US011554141B2

(12) United States Patent
Mata-Fink et al.

(10) Patent No.: US 11,554,141 B2
(45) Date of Patent: Jan. 17, 2023

(54) METHODS AND COMPOSITIONS FOR IMMUNOMODULATION

(71) Applicant: RUBIUS THERAPEUTICS, INC., Cambridge, MA (US)

(72) Inventors: Jordi Mata-Fink, Somerville, MA (US); John Round, Cambridge, MA (US); Noubar B. Afeyan, Lexington, MA (US); Avak Kahvejian, Arlington, MA (US)

(73) Assignee: Rubius Therapeutics, Inc., Cambridge, MA (US)

( * ) Notice: Subject to any disclaimer, the term of this patent is extended or adjusted under 35 U.S.C. 154(b) by 524 days.

(21) Appl. No.: 15/911,924

(22) Filed: Mar. 5, 2018

(65) Prior Publication Data

US 2018/0271910 A1 Sep. 27, 2018

Related U.S. Application Data

(63) Continuation of application No. 15/301,046, filed as application No. PCT/US2015/020614 on Mar. 13, 2015, now Pat. No. 10,869,898.

(60) Provisional application No. 62/059,100, filed on Oct. 2, 2014, provisional application No. 62/025,367, filed on Jul. 16, 2014, provisional application No. 62/006,828, filed on Jun. 2, 2014, provisional application No. 62/006,825, filed on Jun. 2, 2014, provisional application No. 62/006,829, filed on Jun. 2, 2014, provisional application No. 62/006,832, filed on Jun. 2, 2014, provisional application No. 61/991,319, filed on May 9, 2014, provisional application No. 61/973,763, filed on Apr. 1, 2014, provisional application No. 61/973,764, filed on Apr. 1, 2014.

(51) Int. Cl.
| | |
|---|---|
| *C12N 5/10* | (2006.01) |
| *C12N 5/078* | (2010.01) |
| *A61K 39/00* | (2006.01) |
| *A61K 38/17* | (2006.01) |
| *A61K 48/00* | (2006.01) |
| *A61K 35/28* | (2015.01) |
| *C12N 5/07* | (2010.01) |
| *A61K 35/12* | (2015.01) |

(52) U.S. Cl.
CPC ............ *A61K 35/28* (2013.01); *A61K 48/00* (2013.01); *C12N 5/06* (2013.01); *C12N 5/0641* (2013.01); *C12N 5/0644* (2013.01); *A61K 2035/122* (2013.01); *A61K 2035/124* (2013.01)

(58) Field of Classification Search
None
See application file for complete search history.

(56) References Cited

U.S. PATENT DOCUMENTS

| | | | |
|---|---|---|---|
| 4,327,710 A | 5/1982 | DeLoach et al. |
| 5,258,499 A | 11/1993 | Konigsberg et al. |
| 5,648,248 A | 7/1997 | Zenke et al. |
| 5,676,954 A | 10/1997 | Brigham |
| 5,677,176 A | 10/1997 | Nicolau et al. |
| 5,753,221 A | 5/1998 | Magnani et al. |
| 5,811,301 A | 9/1998 | Cameron |
| 5,891,468 A | 4/1999 | Martin et al. |
| 6,139,836 A | 10/2000 | Magnani et al. |
| 6,165,787 A | 12/2000 | Crabtree et al. |
| 6,225,290 B1 | 5/2001 | German et al. |
| 6,326,205 B1 | 12/2001 | Murray et al. |
| 6,350,466 B1 | 2/2002 | Li et al. |
| 6,361,998 B1 | 3/2002 | Bell et al. |
| 6,660,525 B2 | 12/2003 | Martin et al. |
| 6,984,379 B1 | 1/2006 | Kohn et al. |
| 7,427,603 B2 | 9/2008 | Zon et al. |
| 7,462,485 B2 | 12/2008 | Glaser |
| 7,531,341 B1 | 5/2009 | Vellard et al. |
| 7,534,595 B2 | 5/2009 | Vellard et al. |
| 7,537,923 B2 | 5/2009 | Kakkis et al. |
| 7,560,263 B2 | 7/2009 | Kakkis et al. |
| 7,767,202 B2 | 8/2010 | Pardoll et al. |
| 8,211,656 B2 | 7/2012 | Hyde et al. |
| 8,529,944 B2 | 9/2013 | de Almeida Moreira et al. |
| 8,617,840 B2 | 12/2013 | Godfrin |
| 8,673,293 B2 | 3/2014 | Martin et al. |
| 8,852,880 B2 | 10/2014 | Godfrin |
| 8,974,802 B2 | 3/2015 | Dufour et al. |
| 9,125,876 B2 | 9/2015 | Godfrin et al. |
| 9,260,692 B2 | 2/2016 | Martin et al. |
| 9,364,504 B2 | 6/2016 | Godfrin et al. |
| 9,644,180 B2 | 5/2017 | Kahvejian et al. |
| 9,814,780 B2 | 11/2017 | Hubbell et al. |
| 10,253,296 B2 | 4/2019 | Kahvejian et al. |
| 10,260,038 B2 | 4/2019 | Swee et al. |

(Continued)

FOREIGN PATENT DOCUMENTS

| | | |
|---|---|---|
| CN | 101068574 | 11/2007 |
| CN | 101985634 | 3/2011 |

(Continued)

OTHER PUBLICATIONS

Phua et al, Whole Blood Cells Loaded With Messenger RNA as an Anti-Tumor Vaccine, Adv Healthc Mater. Jun. 2014 ; 3(6): 837-842.*

(Continued)

*Primary Examiner* — Maria Marvich

(74) *Attorney, Agent, or Firm* — Fish & Richardson P.C.

(57) ABSTRACT

Provided are cells containing exogenous antigen and uses thereof.

18 Claims, 27 Drawing Sheets

Specification includes a Sequence Listing.

(56) References Cited

U.S. PATENT DOCUMENTS

| | | | |
|---|---|---|---|
| 10,301,593 B2 | 5/2019 | Kahvejian et al. |
| 10,301,594 B1 | 5/2019 | Kahvejian et al. |
| 10,329,531 B2 | 6/2019 | Kahvejian et al. |
| 10,344,263 B2 | 7/2019 | Kahvejian et al. |
| 10,456,421 B2 | 10/2019 | Kahvejian et al. |
| 10,471,099 B2 | 11/2019 | Lodish et al. |
| 10,517,897 B1 | 12/2019 | Kahvejian et al. |
| 10,557,119 B2 | 2/2020 | Kahvejian et al. |
| 10,568,910 B2 | 2/2020 | Kahvejian et al. |
| 10,869,898 B2 | 12/2020 | Mata-Fink et al. |
| 2001/0006772 A1 | 9/2001 | Rainin et al. |
| 2003/0133922 A1 | 7/2003 | Kasha |
| 2003/0207247 A1 | 11/2003 | Stassinopoulos et al. |
| 2004/0133922 A1 | 7/2004 | Okamoto et al. |
| 2004/0142468 A1 | 7/2004 | Pardoll et al. |
| 2006/0188490 A1 | 8/2006 | Hoerr et al. |
| 2006/0228798 A1 | 10/2006 | Verfaillie et al. |
| 2006/0270030 A1 | 11/2006 | Voigt et al. |
| 2007/0082392 A1 | 4/2007 | Glaser |
| 2007/0218552 A1 | 9/2007 | Giarratana et al. |
| 2007/0243137 A1 | 10/2007 | Hainfeld |
| 2008/0008695 A1 | 1/2008 | Vellard et al. |
| 2008/0261262 A1 | 10/2008 | Godfrin |
| 2008/0274092 A1 | 11/2008 | Godfrin et al. |
| 2010/0040546 A1 | 2/2010 | Hyde et al. |
| 2010/0203024 A1 | 8/2010 | Terman et al. |
| 2010/0297177 A1* | 11/2010 | Buening .......... G01N 33/56983 424/233.1 |
| 2010/0310612 A1 | 12/2010 | DuFour et al. |
| 2010/0316620 A1 | 12/2010 | Bourgeaux et al. |
| 2011/0027235 A1 | 2/2011 | Gregory et al. |
| 2011/0070153 A1* | 3/2011 | Hyde ................ A61K 41/0071 424/1.17 |
| 2011/0274669 A1 | 11/2011 | Leboulch et al. |
| 2012/0009140 A1 | 1/2012 | Godfrin et al. |
| 2012/0129210 A1 | 5/2012 | Bourgeaux et al. |
| 2012/0207745 A1 | 8/2012 | Godfrin et al. |
| 2013/0028962 A1 | 1/2013 | Zhang et al. |
| 2014/0010795 A1 | 1/2014 | Bourgeaux et al. |
| 2014/0024118 A1 | 1/2014 | Nakamura et al. |
| 2014/0363413 A1 | 12/2014 | Bourgeaux et al. |
| 2015/0086521 A1 | 3/2015 | Godfrin |
| 2015/0118265 A1 | 4/2015 | Edinger et al. |
| 2015/0133531 A1 | 5/2015 | Wiegand |
| 2015/0182588 A1 | 7/2015 | Kahvejian et al. |
| 2015/0306212 A1 | 10/2015 | Kahvejian et al. |
| 2016/0051648 A1 | 2/2016 | Kraus et al. |
| 2016/0082046 A1 | 3/2016 | Lodish et al. |
| 2016/0095884 A1 | 4/2016 | Godfrin et al. |
| 2016/0120956 A1 | 5/2016 | Godfrin et al. |
| 2016/0122707 A1 | 5/2016 | Swee et al. |
| 2016/0257932 A1 | 9/2016 | Kahvejian et al. |
| 2016/0340665 A1 | 11/2016 | Falb et al. |
| 2016/0361361 A1 | 12/2016 | Godfrin et al. |
| 2017/0020926 A1 | 1/2017 | Mata-Fink et al. |
| 2017/0369843 A1 | 12/2017 | Kahvejian et al. |
| 2018/0030411 A1 | 2/2018 | Kahvejian et al. |
| 2018/0085402 A1 | 3/2018 | Kahvejian et al. |
| 2018/0119101 A1 | 5/2018 | Kahvejian et al. |
| 2018/0135012 A1 | 5/2018 | Mata-Fink et al. |
| 2018/0153989 A1 | 6/2018 | Kahvejian et al. |
| 2018/0187153 A1 | 7/2018 | Kahvejian et al. |
| 2018/0187154 A1 | 7/2018 | Kahvejian et al. |
| 2018/0187155 A1 | 7/2018 | Kahvejian et al. |
| 2018/0193385 A1 | 7/2018 | Kahvejian et al. |
| 2018/0208897 A1 | 7/2018 | Kahvejian et al. |
| 2018/0216067 A1 | 8/2018 | Kahvejian et al. |
| 2018/0265847 A1 | 9/2018 | Kahvejian et al. |
| 2018/0271910 A1 | 9/2018 | Mata-Fink et al. |
| 2018/0344770 A1 | 12/2018 | Wickham et al. |
| 2019/0062788 A1 | 2/2019 | Harandi et al. |
| 2019/0083540 A1 | 3/2019 | Kahvejian et al. |
| 2019/0144827 A1 | 5/2019 | Kahvejian et al. |
| 2019/0160102 A1 | 5/2019 | Hoffman et al. |
| 2019/0161730 A1 | 5/2019 | Kahvejian et al. |
| 2019/0201548 A1 | 7/2019 | Kahvejian et al. |
| 2019/0247440 A1 | 8/2019 | Mata-Fink et al. |
| 2019/0264177 A1 | 8/2019 | Kahvejian et al. |
| 2019/0309261 A1 | 10/2019 | Kahvejian et al. |
| 2019/0309262 A1 | 10/2019 | Kahvejian et al. |
| 2019/0316090 A1 | 10/2019 | Kahvejian et al. |
| 2019/0316091 A1 | 10/2019 | Kahvejian et al. |
| 2019/0330591 A1 | 10/2019 | Yu et al. |
| 2019/0376034 A1 | 12/2019 | Kahvejian et al. |
| 2019/0388473 A1 | 12/2019 | Mata-Fink et al. |
| 2020/0002674 A1 | 1/2020 | Kahvejian et al. |
| 2020/0016209 A1 | 1/2020 | Kahvejian et al. |

FOREIGN PATENT DOCUMENTS

| | | |
|---|---|---|
| CN | 102199199 | 9/2011 |
| CN | 102782142 | 11/2012 |
| CN | 103224957 A | 7/2013 |
| CN | 2003224957 | 7/2013 |
| DE | 102004054536 A1 | 5/2006 |
| JP | 2013/508442 | 5/2012 |
| JP | 2008/501333 | 1/2013 |
| WO | WO 1992/021378 | 12/1992 |
| WO | 2005118780 A1 | 12/2005 |
| WO | 2006016247 A2 | 2/2006 |
| WO | 2006114691 A1 | 11/2006 |
| WO | 2007039150 A2 | 4/2007 |
| WO | 2007042647 A1 | 4/2007 |
| WO | 2009019317 A1 | 2/2009 |
| WO | 2009080837 A1 | 7/2009 |
| WO | 2009101467 A1 | 8/2009 |
| WO | 2009112493 A1 | 9/2009 |
| WO | 2010052315 A1 | 5/2010 |
| WO | 2010075072 A2 | 7/2010 |
| WO | 2010115880 A1 | 10/2010 |
| WO | 2010133298 A1 | 11/2010 |
| WO | 2011051346 A1 | 5/2011 |
| WO | WO 2011/107409 | 9/2011 |
| WO | WO 2013/059343 | 4/2013 |
| WO | 2013121296 A1 | 8/2013 |
| WO | 2013138314 A1 | 9/2013 |
| WO | 2013139906 A1 | 9/2013 |
| WO | 2014066945 A1 | 5/2014 |
| WO | 2014181309 A1 | 11/2014 |
| WO | 2014183066 A2 | 11/2014 |
| WO | 2014183071 A2 | 11/2014 |
| WO | 2015073587 A2 | 5/2015 |
| WO | WO 2001/5073587 | 5/2015 |
| WO | 2015153102 A1 | 10/2015 |
| WO | WO 2015153102 | 10/2015 |
| WO | 2017114966 A1 | 7/2017 |
| WO | WO 2017114966 | 7/2017 |

OTHER PUBLICATIONS

Eixarch et al, Tolerance Induction in Experimental Autoimmune Encephalomyelitis Using Non-myeloablative Hematopoietic Gene Therapy With Autoantigen, Molecular Therapy, 2009, pp. 897-905.*

Meacham et al, Physical Methods for Intracellular Delivery: Practical Aspects from Laboratory Use to Industrial-Scale Processing, J Lab Autom. Feb. 2014 ; 19(1): 1-18.*

Larsson and Lernmark, Vaccination against type 1 diabetes, Intern Med. Jun. 2011 ; 269(6): 626-635.*

Papke and Grosman, The Role of Intracellular Linkers in Gating and Desensitization of Human Pentameric Ligand-Gated Ion Channels, • The Journal of Neuroscience, May 21, 2014 • 34(21):7238-7252.*

Abell et al., "The Effects of Phenylalanine Ammonia-Lyase on Leukemic Lymphocytes in Vitro," Cancer Research (1972) vol. 32, pp. 285-290.

Adriaenssens et al., "Use of Enzyme-loaded Erythrocytes in In-Vitro Correction of Arginase-Deficient Erythrocytes in Familial Hyperargininemia," Clin Chem (1976) vol. 22, No. 3, pp. 323-326.

Bardag-Gorce et al., "Delta-aminolevulinic dehydratase is a proteasome interacting protein," Experimental and Molecular Pathology (2011) vol. 91, pp. 485-489.

(56) References Cited

OTHER PUBLICATIONS

Bergink et al., "Erythropoietic Defect Associated with Reduced Cell Proliferation in Mice Lacking the26S Proteasome Shuttling Factor Rad23b," Molecular and Cellular Biology (2013) vol. 33, No. 19, pp. 3879-3892.
Bogle et al., "Identification of inhibitors of nitric oxide synthase that do not interact with the endotelial cell L-arginine transporter," Br J Pharmacol (1992) vol. 105, pp. 768-770.
Bosmann et al., "Inhibition of Glycoprotein Synthesis in L5178Y Mouse Leukaemic Cells by L-Asparaginase in vitro," Nature (1970) vol. 226, pp. 850-851.
Bryk et al., "Quantitative Analysis of Human Red Blood Cell Preotome," J Proteome Res (2017) vol. 16, pp. 2752-2761.
Caufield et al "SLC2A9 Is a High-Capacity Urate Transporter in Humans" PLOS Medicine (2008) vol. 5, Issue 10, e197, pp. 1509-1522.
Eagle, "Nutrition Needs of Mammalian Cells in Tissue Culture," Science (1955) vol. 122, No. 3168, pp. 501-504.
Gabison et al., "Structural analysis of urate oxidase in complex with its natural substrate inhibited by cyanide Mechanistic implications," BMC Structural Biology (2008) vol. 8, Article 32, 8 pages.
Guo et al., "240-kDa Proteasome Inhibitor (CF-2) Is Identical to delta-Aminolevulinic Acid Dehydratase," J Biol Chem (1994) vol. 269, No. 17, pp. 12399-12402.
Gutiérrez Millán et al., "Cell-based drug-delivery platforms," Therapeutic Delivery (2012) vol. 3, No. 1, pp. 25-41.
Hagihira et al., "Metabolism of L-Lysine by Bacterial Enzymes," J Biochem (1960) vol. 48, No. 2, pp. 267-276.
Hagiya et al. "Pivotal roles of peptide transporter PEPT1 and ATP-binding cassette (ABC) transporter ABCG2 in 5-aminolevulinic acid (ALA)-based photocytotoxicity of gastric cancer cells in vitro" Photodiagnosis and Photodynamic Therapy (2012) vol. 9, pp. 204-214.
Ihler et al. "Enxymatic degratation of uric acid by uricase-loaded human erythrocytes" J Clin Invest (1975) vol. 56, No. 3, pp. 595-602.
Jayaram et al., "Enzyme Applications, Therapeutic," in Kirk-Othmer Encyclopedia of Chemical Technology (2000) John Wiley & Sons, p. 1-22.
Johnson et al. "Uricase Inhibition in the Rat by s-Triazines: An Animal Model for Hyperuricemia and Hyperuricosuria" PSEBM (1969) vol. 131, pp. 8-12.
Kanai et al "Expression Cloning and Characterization of a Transporter for Large Neutral Amino Acids Activated by the Heavy Chain of 4F2 Antigen (CD98)" The Journal of Biological Chemistry (1998) vol. 273, pp. 23629-23632.
Kristensen et al. "Protein synthesis rate is the predominant regulator of protein expression during differentiation" Molecular Systems Biology (2013) vol. 9, No. 689, pp. 1-12.
Kurita et al., "Establishment of Immortalized Human Erythroid Progenitor Cell Lines Able to Produce Enucleated Red Blood Cells," PLOS One (2013) vol. 8, Issue 3, Article e59890, 15 pages.
Malik et al., "An In Vitro Model of Human Red Blood Cell Production From Hematopoietic Progenitor Cells," Blood (1998) vol. 91, No. 8, pp. 2664-2671.
Mochizuki et al, "Long-term correction of hyperphenylalaninemia by AAV-mediated gene transfer leads to behavioral recovery in phenylketonuria mice" Gene Therapy (2004) vol. 11, pp. 1081-1086.
Monico et al. "Phenotypic and Functional Analysis of Human SLC26A6 Variants in Patients With Familial Hyperoxaluria and CalciumOxalate Nephrolithiasis" American Journal of Kidney Diseases (2008) vol. 52, No. 6, pp. 1096-1103.
Moore et al., "Malaria vaccines: where are we and where are we going?," Lancet Infect Dis (2002) vol. 2, pp. 737-743.
Moran et al., "Erythrocyte entrapped thymidine phosphorylase (EE-TP) therapy for mitochondrial neurogastrointestinal encephalopathy," J Neurol Neurosurg Psychiatry (2012) vol. 83, p. 12, Abstract 099.
Müller et al., "Reduction of lysine intake while avoiding malnutrition—Major goals and major problems in dietary treatment of glutaryl-CoA dehydrogenase deficiency," J Inherit Metab Dis (2004) vol. 27, pp. 903-910.
Persons et al., "Use of the green fluorescent protein as a marker to identify and track genetically modified hematopoietic cells," Nature Medicine (1998) vol. 4, No. 10, pp. 1201-1205.
Raghaven et al. "Degradation of oxalate in rats implanted with immobilized oxalate oxidase" FEBS (1986) vol. 195, No. 1,2, pp. 101-105.
Saurabh et al. "Drug Targeting by Erythrocytes: A Carrier System" Scholars Academic Journal of Pharmacy (2013) vol. 2, No. 2, pp. 144-156.
Schrek et al., "L-Asparaginase: Toxicity to Normal and Leukemic Human Lymphocytes," Science (1967) vol. 155, pp. 329-330.
Sen et al., "Cystathionine-β-synthase gene transfer and 3-deazaadenosine ameliorate inflammatory response in endothelial cells," Am J Physiol Cell Physiol (2007) vol. 293, pp. C1779-C1787.
Singh et al., "Relative Contributions of Cystathionine β-Synthase and gamma-Cystathionase to H2S Biogenesis via Alternative Transsulfuration Reactions," J Biol Chem (2009) vol. 284, No. 33, pp. 22457-22466.
Snell et al., "Enzymic imbalance in serine metabolism in human colon carcinma and rat sarcoma," Br J Cancer (1988) vol. 57, pp. 87-90.
Snyder et al., "Effect of Hydrogen Peroxide Exposure on Normal Human Erythrocyte Deformability, Morphology, Surface Characteristics, and Spectrin-Hemoglobin Cross-linking," J Clin Invest (1985) vol. 76, pp. 1971-1977.
Steffes et al., "The lysP Gene Encodes the Lysine-Specific Permease," Journal of Bacteriology (1992) vol. 174, No. 10, pp. 3242-3249.
Stith et al. "Effects of Phenylalanine Ammonia-Lyase and Phenylalanine Deprivation on Murine Leukemic Lymphoblasts in Vitro" Cancer Research (1973) vol. 33, pp. 966-971.
Sun et al. "Nanoliposome-mediated FL/TRAIL double-gene therapy for colon cancer: In vitro and invivo evaluation" Cancer Letters (2012) vol. 315, pp. 69-77.
Torres-Torronteras et al., "Hematopoietic gene therapy restores thymidine phosphorylase activity in a cell culture and a murine model of MNGIE," Gene Therapy (2011) vol. 18, pp. 795-806.
Tsitsiou et al "Homocysteine transport by systems L, A and y+L across the microvillous plasma membrane of human placenta" J Physiol (2009) vol. 587, No. 16, pp. 4001-4013.
Veyssier et al. "Rapid Analysis of 5-aminolevulinic acid" Biochrom (2009) Application Note B30.17.
Wang et al. "Modulation of Cystathionine Beta-Synthase Level Regulates Total Serum Homocysteine in Mice" Circulation Research (2004) vol. 94, pp. 1318-1324.
Yamamoto et al., "Characterization of rapid and high-affinity uptake of L-serine in neurons and astocytes in primary culture," FEBS Letters (2003) vol. 548, pp. 69-73.
Yang et al., "Cystathionine gamma-Lyase Overexpression Inhibits Cell Proliferation via a H2S-dependent Modulation of ERK1/2 Phosphorylation and p21Cip/WAK-1," J Biol Chem (2004) vol. 279, No. 47, pp. 49199-49205.
Yokota et al., "Degradation of Overexpressed Wild-type and Mutant Uricase Proteins in Cultured Cells," The Journal of Histochemistry & Cytochemistry (1999) vol. 49, No. 9, pp. 1133-1139.
Liu et al., "Membrane Remodeling During Reticulocyte Maturation", Blood, 115(10):2021-7, Mar. 11, 2010.
Luo et al. "ECDI-fixed allogeneic splenocytes induce donor-specific tolerance for long-term survival of islet transplants via two distinct mechanisms" PNAS (2008) vol. 105, No. 38, pp. 14527-14532.
Luo, Biao et al., "Highly Parallel Identification of Essential Genes in Cancer Cells." PNAS, 2008, pp. 69-74, vol. 105, No. 105.
Lutterotti et al., "Antigen-Specific Tolerance by Autologous Myelin Peptide Coupled Cells: A Phase 1 Trial in Multiple Sclerosis," Sci Trans Med, 2013, vol. 5, No. 188. Doi:10.1126/scitranslmed. 3006168.
Ma, F. et al., "Generation of Functional Erythrocytes from Human Embryonic Stem Cell-Derived Definitive Hematopoiesis," Proceedings of the National Academy of Sciences of the United States of America, 2008, pp. 13087-1392, vol. 105, No. 35.

(56) References Cited

OTHER PUBLICATIONS

Maria-Grazia, R. et al., Regulatory T-Cell Immunotherapy for Tolerance to Self Antigens and Alloantigens in Humans, The Journal of Immunology (2007) vol. 7, No. 8, pp. 585-598.

McCaughan, J. A. et al., "The Complement Cascade in Kidney Disease: from Sideline to Center Stage," American Journal of Kidney Diseases : the Official Journal of the National Kidney Foundation, 2013, pp. 604-614, vol. 62, No. 3. doi:1 0.1 053/j.ajkd. 2012.12.033.

McGrogan, A. et al., "The Incidence of Primary Glomerulonephritis Worldwide: a Systematic Review of the Literature," Nephrology, Dialysis, Transplantation: Official Publication of the European Dialysis and Transplant Association—European Renal Association, 2011, pp. 414-430, vol. 26, No. 2. doi:1 0.1 093/ndt/gfq665.

Miharada, K. et al., "Efficient Enucleation of Erythroblasts Differentiated In Vitro from Hematopoietic Stem and Progenitor Cells," Nature Biotechnology, 2006, pp. 1255-1256, vol. 24, No. 10. doi: 10.1 038/nbt1245.

Millan, C.G. et al., "Drug, Enzyme and Peptide Delivery Using Erythrocytes as Carriers", Journal of Controlled Release, Elsevier, Amsterdam, NL, vol. 95, No. 1, Feb. 20, 2004.

Miller, Stephen, et al., "The Induction of Cell-Mediated Immunity and Tolerance with Protein Antigens Coupled to Syngeneic Lymphoid Cells" J. Exp. Med., pp. 758-773, vol. 149, 758-773.

Mukthavaram, R. et al., "Targeting and Depletion of Circulating Leukocytes and Cancer Cells by Lipophilic Antibody-Modified Erythrocytes," Journal of Controlled Release: Official Journal of the Controlled Release Society, 2014, pp. 146-153, vol. 183. doi: 10.1 016/j.jconrel.2014.03.038.

Murciano, J. et al., "Prophylactic Fibrinolysis Through Selective Dissolution of Nascent Clots by tPA-Carrying Erythrocytes," Nature Biotechnology, 2003, pp. 891-896, vol. 21, No. 8.

Muzykantov, V. R., "Drug Delivery by Red Blood Cells: Vascular Carriers Designed by Mother Nature," Expert Opinion on Drug Delivery, 2011, pp. 403-427, vol. 7, No. 4. doi:1 0.1517/ 1742524100361 0633.Drug.

Muzykantov, V. R., "Drug Delivery Carriers on the Fringes: Natural Red Blood Cells Versus Synthetic Multilayered Capsules," Expert Opinion on Drug Delivery, 2013, pp. 1-4, vol. 10, No. 1.

Neildez-Nguyen, T. M.A. et al., "Human Erythroid Cells Produced Ex Vivo at Large Scale Differentiate into Red Blood Cells In Vivo," Nature Biotechnology, 2002, pp. 467-472, vol. 20, No. 5.

O'Keefe "Nucleic Acid Delivery: Lentiviral and Retroviral Vectors" Materials and Methods (2013) vol. 3, No. 174, pp. 1-17.

Olivier, E. N. et al., "Large-Scale Production of Embryonic Red Blood Cells from Human Embryonic Stem Cells," Experimental Hematology, 2006, pp. 1635-1642, vol. 34, No. 12. doi:10.1016/j. exphem.2006.07.003.

Pasini, E. M. et al., "Red Blood Cell (RBC) Membrane Proteomics—Part 1: Proteomics and RBC Physiology," Journal of Proteomics, 2010, pp. 403-442, vol. 73, No. 3. doi:1 0.1 016/j.jprot.2009.06.005.

Plaimauer, B. et al., "Recombinant ADAMTS13 Normalizes von Willebrand Factor-Cleaving Activity in Plasma of Acquired TTP Patients by Overriding Inhibitory Antibodies," Journal of Thrombosis and Haemostasis: JTH, 2011, pp. 936-944, vol. 9, No. 5. doi:10.1111/j.1538-7836.2011.04224.x.

Polmar, S.H. et al., "Enzyme Replacement Therapy for Adenosine Deaminase Deficiency and Severe Combined Immunodeficiency," The New England Journal of Medicine, Dec. 9, 1976, pp. 1337-1343.

Popov, M. et al., "Transmembrane Folding of the Human Erythrocyte Anion Exchanger (AE1, Band 3) Determined by Scanning and Insertional N-Giycosylation Mutagenesis," Biochem J, 1999, pp. 269-279, vol. 339.

Pries et al., "Biophysical aspects of blood flow in the microvasculature," Cardiovascular Research, 1996, pp. 654-667.

Rahman, A. et al., "Systemic Lupus Erythematosus," New England Journal of Medicine, 2008, pp. 929-939, vol. 358, No. 9.

Repik, A. et al., "A Transgenic Mouse Model for Studying the Clearance of Blood-Borne Pathogens Via Human Complement Receptor 1 (CR 1 )," Clinical and Experimental Immunology, 2005, pp. 230-240, vol. 140, No. 2. doi:10.1111/j.1365-2249.2005.02764. x.

Rodriguez De Cordoba, S. et al. "Complement Dysregulation and Disease: From Genes and Proteins to Diagnostics and Drugs," Immunobiology, 2012, pp. 1034-1046, vol. 217.

Rossi et al., "Erythrocyte-Mediated Delivery of Phenylalanine Ammonia Lyase for the Treatment of Phenylketonuria in BTBR-Pahenu2 mice", Journal of Controlled Release, 194:37-44, Nov. 28, 2014.

Rother, B. R. P. et al., "Expression of Recombinant Transmembrane CD59 in Paroxysmal Nocturnal Hemoglobinuria B Cells Confers Resistance to Human Complement," Blood, 1994, pp. 2604-2611, vol. 84, No. 8.

Ryan, J. J. et al., "Expression and Characterization of Recombinant Rat a 3 (IV) NC1 and its Use in Induction of Experimental Autoimmune Glomerulonephritis," Nephrology, Dialysis, Transplantation: Official Publication of the European Dialysis and Transplant Association—European Renal Association, 2001, pp. 253-261, vol. 16, No. 2.

Sarkissian "A different approach to treatment of phenylketonuria: Phenylalanine degradation with recombinant phenylalanine ammonia lyase" PNAS (1999) vol. 96, pp. 2339-2344.

Sherer, Y. et al., "Intravenous Immunoglobulin Therapy of Antiphospholipid Syndrome," Rheumatology, 2000, pp. 421-446, vol. 39, No. 4.

Shi, J. et al., "Engineered Red Blood Cells as Carriers for Systemic Delivery of a Wide Array of Functional Probes," Proceedings of the National Academy of Sciences of the United States of America, 2014, pp. 10131-10136, vol. 111, No. 28. doi:1 0.1 073/pnas. 1409861111.

Shiozawa, Y. et al., "Cancer Stem Cells and Their Role in Metastasis", Pharmacology & Therapeutics, 2013, pp. 285-293, vol. 138, No. 2. doi:1 0.1 016/j.pharmthera.2013.01.014.

Smarr et al., "Antigen-Fixed Leukocytes Tolerize Th2 Responses in Mouse Models of Allergy," J Immunol, 2011, vol. 187, No. 5090-5098. doi:10.4049/jimmunol.1100608.

Smith, B. W. et al., "The Aryl Hydrocarbon Receptor Directs Hematopoietic Progenitor Cell Expansion and Differentiation," Blood, 2013, pp. 376-385, vol. 122, No. 3. doi:1 0.1182/blood-2012-11-466722.

Sprandel et al. "In Vitro Studies on Resealed Erythrocyte Ghosts as Protein Carriers" Res. Exp. Med. (Berl.) vol. 175, pp. 239-245 (1979).

Sprandel et al., "Biochemical Studies of Phenylalanine Ammonia-Lyase Encapsulated in Erythrocytes", Biochemical Society Transactions, 18(4):654-655, Aug. 1990.

Stein, S. C. et al., "Erythrocyte-Bound Tissue Plasminogen Activator is Neuroprotective in Experimental Traumatic Brain Injury," Journal of Neurotrauma, 2009, pp. 1585-1592, vol. 26, No. 9.

Suzuki, H. et al., "The Pathophysiology of IgA Nephropathy," Journal of the American Society of Nephrology: JASN, 2011, pp. 1795-1803, vol. 22, No. 10. doi:1 0.1681/ASN.2011050464.

Timmins, N. E. et al., "Manufactured RBC—rivers of blood, or an oasis in the desert?", Biotechnology Advances, 2011, pp. 661-666, vol. 29, No. 6. doi:1 0.1 016/j.biotechadv.2011.05.002.

Toong, C. et al., "Clearing the Complexity: Immune Complexes and Their Treatment in Lupus Nephritis," International Journal of Nephrology and Renovascular Disease, 2011, pp. 17-28, vol. 4. doi:10. 2147/IJNRD.S10233.

Vilchez et al. "Display of Biologically Functional Insecticidal Toxin on the Surface of I Phage" Applied and Environmental Microbiology (2004) Bol 70, No. 11, pp. 6587-6594.

Wang, J. et al., "In Vitro Hematopoietic Differentiation of Human Embryonic Stem Cells Induced by Co-Culture with Human Bone Marrow Stromal Cells and Low Dose Cytokines," Cell Biology International, 2005, pp. 654-661, vol. 29, No. 8. doi:1 0.1 016/j. cellbi.2005.03.019.

Aledort, L. M. et al., "Efficacy and Safety of Intravenous Anti-D Immunoglobulin (Rhophylac) in Chronic Immune Thrombocytopenic Purpura," Hematology (Amsterdam, Netherlands), 2007, pp. 289-295, vol. 12, No. 4. doi:1 0. 1080/10245330701383908.

(56) References Cited

OTHER PUBLICATIONS

Anstee "The functional importance of blood group-active molecules in human red blood cells" Vox Sanguinis (2011) vol. 100, pp. 140-149.
Asherson, R. A., "Multiorgan Failure and Antiphospholipid Antibodies: the Catastrophic Antiphospholipid (Asherson's) Syndrome," Immunobiology, doi:10.1016/j.imbio.2005.10.002, 2005, pp. 727-733, vol. 210, No. 10.
Avramis et al. "Asparaginase (native ASNase or pegylated ASNase) in the treatment of acute lymphoblastic leukemia" International Journal of Nanomedicine (2006) vol. 1, No. 3, pp. 241-254.
Banzato, A. et al., "Clinical Relevance of Beta-2-Glycoprotein-1 Plasma Levels in Antiphospholipid Syndrome (APS)," Current Rheumatology Reports, 2014, 424, 5 pages, vol. 16, No. 6. doi:10.1007/s11926-014-0424-9.
Barnhart et al. "Changes in Cellular mRNA Stability, Splicing and Polyadenylation through HuR Protein Sequestration by a Cytoplasmic RNA Virus" Cell Reports (2013) vol. 5, No. 4, pp. 1-16.
Beck, L. et al., "M-Type Phospholipase A2 Receptor as Target Antigen in Idiopathic Membranous Nephropathy," New England Journal of Medicine, Jul. 2, 2009, pp. 11-21, vol. 361, No. 1. Retrieved from http://www.nejm.org/doi/full/1 0.1056/NEJMoa0810457.
Beck, L. H. & Salant, D. J. "Review Series: Membranous Nephropathy: from Models to Man," Journal of Clinical Investigation, 2014, pp. 2307-2314, vol. 124, No. 6. doi:10.1172/JCI72270.Review.
Bhowmik, D. et al., "Clinical Approach to Rapidly Progressive Renal Failure: Role of Kidney Biopsy," J Assoc Physicians India, Jan. 2011, pp. 38-41, vol. 59.
Bollmann, F. Mathias, "Rheumatic Autoimmune Diseases: Proposed Elimination of Autoreactive B-cells with Magnetic Nanoparticle-Linked Antigens", Medical Hypotheses Eden Press Penrith US, vol. 78, No. 4, Jan. 6, 2012.
Booth, C. et al., "Pegademase Bbovine (PEG-ADA) for the Treatment of Infants and Children with Severe Combined Immunodeficiency ( SCID )," Biologics, 2009, pp. 349-358, vol. 3.
Braley-Mullen, et al., "Suppression of experimental autoimmune thyroiditis in guinea pigs by pretreatment with thyroglobulin-coupled spleen cells," Cellular Immunology (1980) vol. 51, No. 2, pp. 408-413.
Burger et al. "CD4 functions as a molecular switch for erythrocyte phagocytosis" Blood (2012) vol. 119, No. 23, pp. 5512-5521.
Caras, I. W. et al., "Analysis of the Signal for Attachment of a Glycophospholipid Membrane Anchor," Journal of Cell Biology, Apr. 1989, pp. 1387-1396, vol. 108.
Chen, E. H. et al., "Hereditary Overexpression of Adenosine Deaminase in Erythrocytes: Studies in Erythroid Cell Lines and Transgenic Mice," Blood, 1994, pp. 2346-2353, vol. 84, No. 7.
Chen, Z. et al., "Circulation DNA: Biological Implications for Cancer Metastasis and Immunology," Medical Hypotheses, 2005, pp. 956-961, vol. 65, No. 5 doi:1 0.1 016/j.mehy.2005.04.042.
Cremel, M. et al., "Red Blood Cells as Innovative Antigen Carrier to Induce Specific Immune Tolerance," International Journal of Pharmaceutics, 2013, pp. 39-49, vol. 443, No. 1-2. doi:10.1016/j.ijpharm.2012.12.044.
Dember, L., "Emerging Treatment Approaches for the Systemic Amyloidoses," Kidney International, 2005, pp. 1377-1390, vol. 68, No. 3.
European Search Report for European Application No. EP 14824599.6 dated Aug. 7, 2017.
Ferri, C. et al., "Mixed Cryoglobulinemia: Demographic, Clinical, and Serologic Features and Survival in 231 Patients," Semin Arthritis Rheum, 2004, pp. 355-374, vol. 33, No. 6. doi:10.1053/S0049-0172(03)00179-3.
Fujimi, A. et al., "Ex Vivo Large-Scale Generation of Human Red Blood Cells from Cord Blood CD34+ Cells by Co-Culturing with Macrophages," International Journal of Hematology, 2008, pp. 339-350, vol. 87, No. 4. doi:10.1007/ s12185-008-0062-y.
Furtado, P. B. et al., "The Partly Folded Back Solution Structure Arrangement of the 30 SCR Domains in Human Complement Receptor Type 1 (CR1) Permits Access to its C3b and C4b Ligands," Journal of Molecular Biology, 2008, pp. 102-118, vol. 375, No. 1. doi: 10.1 016/j.jmb.2007.09.085.
GenBank Accession No. BAJ17655.1 (2011).
Giarratana, M.C. et al., "Ex Vivo Generation of Fully Mature Human Red Blood Cells from Hematopoietic Stem Cells," Nature Biotechnology, 2005, pp. 69-74, vol. 23, No. 1. doi:10.1038/nbt1047.
Giarratana, M.C. et al., "Proof of Principle for Transfusion of in Vitro-Generated Red Blood Cells," Blood, 2011, pp. 5071-5079, vol. 118, No. 19. doi:10.1182/blood-2011-06-362038.
Hamidi et al. "Applications of carrier erythrocytes in delivery of biopharmaceuticals" Journal of Controlled Release (2007) vol. 118, pp. 145-160.
Hamidi et al. "Carrier Erythrocytes: An Overview" Drug Delivery (2003) vol. 10, pp. 9-20.
Hattangadi, S.M. et al., "From Stem Cell to Red Cell: Regulation of Erythropoiesis at Multiple Levels by Multiple Proteins, RNAs, and Chromatin Modifications," Blood, 2011, pp. 6258-6668, vol. 118, No. 24. doi:10.1182/blood-2011-07-356006.
Hebert, L.A. et al., "Differential Diagnosis of Glomerular Disease: a Systematic and Inclusive Approach," American Journal of Nephrology, 2013, pp. 253-266, vol. 38, No. 3. doi: 10.1159/000354390.
Hermansen "Nucleated red blood cells in fetus and newborn" Arch. Dis. Child. Fetal. Neonatal Ed. (2001) vol. 81, pp. F211-F215.
Hu, C.M. J. et al., "Erythrocyte Membrane-Camouflaged Polymeric Nanoparticles as a Biomimetic Delivery Platform," Proceedings of the National Academy of Sciences of the United States of America, 2011, pp. 10980-10985, vol. 108, No. 27. doi:1 0.1 073/pnas.11 06634108.
Hu, J. et al., "Isolation and Functional Characterization of Human Erythroblasts at Distinct Stages: Implications for Understanding of Normal and Disordered Erythropoiesis in Vivo," Blood, 2013, pp. 3246-3253, vol. 121, No. 16. doi:10.1182/blood-2013-01-476390.
Huang, X. et al., "Extensive Ex Vivo Expansion of Functional Human Erythroid Precursors Established from Umbilical Cord Blood Eells by Defined Factors," Molecular Therapy: the Journal of the American Society of Gene Therapy, 2014, pp. 451-463, vol. 22, No. 2. doi: 10.1038/mt.2013.201.
Imai et al. "Chimeric receptors with 4-1BB signaling capacity provoke potent cytotoxicity against acute lymphoblastic leukemia" Leukemia (2004) vol. 18, pp. 676-684.
Inada, Y. et al., "In Vivo Binding of Circulating Immune Complexes by C3b Receptors (CR1) of Transfused Erythrocytes," Annals of the Rheumatic Disease, 1989, pp. 287-294, vol. 48, No. 4.
Kafri et al. "A Packaging Cell Line for Lentivirus Vectors" Journal of Virology (1999) vol. 73, No. 1, pp. 576-584.
Kallenberg, C. G. M. et al., "Complement is Crucial in the Pathogenesis of ANCA Associated Vasculitis," Kidney International, 2013, pp. 16-18, vol. 83, No. 1. doi:1 0.1 038/ki.2012.371.
Keerthivasan, G. et al., "Erythroblast Enucleation,"Stem Cells International, 2011, Article ID139851, pp. 1-9. doi:10.4061/2011/139851.
Kim, J. Y. et al., "Treatment of Myasthenia Gravis Based on Its Immunopathogenesis Symptom-Relieving Treatments," Journal of Clinical Neurology, 2011, pp. 173-183, vol. 7, No. 4.
Kontos, S. et al., "Engineering Antigens for in situ Erythrocyte Binding Induces T-cell Deletion," Proceedings of the National Academy of Sciences of the United States of America, 2013, pp. E60-E68, vol. 110, No. 1. doi:10.1073/pnas.1216353110.
Kwon et al. "L-Asparaginase Encapsulated Intact Erythrocytes for Treatment of Acute Lymphoblastic Leukemia (ALL)" Journal of Controlled Release (2009) vol. 139, No. 3, pp. 182-189.
Leberbauer, C. et al., "Different Steroids Co-Regulate Long-Term Expansion Versus Terminal Differentiation in Primary Human Erythroid Progenitors," Blood, 2005, pp. 85-94, vol. 105, No. 1. doi:10.1182/blood-2004-03-1002.
Liepkalns, J. S. et al., "Resistance of a Subset of Red Blood Cells to Clearance by Antibodies in a Mouse Model of Incompatible Transfusion,"Transfusion, 2013, pp. 1319-1327, vol. 53, No. 6. doi:10.1111/j.1537-2995.2012.03910.x.
AU Office Action in Australian Appln. No. 2019208203, dated Jun. 26, 2020, 4 pages.

(56) References Cited

OTHER PUBLICATIONS

BR Office Action in Brazilian Appln. No. 112016022814-6, dated Aug. 18, 2020, 5 pages (with English Translation).
CN Office Action in Chinese Appln. No. 201580024460.0. dated Jun. 12, 2020, 15 pages.
Khochenkov et al., "Interaction between dendritic cells and B cells during immune response to T cell-independent antigens," *Meditsinskaya Immunologiya* 14(1-2):51-58, 2012, English Abstract.
Pan et al., "Establishment and Optimization of Efficient Red Blood Cell-Specific Expression System," *J. Transl. Med.* 2(1):4-10, 2013, English, abstract only.
RU Office Action in Russian Appln. No. 2016142671, dated Jun. 2, 2020, 16 pages (with English Translation).
Samsel et al., "Imaging flow cytometry for the study of erythroid cell biology and pathology," *J. Immunol. Methods*, 423:52-59, 2015.
Weiss et al., "Chaperoning erythropoiesis," *Blood*, 113(10):2136-44, 2009.
[No Author Listed] Addgene Vector Database {pEGFP-N1, https://www.addgene.org/vector-database/2491/?Jclid=EAlalQobChMlmv72x9eF5glVl-eGCh0q_A5NEAAYASAAEgliK_D_BwE; last visited Nov. 25, 2019).
Amersdorfer et al., "Molecular Characterization of Murine Humoral Immune Response to Botulinum Neurotoxin Type A Binding Domain as Assessed by Using Phage Antibody Libraries," *Inf Immunity* 65(9):3743-52, 1997.
AU Office Action is Australian Appln. No. 2015241422, dated Nov. 21, 2019, 4 pages.
Bakker-Woudenberg et al., "Liposomes in the Treatment of Infections," *J. Drug Target* 1994, 2(5):363-371, 1994.
Bax et al., "Clinical and Biochemical Improvements in a Patient with MNGIE Following Enzyme Replacement," *Neurology* 81:1269-1271, 2013.
Betageri et al., "Fc-receptor-mediated Targeting of Antibody-Bearing Liposomes Containing Dideoxycytidine Triphosphate to Human Monocyte/Macrophages," *J. Pharm. Pharmacol.* 45(1):48-53, 1993.
Bhaduri et al., "Optical Assay of Erythrocyte Function in Banked Blood," *Sci. Reports* 4:6211, 2014, 6 pages.
Bomalaski et al., "Uricase Formulated with Polyethylene Glycol (Uricase-PEG 20): Biochemical Rationale and Preclinical Studies," *J. Rheumatol.* 29:1942-1949, 2002.
Bose et al., "Characterization and Molecular Modeling of a Highly Stable anti-Hepatitis B Surface Antigen scFv,"*Mol. Immunol.* 40(9):617-31, 2003.
Brasseur et al., "Receptor-mediated Targeting of Phthalocyanines to Macrophages via Covalent Coupling to Native or Maleylated Bovine Serum Albumin," *Photochem. Photobiol.* 69(3):345-352, 1999.
Bryan et al., "Measuring Single Cell Mass, Volume and Density With Dual Suspended Microchannel Resonators," *Lab Chip* 14(3):569-76, 2014.
Byun et al., "Characterizing Deformability and Surface Friction of Cancer Cells," *Proc. Natl. Acad. Sci. U.S.A.* 110(19):7580-5, 2013.
Chakrabartv et al., "Neoglycoproteins as Carriers for Receptor-Mediated Drug Targeting in the Treatment of Experimental Visceral Leishmaniasis," *J. Protozool.* 37(5):358-364, 1990.
Chu et al., "Adjuvant-free in Vivo Targeting. Antigen Delivery by Alpha 2-macroglobulin Enhances Antibody Formation," *J. Immunol.* 152(4):1538-1545, 1994.
Corinti et al., "Erythrocytes deliver Tat to interferon-gamma-treated human dendritic cells for efficient initiation of specific type 1 immune responses in vitro," *J. Leukocyte Biology* 71:652-658, 2002.
Cramer et al., "Ulfrastructure of Platelet Formation by Human Megakaryocytes Cultured With the Mpl Ligand," *Blood* 89(7):2336-2346, 1997.
De Flora et al., "Construction of glucose oxidase-loaded human erythrocytes: a model of oxidative cytotoxicity," *Ital. Biochem.* 35(5)361-367, 1986, Abstract Only.

Delgade et al., "Intracellular Water Exchange for Measuring the Dry Mass, Water Mass and Changes in Chemical Composition of Living Cells," *PLoS One* 8(7):e67590, 2013, 11 pages.
Dreier et al., "Recombinant Immunocytokines Targeting the Mouse Transferrin Receptor: Construction and Biological Activities," *Bioconjug. Chem.* 9(4):482-489, 1998.
Figueiredo, "Gene Therapy: A New Approach for Preventing Calcium Oxalate Stones," Thesis Submitted to the raculty of University of Minnesota, pp. 1-50, 2014.
Frankel et al., "Lectin-deficient Ricin Toxin Intoxicates Cells Bearing the D-mannose Receptor," *Carbohydr. Res.* 300(3):251-258, 1997.
Ghaffari, "Oxidative Stress in the Regulation of Normal and Neoplastic Hematopoiesis," *Antioxid. Redox Signal.* 10(11):1923-1940, 2008.
Goswami et al., "An overview on alcohol oxidases and their potential applications," *Appl. Microbiol. Biotechnol.* (97):4259-4275, 2013.
Green et al., "Immunogenic and Tolerogenic Cell Death," *Nat. Rev. Immunol.* 9(5):353-63, 2009.
Griffith et al., "Cell Death in the Maintenance and Abrogation of Tolerance: The Five Ws of Dying Cells," *Immunity* 35(4):456-66, 2011.
Haidekker et al., "New Fluorescent Probes for the Measurement of Cell Membrane Viscosity," *Chem. Biol.* 8(2)123-31, 2001.
Hamblin et al., "Photosensitizer Targeting in Photodynamic Therapy. I. Conjugates of Haematoporphyrin With Albumin and Transferrin," *J. Photochem. Photobiol.* 26(1):45-56, 1994.
Harris et al., "Methemoglobinemia Resulting From Absorption of Nitrates," *JAMA* 242:2869-2871, 1979.
Hirose et al., "Immortalization of Erythroblasts by c-MYC and BCL-XL Enables Large-Scale Erythrocyte Production From Human Pluripotent Stem Cells," *Stem Cell Report* 1(6):499-508, 2013.
Johnson et al., "Red cells from glutathione peroxidase-1-deficient mice have nearly normal defenses against exogenous peroxides," *Blood* 96:1985-1988, 2000.
JP Office Action in Japanese Appln. No. 2019-143575, dated Feb. 15, 2019, 5 pages.
JP Office Acton in Japanese Appln. No. 2016-560527, dated Dec. 26, 2019, 7 pages (with English Translation).
JP Office Acton in Japanese Appln. No. 2016-560527, dated Feb. 15, 2019, 6 pages (with English Translation).
Kay et al., "Mechanism of Removal of Senescent Cells by Human Macrophages in Situ," Proc. Natl. Acad. Sci. U.S.A. 72(9):3521-5, 1975.
Kooyman et al., "In Vivo Transfer of GPI-linked Complement Restriction Factors From Erythrocytes to the Endothelium," *Science* 269(5220):89-92, 1995.
Lach-Trifilieff et al., "Complement Receptor 1 (CD35) on Human Reticulocytes: Normal Expression in Systemic Lupus Erythematosus and HIV-infected Patients," *J. Immunol.* 162(12):7549-54, 1999.
Lin et al., "Expression of human phenylalanine hydroxylase activity in T lymphocytes of classical phenylketonuria children by retroviral-mediated gene transfer," *J. Int. Metab. Dis.* 20:742-754, 1997.
Liu et al., "Bacterial Glycosidases for the Production of Universal Red Blood Cells," *Nat. Biotech.* 25(4):454-464, 2007.
Lukasheva et al., "L-Lysine alpha-Oxidase: Physicochemical and Biological Properties," *Biochemistry* (Moscow) 67(10): 1152-1158, 2002.
Maeda et al., "Role of Polyamines Derived from Arginine in Differentiation and Proliferation of Human Blood Cells," *Biol. Pharm. Bull.* 29(2):234-239, 2006.
Magnani et al., "Methanol detoxification by enzyme-loaded erythrocytes," *Biotechnol. Appl. Biochem.* 18:217-226, 1993, Abstract Only.
Mankertz et al., "Low Density Lipoproteins as Drug Carriers in the Therapy of Macrophage-Associated Diseases," *Biochem. Biophys. Res. Comm.* 240(1):112-115, 1997.
Migliaccio et al., "The Potential of Stem Cells as an In Vitro Source of Red Blood Cells for Transfusion," *Cell Stem Cell* 10:115-119, 2012.

(56) References Cited

OTHER PUBLICATIONS

Munoz-Pinedo et al., "Apoptosis of haematopoietic cells upon thymidylate synthase inhibition is independent of p53 accumulation and CD95-CD95 ligand interaction," *Biochem. J.* 353:101-108, 2001.

Noble et al., "Reticulocytes. I. Isolation and in Vitro Maturation of Synchronized Populations," *Blood* 74(1)475-481, 1989.

Nuki et al., "A concise history of gout and hyperuricemia and their treatment," *Arthritis Research & Therapy* 8(Supp. 1) 2006, 5 pages.

Penrose, "Data for the Study of Linkage in Man: Phenylketonuria and the ABO and MN Loci," *Annal. Eugenics* 16(1):241-248, 1951.

Pittet et al., "Lymphoscintigraphy via the Targeting of Macrophages With 99mTc-J001X Poly-Galactoside in a Model of Pyogranulomas Developed in Sheep Lymph Nodes," *Nucl. Med. Biol.* 22(3):355-365, 1995.

Rieu et al., "The A-domain of Beta 2 Integrin CR3 (CD1lb/CD18) Is a Receptor for the Hookworm-Derived Neutrophil Adhesion Inhibitor NIF," *J. Cell Biol.* 127:2081-91, 1994.

Rojanasakul et al., "Targeted Gene Delivery to Alveolar Macrophages via Fc Receptor-Mediated Endocytosis," *Pharm. Res.* 11(12):1731-6, 1994.

Rossi et al., "Normalization of Hyperglycemia in Diabetic Mice by Enzyme-Loaded Erythrocytes," in Magnani et al. eds., The Use of Resealed Erythrocytes as Carriers and Bioreactors, Advances in Experimental Medicine and Biology, vol. 326, pp. 183-188, 1992, Abstract only.

Schenkein et al., "The use of glucose oxidase as a generator of $H_2O_2$ in the enzymatic radioiodination of components of cell surfaces," *Cellular Immunol.* 5(3):490-493, 1972, Abstract only.

Shima et al., "L-arginine import via cationic amino acid transporter CAT1 is essential for both differentiation and proliferation of erythrocytes," *Blood* 107:1352-1356, 2006.

Szeto et al., "Microfluidic squeezing for intracellular antigen loading in polyclonal B-cells as cellular vaccines," *Scientific Reports*, vol. 5, Article 10276, 2015, 13 pages.

Tabas et al., "The Influence of Particle Size and Multiple Apoprotein E-receptor Interactions on the Endocytic Targeting of beta-VLDL in Mouse Peritoneal Macrophages," *J. Cell Biol.* 115(6):1547-1560, 1991.

Toth et al., "Intact human erythrocytes prevent hydrogen peroxide-mediated damage to isolated perfused rat lungs and cultured bovine pulmonary artery endothelial cells," *J. Clin. Invest.* 74(1):292-295, 1984.

Turrini et al., "Clustering of Integral Membrane Proteins of the Human Erythrocyte Membrane Stimulates Autologous IgG Binding, Complement Deposition, and Phagocytosis," *J. Biol. Chem.* 266(35):23611-7, 1991.

Vilchez et al., "Display of Biologically Functional Insecticidal Toxin on the Surface of I Phage," Appl. Env. Microbiol. 70(11):6587-6594, 2004.

Von Baeyer et al., "Covalent Coupling of Nucleosides to Low Density Lipoprotein (LDL) Generates Macrophage Specific (Drug)-Carriers," *Int. J. Clin. Pharmacol. Ther. Toxicol.* 31(8):382-386, 1993.

Yang et al., "Pro-apoptotic effect of endogenous $H_2S$ on human aorta smooth muscle cells," *FASEB J.* 20(3):553, 2006, 21 pages.

Zakeri et al., "Spontaneous Intermolecular Amide Bond Formation Between Side Chains for Irreversible Peptide Targeting," *JACS* 132(13):4526-7, 2010.

Zubizarreta et al, "Immune tolerance in multiple sclerosis and neuromyelitis optica with peptide-loaded tolerogenic dendritic cells in a phase 1b trial," *Proc. Natl. Acad. Sci. U.S.A.* 1161(17):18463-8470, 2019.

Weisman, H.F. et al., "Soluble Human Complement Receptor Type 1: In Vivo Inhibitor of Complement Suppressing Post-Ischemic Myocardial Inflammation and Necrosis," Science, 1990, pp. 146-151, vol. 249, No. 4965.

Xi et al. "In Vitro Large Scale Production of Human Mature Red Blood Cells from Hematopoietic Stem Cells by Coculturing with Human Fetal Liver Stromal Cells" BioMed Research International (2013) vol. 2013, pp. 1-12.

Yew, N. S. et al., "Erythrocytes Encapsulated with Phenylalanine Hydroxylase Exhibit Improved Pharmacokinetics and Lowered Plasma Phenylalanine Levels in Normal Mice," Molecular Genetics and Metabolism, 2013, pp. 339-344, vol. 109, No. 4. doi:1 0.1 016/j.ymgme.2013.05.011.

Zhu et al. "Use of RhD Fusion Protein Expressed on K562 Cell Surface in the Study of Molecular Basis for D Antigenic Epitopes" The Journal of Biological Chemistry (1999) vol. 274, No. 9, pp. 5731-5737.

Zimring, J.C., "Fresh Versus Old Blood: Are There Differences and Do They Matter?", Hematology—The Education Program of the American Society of Hematology, 2013, pp. 651-655. doi: 10.1182/asheducation-2013.1.651.

Agarwal et al., "Retroviral gene therapy with an immunoglobulin-antigen fusion construct protects from experimental autoimmune uveitis," *J. Clin. Invest.* 106(2):245-252, Jul. 2000.

Blanchfield et al., "A GMCSF-neuroantigen fusion protein is a potent tolerogen in experimental autoimmune encephalomyelitis (EAE) that is associated with efficient targeting of neuroantigen to APC," *J. Leukocyte Biol.* 87:509-521, Mar. 2010.

Chang et al., "Stem cell-derived erythroid cells mediate long-term systemic protein delivery," *Nature Biotechnol.* 24(8):1017-1021, Aug. 2006.

Lee et al., "A comparative study on the efficiency of two enucleation methods in pig somatic cell nuclear transfer: effects of the squeezing and the aspiration methods," *Ann. Biotechnol.* 19(2):71-79, 2008.

Milo et al., "What is the total number of protein molecules per cell volume? A call to rethink some published values," *Bioessays* 35:1050-1055, 2013.

Yu et al., "Specific T Regulatory Ceils Display Broad Suppressive Functions against Experimental Allergic Encephalomyelitis upon Activation with Cognate Antigen," *J. Immunol.* 174:6772-6780, 2005.

Godfrin et al., "International seminar on the red blood cells as vehicles for drugs," Expert Opinion on Biological Therapy, 12(1):127-133, 2012.

\* cited by examiner

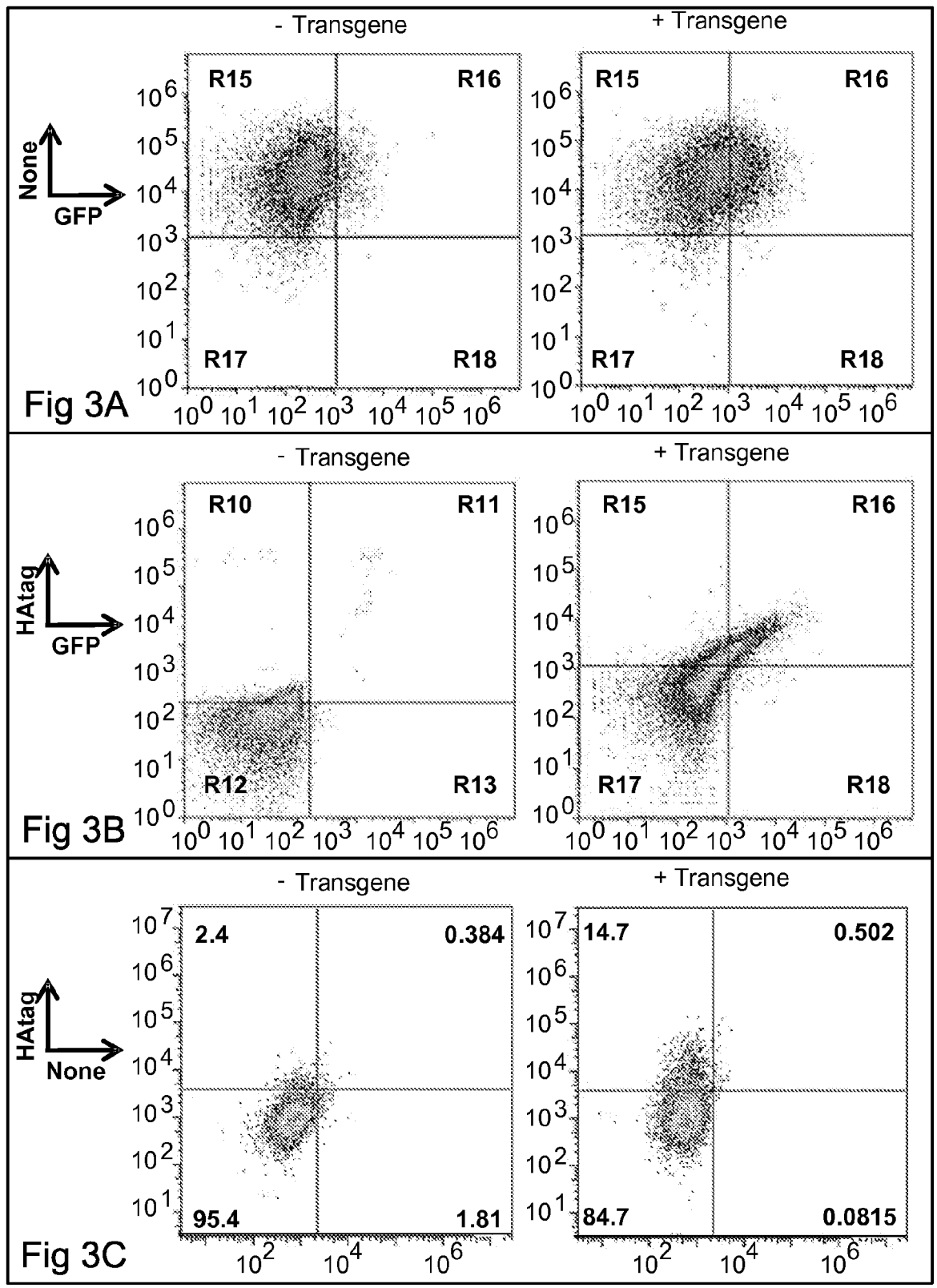

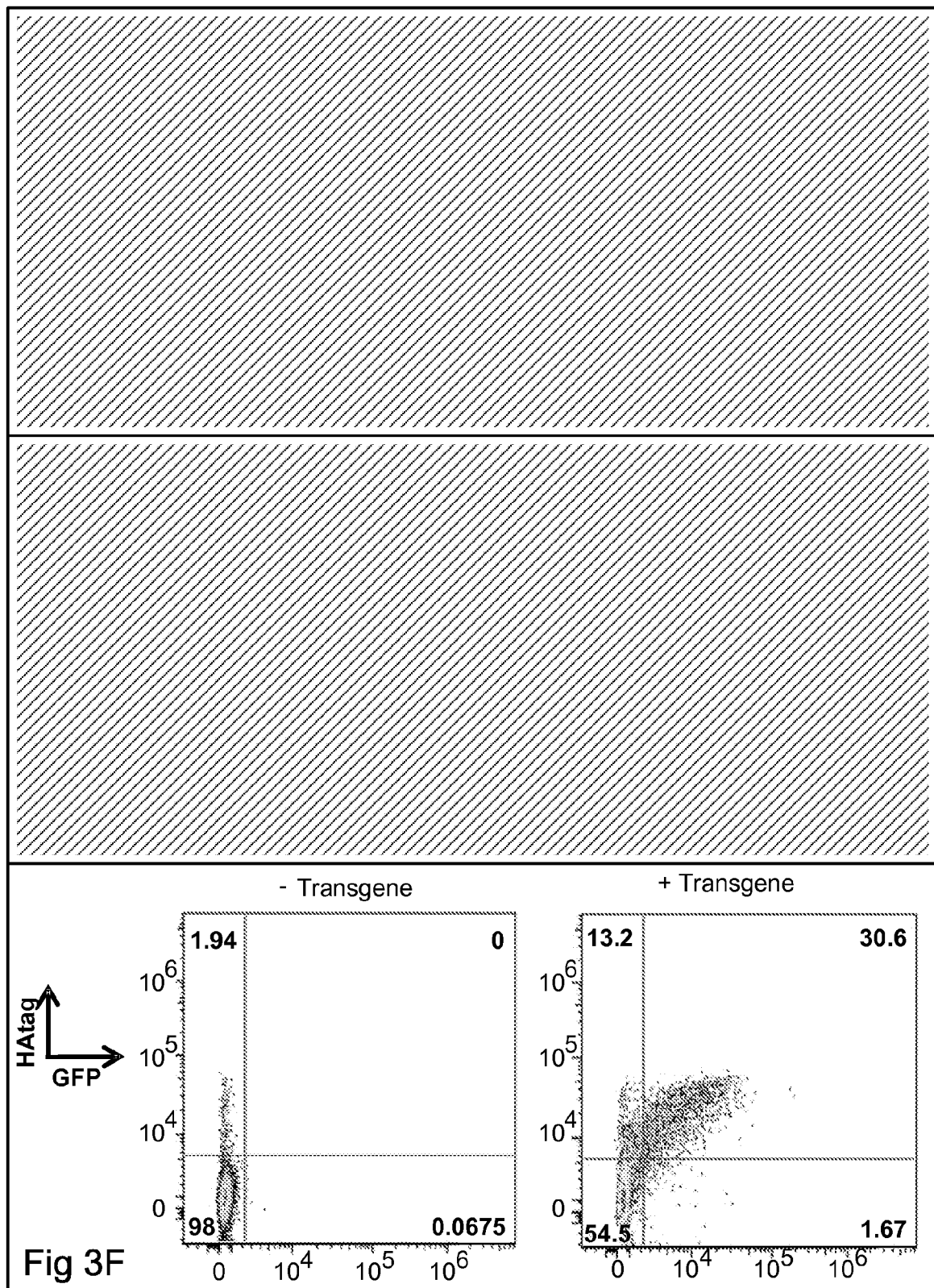

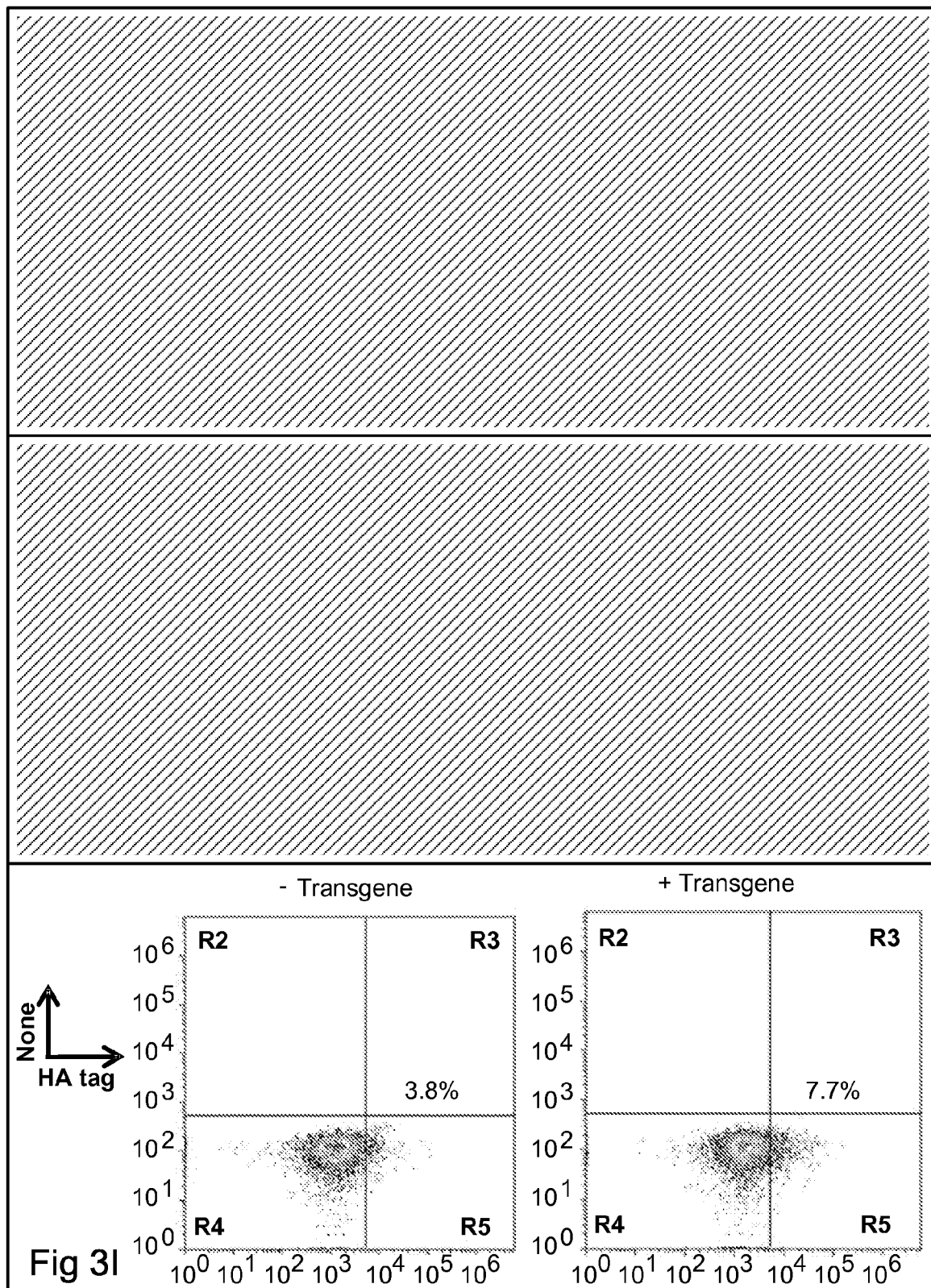

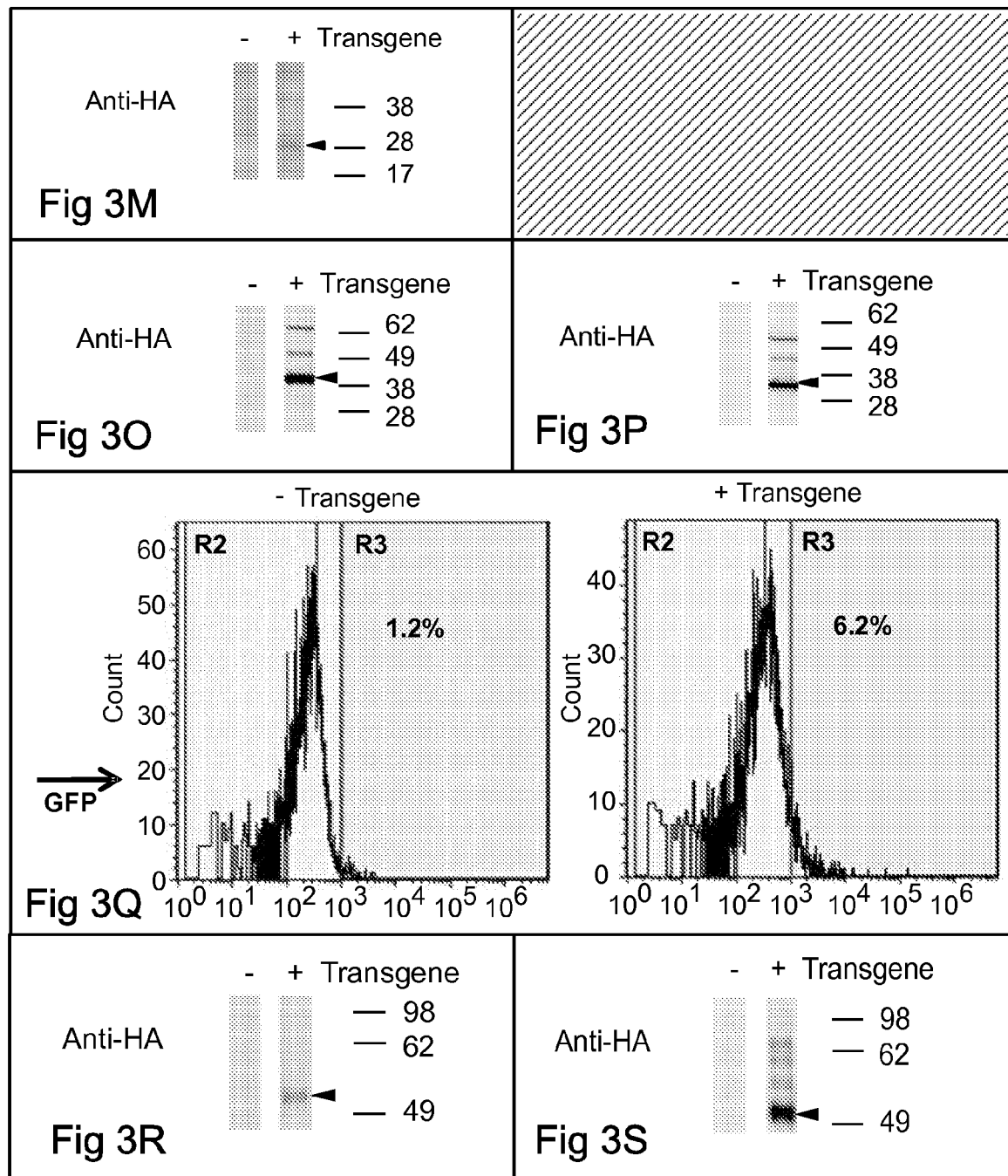

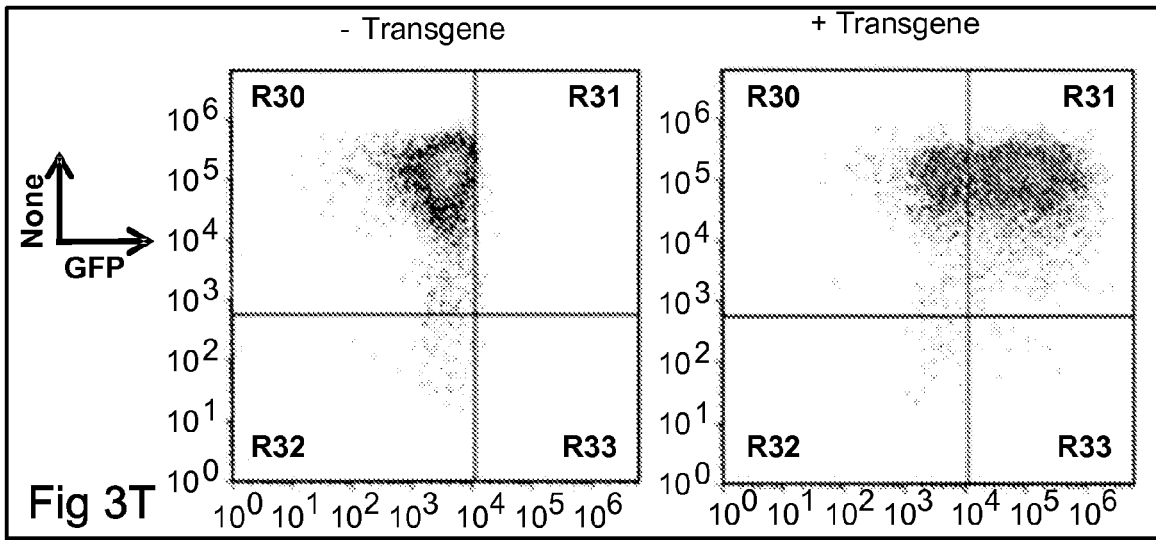
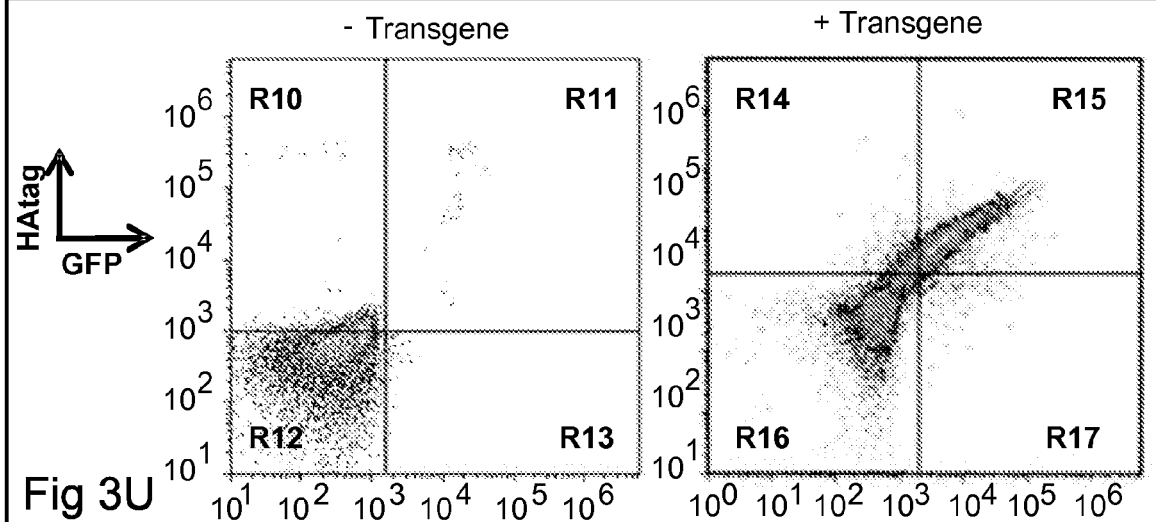
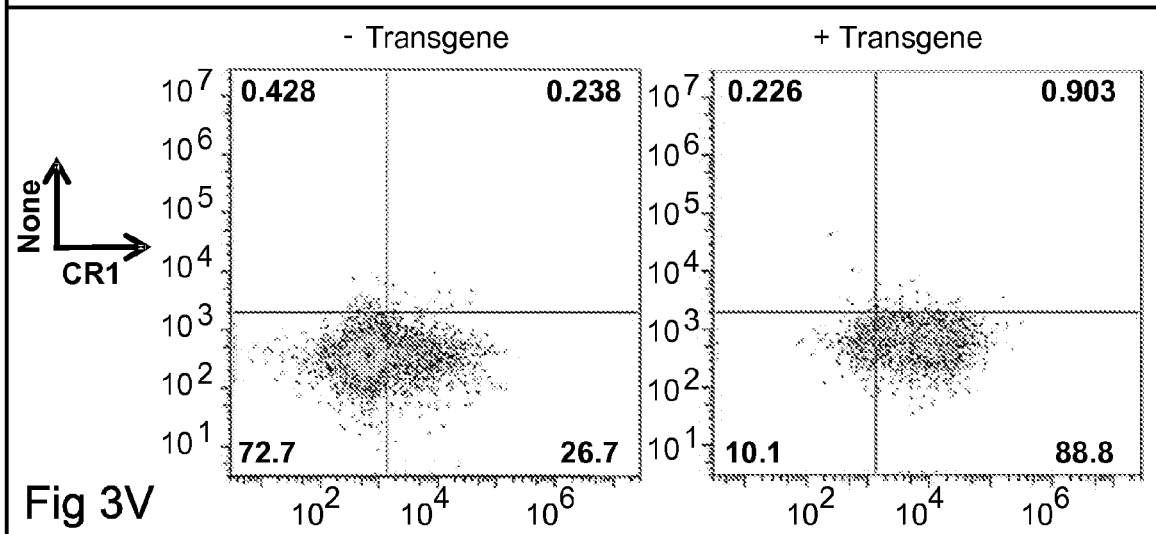

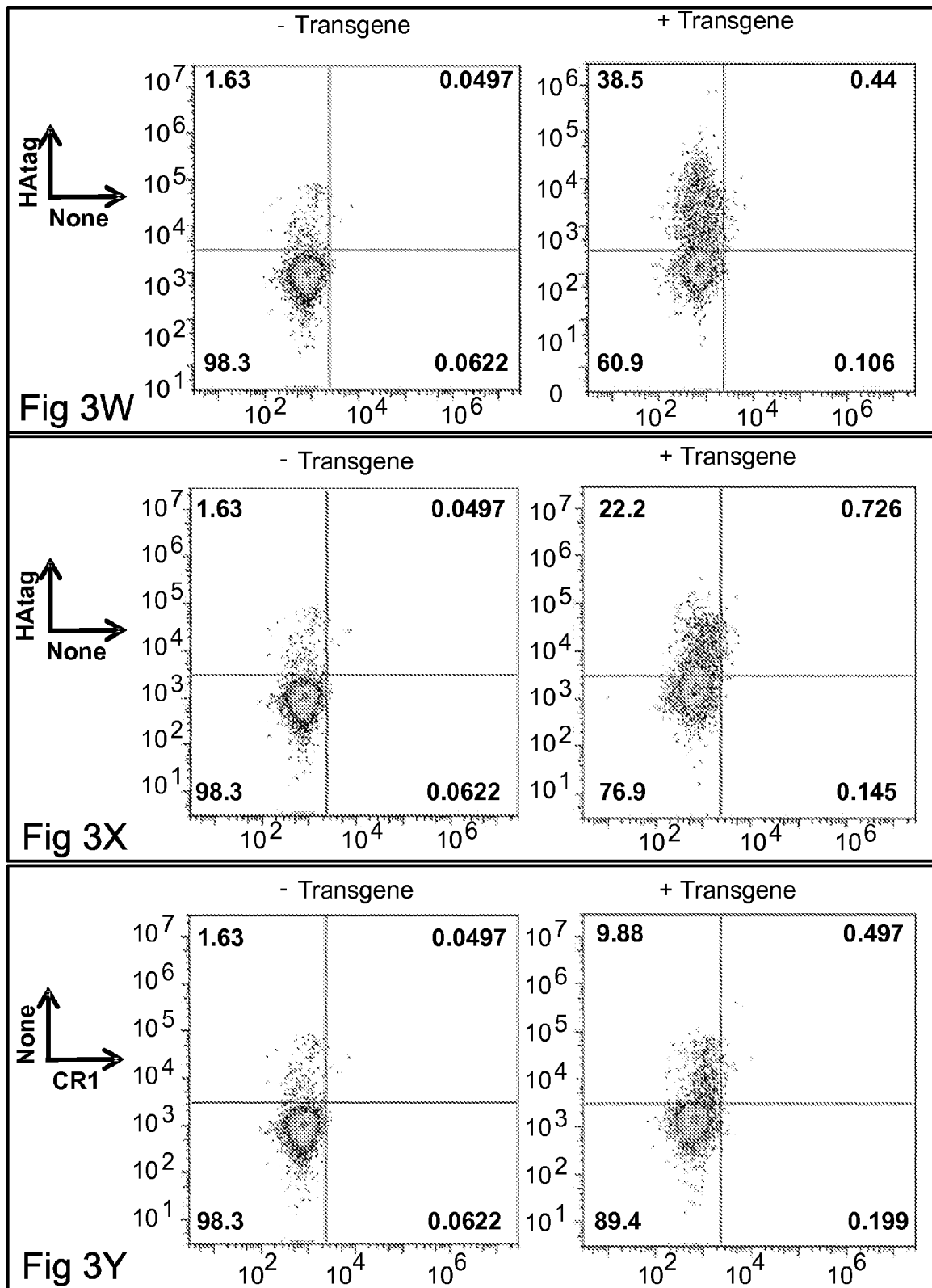

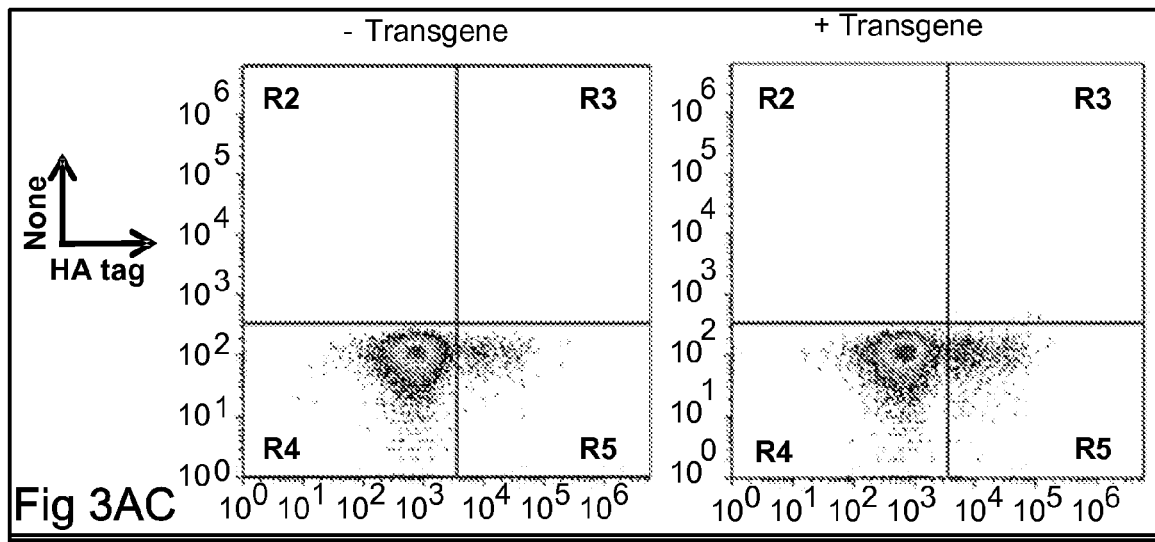
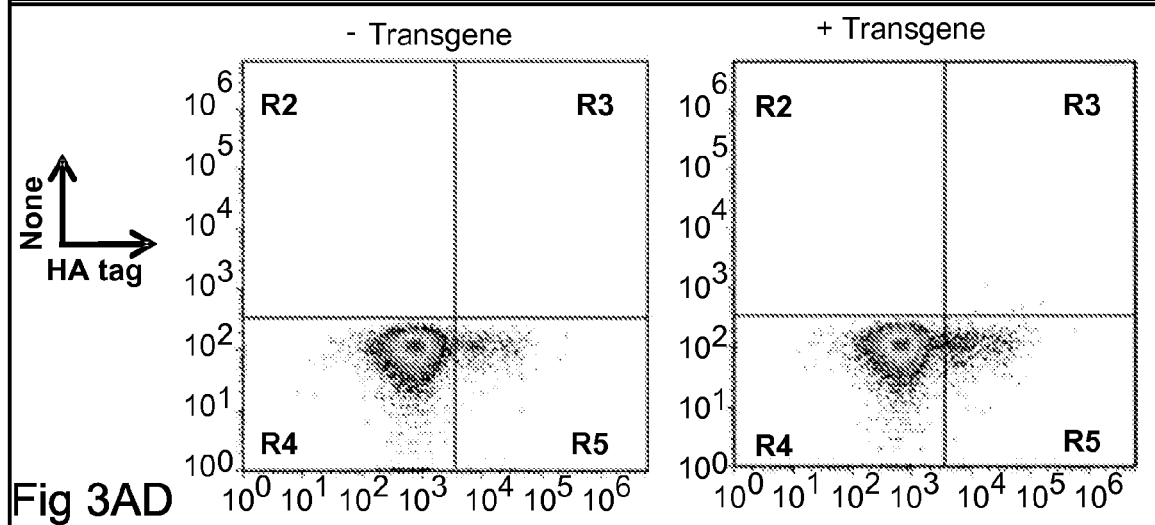
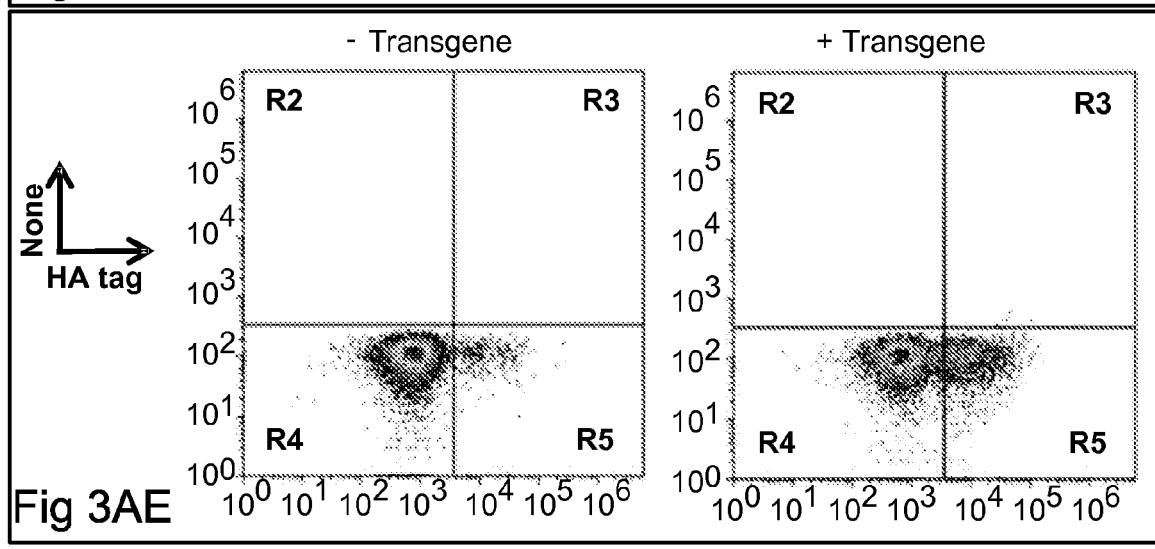

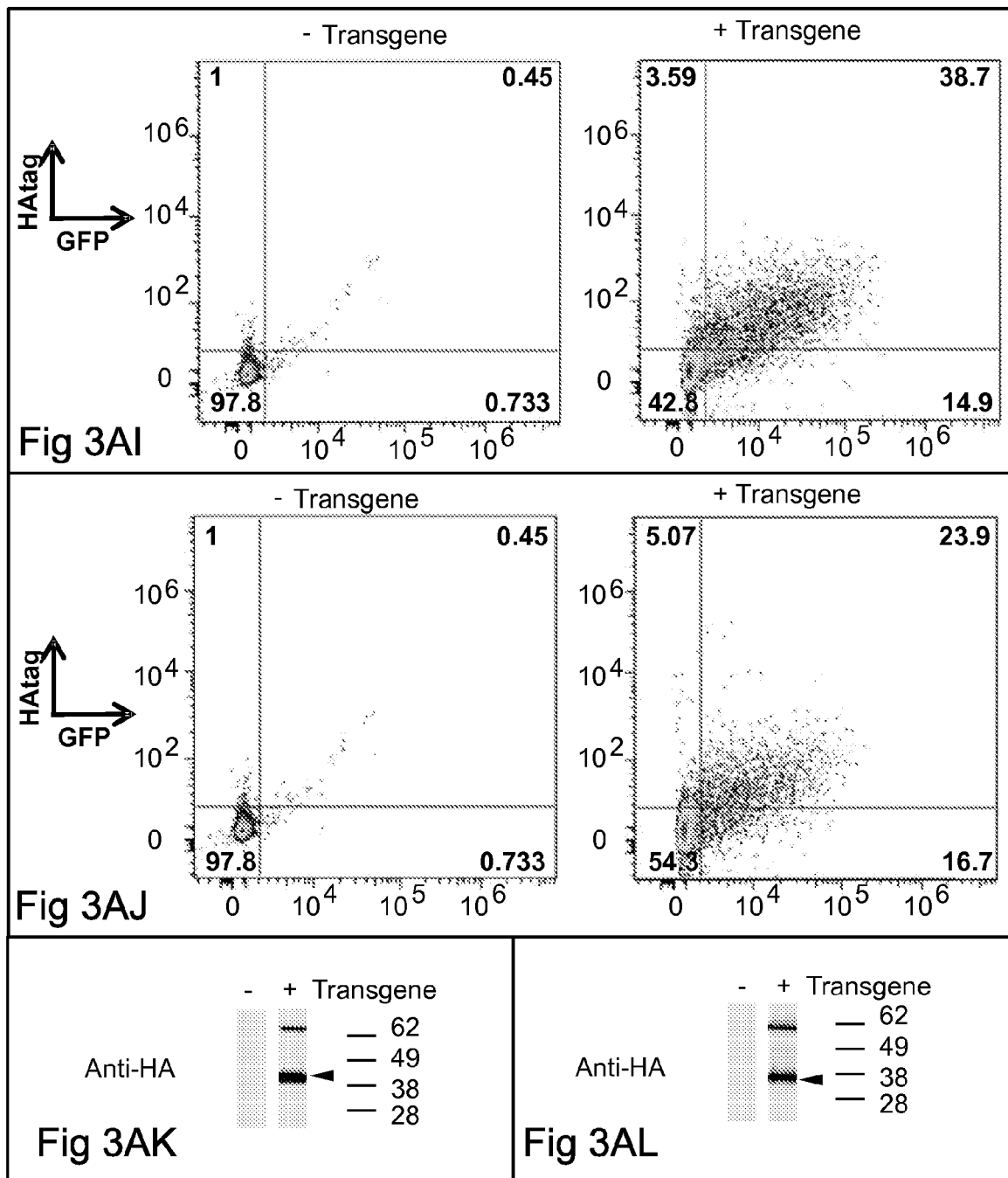

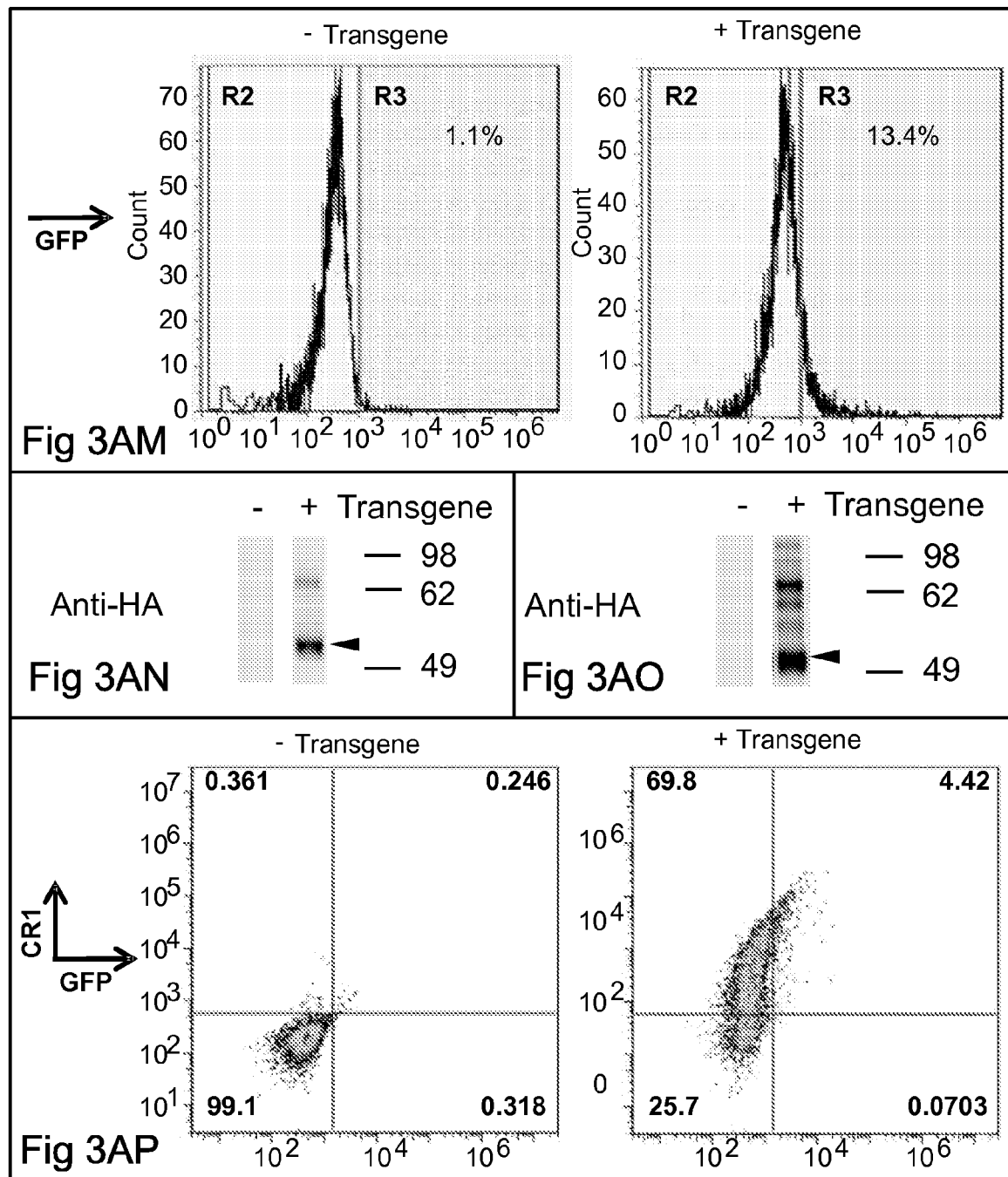

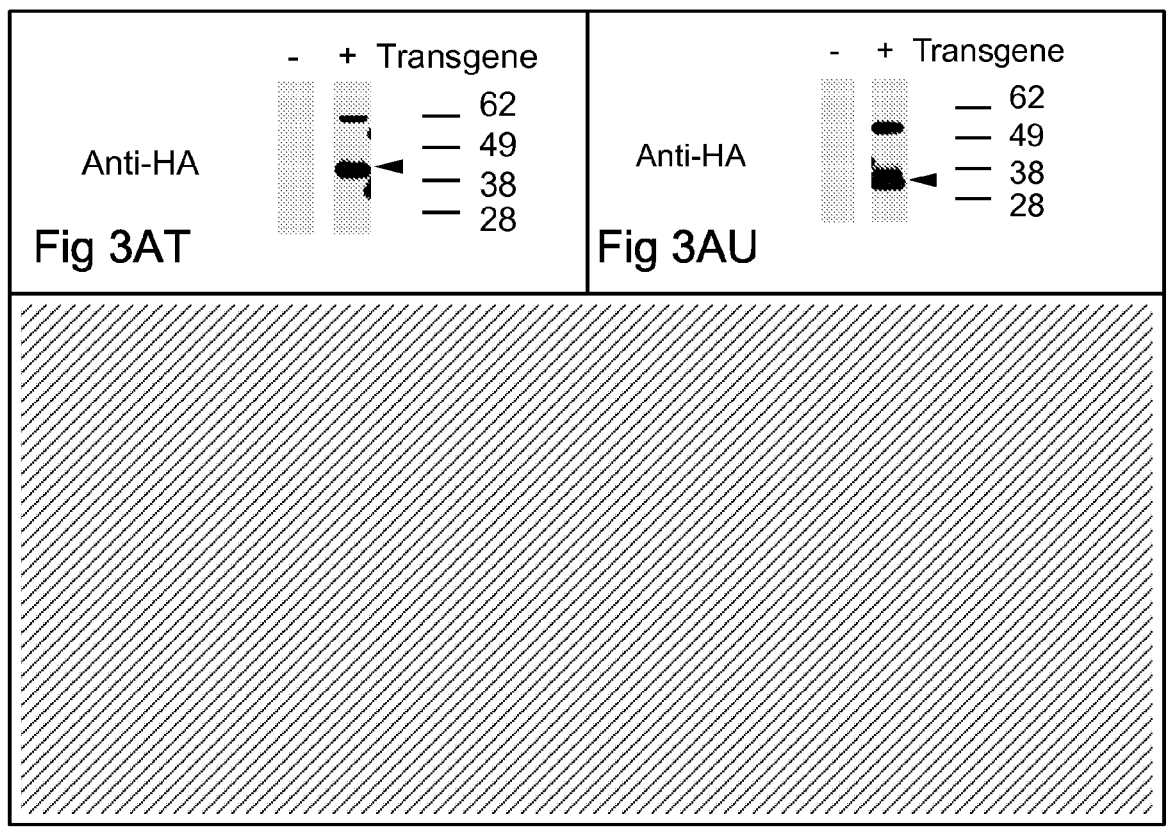

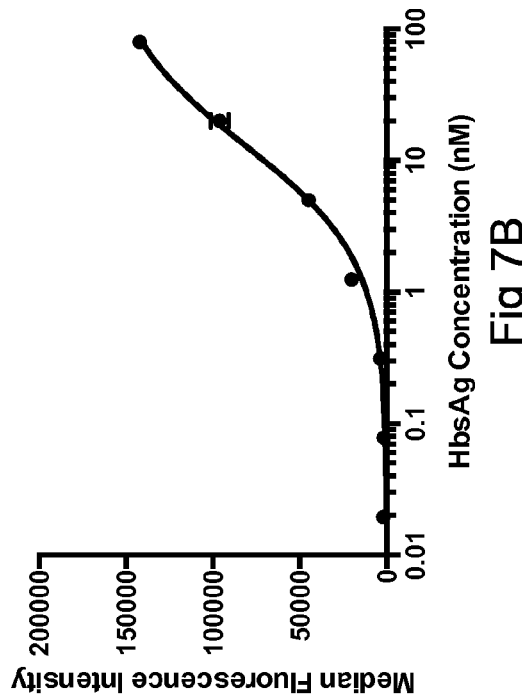
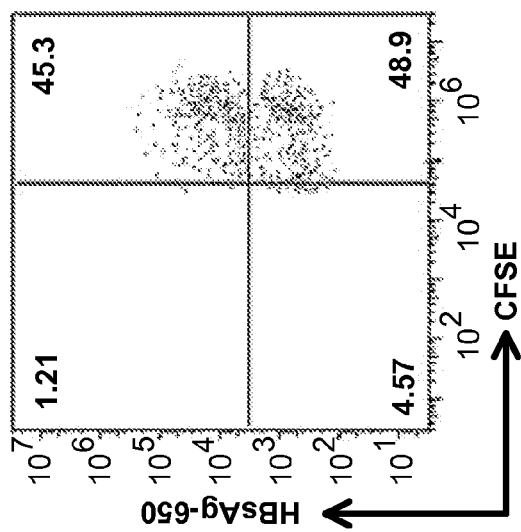
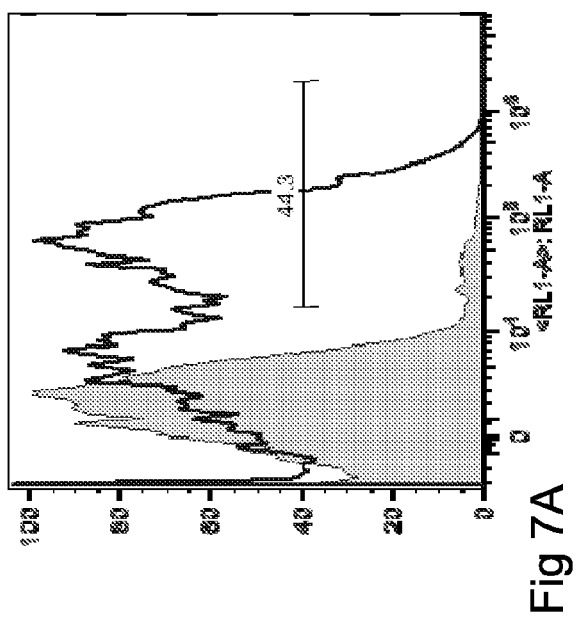
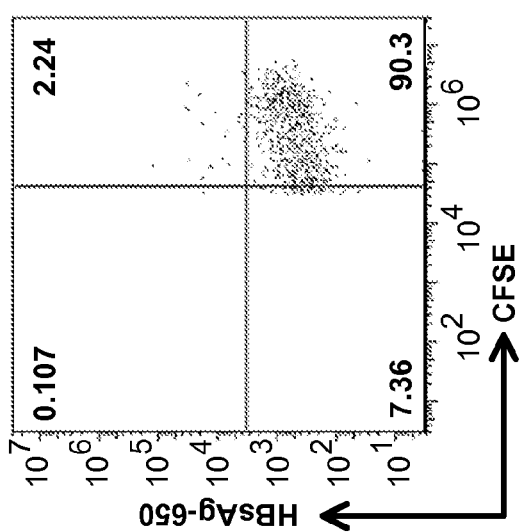

Methods of Exogenous Antigen Expression
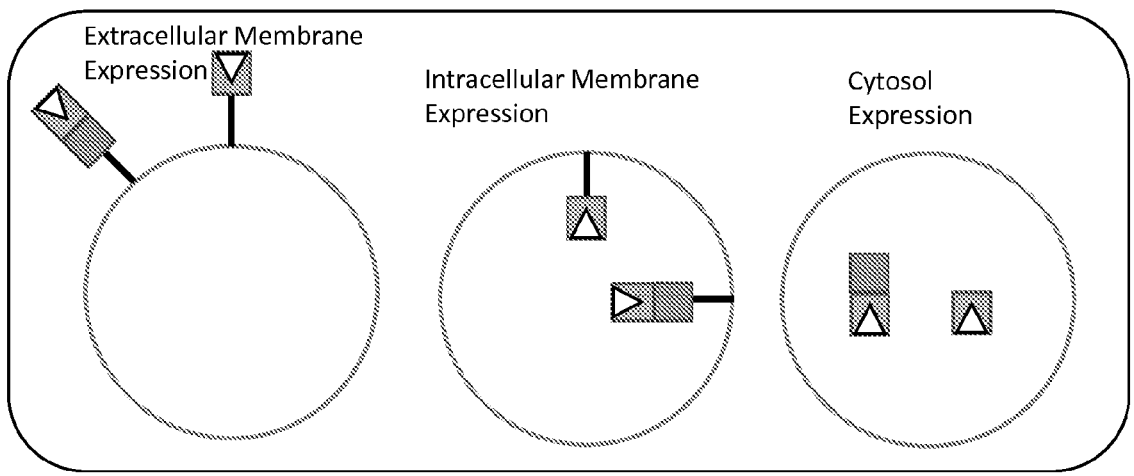
Fig 13A
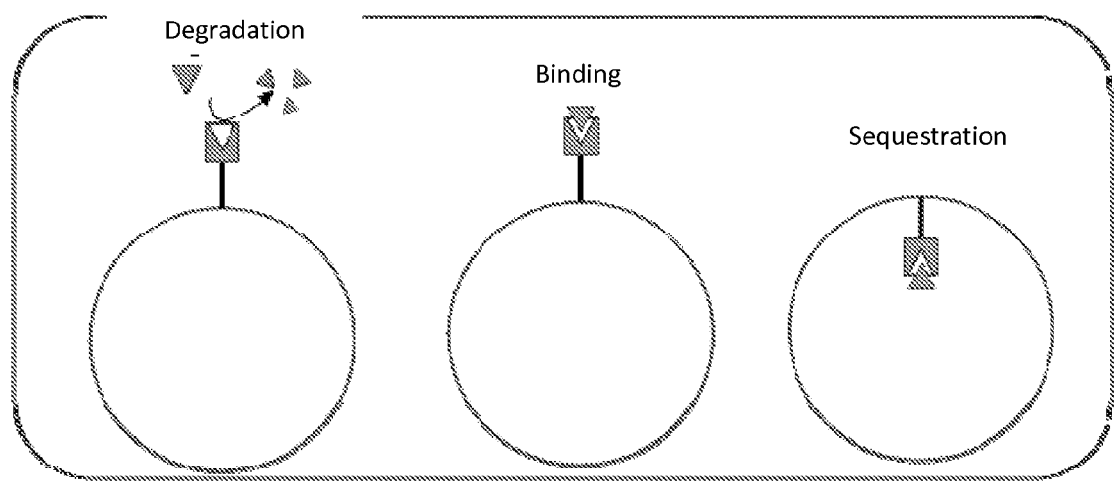
Fig 13B
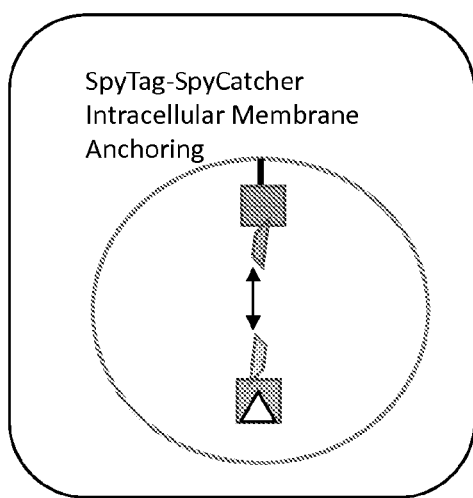
Fig 13C
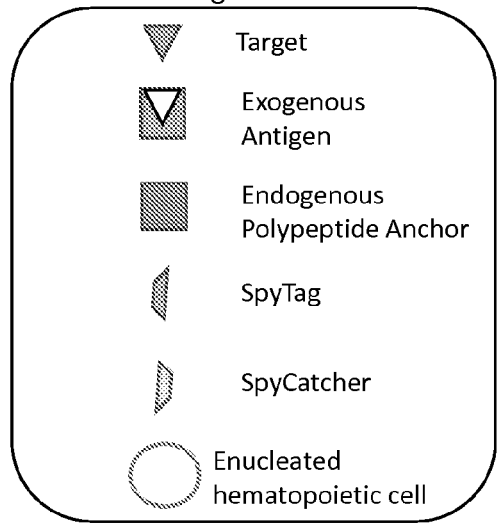

METHODS AND COMPOSITIONS FOR IMMUNOMODULATION

RELATED APPLICATIONS

The present application is a continuation of U.S. Ser. No. 15/301,046, filed Sep. 30, 2016 (issued as U.S. Pat. No. 10,869,898), which is a U.S. National Stage Application under 35 U.S.C. § 371 of International Application No. PCT/US2015/020614, filed Mar. 13, 2015, which claims priority under 35 U.S.C. § 119 to U.S. Provisional Application No. 61/973,764, filed Apr. 1, 2014, U.S. Provisional Application No. 61/973,763, filed Apr. 1, 2014, U.S. Provisional Application No. 61/991,319, filed May 9, 2014, U.S. Provisional Application No. 62/006,825, filed Jun. 2, 2014, U.S. Provisional Application No. 62/006,828, filed Jun. 2, 2014, U.S. Provisional Application No. 62/006,829, filed Jun. 2, 2014, U.S. Provisional Application No. 62/006,832, filed Jun. 2, 2014, U.S. Provisional Application No. 62/025,367, filed Jul. 16, 2014, U.S. Provisional Application No. 62/059,100, filed Oct. 2, 2014, and International Application No. PCT/US2014/065304, filed Nov. 12, 2014. The entire contents of each of the foregoing applications are incorporated herein by reference.

SEQUENCE LISTING

The instant application contains a Sequence Listing which has been submitted electronically in ASCII format and is hereby incorporated by reference in its entirety. Said ASCII copy, created on Jun. 6, 2018, is named R2081-700320_SL.txt and is 66,425 bytes in size.

FIELD OF THE INVENTION

The field of the invention is pharmaceutical compositions for the treatment of diseases and disorders.

BACKGROUND OF THE INVENTION

Aberrant immune activation is a hallmark of many human diseases and conditions. Autoimmune diseases arise when the body's immune system improperly senses an autologous antigen as non-self and attacks the body's own tissues. Inflammatory diseases and allergies can arise when the body's immune system is improperly triggered by common food-borne or environmental antigens. Polypeptides and proteins used to treat a range of human diseases are often destroyed, neutralized, or otherwise rendered ineffective by immune cells that respond to them as though they were foreign antigens.

Current treatment of diseases of improper immune activation involves immunosuppression with chemical agents like corticosteroids, or inhibitors of inflammatory mediators like anti-histamines, antibodies, or cytokines. These generalized treatments are associated with significant morbidities, such as susceptibility to infection, because they broadly suppress the immune system.

For some severe allergies, clinical testing is underway to induce "tolerance" to allergens by exposure to slowly increasing doses of the offending protein over time. To date theses treatments lack long-term efficacy and are associated with a risk of severe anaphylaxis.

There is a need for novel therapeutics to treat these diseases.

SUMMARY OF THE INVENTION

The invention, in certain aspects, relates to isolated enucleated hematopoietic cells expressing an antigen. Enucleated hematopoietic cells will be referred to herein as "EHCs" (or in its singular form: "EHC"). In some embodiments, the enucleated hematopoietic cells or EHCs lack nuclear material. For example, the EHCs can be are erythroid cells or thromboid cells. In some embodiments, EHCs lacking nuclear material are red blood cells, erythrocytes, reticulocytes, or platelets. In some embodiments, the enucleated hematopoietic cells or EHCs are nucleated precursor erythroid cells or precursor thromboid cells that are, e.g., induced to lose their nuclear material or are rendered functionally enucleated and incapable of replication. In some embodiments, the exogenous antigen-expressing EHC is a circulating cell, such as a red blood cell. In some embodiments, the exogenous antigen-expressing EHC is cultured from a hematopoietic precursor using defined factors. In some embodiments, the exogenous antigen-expressing EHC is a thromboid cell, such as a platelet. In some embodiments the thromboid cell is cultured from a hematopoietic precursor using defined factors. In some embodiments, the exogenous antigen-expressing EHC is a primary cell isolated from a patient, for either autologous or allogeneic use, that is contacted with an antigen.

Certain aspects of the invention relate to exogenous antigen-expressing EHCs that are capable of inducing immune tolerance when administered to a subject, e.g. in form of a pharmaceutical composition comprising the exogenous antigen-expressing EHCs. The exogenous antigen expressed by the EHCs can be tailored to a specific disease, disorder or condition. The exogenous antigen-expressing EHCs can comprise antigen in multiple ways, such as e.g. surface display, intracellular expression, intracellular loading, or surface conjugation, of the antigen of interest. The exogenous antigen-expressing EHCs may manage diseases of aberrant immune activation more effectively and/or with fewer side effects than existing treatments. For example, exogenous antigen-expressing EHCs may selectively modulate the immune system while leaving the broader immune system physiology substantially unperturbed. In some embodiments, exogenous antigen-expressing EHCs may induce the destruction, deactivation, and/or anergy of antigen-specific T and B lymphocytes. Alternatively or in addition, exogenous antigen-expressing EHCs may induce the proliferation of antigen-specific regulatory T lymphocytes.

Certain aspects of the invention relate to exogenous antigen-expressing EHCs that comprise exogenous antigen that is recognized by immune cells in autoimmune diseases, such as, e.g. multiple sclerosis, type 1 diabetes, rheumatoid arthritis, and membranous nephritis.

Certain aspects of the invention relate to exogenous antigen-expressing EHCs that comprise exogenous antigen that is recognized by immune cells in inflammatory diseases, such as, e.g. Crohn's disease, ulcerative colitis, celiac disease, or other idiopathic inflammatory bowel diseases.

Certain aspects of the invention relate to exogenous antigen-expressing EHCs that comprise exogenous antigen that is recognized by immune cells in human leukocyte antigen (HLA) mismatch-mediated diseases, such as, e.g. graft-versus-host disease or organ transplant rejection.

Certain aspects of the invention relate to exogenous antigen-expressing EHCs that comprise exogenous antigen that is recognized by immune cells in allergic diseases, such as, e.g. asthma, peanut allergy, shellfish allergy, pollen allergy, milk protein allergy, insect sting allergy, and latex allergy.

Certain aspects of the invention relate to exogenous antigen-expressing EHCs that comprise exogenous antigen that is a therapeutic protein whose efficacy or potency is reduced or impaired by immune cells, such as, e.g., clotting factor VIII in hemophilia A, clotting factor IX in hemophilia B, anti-tumor necrosis factor alpha (TNFα) antibodies in rheumatoid arthritis and other inflammatory diseases, glucocerebrosidase in Gaucher's disease, or asparaginase in acute lymphoblastic leukemia (ALL).

Certain aspects of the invention relate to exogenous antigen-expressing EHCs that comprise exogenous antigen that comprises full-length, truncations, and chimeric fusions of polypeptides that a) mediate complement regulation, b) that mediate binding and sequestration of immune complexes, c) autoimmune antibodies, or d) pathogenic particles. In some embodiments, the exogenous antigen comprises full-length, truncations, and chimeric fusions of polypeptides that are enzymatically active in the conversion of one small molecule substrate into another small molecule product or of one polypeptide substrate into a second polypeptide product, including, e.g., cleavage of the polypeptide substrate.

The invention, in certain aspects, also provides methods of treatment of disease using the exogenous antigen-expressing EHCs and pharmaceutical compositions thereof provided herein.

In some aspects, disclosed herein is a method of inducing immune tolerance. The method comprises administering to a human subject suffering from or at risk of developing an autoimmune disease, disorder or condition, a pharmaceutical composition comprising an enucleated hematopoietic cell expressing an exogenous antigen, wherein the pharmaceutical composition is administered in an amount effective to induce immune tolerance in the subject to the antigen mediating the autoimmune disease, disorder or condition.

In some embodiments, the autoimmune disease is selected from the group consisting of multiple sclerosis, type 1 diabetes, and those listed in Table F.

In some embodiments, the method further comprises administering the pharmaceutical composition at least twice over a treatment period such that the autoimmune disease, disorder or condition is treated, or a symptom thereof is decreased.

In certain embodiments, the method further comprises administering the pharmaceutical composition at least twice over a treatment period such that the autoimmune disease, disorder or condition is prevented.

In other embodiments, the method further comprises administering the pharmaceutical composition a sufficient number of times over a treatment period such that the percentage of antigen-specific immune cells is substantially decreased during the treatment period.

In some embodiments, the immune cell is a T cell. In some embodiments, the immune cell is a B cell.

In some embodiments, the decrease in concentration of antigen-specific immune cells is measured by flow-cytometry from a biological sample taken from the subject.

In some embodiments, the biological sample is a lymph node biopsy, a spleen sample, or peripheral blood.

In some embodiments, the concentration of antigen-specific immune cells is decreased by at least about 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9%, 99.99%, or greater than 99.99% during part or the entirety of the treatment period.

In other embodiments, the concentration of antigen-specific immune cells is decreased by at least about 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9%, 99.99%, or greater than 99.99% within about 1, 5, 10, 15, 20, 30, 40, or 50 minutes, or about 1, 2, 3, 4, 5, 6, 7, 8, 9, 10, 11, 12, 13, 14, 15, 16, 17, 18, 19, 20, 21, 22, or 23 hours, or 1, 2, 3, 4, 5, or 6 days or about 1, 2, 3, 4, 5, or 6 weeks of the administration.

In some embodiments, the pharmaceutical composition is administered a sufficient number of times over a treatment period such that the concentration of antigen-specific immune cells is substantially decreased for at least about one week, two weeks, three weeks, four weeks, one month, two months, three months, four months, five months, six months, or greater than six months.

In certain embodiments, the pharmaceutical composition is administered a sufficient number of times over a treatment period such that the concentration of antigen-specific immune cells is substantially decreased for a period of time at least as long as the treatment period.

In some embodiments, the pharmaceutical composition is administered a sufficient number of times over a treatment period such that the concentration of antigen-specific antibodies in circulation is substantially decreased during the treatment period.

In some embodiments, the concentration of antigen-specific antibodies in circulation is measured by ELISA.

In some embodiments, the concentration of antigen-specific circulating antibody is decreased by at least about 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9%, 99.99%, or greater than 99.99% during part or the entirety of the treatment period.

In some embodiments, the concentration of antigen-specific antibody is decreased by at least about 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9%, 99.99%, or greater than 99.99% within about 1, 5, 10, 15, 20, 30, 40, or 50 minutes, or about 1, 2, 3, 4, 5, 6, 7, 8, 9, 10, 11, 12, 13, 14, 15, 16, 17, 18, 19, 20, 21, 22, or 23 hours, or 1, 2, 3, 4, 5, or 6 days or about 1, 2, 3, 4, 5, or 6 weeks of the administration.

In certain embodiments, the pharmaceutical composition is administered a sufficient number of times over a treatment period such that the concentration of antigen-specific circulating antibody is substantially decreased for at least about one week, two weeks, three weeks, four weeks, one month, two months, three months, four months, five months, six months, or greater than six months.

In certain embodiments, the pharmaceutical composition is administered a sufficient number of times over a treatment period such that the concentration of antigen-specific circulating antibody is substantially decreased for a period of time at least as long as the treatment period.

In some embodiments, the pharmaceutical composition is administered a sufficient number of times over a treatment period such that the percentage of antigen-specific regulatory T cells is substantially increased during the treatment period.

In some embodiments, the decrease in concentration of antigen-specific immune cells is measured by flow-cytometry from a biological sample taken from the subject.

In some embodiments, the biological sample is a lymph node biopsy, a spleen sample, or peripheral blood.

In certain embodiments, the concentration of antigen-specific regulatory T cells is increased by at least about 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9%, 99.99%, or greater than 99.99% during part or the entirety of the treatment period.

In certain embodiments, the concentration of antigen-specific regulatory T cells is increased by at least about 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9%, 99.99%, or greater than 99.99% within about 1, 5, 10, 15, 20, 30, 40, or 50 minutes, or about 1, 2, 3, 4, 5, 6, 7, 8, 9, 10, 11, 12, 13, 14, 15, 16, 17, 18, 19, 20, 21, 22, or 23 hours, or 1, 2, 3, 4, 5, or 6 days or about 1, 2, 3, 4, 5, or 6 weeks of the administration.

In some embodiments, the pharmaceutical composition is administered a sufficient number of times over a treatment period such that the concentration of antigen-specific regulatory T cells is substantially increased for at least about one week, two weeks, three weeks, four weeks, one month, two months, three months, four months, five months, six months, or greater than six months.

In some embodiments, the pharmaceutical composition is administered a sufficient number of times over a treatment period such that the concentration of antigen-specific regulatory T cells is substantially increased for a period of time at least as long as the treatment period.

In some embodiments, the pharmaceutical composition is administered a sufficient number of times over a treatment period such that one or more symptoms of the autoimmune disease, disorder or condition is prevented, decreased or delayed.

In some embodiments, the treatment period is not longer than a year, six months, three months, two months, one month, two weeks, one week, three days, two days, one day.

In certain embodiments, the time interval between administrations within the treatment period is no longer than the period in which the number of enucleated hematopoietic cells expressing an exogenous antigen is reduced to less than about 5%, 10%, 15%, 20%, 25%, 30%, 35%, 40%, 45%, 50%, 55%, 60%, 65%, 70%, 75%, 80%, 85%, 90%, or 95% of the number of enucleated hematopoietic cells expressing an exogenous antigen present in the administered pharmaceutical composition.

In some embodiments, the frequency of administration is sufficient to effectively reduce the concentration of antigen-specific immune cells below a level that is associated with a symptom of autoimmune disease, disorder or condition.

In certain embodiments, the frequency of administration is sufficient to effectively reduce the concentration of antigen-specific circulating antibody below a level that is associated with a symptom of autoimmune disease, disorder or condition.

In certain embodiments, the frequency of administration is sufficient to effectively increase the concentration of antigen-specific, regulatory T cells above a threshold level that is associated with a symptom of autoimmune disease, disorder or condition.

In some embodiments, the enucleated hematopoietic cell is an erythroid cell, a thromboid cell, or a precursor thereof. In some embodiments, the erythroid cell is an erythrocyte or a reticulocyte. In some embodiments, the thromboid cell is a platelet.

In some embodiments, the enucleated hematopoietic cell is isolated from a donor. In some embodiments, the enucleated hematopoietic cell is autologously derived from the subject. In some embodiments, the enucleated hematopoietic cell is allogeneically derived. In some embodiments, the enucleated hematopoietic cell is xenogeneically derived.

In some embodiments, the enucleated hematopoietic cell is derived from a nucleated precursor cell by a culture-based process that induces the expulsion of its nucleus. In some embodiments, the enucleated hematopoietic cell is generated from a nucleated precursor cell that is chemically or physical manipulated to remove its nucleus.

In some embodiments, the enucleated hematopoietic cell is generated by irradiation or chemical destruction of the nucleus of a nucleated precursor cell. In some embodiments, the chemical destruction is carried out with Cytochalasin B. In some embodiments, the irradiation is carried out with at least 5 Gy, 7 Gy, 10 Gy, 15 Gy, 25 Gy, 30 Gy, 40 Gy or at least 50 Gy.

In some embodiments, the exogenous antigen is a polypeptide encoded by an exogenous nucleic acid.

In some embodiments, the exogenous antigen is associated with the cell membrane of the enucleated hematopoietic cell.

In some embodiments, the exogenous antigen is a fusion or a chimera polypeptide.

In some embodiments, the fusion or chimera comprises at least one of an S domain, an A domain or a U domain, wherein the S domain is a surface domain on the enucleated hematopoietic cell, wherein the A domain is an anchor in or on the cell membrane, wherein the U domain faces the intracellular, unexposed side of the enucleated hematopoietic cell, and wherein the S domain, the A domain, and/or the U domain are of different polypeptide origin.

In some embodiments, the S domain and/or the A domain comprises at least 5, 6, 7, 8, 9, 10, 15, 20, 25, 30, 40, 50, 60, 70, 80, 90, 100, 150, 200, 250, or at least 500 amino acids. In some embodiments, the S domain and/or A domain comprises at least 500, 750, or at least 1,000 amino acids.

In some embodiments, the exogenous antigen is selected from the group consisting of myelin basic protein, proteolipid protein, myelin oligodendrocyte glycoprotein, pancreatic beta cell antigen, insulin, and those listed in Table F, Table 6, and Table 8.

In some embodiments, the enucleated hematopoietic cell comprises at least 10 copies, 100 copies, 1,000 copies, 10,000 copies, 25,000 copies, 50,000 copies, 100,000 copies, 500,000 copies, 1,000,000 copies, or 2,000,000 copies of the exogenous antigen.

In some embodiments, the pharmaceutical composition further comprises a pharmaceutically active agent.

In some embodiments, the method further comprises the step of administering a pharmaceutically active agent, wherein the pharmaceutically active agent is administered prior to, after, or concurrent with the pharmaceutical composition.

In some embodiments, the pharmaceutical composition is administered intravenously.

In some embodiments, the pharmaceutically active agent is selected from a biological agent, a small molecule agent, or a nucleic acid agent.

In some embodiments, the pharmaceutical composition further comprises a pharmaceutically acceptable carrier.

In certain embodiments, the method further comprises the step of selecting for treatment a subject suffering from or at risk of an autoimmune disease, disorder or condition selected from the group consisting of: thrombotic thrombocytopenic purpura, CAPS, APS, myasthenia gravis, Goodpasture's syndrome, membraneous nephritis, type 1 diabetes, rheumatoid arthritis, multiple sclerosis, Crohn's disease, or those listed in Table F and Table G.

In some aspects, disclosed herein is a pharmaceutical composition comprising an enucleated hematopoietic cell expressing an exogenous antigen, wherein administration of an effective amount of the pharmaceutical composition is capable of inducing immune tolerance in a human subject suffering from or at risk of developing an autoimmune disease, disorder or condition administered by the method of any one of the preceding claims.

In some embodiments, the pharmaceutical composition further comprises a pharmaceutically acceptable carrier.

In some embodiments, the pharmaceutical composition comprises a population of hematopoietic cells expressing an exogenous antigen. In some embodiments, the pharmaceutical composition comprises at least 1×103 hematopoietic cells expressing an exogenous antigen.

In certain embodiments of the pharmaceutical composition, the hematopoietic cells expressing an exogenous antigen are provided in a volume of about 10 nl, 100 nl, 1 µl, 10 µl, 100 µl, 1 ml, 10 ml, 20 ml, or 50 ml. In other embodiments of the pharmaceutical composition, the hematopoietic cells expressing an exogenous antigen are provided in a volume of about 1 ml, 10 ml, 20 ml, 50 ml, 100 ml, 250 ml, or 500 ml.

In some embodiments of the pharmaceutical composition, the composition is formulated for long-term storage. In some embodiments of the pharmaceutical composition, the composition is frozen. In some embodiments, the pharmaceutical composition comprises a pharmaceutically active agent.

In certain embodiments of the pharmaceutical composition, the pharmaceutically active agent is selected from a biological agent, a small molecule agent, or a nucleic acid agent.

In some aspects, disclosed herein is a dosage form comprising the compositions described herein formulated as a liquid suspension for intravenous injection.

In some aspects, disclosed herein is a medical device comprising a container holding the pharmaceutical compositions described herein and an applicator for intravenous injection of the pharmaceutical composition to the subject.

In some aspects, disclosed herein is a medical kit comprising the pharmaceutical compositions described herein and a medical device for intravenous injection of the pharmaceutical composition to the subject.

In some aspects, disclosed herein are hematopoietic cells expressing an exogenous antigen of the pharmaceutical composition administered by any of the methods described herein.

In some aspects, disclosed herein is a population of hematopoietic cells expressing an exogenous antigen as disclosed herein.

In some embodiments, the population of hematopoietic cells expressing an exogenous antigen is formulated as a liquid.

In some embodiments, the population of hematopoietic cells expressing an exogenous antigen is frozen.

In some aspects, disclosed herein is an isolated antigen expressed by the hematopoietic cell population described herein.

In some aspects, disclosed herein is an exogenous nucleic acid encoding the exogenous antigen described herein.

In some aspects, disclosed herein is an enucleated hematopoietic cell comprising an exogenous antigen that comprises at least one of an S domain, an A domain or a U domain, wherein the S domain is an extracellular surface domain, the A domain is an anchor, and the U domain is intracellularly localized, and wherein the enucleated hematopoietic cell is capable of inducing immune tolerance when administered to a subject.

In some embodiments of the enucleated hematopoietic cell disclosed herein, the exogenous antigen is a fusion or a chimeric polypeptide.

In some embodiments of the enucleated hematopoietic cell disclosed herein, the S domain, the A domain, and/or the U domain are of different polypeptide origin.

In certain embodiments of the enucleated hematopoietic cell disclosed herein, the S domain and/or the A domain comprises at least 5, 6, 7, 8, 9, 10, 15, 20, 25, 30, 40, 50, 60, 70, 80, 90, 100, 150, 200, 250, or at least 500 amino acids.

In certain embodiments of the enucleated hematopoietic cell disclosed herein, the S domain and/or A domain comprises at least 500, 750, or at least 1,000 amino acids.

In some embodiments of the enucleated hematopoietic cell disclosed herein, the exogenous antigen is selected from the group consisting of myelin basic protein, proteolipid protein, myelin oligodendrocyte glycoprotein, pancreatic beta cell antigen, insulin, and those listed in Table F, Table 6, and Table 8.

In some embodiments, the enucleated hematopoietic cell comprises at least 10 copies, 100 copies, 1,000 copies, 10,000 copies, 25,000 copies, 50,000 copies, 100,000 copies, 500,000 copies, 1,000,000 copies, or 2,000,000 copies of the exogenous antigen.

In certain embodiments, the enucleated hematopoietic cell is an erythroid cell, a thromboid cell, or a precursor thereof. In some embodiments, the erythroid cell is an erythrocyte or a reticulocyte. In some embodiments, the thromboid cell is a platelet.

In some embodiments, the enucleated hematopoietic cell is isolated from a donor. In some embodiments, the enucleated hematopoietic cell is autologously derived from the subject. In some embodiments, the enucleated hematopoietic cell is allogeneically derived. In some embodiments, the enucleated hematopoietic cell is xenogeneically derived.

In certain embodiments, the enucleated hematopoietic cell is derived from a nucleated precursor cell by a culture-based process that induces the expulsion of its nucleus.

In certain embodiments, the enucleated hematopoietic cell is generated from a nucleated precursor cell that is chemically or physical manipulated to remove its nucleus.

In certain embodiments, the enucleated hematopoietic cell is generated by irradiation or chemical destruction of the nucleus of a nucleated precursor cell. In some embodiments, the chemical destruction is carried out with Cytochalasin B. In some embodiments, the irradiation is carried out with at least 5 Gy, 7 Gy, 10 Gy, 15 Gy, 25 Gy, 30 Gy, 40 Gy or at least 50 Gy.

In some embodiments of the enucleated hematopoietic cell disclosed herein, the exogenous antigen is a polypeptide encoded by an exogenous nucleic acid.

In some embodiments of the enucleated hematopoietic cell disclosed herein, the cell is derived from a human source.

In some embodiments of the enucleated hematopoietic cell disclosed herein, the cell is derived from a non-human source, selected from the group consisting of pig, chimpanzee, macaque, a non-human primate, and a non-primate mammal.

In some embodiments of the enucleated hematopoietic cell disclosed herein, the polypeptide antigen is localized intracellularly. In some embodiments of the enucleated hematopoietic cell disclosed herein, the polypeptide antigen is localized extracellularly on the surface of the cell. In some embodiments of the enucleated hematopoietic cell disclosed herein, the polypeptide antigen is fused to an endogenous cell protein. In some embodiments of the enucleated hematopoietic cell disclosed herein, the polypeptide antigen is fused to an intracellular region of an endogenous transmembrane protein. In some embodiments of the enucleated hematopoietic cell disclosed herein, the polypeptide antigen is fused to an extracellular region of an endogenous transmembrane protein. In some embodiments of the enucleated hematopoietic cell disclosed herein, the polypeptide antigen is fused to a glycosylphosphatidylinisotol (GPI) anchored protein.

In some aspects, disclosed herein is a tissue culture batch comprising the enucleated hematopoietic cells described herein.

In some aspects, disclosed herein is a population of the enucleated hematopoietic cells described herein.

In some aspects, disclosed herein is a pharmaceutical composition comprising the cell populations described herein.

In some aspects, disclosed herein is a method of inducing immune tolerance comprising administering to a subject in need thereof the pharmaceutical compositions described herein in an amount and/or a frequency sufficient to induce immune tolerance in the subject.

In some aspects, disclosed herein is a method of treating an immune activation disease comprising administering to a subject in need thereof the pharmaceutical compositions described herein in an amount and/or frequency sufficient to treat the immune activation disease.

In some embodiments, the disease is selected from the group consisting of a self-antibody mediated disease, an autoimmune disease, an inflammatory disease, an allergic disease, an HLA-mismatch mediated disease, and a disease treatable by an immunogenic therapeutic protein.

In some aspects, disclosed herein is a method of reducing or alleviating an immune activation in response to a therapeutic protein treatment regimen comprising administering to a subject in need thereof the pharmaceutical compositions described herein in an amount and/or frequency sufficient to substantially reduce or alleviate the immune activation.

In some embodiments, the therapeutic protein is selected from the group consisting of those listed in Table I, Table J, and Table 7.

In some aspects, disclosed herein is an expression vector comprising a nucleic acid sequence encoding an endogenous erythroid cell protein fused with one or more exogenous polypeptide antigens selected from the group consisting of those listed in Table F, Table G, Table H, Table I, Table J, Table 6, Table 7, and Table 8.

In some aspects, disclosed herein is a messenger RNA comprising a nucleic acid sequence encoding an endogenous erythroid cell protein fused with one or more exogenous polypeptide antigens selected from the group consisting of those listed in Table F, Table G, Table H, Table I, Table J, Table 6, Table 7, and Table 8.

In some aspects, disclosed herein is a method of inducing immune tolerance comprising administering to a human subject suffering from or at risk of developing an allergen-mediated disease, disorder or condition, a pharmaceutical composition comprising an enucleated hematopoietic cell expressing an exogenous antigen, wherein the pharmaceutical composition is administered in an amount effective to induce immune tolerance in the subject to the allergen mediating the disease, disorder or condition.

In certain embodiments, the exogenous antigen is selected from the group consisting of Ara h2, 2S albumin, hyalauronidase, and those listed in Table H.

In certain embodiments, the allergen-mediated disease, disorder or condition is selected from the group consisting of peanut allergy, tree nut allergy, insect venom allergy, and those listed in Table H.

In some aspects, disclosed herein is a method of inducing immune tolerance comprising administering to a human subject suffering from or at risk of developing a human leukocyte antigen (HLA) mismatch-mediated disease, disorder or condition, a pharmaceutical composition comprising an enucleated hematopoietic cell expressing an exogenous antigen, wherein the pharmaceutical composition is administered in an amount effective to induce immune tolerance in the subject to the HLA mediating the disease, disorder or condition.

In some aspects, disclosed herein is a method of inducing immune tolerance comprising: administering to a human subject suffering from or at risk of developing a disease, disorder or condition that can be treated by an immunogenic therapeutic molecule, a pharmaceutical composition comprising an enucleated hematopoietic cell expressing an exogenous antigen, wherein the pharmaceutical composition is administered in an amount effective to induce immune tolerance in the subject to the immunogenic therapeutic molecule used to treat the disease, disorder or condition.

In some embodiments, the therapeutic molecule is selected from the group consisting of Recombinant (factor VIII), Benefix (factor IX), Humira (anti-TNFα), and those listed in Table I, Table J, and Table 7.

BRIEF DESCRIPTION OF THE FIGURES

FIGS. 3 A-C, F, I-M, O-Z, and AA-AU is a collection of flow cytometry plots and Western blots that demonstrate the expression of a vast array of exemplary antigens on the surface, in the cytoplasm, as fusions, and as intact proteins, in three cell types, enucleated erythroid cells, nucleated erythroid precursor cells, and erythroleukemic cells.

FIGS. 3 A-C, F, I-M, and O-S shows the exogenous expression of surface and cytoplasmic proteins on enucleated cultured erythroid cells.

FIG. 3B—Expression of glycophorin A with an HA epitope tag at the N terminus between the leader sequence and the body of the gene assessed by anti-HA staining.

FIG. 3C—Expression of complement receptor 1-derived fragment of ~70 kDa with an HA epitope tag at the N terminus assessed by anti-HA staining.

FIG. 3F—Expression of antibody scFv as N terminal fusion to glycophorin A assessed by anti-HA staining.

FIG. 3I—Expression of antibody scFv fused to C terminus of Kell-derived fragment of 71 amino acids assessed by anti-HA staining.

FIG. 3M—Expression of antibody scFv fused to N-terminus of CD55-derived fragment of 37 amino acids, assessed by anti-HA Western blot.

FIG. 3O—Cytoplasmic expression of adenosine deaminase fused to HA tag assessed by anti-HA Western blot. Expected size approximately 40 kDa.

FIG. 3P—Cytoplasmic expression of phenylalanine hydroxylase fused to HA tag assessed by anti-HA Western blot. Expected size approximately 33 kDa.

FIG. 3Q—Cytoplasmic expression of phenylalanine hydroxylase fused to adenosine deaminase and an HA tag assessed by anti-HA Western blot.

FIG. 3R—Cytoplasmic expression of adenosine deaminase fused to the intracellular C terminus of glycophorin A assessed by anti-HA Western blot. Expected size approximately 55 kDa.

FIG. 3S—Cytoplasmic expression of phenylalanine hydroxylase fused to the intracellular C terminus of glycophorin A assessed by anti-HA Western blot. Expected size approximately 50 kDa.

FIGS. 3 T-AO shows the exogenous expression of surface and cytoplasmic proteins on nucleated cultured erythroid precursor cells.

FIG. 3T—Expression of glycophorin A with an HA epitope tag at the cytoplasmic C terminus assessed by expression of co-translated GFP.

FIG. 3U—Expression of glycophorin A with an HA epitope tag at the N terminus between the leader sequence and the body of the gene assessed by anti-HA staining.

FIG. 3V—Overexpression of complement receptor 1 assessed by anti-CR1 staining.

FIG. 3W—Expression of complement receptor 1-derived fragment of ~70 kDa with an HA epitope tag at the N terminus assessed by anti-HA staining.

FIG. 3X—Expression of complement receptor 1-derived fragment of ~210 kDa with an HA epitope tag at the N terminus assessed by anti-HA staining.

FIG. 3Y—Expression of complement receptor 1-derived fragment of ~230 kDa fused to the N terminus of glycophorin A with an HA epitope tag at the N terminus assessed by anti-HA staining.

FIG. 3AA—Expression of antibody scFv fused to the extracellular C terminus of Kell, assessed by anti-HA staining. Expected size approximately 108 kDa.

FIG. 3AB—Expression of HA tag fused to the extracellular C terminus of Kell, assessed by anti-HA staining.

FIG. 3AC—Expression of Kell-derived fragment of 71 amino acids with HA tag at the C (extracellular) terminus assessed by anti-HA staining.

FIG. 3AD—Expression of Kell-derived fragment of 79 amino acids with HA tag at the C terminus assessed by anti-HA staining.

FIG. 3AE—Expression of antibody scFv fused to C terminus of Kell-derived fragment of 71 amino acids assessed by anti-HA staining.

FIG. 3AF—Expression of antibody scFv fused to C terminus of Kell-derived fragment of 79 amino acids assessed by anti-HA staining.

FIG. 3AG—Expression of CD55 with HA epitope tag at the extracellular N terminus after the leader sequence assessed by anti-HA staining.

FIG. 3AH—Expression of CD59 with HA epitope tag at the extracellular N terminus after the leader sequences assessed by anti-HA staining.

FIG. 3AI—Expression of antibody scFv fused to N-terminus of CD55-derived fragment of 37 amino acids, assessed by anti-HA staining.

FIG. 3AJ—Expression of antibody scFv fused to N-terminus of CD59 assessed by anti-HA staining.

FIG. 3AK—Cytoplasmic expression of adenosine deaminase fused to HA tag assessed by anti-HA Western blot. Expected size approximately 40 kDa.

FIG. 3AL—Cytoplasmic expression of phenylalanine hydroxylase fused to HA tag assessed by anti-HA Western blot. Expected size approximately 33 kDa.

FIG. 3AM—Cytoplasmic expression of phenylalanine hydroxylase fused to adenosine deaminase and an HA tag assessed by flow cytometry for fluorescence from co-translated GFP.

FIG. 3AN—Cytoplasmic expression of adenosine deaminase fused to the intracellular C terminus of glycophorin A assessed by anti-HA Western blot. Expected size approximately 55 kDa.

FIG. 3AO—Cytoplasmic expression of phenylalanine hydroxylase fused to the intracellular C terminus of glycophorin A assessed by anti-HA Western blot. Expected size approximately 50 kDa.

FIGS. 3 AP-AU shows the exogenous expression of surface and cytoplasmic proteins on K562 erythroleukemia cells.

FIG. 3AP—Overexpression of complement receptor 1 assessed by anti-CR1 staining.

FIG. 3AQ—Expression of antibody scFv as N terminal fusion to glycophorin A assessed by anti-HA staining.

FIG. 3AR—Expression of antibody scFv fused to N-terminus of CD55-derived fragment of 37 amino acids, assessed by anti-HA staining.

FIG. 3AS—Expression of antibody scFv fused to N-terminus of CD59 assessed by anti-HA staining.

FIG. 3AT—Cytoplasmic expression of adenosine deaminase fused to HA tag assessed by anti-HA Western blot. Expected size approximately 40 kDa.

FIG. 3AU—Cytoplasmic expression of phenylalanine hydroxylase fused to HA tag assessed by anti-HA Western blot. Expected size approximately 33 kDa.

(FIG. 4A) Untransfected platelets. (FIG. 4B) Platelets transfected with 3 ug GFP mRNA. (FIG. 4C) Platelets transfected with 6.8 ug GFP mRNA.

(FIG. 5A) is a Western blot of exogenously expressed adenosine deaminase detected with an anti-HA antibody over the course of differentiation, from nucleated precursor cells ("Diff I D5") through to enucleated erythroid cells ("Diff III D8"). (FIG. 5B) is a bar chart of inosine produced from adenosine by intact adenosine deaminase-expressing 293T cells. (FIG. 5C) is a Western blot of the exogenously expressed phenylalanine hydroxylase detected with an anti-HA antibody at various time points over the course of differentiation, from nucleated precursor cells ("Diff I D5") through to enucleated erythroid cells ("Diff III D8"). (FIG. 5D) is a bar chart of tyrosine produced from phenylalanine by lysates of cultured phenylalanine hydroxylase-expressing enucleated erythroid cells.

(FIG. 6A) is a flow cytometry plot that shows the capture of fluorescent immune complexes (white histogram) and complement-deficient immune complexes (shaded histogram) by cultured erythroid cells that overexpress CR1. (FIG. 6B) is a bar chart of flow cytometry data assessing the uptake of fluorescent immune complexes (hashed bars), complement deficient immune complexes (gray bars), or no immune complexes (black bars) by macrophages (left set) or macrophages incubated with cultured erythroid cells that overexpress CR1 (right set).

FIGS. 7A-7D show the activity of an antibody scFv that binds hepatitis B surface antigen (scFv) on the surface of a cultured erythroid cell. (FIG. 7A) is a flow cytometry histogram showing binding of 450 nM antigen (white histogram) or no antigen (gray histogram). (FIG. 7B) is a titration of binding signal assessed by flow cytometry for a range of antigen concentrations. (FIGS. 7C-D) are flow cytometry plots of blood cells from mice that had been injected with fluorescent antigen and cultured erythroid cells that (FIG. 7C) do not or (FIG. 7D) do express scFv. The y-axis measures antigen fluorescence. The x-axis measures fluorescence of the cultured cells.

(FIG. 8A) is a set of flow cytometry plots that show no binding (top) and binding (bottom) of circulating Dylight650-labeled mouse anti-HA antibody to CFSE-labeled cultured human erythroid cells isolated from a recipient mouse that either do not (top) or do (bottom) express HA epitope tag on their surface. The x-axis measures CFSE fluorescence. The y-axis measures anti-HA antibody Dylight650 fluorescence. (FIG. 8B) is data from an HA epitope tag substrate ELISA comparing anti-HA antibody levels over time in plasma collected from mice injected with anti-HA antibody (open circles, solid line), anti-HA antibody followed by cultured human erythroid cells that do not express HA epitope tag (dashed line), or anti-HA antibody followed by cultured human erythroid cells that do express HA epitope tag (dotted line). (FIG. 8C) is a set of flow cytometry plots that show no binding (top) and binding (bottom) of Dylight650-labeled mouse anti-biotin antibody to CFSE-labeled primary human erythrocytes that either are not (top) or are (bottom) conjugated with biotin on their surface. The x-axis measures CFSE fluorescence. The y-axis measures anti-biotin antibody Dylight650 fluorescence. (FIG. 8D) is data from a biotin substrate ELISA comparing anti-biotin antibody levels over time in plasma collected from mice injected with anti-biotin antibody (open circles, solid line), anti-biotin antibody followed by cultured human erythroid cells that are not conjugated to biotin (dashed line), or anti-biotin antibody followed by cultured human erythroid cells that are conjugated to biotin (dotted line).

(FIG. 9A) is a representative flow cytometry dot-plot of drawn blood, stained for human glycophorin A (y-axis) and CFSE (x-axis), in which human cultured cells are double-positive. (FIG. 9B) is a plot of the clearance rate over time as a percentage of double-positive cells remaining after NSG mice were injected with human red blood cells (solid circles), cultured enucleated erythroid cells (dashed diamonds), cultured enucleated erythroid cells that express an intracellular exogenous protein (dotted squares) and cultured enucleated erythroid cells that express a surface exogenous protein (open triangles).

(FIGS. 10A-B) show levels of (FIG. 10A) fibrinopeptide A and (FIG. 10B) fibrinopeptide B assessed by ELISA in plasma collected from mice 20 minutes (black), 6 hours (gray), and 48 hours (white) after injection with (1) human red blood cells, (2) cultured human erythroid cells, (3) cultured human erythroid cells expressing an exogenous cytoplasmic protein, (4) cultured human erythroid cells expressing an exogenous surface transgene, or (5) recombinant protein. (FIGS. 10C-D) show microscope images of histologically stained sections of spleen for mice injected with (G FIG. 10C) cultured human erythroid cells and (FIG. 10D) recombinant protein.

(FIG. 11A) is flow cytometry data of blood drawn from a mouse that was injected with cultured human erythroid cells expressing an exogenous surface protein, showing the percent of cultured human erythroid cells that are HA-positive over time. (FIG. 11B) is a Western blot of blood drawn from two mice, wherein one mouse was injected with cultured human erythroid cells expressing an exogenous cytoplasmic protein, and wherein the other mouse was injected with the purified recombinantly-produced exogenous protein in the absence of any cells, showing the level of HA-containing protein in the blood over time.

(FIG. 12A) is a plot of expansion rates for distinct cultures of in vitro differentiated erythroid cells that contain transgenes (dashed line and dotted line) and cells that do not contain a transgene (solid line). (FIG. 12B) is a flow cytometry plot of cell surface markers GPA and CKIT for distinct cultures of cultured human erythroid cells that do not (left) or do (right) contain a transgene. (FIG. 12C) is a flow cytometry plot of cultured human erythroid cells that do not (left) or do (right) contain a transgene, wherein the cells are stained with DNA stain DRAQ5 (y-axis) and anti-glycophorin A (x-axis), which identifies distinct populations of (1) enucleated cells, (2) nucleated cells, and (3) nuclei.

FIG. 13A is a schematic of three ways in which an antigen may be localized in an exogenous antigen-expressing EHC. FIG. 13B is a schematic of three ways in which an antigen localized in or on an exogenousan exogenous antigen-expressing EHC may act on a target in circulation. FIG. 13C is a schematic of an auto-catalytic fusion of an endogenous polypeptide anchor to an antigen utilizing a SpyTag-SpyCatcher mechanism.

DETAILED DESCRIPTION OF THE INVENTION

Figure 1:
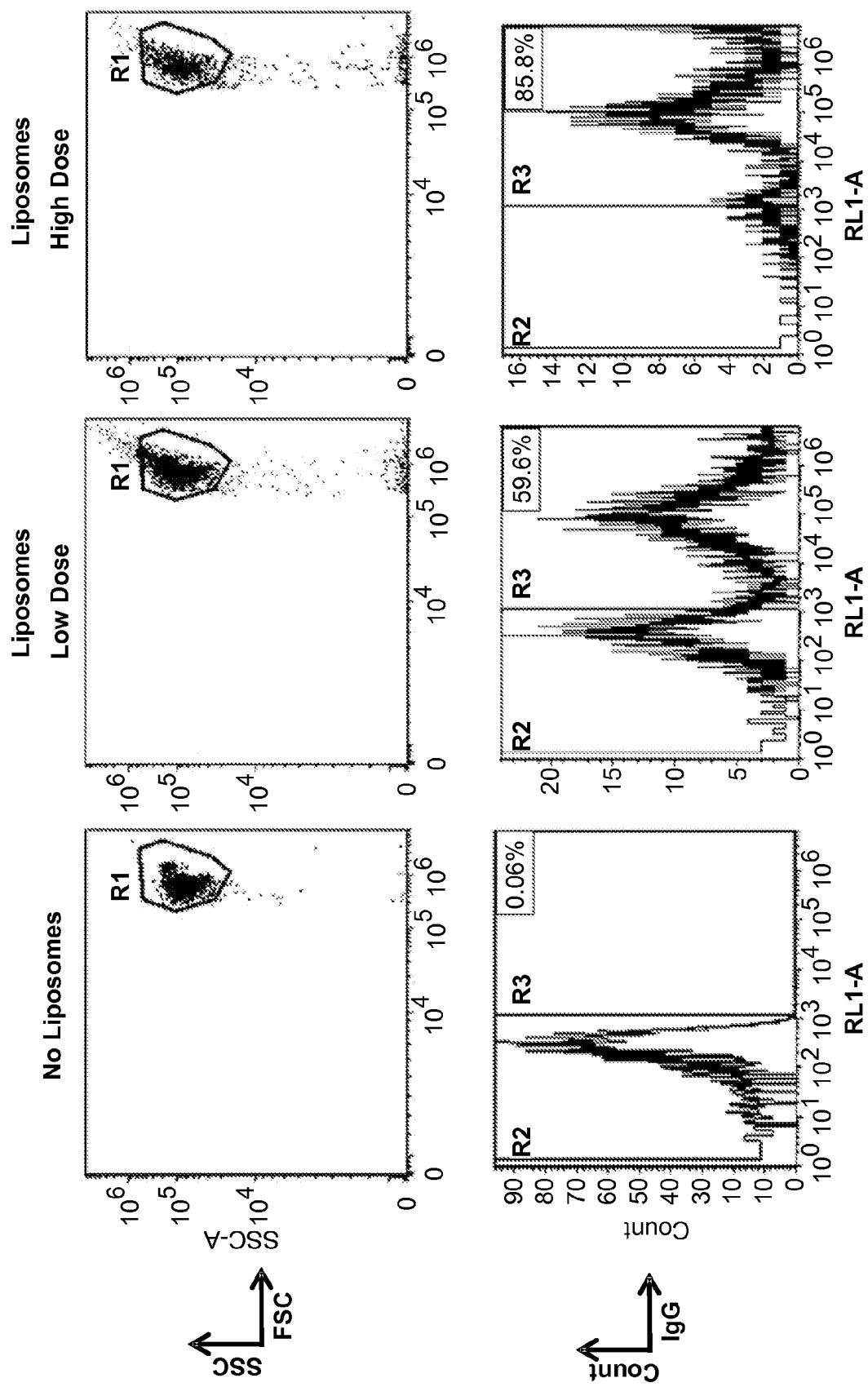
FIG. 1 is a collection of flow cytometry plots of red blood cells contacted with fluorescently labeled IgG encapsulated within liposomes. Cells are shown that are incubated with no liposomes (left), a low dose of liposomes (center), and a high dose of liposomes (left). On the bottom histograms, the percentage of cells that are fluorescent is shown.

The invention, in certain aspects, provides isolated cells that are engineered or modified to contain exogenous antigens of interest. In certain aspects, isolated EHCs of the invention comprise one or more antigens that comprise or consist of polypeptides. In some embodiments, the antigen is a full-length protein. In some embodiments, the antigen is comprised of one or more polypeptides contained within the full-length protein, of any length greater than approximately 7 amino acids. The polypeptides comprising the antigen may comprise one or more immunological epitopes which may be conformational epitopes or may be linear epitopes. The antigen may be comprised of one or more polypeptides from one or more different proteins. In certain aspects, EHCs of the invention comprise one or more antigens that comprise or consist of carbohydrates. In certain aspects, EHCs of the invention comprise one or more antigens that comprise or consist of lipids. In certain aspects, EHCs of the invention comprise one or more antigens that comprise or consist of one or more polypeptides, lipids, and/or carbohydrates, and any combination thereof. The cells can be circulating cells, such as EHCs. The EHCs can be cultured from hematopoietic precursors using defined factors such as e.g. stem cell factor, cytokines such as IL-3 and IL-6, insulin, transferrin, erythropoietin, hydrocortisone, and estrogens.

Aspects of the invention relate to methods of culturing EHCs to comprise exogenous antigens of interest. The exogenous antigens of interest can be introduced by a number of methods, such as, e.g. intracellular expression, cell-surface expression, fusion to an endogenous protein, conjugation by chemical or enzymatic means to a cell surface protein, or physical loading into the intracellular space. The antigen-comprising cells of the invention may be used as therapeutic agents.

Aspects of the invention relate to the use of these antigen-comprising cells in the treatment of diseases of immune activation by the induction of peripheral tolerance. In some aspects, induction of peripheral tolerance means the deletion or inactivation of antigen-specific immune cells, such as, e.g. CD8 T lymphocytes (CD8 T cells), CD4 T lymphocytes (CD4 T cells), CD4 T regulatory lymphocytes (Treg), or B lymphocytes (B cells). Diseases of immune activation include autoimmune diseases, such as, e.g. multiple sclerosis, type 1 diabetes, rheumatoid arthritis, and membranous nephritis. Diseases of immune activation also include inflammatory diseases, such as, e.g. Crohn's disease, ulcerative colitis, celiac disease, or other idiopathic inflammatory bowl diseases. Diseases of immune activation also include allergic diseases, such as, e.g. asthma, peanut allergy, shellfish allergy, pollen allergy, milk protein allergy, insect sting allergy, and latex allergy. Diseases of immune activation also include immune activation in response to a therapeutic protein, administered to treat a primary condition, that lessens the efficacy of the therapeutic protein, such as, e.g., clotting factor VIII in hemophilia A, clotting factor IX in hemophilia B, anti-tumor necrosis factor alpha (TNFa) antibodies in rheumatoid arthritis and other inflammatory diseases, glucocerebrosidase in Gaucher's disease, or asparaginase in acute lymphoblastic leukemia (ALL).

Biology of Immune Tolerance

The body has evolved sophisticated mechanisms for the prevention of aberrant immune activation and autoimmune disease, collectively termed immune tolerance. Central tolerance refers to the antigen-specific deletion of autoreactive T cells and B cells during development in the primary lymphoid organs, e.g. thymus and bone marrow. Peripheral tolerance refers to the deletion or inactivation of mature T and B lymphocytes outside of the primary lymphoid organs. Peripheral tolerance includes the suppression of autoreactive lymphocytes by regulatory T cells (Tregs) or the induction of anergy or non-responsiveness in antigen-specific effector lymphocytes by exposure to continuous low doses of antigen in the absence of costimulatory "danger" signals. Both Treg activation and lymphocyte anergy can be induced by the secretion of inhibitory factors such as, for example, TGF-beta, IL-10, and IL-4.

Immune activation in response to antigen often requires a secondary "danger" signal, such as a toll-like receptor ligand, often derived from microbial or viral pathogens (Matzinger, Annu Rev Immuno 1994). Such danger signals include double-stranded RNA, single-stranded DNA, lipopolysaccharide, bacterial lipoproteins, flagellin, zymosan, and others. Antigen presenting cells that receive both antigen and danger signal display costimulatory molecules on their surface, like CD80 and CD86, in addition to the antigenic peptides. T cells that recognize both the antigenic peptide and the costimulatory molecules become activated. Those that receive just the antigenic peptide signal become anergic.

Therapeutic strategies that take advantage of antigen presentation in the absence of danger signals to induce immune tolerance have been developed for the experimental treatment of many food allergies. The studies take the form of prolonged exposure to increasing doses of allergen with the intent to induce tolerance. Thirteen studies since 2007 have tested a variety of common food allergens like peanut, milk, and egg, in this format. 50-100% of patients become sensitized, that is, able to survive a food challenge without anaphylaxis. However, long term tolerance is less successful, with only 25-50% of patients able to tolerate antigen after one month off therapy. See, e.g. Burks et al., New England Journal of Medicine 2012.

It is thought that allergy is IgE mediated, with activation of mast cells and basophils. Oral administration of the allergen in low dose, such as continuous feeding, induces Tregs via $CD11c^+$ dendritic cell presentation of antigen and secretion of TGF-beta, IL-10, and IL-4. Oral administration at high doses induces antigen-specific T cell deletion and anergy via plasmacytoid dendritic cells. In human studies, oral administration of allergen results in a decrease in IgE, mast cells, and basophils, an increase in IgG4, TGF-beta, IL-10, and a temporary uptick in Tregs at the start of therapy. See, e.g. Herzog, Adv Drug Deliv Rev 2013.

While not wishing to be limited to any particular mechanism, it is believed that peripheral immunologial tolerance can be induced by self antigens from apoptosing cells (Griffith and Ferguson, Immunity 2011; Green et al., Nat Rev Immunol 2009). Though the exact mechanisms are not fully understood from a molecular perspective, self proteins such as HSP90 and other damage-associated molecular patterns facilitate uptake by dendritic cells. Dendritic cell receptors like CD205 recognize these signals, cross-present antigen, and induce tolerogenic cytokines and suppress costimulatory protein expression (Bonifaz, J Exp Med 2002).

Therapeutic strategies that harness the tolerogenic potential of apoptosing cells to induce peripheral immune tolerance are under investigation. These strategies typically involve the chemical coupling of antigens of interest to the surface of cells. In studies in mice, rat, and guinea pigs, a variety of protein antigens are chemically attached to the surface of splenocytes and leukocytes. See, e.g., Miller et al., J Exp Med 1979; Braley-Mullen et al., Cell Immunol 1980; Luo et al., PNAS 2008; Smarr et al., J Immunol 2011.

In a recent phase I clinical study in humans, a cocktail of peptide antigens associated with multiple sclerosis were chemically coupled to autologous peripheral blood mononuclear cells and reinfused into patients (Lutterotti and Martin, Sci Trans Med 2013). The cells were well tolerated, and there was evidence of a decrease in antigen-specific T cell responses.

EHCs are a prominent source of dying cells. A large number of erythrocytes are cleared after apoptosis-like programmed cell death, called eryptosis, each day (more than 1% per day in humans, approximately $1 \times 10^{11}$ cells). Although the exact triggers of erythrocyte clearance remain unclear, eryptotic erythrocytes are characterized by phosphatidylserine asymmetry, membrane heterogeneity, and annexin-V binding, analogous to apoptotic nucleated cells.

EHCs are also persistent in the body. Erythrocytes circulate for up to 120 days in the adult human. As such, EHCs that comprise an antigen of interest may enable the persistent exposure of the antigen to the host. As described above, though the exact molecular mechanisms are not fully understood, it is thought that persistent exposure to antigen can induce peripheral tolerance through antigen presentation in the absence of costimulatory signals, leading to the expansion of regulatory T cells, the deletion and anergy of effector T and B cells, and the secretion of anti-inflammatory and pro-tolerogenic cytokines.

The induction of peripheral tolerance by taking advantage of erythrocytes have been explored experimentally as well. In preliminary work, the model antigen ovalbumin has been shown to induce antigen-specific CD8 T cell deletion and antigen-specific Treg induction when non-covalently attached to erythrocytes (Kontos et al., PNAS 2013) or osmotically loaded into erythrocytes (Cremel and Godfrin, Int J Pharm 2013).

Cultured EHCs of the invention comprising an exogenous antigen of interest may have distinct advantages over antigen that is non-covalently attached to erythrocytes, e.g. via a polypeptide binding domain. One advantage may be that the bio-distribution of an EHC comprising an exogenous antigen of interest is more defined than that of a polypeptide composition of antigen with targeting domain. The EHC comprising an exogenous antigen of interest will be confined to the vasculature and to places that erythrocytes typically reside, e.g. spleen. EHCs comprising an exogenous antigen of interest will not be filtered out of the kidney or exit into peripheral tissue, problems that may arise when polypeptide antigen compositions are administered. The dose of exogenous antigen per EHC may be significantly higher if the cells comprising an exogenous antigen of interest are cultured than if a polypeptide antigen is directly injected into the bloodstream and distributed across approximately 10 trillion erythrocytes in the bloodstream. In some instances, it may be preferable to have the exogenous antigen of interest confined in the intracellular compartment of the EHC. For example, if the antigen is immunogenic, intracellular localization may be advantageous because it may mask the immunogenic antigen from the immune system and thus prevent or reduce immune activation. This configuration is not possible with a polypeptide antigen composition.

Cultured EHCs that express an exogenous antigen of interest may have distinct advantages over antigen that is osmotically loaded into EHCs. The cultured EHCs comprising an exogenous antigen of interest will have cell membranes and cytoskeleton that are substantially unaltered, in contrast to the product of an osmotic loading procedure, in which large pores breach the integrity of the cell membrane and cytoskeleton. The morphology and biophysical characteristics of EHCs are crucial determinants of the cell's bio-distribution, circulation, and interaction with the vasculature and immune cells (e.g. Pries et al., Cardiovasc. Res. 1996), and hence maintaining cell integrity may be crucial to retain efficaciousness. Exogenous antigen that is physically attached to a cultured EHC, for example by direct fusion to an endogenous cytoplasmic protein or fusion to an endogenous transmembrane protein, will not leak out of the cell and be exposed to the immune system until the EHC is consumed. The problem of leakage may arise if the cell is contacted with the antigen using an osmotic loading procedure in which the cell membrane can be damaged.

Cultured EHCs that express an antigen of interest can be administered directly to a subject in need of the antigen. A separation and purification of the antigen during manufacture of the product is not required. This is in contrast to an osmotic loading product, in which the antigen must be synthesized and purified separately and then combined with the cell, and may provide a significant cost and time advantage in the manufacture of the product. The cultured EHCs that express an antigen of interest can be scaled up by propagation in culture. Large, industrial-size batches of cells may be produced to generate a substantially uniform pharmaceutical composition of EHCs for a given antigen that can be used to universally treat many subjects. In contrast, osmotic loading is generally limited to a one-donor-to-one-subject scale.

Acquisition of Cells

Exogenous antigen-expressing enucleated hematopoietic cells of the invention can be generated by any method described herein. In some embodiments, the steps comprise contacting isolated optionally cultured cells derived from hematopoietic stem cells with an antigen. Hematopoietic stem cells give rise to all of the blood cell types found in mammalian blood including myeloid (monocytes and macrophages, neutorphils, basophils, eosinophils, erythrocytes, megakaryocytes/platelets, dendritic cells) and lymphoid lineages (T-cells, B-cells, NK-cells). Hematopoietic stem cells may be isolated from the bone marrow of adult bones including, for example, femur, hip, rib, or sternum bones. Cells may be obtained directly from the hip, for example, by removal of cells from the bone marrow using aspiration with a needle and syringe. Alternatively, hematopoietic stem cells may be isolated from normal peripheral blood following pre-treatment with cytokines such as, for example, granulocyte colony stimulating factor (G-CSF). G-CSF mobilizes the release of cells from the bone marrow compartment into the peripheral circulation. Other sources of hematopoietic stem cells include umbilical cord blood and placenta.

Isolated hematopoietic stem cells may be cultured, expanded and differentiated ex vivo to provide a variety of source material to generate exogenous antigen-expressing EHCs. For example, hematopoietic stem cells isolated from bone marrow, cytokine-stimulated peripheral blood or umbilical cord blood may be expanded and differentiated ex vivo into mature erythrocytes (Giarratana et al., Nature Biotech. 23:69-74 (2005); U.S. Patent Application 2007/0218552). As such, CD34+ cells are isolated from bone marrow or peripheral or cord blood using, for example, magnetic microbead selection and Mini-MACS columns (Miltenyi Biotech). In one example, the cells are subsequently cultured in modified serum-free medium supplemented with 1% bovine serum albumin (BSA), 120 µg/ml iron-saturated human transferrin, 900 ng/ml ferrous sulfate, 90 ng/ml ferric nitrate and 10 rig/ml insulin and maintained at 37° C. in 5% carbon dioxide in air. Expansion and differentiation of the cell culture may occur in multiple steps. For example, in the initial growth step following isolation, the cells may be expanded in the medium described herein in the presence of multiple growth factors including, for example, hydrocortisone, stem cell factor, IL-3, and erythropoietin. In the second stage, the cells may optionally be co-cultured, for example, on an adherent stromal layer in the presence of erythropoietin. In a third stage, the cells may be cultured on an adherent stromal layer in culture medium in the absence of exogenous factors. The adherent stromal layer may be murine MS-5 stromal cells, for example. Alternatively, the adherent stromal layer may be mesenchymal stromal cells derived from adult bone marrow. The adherent stromal cells may be maintained in RPMI supplemented with 10% fetal calf serum, for example. In some embodiments, the erythroid precursor cells and cell populations derived therefrom are not co-cultured with non-EHCs, e.g., with an adherent stromal layer, i.e. they are cultured in the absence of non-EHCs. In some embodiments, EHCs comprising an antigen are cultured in the absence of non-EHCs and are differentiated so that greater than 10%, 15%, 20%, 25%, 30%, 35%, 40%, 45%, 50%, 55%, 60%, 65%, 70%, 75%, 80%, 85%, 90%, 95% or greater than 98% of EHCs are enucleated and the population of enucleated cells is obtained without an enrichment step, such as gravitational separation, magnetic or fluorescent sorting, irradiation, poisoning of nucleated cells, and the like to select for enucleated cells.

In some instances, it may be desirable to expand and partially differentiate the CD34+ hematopoietic stem cells in vitro and to allow terminal differentiation into mature erythrocytes to occur in vivo (See, e.g., Neildez-Nguyen et al., Nature Biotech. 20:467-472 (2002)). Isolated CD34+ hematopoietic stem cells may be expanded in vitro in the absence of the adherent stromal cell layer in medium containing various factors including, for example, Flt3 ligand, stem cell factor, thrombopoietin, erythropoietin, and insulin growth factor. The resulting erythroid precursor cells may be characterized by the surface expression of CD36 and GPA, and may be transfused into a subject where terminal differentiation to mature erythrocytes is allowed to occur.

In some embodiments, the EHC population comprises a plurality of enucleated EHCs that comprise an antigen polypeptide that is retained during enucleation. The resulting isolated enucleated EHC comprising an antigen polypeptide exhibits substantially the same osmotic membrane fragility as a corresponding isolated, unmodified, uncultured EHC.

In some embodiments, the EHC population comprises a plurality of erythrocyte precursor cells in substantially the same stage of differentiation and/or cell cycle stage, wherein the precursor cells comprise a recombinant nucleic acid encoding an antigen. The majority of erythrocyte precursor cells that comprise a recombinant nucleic acid encoding an antigen are capable of differentiating into mature erythrocytes that retain the antigen without retaining the recombinant nucleic acid.

In some embodiments, the primary cells may be collected through venipuncture, capillary puncture, or arterial puncture. From the collected whole blood erythrocytes, platelets or other cells may then be isolated using one, or a combination of techniques including plasma depletion, density gradient, Hetastarch, PrepaCyte-CB, and centrifugation.

Allogeneic/ and Autologous Sourcing

In some embodiments, generating an exogenousan exogenous antigen-expressing EHC comprises contacting isolated optionally cultured cells that are autologous and/or allogeneic to the subject with an antigen. For example, erythrocytes allogeneic to the subject include one or more of blood type specific erythrocytes or one or more universal donor erythrocytes. In some embodiments, exogenous antigen-expressing EHCs may be generated through fusion of erythrocytes, e.g., between erythrocytes autologous to the subject and one or more allogeneic erythrocytes, liposomes, and/or artificial vesicles.

In certain embodiments, autologous transfusion of exogenous antigen-expressing EHCs includes isolating erythrocytes, reticulocytes or hematopoietic stem cells from a subject, generating a suitable exogenous antigen-expressing EHC by contacting the cell with an antigen by methods described herein and administering (e.g., by transfusion) the exogenous antigen-expressing EHC into the same subject.

In certain embodiments, allogeneic transfusion of exogenous antigen-expressing EHCs includes isolating erythrocytes, reticulocytes or hematopoietic stem cells from a donor, generating a suitable exogenous antigen-expressing EHC by contacting the cell with an antigen by methods described herein and administering (e.g., by transfusion) the exogenous antigen-expressing EHC into a subject that is different from the donor. Where allogeneic cells are used for transfusion, care needs to be taken to use a compatible ABO blood group to prevent an acute intravascular hemolytic transfusion reaction which is characterized by complement activation and lysis of incompatible erythrocytes. The ABO blood types are defined based on the presence or absence of the blood type antigens A and B, monosaccharide carbohydrate structures that are found at the termini of oligosaccharide chains associated with glycoproteins and glycolipids on the surface of the erythrocytes (reviewed in Liu et al., Nat. Biotech. 25:454-464 (2007)). Group O erythrocytes lack either of these antigenic monosaccharide structures. Subjects with group A erythrocytes have naturally occurring antibodies to group B erythrocytes whereas subjects with group B erythrocytes have antibodies to group A erythrocytes. Blood group AB subjects have neither antibody and blood group O individuals have both. Subjects with either anti-A and/or anti-B antibodies cannot receive a transfusion of blood containing the corresponding antigen. Because group O erythrocytes contain neither A nor B antigens, they can be safely transfused into recipients of any ABO blood group, e.g., group A, B, AB, or O recipients. Group O erythrocytes are considered universal and may be used in all blood transfusions. In contrast, group A erythrocytes may be given to group A and AB recipients, group B erythrocytes may be given to group B and AB recipients, and group AB erythrocytes may only be given to AB recipients. In embodiments in which exogenous antigen-expressing EHCs are generated by contecting erythrocytes or their precursors with an antigen the sourced erythrocytes or their precursors are matched for compatibility with the recipient.

In some instances, it may be beneficial to convert an exogenous antigen-expressing EHC comprising a non-group O erythrocyte to a universal blood type. Enzymatic removal of the immunodominant monosaccharides on the surface of group A and group B erythrocytes may be used to generate a population of group O-like exogenous antigen-expressing EHCs (See, e.g., Liu et al., Nat. Biotech. 25:454-464 (2007)). Group B exogenous antigen-expressing EHCs may be converted using an α-galactosidase derived from green coffee beans. Alternatively or in addition, α-N-acetylgalactosaminidase and α-galactosidase enzymatic activities derived from E. meningosepticum bacteria may be used to respectively remove the immunodominant A and B antigens (Liu et al., Nat. Biotech. 25:454-464 (2007)), if present on the exogenous antigen-expressing EHCs. In one example, packed red blood cells isolated as described herein, are incubated in 200 mM glycine (pH 6.8) and 3 mM NaCl in the presence of either α-N-acetylgalactosaminidase and α-galactosidase (about 300 μg/ml packed red blood cells) for 60 min at 26° C. After treatment, the red blood cells are washed by 3-4 rinses in saline with centrifugation and ABO-typed according to standard blood banking techniques.

In specific embodiments, the exogenous antigen-expressing EHCs described herein may be generated in the following way. First, erythroid precursor cells are isolated. These cells may alternatively be autologous to the patient or from substantially universal donor blood. For example, the cells may be ABO type O, rhesus factor Rh r/r, Duffy −/−, and large Kell antigen K1 negative. In the course of differentiation from erythroid precursor cell to EHC, a recombinant nucleic acid encoding the antigen is introduced. The recombinant nucleic acid encoding the antigen can be under the control of an erythroid-specific promoter, such as a GATA-1 promoter (see e.g., Repik et al., Clin Exp Immunol 2005, 140:230). The recombinant nucleic acid encoding the antigen can be introduced in any way known in the art, for example, as plasmid DNA, virus, or mRNA. Nucleic acid introduction can be achieved by a variety of standard methods, e.g., transfection, transduction, or electroporation.

Platelet Derivation and Maturation

In specific embodiments, the exogenous antigen-expressing EHCs described herein may be generated by contacting platelets with an antigen. Each day an adult human produces $2 \times 10^{11}$ red blood cells, and about one-half as many white cells and platelets. In humans, nearly all blood cell production occurs in the red bone marrow that represents a hierarchical developmental system composed of hematopoietic stem cells, intermediate level progenitors and maturing cells committed to each lineage.

Although the morphology of all the major blood cell types is similar through their initial development stages, megakaryocytes, cells committed to platelet production, are marked by an obvious structural and functional departure beyond the blast cell level of differentiation growing to a size 10 times the diameter of most other bone marrow and blood cells, and containing up to 128 times the normal chromosomal complement, these cells give rise to blood platelets. After a series of normal cell divisions, the developing megakaryocyte precursor enters a unique cell cycle characterized by a brief (about 1 h) G1 phase, a typical (7 h) S phase, a very brief (~45 min) G2 phase, followed by the endomitotic phase (an aborted M phase). Once the cell develops a highly polyploid nucleus, it also develops demarcation membranes necessary for cytoplasmic fragmentation. This event is accompanied by expression of glycoprotein GPIIbIIIa (platelet fibrinogen receptor; Papayannopoulou et al., Exp. Hematol., 24: 660-9, 1996) and GPIb (von Willibrand factor receptor; Kaushansky et al., Nature, 369: 568-571, 1994), the granules that contain ADP, serotonin, -thromboglobulin, and other substances critical for mature platelet function. Finally, highly polyploid megakaryocytes undergo cytoplasmic partitioning, allowing the release of thousands of platelets (Choi et al., Blood, 85: 402-413, 1995; Cramer et al., Blood, 89: 2336-2346, 1997).

Like all blood cell precursors, megakaryocytes are derived from pluripotent marrow stem cells that retain the capacity to extensively self-renew, or to differentiate into all of the elements of the blood. Platelet production is in part regulated by signaling mechanisms induced by interaction between thrombopoietin (TPO) and its cellular receptor TPOR/MPUc-MPL.

Thrombopoietin (TPO) is a hematopoietic growth factor involved in stimulation of megakaryocytopoiesis and platelet production. TPO is expressed in liver and kidney, and, in response to platelet demand, its expression may be also upregulated in the bone marrow microenvironment (Kato et al., Stem Cells, 16: 322-328, 1998; McCarty et al., Blood, 86:3668-3675, 1995). As TPO expression is mostly constitutive, the TPO levels are believed to be regulated by sequestering by platelets (Fielder et al., Blood 87: 2154, 1996).

The gene encoding TPO has been cloned and characterized (Kuter et al., Proc. Natl. Acad. Sci. USA, 91:11104-11108, 1994; Bartley et al., Cell, 77:1117-1124, 1994; Kaushansky et al., Nature, 369:568-571, 1994; Wendling et al., Nature, 369:571-574, 1994, and de Sauvage et al., Nature, 369:533-538, 1994). Human TPO (hTPO) cDNA encodes a 353 amino acid-long polypeptide. The full-length hTPO secreted from mammalian cells after cleavage of the signal peptide consists of 332 amino acids. Although the predicted molecular mass of this protein is 38 kDa, the molecular masses reported from measurements of material in serum or in culture fluid from recombinant cells vary from 18 to 85 kD (glycosylation, and post-translational proteolytic processing).

The cell surface receptor for TPO (TPOR/MPL/c-MPL) is a product of the protooncogene c-mpl, a homologue of v-mpl, an envelope protein of the myeloproliferative leukaemia virus (MPLV) shown to induce a pan-myeloid disorder (Wendling, Virol., 149:242-246, 1986). The human c-mpl gene codes for a protein of 635 aa having a predicted molecular weight of 71 kD (Vigon et al., Proc. Natl. Acad. Sci. USA, 89:5640-44, 1992; Mignotte et al., Genomics, 20: 5-12, 1994).

Mice rendered null for the expression of either TPO or its receptor (TPOR/MPL/c-MPL) manifest a severe thrombocytopenic phenotype (Gurney et al., Science, 265: 1445, 1994; Kaushansky et al., J. Clin. Invest., 96: 1683, 1995; de Sauvage et al., J. Exp. Med., 183: 651, 1996).

Multiple cytokines (e.g., stem cell factor [SCF], IL-1, IL-3, IL-6, IL-11, leukaemia inhibiting factor [LIF], G-CSF, GM-CSF, M-CSF, erythropoietin (EPO), kit ligand, and -interferon) have been shown to possess thrombocytopoietic activity.

Platelet Activation

The resulting platelets are small disc-shaped cell fragments which undergo a rapid transformation when they encounter sites of vascular damage. They become more spherical and extrude pseudopodia, their fibrinogen receptors are activated leading to aggregation, and they release their granule contents and eventually they form a plug which is responsible for primary hemostasis (Siess, W., Physiol. Rev. 69: 58-178, 1989). Activation of platelets is also implicated in the pathogenesis of unstable angina, myocardial infarction and stroke (Packham, M. A., Can J. Physiol Pharmacol. 72: 278-284).

Several physiological substances are involved in the activation of platelets such as collagen, which is exposed at the subendothelial surfaces, thrombin, generated by the coagulation cascade, and thromboxane A2 ($TXA_2$) and ADP, which are released from activated platelets. Collagen binds to several platelet membrane proteins including integrin α2 β1 leading to platelet activation through the release of $TXA_2$ and ADP (Shattil, S. J., et al., Curr. Opin. Cell Biol. 6: 695-704, 1994). In contrast, thrombin, $TXA_2$, and ADP, activate G-protein coupled receptors directly and induce platelet aggregation and granule release (Hourani, S. M, and Cusack, N. J., Pharmacol. Rev. 43: 243-298, 1991). The major events involved in platelet activation are believed to be the result of the activation of β-isoforms of phospholipase C (PLC) leading to the generation of inositol 1,4,5 triphosphate and diacylglycerol. Platelets mainly contain two isoforms, PLC-β2 and PLC-β3.

Platelet receptors which mediate platelet adhesion and aggregation are located on the two major platelet surface glycoprotein complexes. These complexes are the glycoprotein Ib-IX complex which facilitates platelet adhesion by binding von Willebrand factor (vWF), and the glycoprotein IIb-IIIa complex which links platelets into aggregates by binding to fibrinogen. Patients with the Bernard-Soulier syndrome, a congenital bleeding disorder, show deficient platelet adhesion due to a deficiency in the glycoprotein Ib-IX complex which binds vWF, mild thrombocytopenia, and large lymphocoid platelets.

Glycoprotein V (GPV) is a major (≈12,000 molecules/platelet), heavily glycosylated platelet membrane protein (Mr 82,000). Exposure of platelets to thrombin liberates a 69 kDa soluble fragment termed GPVfl. GPV can interact non-covalently with the GPIb-IX complex a complex formed by the non-covalent association of GPIb (consisting of GPIbα, a 145 kDa protein, disulfide linked to GPIbβ, a 24 kDa protein) with GPIX (a 22 kDa protein). The binding sites for von Willebrand factor and for thrombin on the GPIb-IX complex have been localized on GPIbα. Since thrombin is now known to activate platelets by cleaving the thrombin receptor (Vu et. al., Cell 64:1057-1068 (1990)), a G-protein coupled receptor, it is unknown whether thrombin cleaves GPV incidentally as a consequence of thrombin binding to GPIbα, or whether this cleavage has a physiological role. GPIBα, GPIBβ, and GPIX contain one or more homologous 24 amino acid leucine-rich domains. These domains are also found in a large family of leucine-rich glycoproteins (LRG).

GPV is a marker for the megakaryocytic cell lineage. A monoclonal antibody specific for GPV (SW16) does not bind to red cells, leukocytese endothelial cells, or cell lines such as HEL or MEG-01 which are known to express platelet megakaryocyte markers.

Mature GPV is composed of 543 amino acids which contain a single transmembrane domain, a short cytoplasmic domain (16 residues) and a large extracellular domain with 8 potential N-glycosylation sites. Analysis of the extracellular domain revealed the presence of 15 tandem Leu-rich repeats of 24 amino acids with homology to GPIbα, and identified a cleavage site for thrombin near the C-terminus with homology to the Aα chain of fibrinogen.

Culturing Conditions

Sources for generating exogenous antigen-expressing EHCs described herein include circulating cells such as EHCs. A suitable cell source may be isolated from a subject as described herein from patient-derived hematopoietic or erythroid progenitor cells, derived from immortalized EHC lines, or derived from induced pluripotent stem cells, optionally cultured and differentiated. Methods for generating erythrocytes using cell culture techniques are well known in the art, e.g., Giarratana et al., Blood 2011, 118:5071, Huang et al., Mol Ther 2013, epub ahead of print September 3, or Kurita et al., PLOS One 2013, 8:e59890. Protocols vary according to growth factors, starting cell lines, culture period, and morphological traits by which the resulting cells are characterized. Culture systems have also been established for blood production that may substitute for donor transfusions (Fibach et al. 1989 Blood 73:100). Recently, CD34+ cells were differentiated to the reticulocyte stage, followed by successful transfusion into a human subject (Giarratana et al., Blood 2011, 118:5071).

Provided herein are culturing methods for EHCs and exogenous antigen-expressing EHCs derived from EHCs. EHCs can be cultured from hematopoietic progenitor cells, including, for example, CD34+ hematopoietic progenitor cells (Giarratana et al., Blood 2011, 118:5071), induced pluripotent stem cells (Kurita et al., PLOS One 2013, 8:e59890), and embryonic stem cells (Hirose et al. 2013 Stem Cell Reports 1:499). Cocktails of growth and differentiation factors that are suitable to expand and differentiate progenitor cells are known in the art. Examples of suitable expansion and differentiation factors include, but are not limited to, stem cell factor (SCF), an interleukin (IL) such as IL-1, IL-2, IL-3, IL-4, IL-5, IL-6, IL-7, IL-8, IL-9, IL-11, IL-12, CSF, G-CSF, thrombopoietin (TPO), GM-CSF, erythropoietin (EPO), Flt3, Flt2, PIXY 321, and leukemia inhibitory factor (LIF).

EHCs can be cultured from hematopoietic progenitors, such as CD34+ cells, by contacting the progenitor cells with defined factors in a multi-step culture process. For example, EHCs can be cultured from hematopoietic progenitors in a three-step process.

The first step may comprise contacting the cells in culture with stem cell factor (SCF) at 1-1000 ng/mL, erythropoietin (EPO) at 1-100 U/mL, and interleukin-3 (IL-3) at 0.1-100 ng/mL. The first step optionally comprises contacting the cells in culture with a ligand that binds and activates a nuclear hormone receptor, such as e.g., the glucocorticoid receptor, the estrogen receptor, the progesterone receptor, the androgen receptor, or the pregnane x receptor. The ligands for these receptors include, for example, a corticosteroid, such as, e.g., dexamethasone at 10 nM-100 µM or hydrocortisone at 10 nM-100 µM; an estrogen, such as, e.g., beta-estradiol at 10 nM-100 µM; a progestogen, such as, e.g., progesterone at 10 nM-100 µM, hydroxyprogesterone at 10 nM-100 µM, 5a-dihydroprogesterone at 10 nM-100 µM, 11-deoxycorticosterone at 10 nM-100 µM, or a synthetic progestin, such as, e.g., chlormadinone acetate at 10 nM-100 µM; an androgen, such as, e.g., testosterone at 10 nM-100 µM, dihydrotestosterone at 10 nM-100 µM or androstenedione at 10 nM-100 µM; or a pregnane x receptor ligand, such as, e.g., rifampicin at 10 nM-100 µM, hyperforin at 10 nM-100 µM, St. John's Wort (hypericin) at 10 nM-100 µM, or vitamin E-like molecules, such as, e.g., tocopherol at 10 nM-100 µM. The first step may also optionally comprise contacting the cells in culture with an insulin-like molecule, such as, e.g., insulin at 1-50 µg/mL, insulin-like growth factor 1 (IGF-1) at 1-50 µg/mL, insulin-like growth factor 2 (IGF-2) at 1-50 µg/mL, or mechano-growth factor at 1-50 µg/mL. The first step further may optionally comprise contacting the cells in culture with transferrin at 0.1-5 mg/mL.

The first step may optionally comprise contacting the cells in culture with one or more interleukins (IL) or growth factors such as, e.g., IL-1, IL-2, IL-4, IL-5, IL-6, IL-7, IL-8, IL-9, IL-11, IL-12, granulocyte colony-stimulating factor (G-CSF), macrophage colony-stimulating factor (M-CSF), granulocyte-macrophage colony-stimulating factor (GM-CSF), thrombopoietin, fibroblast growth factor (FGF), platelet-derived growth factor (PDGF), transforming growth factor beta (TGF-B), tumor necrosis factor alpha (TNF-A), megakaryocyte growth and development factor (MGDF), leukemia inhibitory factor (LIF), and Flt3 ligand. Each interleukin or growth factor may typically be supplied at a concentration of 0.1-100 ng/mL. The first step may also optionally comprise contacting the cells in culture with serum proteins or non-protein molecules such as, e.g., fetal bovine serum (1-20%), human plasma (1-20%), plasmanate (1-20%), human serum (1-20%), albumin (0.1-100 mg/mL), or heparin (0.1-10 U/mL).

The second step may comprise contacting the cells in culture with stem cell factor (SCF) at 1-1000 ng/mL and erythropoietin (EPO) at 1-100 U/mL. The second step may also optionally comprise contacting the cells in culture with an insulin-like molecule, such as e.g., insulin at 1-50 µg/mL, insulin-like growth factor 1 (IGF-1) at 1-50 µg/mL, insulin-like growth factor 2 (IGF-2) at 1-50 µg/mL, or mechano-growth factor at 1-50 µg/mL. The second step may further optionally comprise contacting the cells in culture with transferrin at 0.1-5 mg/mL. The second may also optionally comprise contacting the cells in culture with serum proteins or non-protein molecules such as, e.g., fetal bovine serum (1-20%), human plasma (1-20%), plasmanate (1-20%), human serum (1-20%), albumin (0.1-100 mg/mL), or heparin (0.1-10 U/mL).

The third step may comprise contacting the cells in culture with erythropoietin (EPO) at 1-100 U/mL. The third step may optionally comprise contacting the cells in culture with stem cell factor (SCF) at 1-1000 ng/mL. The third step may further optionally comprise contacting the cells in culture with an insulin-like molecule, such as e.g., insulin at 1-50 µg/mL, insulin-like growth factor 1 (IGF-1) at 1-50 µg/mL, insulin-like growth factor 2 (IGF-2) at 1-50 µg/mL, or mechano-growth factor at 1-50 µg/mL. The third step may also optionally comprise contacting the cells in culture with transferrin at 0.1-5 mg/mL. The third step may also optionally comprise contacting the cells in culture with serum proteins or non-protein molecules such as, e.g., fetal bovine serum (1-20%), human plasma (1-20%), plasmanate (1-20%), human serum (1-20%), albumin (0.1-100 mg/mL), or heparin (0.1-10 U/mL).

The culture process may optionally comprise contacting cells by a method known in the art with a molecule, e.g., a DNA molecule, an RNA molecule, a mRNA, an siRNA, a microRNA, a lncRNA, a shRNA, a hormone, or a small molecule, that activates or knocks down one or more genes. Target genes can include, for example, genes that encode a transcription factor, a growth factor, or a growth factor receptor, including but not limited to, e.g., GATA1, GATA2, CMyc, hTERT, p53, EPO, SCF, insulin, EPO-R, SCF-R, transferrin-R, insulin-R.

In one embodiment, CD34+ cells are placed in a culture containing varying amounts of IMDM, FBS, glutamine, BSA, holotransferrin, insulin, dexamethasone, β-estradiol, IL-3, SCF, and erythropoietin, in three separate differentiation stages for a total of 22 days.

In one embodiment, CD34+ cells are placed in a culture containing varying amounts of IMDM, FBS, glutamine, BSA, holotransferrin, insulin, dexamethasone, β-estradiol, IL-3, SCF, and thrombopoietin, in three separate differentiation stages for a total of 14 days.

In one embodiment, CD34+ cells are placed in a culture containing varying amounts of IMDM, FBS, glutamine, BSA, holotransferrin, insulin, dexamethasone, β-estradiol, IL-3, SCF, and GCSF, in three separate differentiation stages for a total of 15 days.

In certain embodiments, cells that comprise an exogenous antigen of interest may be comprised of or derived from a plurality of circulating cells including, but not limited to, those listed in Table A. In a preferred embodiment, the circulating cells of the invention are EHCs, such as, e.g. nucleated red blood cells, red blood cell precursors or enucleated red blood cells. For example, the EHCs are a cord blood stem cell, a CD34+ cell, a hematopoietic stem cell (HSC), a spleen colony forming (CFU-S) cell, a common myeloid progenitor (CMP) cell, a blastocyte colony-forming cell, a burst forming unit-erythroid (BFU-E), a megakaryocyte-erythroid progenitor (MEP) cell, an erythroid colony-forming unit (CFU-E), a reticulocyte, an erythrocyte, an induced pluripotent stem cell (iPSC), a mesenchymal stem cell (MSC), a polychtomratic normoblast, an orthochtomratic normoblast, or those listed in Table A1, or a combination thereof. In some embodiments, the EHCs are immortal or immortalized cells, for example immortalized erythroblast cells generated by retroviral transduction of CD34+ hematopoietic progenitor cells to express Oct4, Sox2, Klf4, cMyc, and suppress TP53 (e.g. Huang et al., Mol Ther 2013, epub ahead of print September 3).

Erythrocyte compositions are herein provided, wherein a plurality of erythrocytes express an exogenous antigen of interest or a fragment thereof. The cells may be cultured from patient-derived hematopoietic or erythroid progenitor cells, derived from immortalized EHC lines, or derived from induced pluripotent stem cells. Methods for generating erythrocytes in cell culture are known in the art, e.g. Giarratana et al., Blood 2011, 118:5071, Huang et al., Mol Ther 2013, or Kurita et al., PLOS One 2013, 8:e59890. Exogenous antigens can be introduced by transfection of single or multiple copies of genes, transduction with a virus, or electroporation in the presence of DNA or RNA. Methods for expression of exogenous proteins in mammalian cells are well known in the art. For example, expression of exogenous factor IX in hematopoietic cells is induced by viral transduction of CD34+ progenitor cells, see Chang et al., Nat Biotechnol 2006, 24:1017.

The erythrocyte compositions described herein may be generated in the following way. First, erythroid precursor cells are isolated. These cells may alternatively be autologous to the patient or from substantially universal donor blood. For example, the cells may be ABO type O, rhesus factor Rh r/r, Duffy –/–, and large Kell antigen K1 negative. In the course of differentiation from erythroid precursor cell to EHC, the nucleic acids encoding the exogenous antigen are introduced. The nucleic acid encoding the exogenous antigen can be under the control of an erythroid-specific promoter, such as a GATA-1 promoter (see e.g. Repik et al., Clin Exp Immunol 2005, 140:230). The nucleic acid encoding the exogenous antigen, can be introduced in any way known in the art, for example, as plasmid DNA, virus, or mRNA. Nucleic acid introduction can be achieved by a variety of standard methods, e.g. transfection, transduction, or electroporation.

Modification of Progenitor Cells. Nucleic acids such as DNA expression vectors or mRNA for producing the antigen of interest may be introduced into progenitor cells, which can be isolated from an original source or obtained from expanded above via routine recombinant technology as provided herein. In some instances, the expression vectors can be designed such that they can incorporate into the genome of cells by homologous or non-homologous recombination by methods known in the art.

In some instances, a nucleic acid encoding a polypeptide that can selectively target and cut the genome, for example a CRISPR/Cas9, transcriptional activator-like effector nuclease (TALEN), or zinc finger nuclease, is used to direct the insertion of the nucleic acid payload of the expression vector to a particular genomic location, for example the CR1 locus (1q32.2), the hemoglobin locus (11p15.4), or another erythroid-associated protein including, but not limited to, those listed in Table C.

In some instances, the nucleic acid is an RNA molecule, or a DNA molecule that encodes for an RNA molecule, that silences or represses the expression of a target gene. For example, the molecule can be a small interfering RNA (siRNA), an antisense RNA molecule, or a short hairpin RNA (shRNA) molecule.

Methods for transferring expression vectors into progenitor cells include, but are not limited to, viral mediated gene transfer, liposome mediated transfer, transformation, gene guns, transfection and transduction, e.g., viral mediated gene transfer such as the use of vectors based on DNA viruses such as adenovirus, adenoassociated virus and herpes virus, as well as retroviral based vectors. Examples of modes of gene transfer include e.g., naked DNA, CaPO4 precipitation, DEAE dextran, electroporation, protoplast fusion, lipofection, and cell microinjection.

Any of the genetically modified progenitor cells described herein can be cultured under suitable conditions allowing for differentiation into mature enucleated red blood cells, e.g., the in vitro culturing process described herein. The resulting enucleated red blood cells display and express proteins associated with mature erythrocytes, e.g. hemoglobin, glycophorin A, which can be validated and quantified by standard methods (e.g., Western blotting or FACS analysis).

Strategies for Exogenous Antigen Expression

Provided herein are antigens that are exhibited by exogenous antigen-expressing EHCs. In some embodiments, an antigen is capable of interacting with a target, e.g., to associate with or bind to a target. An antigen can comprise or may consist essentially of a polypeptide. In some embodiments, the antigen comprises a polypeptide, a carbohydrate, a nucleic acid, a lipid, a small molecule, or a combination thereof. In some embodiments antigens do not interact with a target but act as payloads to be delivered by the exogenous antigen-expressing EHC to a cell, tissue or other site in the body of a subject.

Antigen Polypeptides, Chimeras and Fusions

In some embodiments, antigens comprise polypeptides. Receiver polypeptides may range in size from 6 amino acids to 3000 amino acids and may exceed 6, 10, 15, 20, 25, 30, 35, 40, 50, 60, 70, 80, 90, 100, 150, 200, 300, 400 or may exceed 500 amino acids. Receiver polypeptides may range in size from about 20 amino acids to about 500 amino acids, from about 30 amino acids to about 500 amino acids or from about 40 amino acids to about 500 amino acids.

In some embodiments, the antigen polypeptide comprises a chimeric or fusion protein which may comprise two or more distinct protein domains. These chimeric antigens are heterologous or exogenous in the sense that the various domains are derived from different sources, and as such, are not found together in nature and can be encoded e.g., by recombinant nucleic acids. Antigen polypeptides can be produced by a number of methods, many of which are well known in the art and also described herein. For example, antigen polypeptides can be obtained by extraction (e.g., from isolated cells), by expression of a recombinant nucleic acid encoding the antigen polypeptide, or by chemical synthesis. Antigen polypeptides can be produced by, for example, recombinant technology, and expression vectors encoding the polypeptide introduced into host cells (e.g., by transformation or transfection) for expression of the encoded antigen polypeptide.

There are a variety of conservative changes that can generally be made to an amino acid sequence without altering activity. These changes are termed conservative substitutions or mutations; that is, an amino acid belonging to a grouping of amino acids having a particular size, charge or other characteristic can be substituted for another amino acid. Substitutions for an amino acid sequence may be selected from other members of the class to which the amino acid belongs. For example, the nonpolar (hydrophobic) amino acids include alanine, leucine, isoleucine, valine, proline, phenylalanine, tryptophan, methionine, and tyrosine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Such alterations are not expected to substantially affect apparent molecular weight as determined by polyacrylamide gel electrophoresis or isoelectric point. Conservative substitutions also include substituting optical isomers of the sequences for other optical isomers, specifically D amino acids for L amino acids for one or more residues of a sequence. Moreover, all of the amino acids in a sequence may undergo a D to L isomer substitution. Exemplary conservative substitutions include, but are not limited to, Lys for Arg and vice versa to maintain a positive charge; Glu for Asp and vice versa to maintain a negative charge; Ser for Thr so that a free ~OH is maintained; and Gln for Asn to maintain a free NH2. Moreover, point mutations, deletions, and insertions of the polypeptide sequences or corresponding nucleic acid sequences may in some cases be made without a loss of function of the polypeptide or nucleic acid fragment. Substitutions may include, e.g., 1, 2, 3, or more residues. Any teaching of a specific amino acid sequence or a recombinant nucleic acid encoding the polypeptide or teaching of the name of the name thereof includes any conservative substitution point mutations, deletions, and insertions of those polypeptide sequences or corresponding nucleic acid sequences and any sequence deposited for the protein or gene in a database that can be made without a loss of function of the polypeptide or nucleic acid fragment.

In some embodiments, the antigen polypeptide is associated with the membrane of the exogenous antigen-expressing EHC. In other embodiments, the antigen polypeptide is not associated with the membrane of the exogenous antigen-expressing EHC.

In one embodiment the mass ratio of lipid to antigen in the exogenous antigen-expressing EHC is less than 1:1000, approximately 1:1000, approximately 1:500, approximately 1:250, approximately 1:100, approximately 1:50, approximately 1:25, approximately 1:10, approximately 1:9, approximately 1:8, approximately 1:7, approximately 1:6, approximately 1:5, approximately 1:4, approximately 1:3, approximately 1:2, approximately 1:1, approximately 2:1, approximately 3:1, approximately 4:1, approximately 5:1, approximately 6:1, approximately 7:1, approximately 8:1, approximately 9:1, approximately 10:1, approximately 25:1, approximately 50:1, approximately 100:1, approximately 250:1, approximately 500:1, approximately 1000:1, approximately 10,000:1, approximately 100,000:1, approximately 1,000,000:1, approximately 10,000,000:1, approximately 100,000,000:1, approximately 1,000,000,000:1 or greater than approximately 1,000,000,000:1.

In one embodiment the mass ratio of non-exogenous antigen polypeptide to antigen in the exogenous antigen-expressing EHC is less than 1:1000, approximately 1:1000, approximately 1:500, approximately 1:250, approximately 1:100, approximately 1:50, approximately 1:25, approximately 1:10, approximately 1:9, approximately 1:8, approximately 1:7, approximately 1:6, approximately 1:5, approximately 1:4, approximately 1:3, approximately 1:2, approximately 1:1, approximately 2:1, approximately 3:1, approximately 4:1, approximately 5:1, approximately 6:1, approximately 7:1, approximately 8:1, approximately 9:1, approximately 10:1, approximately 25:1, approximately 50:1, approximately 100:1, approximately 250:1, approximately 500:1, approximately 1000:1, approximately 10,000:1, approximately 100,000:1, approximately 1,000,000:1, approximately 10,000,000:1, approximately 100,000,000:1, approximately 1,000,000,000:1 or greater than approximately 1,000,000,000:1.

In certain embodiments, the polypeptide antigen is located on the surface and is exposed to the environment around the exogenous antigen-expressing EHC. In some embodiments, the polypeptide antigen is located inside and faces the unexposed side of the exogenous antigen-expressing EHC.

In certain embodiments, the polypeptide antigen comprises at least one of the following domains, an S domain (surface), an A domain (anchor), and/or a U domain (unexposed), wherein the S domain is a surface domain exposed to the environment around the exogenous antigen-expressing EHC, wherein the A domain is an anchor, and wherein the U domain is located within and/or faces the unexposed side of the exogenous antigen-expressing EHC.

Optionally the antigen polypeptide comprises i) one or more additional S domains, termed S' domains, or ii) one or more additional U domains, termed U' domains.

In some embodiments, the S domain and the A domain form part of the same polypeptide chain.

In some embodiments, the A domain and the U domain form part of the same polypeptide chain.

In some embodiments, any one or more of the S, A, U domain is added to the exogenous antigen-expressing EHC externally.

In some embodiments, any one or more of the S, A, U domain is produced within the exogenous antigen-expressing EHC.

In some embodiments, any one or more of the S, A, U domain is a polypeptide.

In some embodiments, any one or more of the S, A, U domain is not a polypeptide.

Schematics of exemplary conformations of antigens within or on exogenous antigen-expressing EHCs are shown in FIGS. 13A, 13B, and 13C.

The A Domain

In certain embodiments, the A domain is a membrane polypeptide. The A domain can be, e.g., an integral membrane polypeptide or a membrane associated polypeptide.

The A domain may be selected from one of the following classes, including but not limited to, for example, alpha-helical bitopic, alpha-helical polytopic, beta-barrel transmembrane, all alpha monotopic/peripheral, all beta monotopic/peripheral, alpha/beta monotopic/peripheral, alpha+beta monotopic/peripheral, alpha helical peptides, beta-hairpin peptides, beta-helical peptides, type 1 transmembrane protein (N-terminus extracellular), type 2 transmembrane protein (N-terminus intracellular), type 3 transmembrane protein, type 4A transmembrane protein, type 4B transmembrane protein, lipid-anchored protein, glycosylphosphatidylinositol (GPI) anchored protein, prenyl chain anchored protein, or peptides of nonregular structure.

In certain embodiments, the A domain is endogenous, e.g., endogenous to an EHC, a platelet, or a hematopoietic cell. In some embodiments, the A domain is endogenous to a mammalian cell.

In certain embodiments, the A domain is exogenous, e.g., exogenous to an EHC, a platelet, or a hematopoietic cell. In some embodiments, the A domain is exogenous to a mammalian cell.

The A domain may be selected from the following molecules or fragments thereof, including but not limited to, CD1, CD2, CD3, CD4, CD5, CD6, CD7, CD8, CD9, CD10, CD11a, CD11b, CD11c, CD12w, CD13, CD14, CD15, CD16, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42, CD43, CD44, CD45, CD46, CD47, CD48, CD49a, CD49b, CD49c, CD49d, CD49e, CD49f, CD53, CD54, CD55, CD56, CD57, CD58, CD59, CD61, CD62E, CD62L, CD62P, CD63, CD68, CD69, CD71, CD72, CD73, CD74, CD80, CD81, CD82, CD83, CD86, CD87, CD88, CD89, CD90, CD91, CD95, CD96, CD100, CD103, CD105, CD106, CD107, CD107a, CD107b, CD109, CD117, CD120, CD122, CD123, CD127, CD132, CD133, CD134, CD135, CD138, CD141, CD142, CD143, CD144, CD147, CD151, CD152, CD154, CD155, CD156, CD158, CD163, CD165, CD166, CD168, CD184, CDw186, CD195, CD197, CDw199, CD209, CD202a, CD220, CD221, CD235a, CD271, CD279, CD303, CD304, CD309, CD326, Ras-Related protein 1A, semaporin 7A precursor, Calcium and integrin-binding protein 1, 55 kDa erythrocyte membrane protein, Flotillin-1, Flotillin-2, Erythroid membrane-associated protein, eukaryotic translation initiation factor 2C 2, cytochrome b5 reductase, cell division control protein 42 homolog, KIAA1363 protein, band3, annexin VII, aquaporin, Ecto-ADP-ribosyltransferase 4, Kell, LFA-3, soulute carrier family 2 member 1, LGALS3 protein, Urea transporter, Rh blood CE group antigen poypeptide, Rh-associated glycoprotein, Dematin, ABO blood groups, Aquaporin 3, Aubergers, Band 3, Basigin, C41, CD44, Cis AB, Colton antigen, Complement Component 4, CR1, DAF, Diego, Duffy, Hh/Bombay antigen, ii antigen, Indian blood group, Kell, Kidd, Lewis antigen, Lutheran antigen, MNS antigen system, Cost group, Er group, Dematin, Stomatin, Tropomyosin, Glucose transporter, Adducin, Rabphilin, C1 tetrahydrofolate synthase, Vel group, Lan antigen, At antigen, Jr antigen, AnWj antigen, Sd antigen, Batty, Bilkes, Box, Christiansen, HJK, HOFM, JFV, JONEs, Jensen, Katagiri, Livesay, Milne, Oldeide, Peters, Rasmussen, Reid, REIT, SARA, Rhesus blood D group, Aldolase, Tropomodulin, Arginase, Creatine kinase, B-Cam protein, Rap1A, Bennett-Goodspeed, P antigen system, Rh blood groupXg antigen system, XK protein, Yt/Cartwright antigen system, CD58, Rh, Scianna, Radin, DARC (Duffy), CR1 Knops-McCoy, DAF Cromer, Gerbich (GYPC), CD47, Glycophorin A, Band 3 (AE3), GYPB Ss, C4A, C4B Chido, Rodgers C4 component of complement, HLA Bg HLA class I, RHAG Rh-associated Ammonium transport, Glycoprotein, Colton (Co) Water channel protein, ACHE Cartwright (Yt) Acetylcholinesterase, Glutathione transferase, Glycophorin C, Aquaporin, Erythroblast associated membrane protein, CD44, Synaptobrevin 2, Ribonuclease, Duodenal cytochrome B, ABO glycosyl transferases, CD59, CD44 Indian (In), AnWj Adhesion receptor, MER2, DOK Dombrock ADP-ribosyltransferase, SEMA7A JMH Putative adhesion receptor, UMOD Sda Tamm-Horsfall protein (uromodulin), Diego (Di), Wright (Wr) Anion channel protein (band 3, AE1), Kidd (Jk) Urea transporter, FUT3 Lewis (Le) alpha(1,3) fucosyltransferase, OK Oka Neurothelin, putative adhesion molecule, LW Adhesion receptor, FUT2 Secretor (Se) alpha(1,2) fucosyltransferase, FUT1 Hh alpha(1,2) fucosyltransferase, LU Lutheran (Lu) Adhesion receptor, P1 Glycosyltransferase, XK Kx Putative neurotransmitter transporter, XG Xg formerly called PBDX, MIC2, Hemoglobin, Ankyrin, Spectrin, KEL Kell (forms K,k,Kp,Js) Metalloproteinase, Torkildsen antigen, coenzyme Q10, Rab 35, Ral A binding protein, Zona pellucida binding protein, Lyn B protein, KIaa1741 protein, DC38, Calcium transporting ATPase, GPIX, GPIba, GPIbb, GPV, GPIb-IX-V, GPVI, GPIa/IIa, GPIIb/IIIa, GPV/IIa.

The S Domain

In some embodiments, the S domain is a protein or a polypeptide. In other embodiments, the S domain is a nucleic acid. In some embodiments, the S domain is a chemical. In certain embodiment the S domain is a small molecule.

In some embodiments, the S domain is a polypeptide selected from or derived from one or more of the following classes, including but not limited to, a flexible linker, an epitope tag, an enzyme, a protease, a nuclease, an antigen, an antibody-like molecule, a ligand of an antibody, a growth factor, a cytokine, a chemokine, a growth factor receptor, a cytokine receptor, a chemokine receptor, an enzymatic recognition sequence, a transpeptidase recognition sequence, a protease recognition sequence, a cleavable domain, an intein, a DNA binding protein, and RNA binding protein, a complement regulatory molecule, a complement cascade molecule, a clotting cascade molecule, a chelator, a complement regulatory domain, an SCR domain, a CCP domain, an immunoglobulin or immunogloblulin-like domain, an armadillo repeat, a leucine zipper, a dealth effector domain, a cadherein repeat, an EF hand, a phosphotyrosine binding domain, a pleckstrin homology domain, an SCR homology 2 domain, a zinc finger domain, a cyclic peptide, a cell-penetrating peptide.

In some embodiments, the S domain is a non-polypeptide molecule, for example a nucleic acid, a carbohydrate, or a small molecule. In some embodiments, the S domain is a nucleic acid selected from one or more of the following classes, including but not limited to, a DNA aptamer, an RNA aptamer, an siRNA, a shRNA, a single-strand RNA probe, a single strand DNA probe, an mRNA, a chemically modified oligonucleotide. In some embodiments, the S domain is a small molecule selected from one or more of the following classes, including but not limited to, a chelator, DOTA, a radionuclide, an isotope, an imaging agent, a fluorescent molecule, a chemiluminescent molecule, a gas.

The U Domain

In some embodiments, the U domain is a protein or a polypeptide. In other embodiments, the U domain is a nucleic acid. In some embodiments, the U domain is a chemical. In certain embodiment the U domain is a small molecule.

In some embodiments, the U domain is a polypeptide selected from or derived from one or more of the following classes, including but not limited to, a flexible linker, an epitope tag, an enzyme, a protease, a nuclease, an antigen, an antibody-like molecule, a ligand of an antibody, a growth factor, a cytokine, a chemokine, a growth factor receptor, a cytokine receptor, a chemokine receptor, an enzymatic recognition sequence, a transpeptidase recognition sequence, a protease recognition sequence, a cleavable domain, an intein, a DNA binding protein, and RNA binding protein, a complement regulatory molecule, a complement cascade molecule, a clotting cascade molecule, a chelator, a complement regulatory domain, an SCR domain, a CCP domain, an immunoglobulin or immunogloblulin-like domain, an armadillo repeat, a leucine zipper, a dealth effector domain, a cadherein repeat, an EF hand, a phosphotyrosine binding domain, a pleckstrin homology domain, an SCR homology 2 domain, a zinc finger domain, a cyclic peptide, a cell-penetrating peptide, a kinase domain, aphosphatase domain, a cytoskeletal protein, a protein that interacts with the cytoskeletal protein, a G-protein coupled receptor, a tyrosine kinase, an ITIM domain, an ITAM domain.

In some embodiments, the U domain is a non-polypeptide molecule, for example a nucleic acid, a carbohydrate, or a small molecule. In some embodiments, the U domain is a nucleic acid selected from one or more of the following classes, including but not limited to, a DNA aptamer, an RNA aptamer, an siRNA, a shRNA, a single-strand RNA probe, a single strand DNA probe, an mRNA, a chemically modified oligonucleotide. In some embodiments, the U domain is a small molecule selected from one or more of the following classes, including but not limited to, a chelator, DOTA, a radionuclide, an isotope, an imaging agent, a fluorescent molecule, a chemiluminescent molecule, a gas.

Examples of Antigen Polypeptides

Examples of antigen polypeptides include: the polypeptide antigen comprises glycophorin A with HA epitope tag at the N terminus; the polypeptide antigen comprises the leader sequence of glycophorin A, HA epitope tag, and the body sequence of glycophorin A; the polypeptide antigen comprises complement receptor 1 (CR1); the polypeptide antigen comprises the leader sequence of CR1, HA epitope tag, the body sequence of CR1; the polypeptide antigen comprises the leader sequence of CR1, HA epitope tag, six SCR domains of LHR-A and LHR-B of CR1, the membrane proximal two SCR domains of CR1, the transmembrane region of CR1, and the intracellular region of CR1; the polypeptide antigen comprises the leader sequence of CR1, HA epitope tag, nine SCR domains of LHR-A and LHR-B and LHR-C of CR1, the membrane proximal two SCR domains of CR1, the transmembrane region of CR1, and the intracellular region of CR1; the polypeptide antigen comprises the leader sequence of CR1, LHR-A of CR1, LHR-B of CR1, LHR-C of CR1, the membrane proximal two SCR domains of CR1, the transmembrane region of CR1, and the intracellular region of CR1; the polypeptide antigen comprises leader sequence of CR1, LHR-A of CR1, LHR-B of CR1, LHR-C of CR1, the membrane proximal two SCR domains of CR1, the transmembrane region and intracellular region of glycophorin A; the polypeptide antigen comprises the leader sequence of glycophorin A, an antibody scFv against hepatitis B surface antigen (scFv), a (Gly3Ser)2 flexible linker (Seq. ID No. 23), HA epitope tag, and the body of glycophorin A; the polypeptide antigen comprises Kell, a (Gly3Ser)2 flexible linker (Seq. ID No. 23), HA epitope tag, and scFv; the polypeptide antigen comprises Kell and HA epitope tag; the polypeptide antigen comprises a 71-amino acid N-terminal fragment of Kell and an HA epitope tag; the polypeptide antigen comprises a 71-amino acid N-terminal fragment of Kell, a (Gly3Ser)2 flexible linker (Seq. ID No. 23), and an HA epitope tag; the polypeptide antigen comprises a 79-amino acid N-terminal fragment of Kell and an HA epitope tag; the polypeptide antigen comprises a 79-amino acid N-terminal fragment of Kell, a (Gly3Ser)2 flexible linker (Seq. ID No. 23), and an HA epitope tag; the polypeptide antigen comprises a 71-amino acid N-terminal fragment of Kell, a (Gly3Ser)2 flexible linker (Seq. ID No. 23), scFv, and an HA epitope tag; the polypeptide antigen comprises a 79-amino acid N-terminal fragment of Kell, a (Gly3Ser)2 flexible linker (Seq. ID No. 23), scFv, and an HA epitope tag; the polypeptide antigen comprises the leader sequence of CD55, scFv, an HA epitope tag, and the terminal 37 amino acids of CD55; the polypeptide antigen comprises the leader sequence of CD55, an HA epitope tag, and the body of CD55. In one embodiment, the polypeptide antigen comprises the leader sequence of CD59, scFv, an HA epitope tag, and the body of CD59; the polypeptide antigen comprises the leader sequence of CD59, and HA epitope tag, and the body of CD59; the polypeptide antigen comprises adenosine deaminase and an HA epitope tag; the polypeptide antigen comprises phenylalanine hydroxylase and an HA epitope tag; the polypeptide antigen comprises adenosine deaminase, a (Gly3Ser)2 flexible linker (Seq. ID No. 23), phenylalanine hydroxylase, and an HA epitope tag; the polypeptide antigen comprises glycophorin A, adenosine deaminase at the cytoplasmic C terminus, and an HA epitope tag; the polypeptide antigen comprises glycophorin A, phenylalanine hydroxylase at the cytoplasmic C terminus, and an HA epitope tag.

In certain embodiments, the antigen is capable or interacting with a macrophage. The antigen polypeptide may comprise one or more of: the complement receptor (Rieu et al., J. Cell Biol. 127:2081-2091 (1994)), the scavenger receptor (Brasseur et al., Photochem. Photobiol. 69:345-352 (1999)), the transferrin receptor (Dreier et al., Bioconjug. Chem. 9:482-489 (1998); Hamblin et al., J. Photochem. Photobiol. 26:4556 (1994)); the Fc receptor (Rojanasakul et al., Pharm. Res. 11:1731-1733 (1994)); and the mannose receptor (Frankel et al., Carbohydr. Res. 300:251-258 (1997); Chakrabarty et al., J. Protozool. 37:358-364 (1990)).

Other antigens capable or interacting with a macrophages include: low density lipoproteins (Mankertz et al., Biochem. Biophys. Res. Commun. 240:112-115 (1997); von Baeyer et al., Int. J. Clin. Pharmacol. Ther. Toxicol. 31:382-386 (1993)), very low density lipoproteins (Tabas et al., J. Cell Biol. 115:1547-1560 (1991)), mannose residues and other carbohydrate moieties (Pittet et al., Nucl. Med. Biol. 22:355-365 (1995)), poly-cationic molecules, such as poly-L-lysine (Hamblin et al., J. Photochem. Photobiol. 26:45-56 (1994)), liposomes (Bakker-Woudenberg et al., J. Drug Target. 2:363-371 (1994); Betageri et al., J. Pharm. Pharmacol. 45:48-53 (1993)) and 2-macroglobulin (Chu et al., J. Immunol. 152:1538-1545 (1994)).

Provided herein are compositions containing EHCs comprising an antigen having functional activities that are either i) not present in native EHCs of the same lineage, or ii) present in native EHCs of the same lineage in reduced levels or reduced activity levels as compared to the EHCs comprising the antigen. Such functional activities include complement inhibition, immune complex clearance, artificial antigen presentation, modulation of the coagulation cascade, oxygen transfer, drug delivery, cytotoxin adsorption, avoidance of phagocytosis, and extension of circulation time.

In some embodiments, EHCs have higher levels of a complement receptor polypeptide, such as CR1, than native EHCs of the same lineage by virtue of comprising a CR-1 antigen. In an alternative embodiment, the EHCs comprising an antigen have higher levels of a complement receptor agonist polypeptide or complement associated polypeptide than native EHCs of the same lineage, including but not limited to, the polypeptides listed in table 6 and table 8. The complement receptor antigen polypeptide comprises a human Complement Receptor-1 (CR1) polypeptide, variant, or functional fragment thereof. The CR1 antigen polypeptide may be derived from one or more than one of the native alleles of CR1, e.g., the A allele (also termed the F allele or CR1*1 allele), the B allele (also termed the S allele or CR1*2 allele), the C allele (also termed the F' allele or CR1*3 allele), or the D allele (also termed the CR1*4 allele). The sequences and database accession numbers for these native forms are provided in table 3. In some embodiments, the CR1 antigen polypeptide contains a domain of a CR1 polypeptide. For example, the CR1 polypeptide may comprise one or more short consensus repeat (SCR) domains, also termed complement control protein (CCP) modules or Sushi domains, e.g., Genbank accession number AAV65577.1. In one embodiment, the CR1 antigen polypeptide comprises one or more Short Consensus Repeats (SCRs), e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or greater than 44 SCRs. In another embodiment, the CR1 antigen polypeptide comprises one or more long homologous repeat (LHR) units of CR1, e.g., LHR-A, LHR-B, LHR-C, or LHR-D, e.g., 1, 2, 3, 4, 5, 6 or greater than 6 LHR domains. In another embodiment, the CR1 antigen polypeptide may comprise one or more than one extracellular domains of CR1 fused to another cell membrane protein, e.g., glycophorin A, glycophorin B, glycophorin C, glycophorin D, kell, band 3, aquaporin 1, glut 1, kidd antigen protein, rhesus antigen, including, but not limited to the cell surface moieties listed in table 1 and table 6.

In some embodiments, an EHC contains a recombinant nucleic acid encoding a complement receptor antigen polypeptide, or alternatively or in combination, a complement receptor agonist antigen polypeptide or complement associated antigen polypeptide including but not limited to, the polypeptides, and agonists to the polypeptides, listed in table 8. In some embodiments, the EHCs further contain an exogenous decay-accelerating factor (CD59, GenBank: CAG46523.1) polypeptide, or an exogenous membrane cofactor (CD46, GenBank: BAA12224.1) polypeptide, or a variant or functional fragment thereof, or a combination thereof.

CR1 activities include binding to C3b-containing immune complexes and shuttling of these immune complexes from circulation to liver and spleen macrophages of the reticuloendothelial system. Upon encounter with cells of the reticuloendothelial system, the immune complex is endocytosed by the phyagocytic cell but the red blood cell is spared to continue its circulation. The removal of the immune complex sometimes results in proteolytic cleavage of CR1 from the surface of the red blood cell. To measure binding activity, one can perform an in vitro binding assay between EHCs and immune complexes. To measure sparing of the EHC, one can perform an in vitro phagocytosis assay with phagocytic cells and immune complex-loaded EHCs. To measure in vivo clearance of circulating immune complexes to the liver, one can perform a clearance and biodistribution assay using radiolabeled immune complexes.

Provided are compositions containing EHCs containing an antigen comprising a native polypeptide at a level greater than that of a hematopoietic cell of the same lineage not comprising the antigen polypeptide. For example, populations of EHCs contain antigens, such as complement receptor 1 levels at least about 1.1, e.g., 1.2, 1.3, 1.4, 1.5, 1.6, 1.7, 1.8, 1.9, 2, 3, 4, 5, 6, 7, 8, 9, 10, 15, 20, 25, 30, 35, 40, 45, 50, 60, 70, 80, 90, 100, 150, 200, 250, 300, 350, 400, 450, 500, 600, 700, 800, 900, 1000, 2000, 3000, 4000, 5000, 6000, 7000, 8000, 9000, 10000, or more than 10000 times greater than corresponding hematopoietic cells of the same lineage that lack the CR1 antigen polypeptide. CR1 levels on reticulocytes and erythrocytes are typically between 50-2000 molecules per cell (Lach-Trifilieff, J Immunol 1999, 162:7549). Provided are compositions that contain populations of EHCs with CR1 levels of at least about 2500, 5000, 6000, 7000, 8000, 9000, 10000, 15000, 20000, 25000, 30000, 40000, 50000, 100000, 200000, 300000, 400000, 500000, 600000, 700000, 800000, 900000, 1000000, or more than 1000000 molecules per cell. CR1 levels in wild-type and exogenous antigen-expressing EHCs can be measured and quantified by, for example, flow cytometry with antibodies specific for CR1.

Provided herein, in some embodiments, are EHCs comprising an antigen, populations of EHCs comprising an antigen, and compositions of EHCs comprising an antigen. In some embodiments, the antigen interacts with a circulating pathogen, such as a virus or a bacterium. In some embodiments, the EHC expresses a recombinant gene encoding an antibody, scFv, or nanobody specific for the circulating pathogen. The antibody, scFv, or nanobody may be expressed as a fusion protein. In other embodiments, the antibody, scFv, or nanobody antigen or another antigen with affinity to circulating pathogens is loaded into or onto the EHC. The antibody, scFv, or nanobody antigen or the other antigen with affinity to circulating pathogens may be localized intracellularly or extracellularly. In some embodiments, the antigen is specific for a viral or bacterial antigen, such as a surface, envelope or capsid antigen.

Provided herein, in certain embodiments, are EHCs comprising an antigen, populations of EHCs comprising an antigen, and compositions of EHCs comprising an antigen. In some embodiments, the antigen interacts with a toxin, preferably a foreign toxin, such as derived from a pathogen or otherwise from the environment. In some embodiments, the EHC expresses a recombinant gene encoding an antigen comprising an amino acid sequence derived from lipopolysaccharide-binding protein (LBP), bactericidal/permeability-increasing protein (BPI), amyloid P component, or a cationic protein. Toxin-binding antigens may be expressed as a fusion protein. In other embodiments, toxin-binding antigens may be loaded into or onto the EHC. Toxin-binding antigens may be localized intracellularly or extracellularly. In some embodiments, the toxin binding antigen is specific for a bacterial toxin such as botulinum or anthrax.

Further, exogenous antigen-expressing EHCs may express an antigen capable of enhancing its ability to sequester a target. Potential sequestration enhancement antigens include the polypeptide transporters including, but not limited to, those in table 1.

In one embodiment, the antigen comprises a polypeptide that comprises an amino acid sequence derived from Duffy Antigen Receptor for Chemokines (DARC). In one embodiment, the EHC expresses a recombinant gene encoding an amino acid sequence derived from Duffy Antigen Receptor for Chemokines (DARC). The DARC antigen may be expressed as a full-length protein or a fragment thereof. DARC may be expressed as a fusion protein. In other embodiments, DARC protein is loaded into or onto the EHC. In some embodiments, the loaded DARC is additionally functionalized or otherwise modified. The DARC antigen molecule may be localized intracellularly or extracellularly.

DARC was identified as a potent multi-ligand chemokine receptor. DARC belongs to the family of rhodopsin-like seven-helix transmembrane proteins. Besides erythrocytes DARC is expressed in post capillary venular endothelial cells, which are the primary site of leukocyte transmigration in most tissues. DARC provides a highly specific binding site for both CC and CXC chemokines. DARC is thought to possess a higher affinity for ELR motif CXC chemokines. CXC chemokines are neutrophil chemoattractants and may potentially be pro-angiogenic.

Interaction between DARC and CXCL8 has demonstrated a dissociation constant ($K_d$) of 5 nmol/L and receptor binding sites estimated at 1000-9000 per erythrocyte (Hadley, Blood, 1997) Unlike other seven-transmembrane chemokine receptors, DARC lacks the highly conserved G protein coupling motif located in the second cytoplasmic loop (Meny, Immunohematology, 2010). DARC is not G-protein coupled and has no known alternative signaling mechanism. The biological role of DARC is not fully understood. DARC is thought to be a) multi-specific; b) unable to initiate intracellular signals, and c) chemokines bound to erythrocyte surface are believed to be inaccessible to their normal target inflammatory cells (Neote, J Biol Chem, 1993). Erythrocytes may play a role in the regulation of inflammatory processes through the presence of DARC Inflammatory signaling molecules, such as cytokines, can trigger local and systemic tissue damage when present in high concentrations. Bursts of cytokines are implicated in the pathogenesis of bacterial sepsis, rheumatoid arthritis, and several other inflammatory diseases. Modified EHCs that exogenously express natural cytokine receptors or synthetic antibody-like receptor mimics can sequester the inflammatory cytokines. An exemplary chemokine receptor is DARC. Provided herein are EHCs comprising an antigen that is a cytokine receptor or chemokine receptor, including, but not limited to DARC. For example, EHCs expressing DARC antigen (thereby increasing the amount present on native erythrocytes) may be used to modulate chemokine levels in circulation and/or within the body's peripheral tissues. The EHCs comprising a DARC antigen can either be marked for destruction or can slowly release the inflammatory mediators back into circulation, but at a low and diffuse concentration. The EHC comprising an antigen that comprises a chemokine or cytokine receptor may act as a reservoir for signal transduction peptides.

In one embodiment, the antigen comprises a polypeptide that comprises an amino acid sequence derived from an antibody. In one embodiment, the EHC expresses a recombinant gene encoding an amino acid sequence derived from an antibody. The antibody antigen may be expressed as a full-length protein or a fragment thereof. The antibody may be expressed as a fusion protein. In other embodiments, the antibody protein is loaded into or onto the EHC. In some embodiments, the loaded antibody is additionally functionalized or otherwise modified. The antibody antigen may be localized intracellularly or extracellularly. In one embodiment, the antigen comprises an antibody amino acid sequence that is specific for a desired target. In some embodiments, the antibody is a scFv. In other embodiments, the antibody is a nanobody.

In certain embodiments, the EHCs comprise an antigen that comprises an antibody or fragment thereof that is specific for a target and is located on the cell surface. For example, a variable fragment (Fv) of an antibody specific for botulinum toxin binding is expressed on the surface of the EHC. Botulinum toxin binding antibodies are known in the art (Amersdorfer, Inf and Immunity, 1997), as is the expression of the Fv portion of an antibody (Hoedemaeker, Journ of Bio Chemistry, 1997). Upon binding, the toxin is retained by the EHC through the Fv region, sequestered and shuttled via the circulatory system to the liver for clearance from the body.

In one embodiment, the antigen comprises a polypeptide that comprises an amino acid sequence derived from a scFv antibody. In one embodiment, the EHC expresses a recombinant gene encoding an amino acid sequence derived from a scFv antibody. The scFv antibody antigen may be expressed as a full-length protein or a fragment thereof. The scFv antibody may be expressed as a fusion protein. In other embodiments, the scFv protein is loaded into or onto the EHC. Suitable scFv antigen polypeptides that may be expressed by EHCs include, but are not limited to, those listed in table 6.

scFv antibodies have been constructed mainly from hybridoma, spleen cells from immunized mice, and B lymphocytes from human. The variable region of an antibody is formed by the noncovalent heterodimer of the variable domains of the V(H) and V(L) domains, which can then be used in the construction of a recombinant scFv antibody.

The production of scFvs is known in the art and require mRNA to first be isolated from hybridoma (or also from the spleen, lymph cells, and bone marrow) followed by reverse transcription into cDNA to serve as a template for antibody gene amplification (PCR). With this method, large libraries with a diverse set of antibody-derived scFvs (a set comparable to that of the original antibodies from which the scFvs are modeled) can be created.

The scFv antigen may be made specific to any target molecule including, but not limited to, those in table 4.

In one example, a scFv antigen specific for anthrax toxin may be expressed on a EHC. Upon administration to a subject in need thereof an effective dose of a population of EHC comprising an antigen molecule specific for anthrax toxin can be used to capture and sequester the anthrax toxin. The EHC migrates to the liver where clearance occurs.

In certain embodiments, erythrocytes comprise an antigen comprising a camelid-derived nanobody expressed on the surface of the cell. Nanobodies are usually 12-15 kDa. They are considerably smaller than antibodies and scFv. Nanobodies may thus be easier to transfect, and the nanobody antigen will be more easily expressed, translated and or transported to the cell surface in an EHC. In certain embodiments, nanobody antigens are employed to minimize immunogenic effects caused by a specific antigen. Nanobodies because of their small size will offer reduced immunogenic potential. In certain embodiments, antigen nanobodies are employed because they limit changes in the mechanical and morphological behavior of the plasma membrane of the EHC. This may allow the EHC to exhibit normal circulatory red blood cell behavior. In certain embodiments, antigen nanobodies are employed because they have an increased ability to recognize hidden or uncommon epitopes compared to standard antibodies. For example, they can bind to small enzymatic cavities of a target and modulate the molecular behavior of the target.

In certain embodiments, EHCs comprise antigen nanobodies with specificity to target epitopes of molecules in the human complement system. Such EHCs may be administered to a subject in need thereof to selectively deplete one or more over-active factors of the complement system. For example, C5 may be targeted by EHCs comprising antigen nanobodies with specificity to target epitopes of C5 and cleared from the system by the EHCs upon administration of the cells into a subject. This approach is suitable to provide a therapeutic effect, e.g., for a complement disorder, such as paroxysmal nocturnal hemoglobinuria. In certain embodiments, EHCs comprise antigen nanobodies with specificity to target epitopes of molecules including, but not limited to, those listed in table 4.

In some embodiments, the antigen comprises a polypeptide that comprises an amino acid sequence derived from one of proteases, nucleases, amylase, lyase (sucrase) or hydrolase (DNase, lipase). In one embodiment, the EHC expresses a recombinant gene encoding an amino acid sequence derived from one of proteases, nucleases, amylase, lyase (sucrase) or hydrolase (DNase, lipase). Antigen proteases, nucleases, amylases, lyases and hydrolases may be expressed as a full-length protein or a fragment thereof. Antigen proteases, nucleases, amylases, lyases and hydrolases may be expressed as a fusion protein. In other embodiments, antigen proteases, nucleases, amylases, lyases or hydrolases are loaded into or onto the EHC. In some embodiments, the loaded antigen proteases, nucleases, amylases, lyases or hydrolases are additionally functionalized or otherwise modified. The antigen protease, nuclease, amylase, lyase or hydrolase antigen molecule may be localized intracellularly or extracellularly.

In certain embodiments, EHCs comprise an antigen comprising a protease, a nuclease, an amylase, a lyase or a hydrolase. The EHC comprising a protease, a nuclease, an amylase, a lyase or a hydrolase antigen is capable of degrading a target on the EHC independent of circulatory clearance, e.g., by macrophages in the liver. In certain embodiments, EHCs comprising an antigen comprising a protease, a nuclease, an amylase, a lyase or a hydrolase may be administered to a subject in need thereof to treat a cancer by selectively degrading metabolites that are essential for cancer cell growth. For example, asparaginase is used to decrease local asparagine levels to treat acute lymphoblastic leukemia and acute myeloid leukemia. Suitable antigens may, e.g., comprise one or both of the two major classes of enzymes capable of degrading target molecules, lyases and hydrolases. In certain embodiments, EHCs are provided comprising an antigen comprising a molecule including but not limited to those listed in table 6.

In certain embodiments, erythrocytes comprise an antigen comprising a lyase. In one embodiment, the lyase is valine decarboxylase. Valine decarboxylase antigen may be expressed within the intracellular space of the EHC. EHCs comprising a valine decarboxylase antigen may be administered to a subject in need thereof to modulate valine levels within the blood. EHCs comprising a valine decarboxylase antigen are suitable to treat valinemia, an inherited disorder that increases levels of the amino acid valine in the blood. Affected individuals typically develop vomiting, failure to thrive, intellectual disability, and fatigue. Valinemia is caused by a deficiency of the valine transaminase enzyme and has an autosomal recessive pattern of inheritance.

In certain embodiments, erythrocytes comprise an antigen comprising a hydrolase. In one embodiment, the hydrolase is deoxyribonuclease I (DNase I). DNase I antigen may be expressed on the surface of the EHC. EHCs comprising a DNase I antigen may be administered to a subject in need thereof to preferentially cleave circulating DNA at phosphodiester linkages adjacent to a pyrimidine nucleotide, yielding 5'-phosphate-terminated polynucleotides with a free hydroxyl group on position 3'. On average tetra-nucleotides are produced. EHCs comprising a DNase I antigen are suitable to treat conditions exacerbated by high levels of immunogenic DNA in circulation, such as systemic lupus erythematosus (SLE).

In certain embodiments the antigen is capable of responding to an external stimulus, e.g., upon binding to a ligand or contacting the stimulus, wherein responding entails, for example, moving, re-folding, changing conformation, forming a dimer, forming a homodimer, forming a heterodimer, forming a multimer, transducing a signal, emitting energy in a detectable form (e.g., fluorescence), functionally interacting with another antigen, or functionally interacting with a non-exogenous antigen polypeptide.

Targets

Provided herein are exogenous antigen-expressing EHCs comprising an exogenous antigen polypeptide capable of interacting with a target. Further provided herein are exogenous antigen-expressing EHCs comprising a non-polypeptide exogenous antigen capable of interacting with a target. The exogenous antigen-expressing EHCs may be administered to a subject in need thereof to modulate the amount or concentration of a target residing in the circulatory system of the subject. A suitable exogenous antigen may be chosen to interact with a specific target. Suitable targets include entities that are associated with a specific disease, disorder, or condition. However, targets may also be chosen independent of a specific disease, disorder, or condition.

In some embodiments, the target is an antibody or antibody-like molecule, for example an autoimmune or a self-antibody, or a foreign antibody, or a therapeutic antibody, including but not limited to, e.g., an antibody against beta-2 glycoprotein 1, an antibody against I/i antigen, an antibody against the NC1 domain of collagen a3(IV), an antibody against platelet glycoprotein, an antibody against phospholipase A2 receptor, an antibody against erythrocyte glycophorin A, B, or C, or an antibody against erythrocyte Rh antigen.

In some embodiments, the target is a molecule of the complement cascade, for example C1, C1r, C1s, C1q, C2, C2a, C2b, C3, C3a, C3b, C4, C4b, C4a, C3bBb, C3bBb3b, C4b2b, C4b2b3b, C5, C5a, C5b, C6, C7, C8, C9, poly-C9, membrane attack complex. Factor B, Factor D, Properdin, C3, C3a, C3b, iC3b, C3c, C3dg, C3dk, C3e, Bb, Factor I, C1q, C1r, C1s, C4, C4a, C4b, C2, C4bp, Mannose-Binding Lectin (MBL), MBL-Associated Serine Protease 1 (MASP1), MBL-Associated Serine Protease 2 (MASP2), C5, C5a, C6, C7, C8, C9, CR1, CR2, CR3, CR4, C3aR, C3eR, Decay-accelerating factor (DAF), Membrane cofactor protein (MCP), CD59, C3 Beta chain Receptor, C1 inhibitor, C4 binding protein, Factor I, Factor H.

In some embodiments, the target is an immune complex, for example an IgG immune complex, an IgA immune complex, an IgM immune complex.

In some embodiments, the target is an amyloid placque, for example a placque comprised of beta amyloid, IAPP (Amylin), alpha-synuclein, PrPSc, huntingtin, calcitonin, atrial natriuretic factor, apolipoprotein AI, serum amyloid A, medin, prolactin, transthyretin, lysozyme, beta 2 microglobulin, gelsolin, keratoepithelin, cystatin, immunoglobulin light chain AL, S-IBM.

In some embodiments, the target is a bacterium, for example *Enterococcus, Streptococcus,* or *Mycobacteria, Rickettsia, Mycoplasma, Neisseria meningitides, Neisseria gonorrheoeae, Legionella, Vibrio cholerae, Streptococci, Staphylococcus aureus, Staphylococcus epidermidis, Pseudomonas aeruginosa, Corynobacteria diphtheriae, Clostridium* spp., enterotoxigenic *Eschericia coli,* and *Bacillus anthracis*. Other pathogens for which bacteremia has been reported at some level include the following: *Rickettsia, Bartonella henselae, Bartonella quintana, Coxiella burnetii, chlamydia, Mycobacterium leprae, Salmonella; shigella; Yersinia enterocolitica; Yersinia pseudotuberculosis; Legionella pneumophila; Mycobacterium tuberculosis; Listeria monocytogenes; Mycoplasma* spp.; *Pseudomonas fluorescens; Vibrio cholerae; Haemophilus influenzae; Bacillus anthracis; Treponema pallidum; Leptospira; Borrelia; Corynebacterium diphtheriae; Francisella; Brucella melitensis; Campylobacter jejuni; Enterobacter; Proteus mirabilis; Proteus*; and *Klebsiella pneumoniae*.

In some embodiments, the target is a virus, including but not limited to, those whose infection involves injection of genetic materials into host cells upon binding to cell surface receptors, viruses whose infection is mediated by cell surface receptors. Non-limiting examples of these viruses can be selected from Paramyxoviridae (e.g., pneumovirus, morbillivirus, metapneumovirus, respirovirus or rubulavirus), Adenoviridae (e.g., adenovirus), Arenaviridae (e.g., arenavirus such as lymphocytic choriomeningitis virus), Arteriviridae (e.g., porcine respiratory and reproductive syndrome virus or equine arteritis virus), Bunyaviridae (e.g., phlebovirus or hantavirus), Caliciviridae (e.g., Norwalk virus), Coronaviridae (e.g., coronavirus or torovirus), Filoviridae (e.g., Ebola-like viruses), Flaviviridae (e.g., hepacivirus or flavivirus), Herpesviridae (e.g., simplexvirus, varicellovirus, cytomegalovirus, roseolovirus, or lymphocryptovirus), Orthomyxoviridae (e.g., influenza virus or thogotovirus), Parvoviridae (e.g., parvovirus), Picomaviridae (e.g., enterovirus or hepatovirus), Poxviridae (e.g., orthopoxvirus, avipoxvirus, or leporipoxvirus), Retroviridae (e.g., lentivirus or spumavirus), Reoviridae (e.g., rotavirus), Rhabdoviridae (e.g., lyssavirus, novirhabdovirus, or vesiculovirus), and Togaviridae (e.g., alphavirus or rubivirus). Specific examples of these viruses include human respiratory coronavirus, influenza viruses A-C, hepatitis viruses A to G, and herpes simplex viruses 1-9.

In some embodiments, the target is a parasite, including but not limited to, for example, intestinal or blood-borne parasites, protozoa, trypanosomes; haemoprotozoa and parasites capable of causing malaria; enteric and systemic cestodes including taeniid cestodes; enteric coccidians; enteric flagellate protozoa; filarial nematodes; gastrointestinal and systemic nematodes and hookworms.

In some embodiments, the target is a fungus, including but not limited to, for example, *Candida albicans, Candida glabrata, Aspergillus, T. glabrata, Candida tropicalis, C. krusei,* and *C. parapsilosis.*

In some embodiments, the target is a bacterial toxin, including but not limited to, for example, AB toxin, alpha toxin, anthrax toxin, bacteriocin, botunlinum toxin, cholesterol-dependent cytolysin, *Clostridium botulinum* C3 toxin, *Clostridium difficile* toxin A, *Clostridium difficile* toxin B, *Clostridium* enterotoxin, *Clostridium perfringens* alpha toxin, *Clostridium perfringens* beta toxin, Cord factor, Cry1Ac, Cryptophycin, Delta endotoxin, Diphtheria toxin, Enterotoxin type B, erythrogenic toxin, exfoliatin, haemolysin E, heat-labile enterotoxin, heat-stable enterotoxin, hemolysin, leukocidin, lipopolysaccharide, Listeriolysin O, microcin, Panton-Valentine leucocidin, pathogenicity island, phenol-soluble modulin, pneumolysin, pore-forming toxin, *Pseudomonas* exotoxin, RTX toxin, sakacin, *Staphylococcus aureus* alpha toxin, *Staphylococcus aureus* beta toxin, *Staphylococcus aureus* delta toxin, Streptolysin, Symplocamide A, tabtoxin, tetanolysin, tetanospasmin, thiol-activated cytolysin, tolaasin, toxic shock syndrome toxin, toxoflavin, trehalose dimycolate, verocytotoxin, and vibriocin.

In some embodiments, the target is a prion protein, including but not limited to, for example, PRP, PRPc, PRPsc, PRPres.

In some embodiments, the target is a cytokine or a chemokine or a growth factor, including but not limited to, for example, acylation stimulating protein, adipokine, albinterferon, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL5, CCL6, CCL7, CCL8, CCL9, colony-stimulating factor, CX3CL1, CX3CR1, CXCL1, CXCL10, CXCL11, CXCL13, CXCL14, CXCL15, CXCL16, CXCL17, CXCL2, CXCL3, CXCL5, CXCL6, CXCL7, CXCL9, erythropoietin, Gc-MAF, granulocyte colony-stimulating factor, granulocyte macrophage colony-stimulating factor, hepatocyte growth factor, IL 10 family, IL 17 family, IL1A, IL1B, interferon, interferon beta 1a, interferon beta 1b, interferon gamma, interferon type I, interferon type II, interferon type III, interleukin, interleukin 1 family, interleukin 1 receptor antagonist, interleukin 10, interleukin 12, interleukin 12 subunit beta, interleukin 13, interleukin 16, interleukin 2, interleukin 23, interleukin 23 subunit alpha, interleukin 34, interleukin 35, interleukin 6, interleukin 7, interleukin 8, interleukin-36, leukemia inhibitory factor, leukocyte-promoting factor, lymphokine, lymphotoxin, lymphotoxin alpha, lymphotoxin beta, macrophage colony-stimulating factor, macrophage inflammatory protein, macrophage-activating factor, monokine, myokine, myonectin, nicotinamide phosphoribosyltransferase, oncostatin M, oprelvekin, platelet factor 4, proinflammatory cytokine, promegapoietin, RANKL, stromal cell-derived factor 1, talimogene laherparepvec, tumor necrosis factor alpha, tumor necrosis factors, XCL1, XCL2, XCR1, angiopoietin, basic fibroblast growth factor, betacellulin, bone morphogenetic protein, brain-derived neurotrophic factor, CCN intercellular signaling protein, CTGF, darbepoetin alfa, endoglin, epidermal growth factor, epoetin alfa, epoetin beta, erythropoietin, FGF15, FGF15/19, fibroblast growth factor, fibroblast growth factor 23, filgrastim, GLIA maturation factor, granulocyte colony-stimulating factor, granulocyte macrophage colony-stimulating factor, growth differentiation factor-9, heberprot-P, hemopoietic growth factors, heparin-binding EGF-like growth factor, hepatocyte growth factor, insulin-like growth factor, insulin-like growth factor 1, insulin-like growth factor 2, keratinocyte growth factor, myostatin, nerve growth factor, neurotrophin-3, neurotrophin-4, oncomodulin, osteopromotive, palifermin, PDGFB, placental growth factor, platelet alpha-granule, platelet-derived growth factor, platelet-derived growth factor receptor, proliferative index, thrombopoietin, transforming growth factor, vascular endothelial growth factor.

In some embodiments, the target is a small molecule, for example a chemical, an amino acid, an atom, an element, an organic acid, <2000 Da, <1000 Da, <500 Da, including but not limited to, for example, iron, copper, calcium, potassium, ethanol, methanol, glycine, alanine, valine, leucine, isoleucine, serine, cysteine, selenocysteine, threonine, methionine, proline, phenylalanine, tyrosine, tryptophan, histidine, lysine, arginine, aspartate, glutamate, asparagine, glutamine.

In some embodiments, the target is a lipid, lipid complex, proteolipid complex, or cholesterol, including but not limited to for example, LDL, VLDL, HDL, HDL2B, triglycerides, LP(a), cholesterol.

In some embodiments, the target is a mammalian cell, including but not limited to, for example, a human cell, a circulating cell, an immune cell, a neutrophil, an eosinophil, a basophil, a lymphocyte, a monocyte, a B cell, a T cell, a CD4+ T cell, a CD8+ T cell, a gamma-delta T cell, a regulatory T cell, a natural killer cell, a natural killer T cell, a macrophage, a Kupffer cell, a dendritic cell, a cancer cell, a cancer stem cell, a circulating tumor cell, a cancer cell from one of the following cancers including, but not limited to, ACUTE lymphoblastic leukaemia (ALL), ACUTE myeloid leukaemia (AML), anal cancer, bile duct cancer, bladder cancer, bone cancer, bowel cancer, brain tumours, breast cancer, cancer of unknown primary, cancer spread to bone, cancer spread to brain, cancer spread to liver, cancer spread to lung, carcinoid, cervical cancer, choriocarcinoma, chronic lymphocytic leukaemia (CLL), chronic myeloid leukaemia (CML), colon cancer, colorectal cancer, endometrial cancer, eye cancer, gallbladder cancer, gastric cancer, gestational trophoblastic tumours (GTT), hairy cell leukaemia, head and neck cancer, hodgkin lymphoma, kidney cancer, laryngeal cancer, leukaemia, liver cancer, lung cancer, lymphoma, melanoma skin cancer, mesothelioma, men's cancer, molar pregnancy, mouth and oropharyngeal cancer, myeloma, nasal and sinus cancers, nasopharyngeal cancer, non hodgkin lymphoma (NHL), oesophageal cancer, ovarian cancer, pancreatic cancer, penile cancer, prostate cancer, rare cancers, rectal cancer, salivary gland cancer, secondary cancers, skin cancer (non melanoma), soft tissue sarcoma, stomach cancer, testicular cancer, thyroid cancer, unknown primary cancer, uterine cancer, vaginal cancer, and vulval cancer.

Antigen Expression, Conjugation, Loading

In certain embodiments, the polypeptide antigen is expressed within the exogenous antigen-expressing EHC. The polypeptide antigen may be exhibited on the surface of the exogenous antigen-expressing EHC or may reside within the exogenous antigen-expressing EHC.

In certain embodiments, the polypeptide antigen is conjugated to the exogenous antigen-expressing EHC. The polypeptide antigen usually is conjugated to the surface of the exogenous antigen-expressing EHC. Conjugation may be achieved chemically or enzymatically, by methods known in the art and described herein. Non-polypeptide antigens may also be conjugated to an exogenous antigen-expressing EHC. In some embodiments, the antigen is not conjugated to the exogenous antigen-expressing EHC.

In certain embodiments, the polypeptide antigen is loaded into the exogenous antigen-expressing EHC. Non-polypeptide antigens may also be loaded within an exogenous antigen-expressing EHC. In some embodiments, the antigen is not loaded into or onto the exogenous antigen-expressing EHC.

In some embodiments, the exogenous antigen-expressing EHC comprises an antigen that is optionally expressed from a recombinant nucleic acid, conjugated to the EHC, loaded into or onto the EHC, and any combination thereof. Optionally, the exogenous antigen-expressing EHC comprises a therapeutic agent or other payload.

In some embodiments, the exogenous antigen-expressing EHC is generated by contacting a suitable isolated cell, e.g., an EHC, a reticulaocyte, an EHC precursor, a platelet, or a platelet precursor, with a recombinant nucleic acid encoding an antigen polypeptide. In some embodiments, the antigen polypeptide is encoded by a DNA, which is contacted with a nucleated erythroid precursor cell or a nucleated platelet precursor cell. In some embodiments, the antigen polypeptide is encoded by an RNA, which is contacted with a platelet, a nucleate EHC, a nucleated platelet precursor cell, or a reticulocyte. In some embodiments, the antigen is a polypeptide, which is contacted with a primary platelet, a nucleated EHC, a nucleated platelet precursor cell, a reticulocyte, or an erythrocyte.

A antigen polypeptide may be expressed from a transgene introduced into an EHC by electroporation, chemical or polymeric transfection, viral transduction, mechanical membrane disruption, or other method; an antigen polypeptide that is expressed from mRNA that is introduced into a cell by electroporation, chemical or polymeric transfection, viral transduction, mechanical membrane disruption, or other method; an antigen polypeptide that is over-expressed from the native locus by the introduction of an external factor, e.g., a transcriptional activator, transcriptional repressor, or secretory pathway enhancer; and/or an antigen polypeptide that is synthesized, extracted, or produced from a production cell or other external system and incorporated into the EHC.

In some embodiments, the antigen is a full-length protein. In some embodiments, the antigen is comprised of one or more polypeptides contained within the full-length protein, of any length greater than approximately 7 amino acids. For example, the polypeptides can be 7, 8, 9, 10, 11, 12, 13, 14, 15, 16, 17, 18, 19, 20, or more than 20 amino acids, e.g 30, 40, 50, 60, 70, 80, 90, 100, or more than 100 amino acids. The polypeptides comprising the antigen may comprise one or more immunological epitopes which may be conformational epitopes or may be linear epitopes. The antigen may be comprised of one or more polypeptides from one or more different proteins.

The antigen of interest can be expressed in the circulating cell by fusion to an endogenous cell protein, including but not limited to those listed in Table B and Table C. Fusion to an endogenous protein may be necessary because it is thought that during the natural process of differentiation and enucleation, the EHC sheds and discards many of the endogenous proteins required for erythropoiesis but not for mature erythrocyte function such as, e.g. c-Kit (SCF receptor) and transferrin. See e.g. Keerthivasan et al., Stem Cells International 2011; Migliaccio, Haematologica 2010. Proteins that are retained include certain membrane proteins such as, e.g. glycophorin A, band 3, and aquaporin; certain cytoplasmic proteins such as, e.g. hemoglobin alpha, hemoglobin beta, and adenosine deaminase; and cytoskeletal proteins.

The antigen of interest can be expressed in the intracellular space of the EHC by a number of methods, including direct expression of the transgene, fusion to an endogenous intracellular protein such as, e.g., hemoglobin, fusion to the intracellular domain of endogenous cell surface proteins such as, e.g. Band 3, glycophorin A, Kell, or fusion to a structural component of the erythroid cytoskeleton.

The antigen of interest can be expressed on the extracellular surface of the EHC by a number of methods, including direct expression of the transgene if it contains a transmembrane domain or other membrane attachment domain, fusion to an endogenous erythroid membrane protein or to the transmembrane domain of said protein such as, e.g. Band 3, glycophorin A, or Kell; or fusion to the GPI-linker acceptor peptide of an endogenous erythroid GPI-linked cell surface protein such as, e.g. acetylcholinesterase, CD55, CD58 or CD59 (see, e.g. Kooyman et al., Science 1995).

The antigen of interest can be conjugated to the surface of a cultured EHC by various chemical and enzymatic means, including but not limited to those listed in Table D, Table D1, and Table E. These methods include chemical conjugation with bifunctional cross-linking agents such as, e.g. an NHS ester-maleimide heterobifunctional crosslinker to connect a primary amine group with a reduced thiol group. These methods also include enzymatic strategies such as, e.g. transpeptidase reaction mediated by a sortase enzyme to connect one polypeptide containing the acceptor sequence LPXTG (Seq. ID No. 24) or LPXTA (Seq. ID No. 25) with a polypeptide containing the N-terminal donor sequence GGG, see e.g. Swee et al., PNAS 2013. The methods also include combination methods, such as e.g. sortase-mediated conjugation of Click Chemistry handles (an azide and an alkyne) on the antigen and the cell, respectively, followed by a cycloaddition reaction to chemically bond the antigen to the cell, see e.g. Neves et al., Bioconjugate Chemistry, 2013.

If desired, a catalytic bond-forming polypeptide domain can be expressed on or in an EHC, either intracellularly or extracellularly. Many catalytic bond-forming polypeptides exist, including transpeptidases, sortases, and isopeptidases, including those derived from Spy0128, a protein isolated from *Streptococcus pyogenes*.

It has been demonstrated that splitting the autocatalytic isopeptide bond-forming subunit (CnaB2 domain) of Spy0128 results in two distinct polypeptides that retain catalytic activity with specificity for each other. The polypeptides in this system are termed SpyTag and SpyCatcher. Upon mixing, SpyTag and SpyCatcher undergo isopeptide bond formation between Asp117 on SpyTag and Lys31 on SpyCatcher (Zakeri and Howarth, JACS 2010, 132:4526). The reaction is compatible with the cellular environment and highly specific for protein/peptide conjugation (Zakeri, B.; Fierer, J. O.; Celik, E.; Chittock, E. C.; Schwarz-Linek, U.; Moy, V. T.; Howarth, M. Proc. Natl. Acad. Sci. U.S.A. 2012, 109, E690-E697). SpyTag and SpyCatcher has been shown to direct post-translational topological modification in elastin-like protein. For example, placement of SpyTag at the N-terminus and SpyCatcher at the C-terminus directs formation of circular elastin-like proteins (Zhang et al, Journal of the American Chemical Society, 2013).

The components SpyTag and SpyCatcher can be interchanged such that a system in which molecule A is fused to SpyTag and molecule B is fused to SpyCatcher is functionally equivalent to a system in which molecule A is fused to SpyCatcher and molecule B is fused to SpyTag. For the purposes of this document, when SpyTag and SpyCatcher are used, it is to be understood that the complementary molecule could be substituted in its place.

A catalytic bond-forming polypeptide, such as a SpyTag/SpyCatcher system, can be used to attach an exogenous antigen of interest to the surface of an EHC. The SpyTag polypeptide sequence can be expressed on the extracellular surface of the EHC. The SpyTag polypeptide can be, for example, fused to the N terminus of a type-1 or type-3 transmembrane protein, e.g. glycophorin A, fused to the C terminus of a type-2 transmembrane protein, e.g. Kell, inserted in-frame at the extracellular terminus or in an extracellular loop of a multi-pass transmembrane protein, e.g. Band 3, fused to a GPI-acceptor polypeptide, e.g. CD55 or CD59, fused to a lipid-chain-anchored polypeptide, or fused to a peripheral membrane protein. The nucleic acid sequence encoding the SpyTag fusion can be expressed within an EHC. An exogenous antigen of interest can be fused to SpyCatcher. The nucleic acid sequence encoding the SpyCatcher fusion can be expressed and secreted from the same EHC that expresses the SpyTag fusion. Alternatively, the nucleic acid sequence encoding the SpyCatcher fusion can be produced exogenously, for example in a bacterial, fungal, insect, mammalian, or cell-free production system. Upon reaction of the SpyTag and SpyCatcher polypeptides, a covalent bond will be formed that attaches the exogenous antigen of interest to the surface of the EHC.

In one embodiment, the SpyTag polypeptide may be expressed as a fusion to the N terminus of glycophorin A under the control of the Gata1 promoter in an EHC. An exogenous antigen of interest, for example the exogenous antigens listed in Table F, Table G, Table H, Table I and Table J, fused to the SpyCatcher polypeptide sequence can be expressed under the control of the Gata1 promoter in the same EHC. Upon expression of both fusion polypeptides, an isopeptide bond will be formed between the SpyTag and SpyCatcher polypeptides, forming a covalent bond between the EHC surface and the exogenous antigen of interest.

In another embodiment, the SpyTag polypeptide may be expressed as a fusion to the N terminus of glycophorin A under the control of the Gata1 promoter in an EHC. An exogenous antigen of interest, for example the exogenous antigens listed in Table F, Table G, Table H, Table I and Table J, fused to the SpyCatcher polypeptide sequence can be expressed in a suitable mammalian cell expression system, for example HEK293 cells. Upon expression of the SpyTag fusion polypeptide on the EHC, the SpyCatcher fusion polypeptide can be brought in contact with the cell. Under suitable reaction conditions, an isopeptide bond will be formed between the SpyTag and SpyCatcher polypeptides, forming a covalent bond between the EHC surface and the exogenous antigen of interest.

A catalytic bond-forming polypeptide, such as a SpyTag/SpyCatcher system, can be used to anchor the exogenous antigen of interest to the intracellular space of an EHC. The SpyTag polypeptide sequence can be expressed in the intracellular space of the EHC by a number of methods, including direct expression of the transgene, fusion to an endogenous intracellular protein such as, e.g., hemoglobin, fusion to the intracellular domain of endogenous cell surface proteins such as, e.g. Band 3, glycophorin A, Kell, or fusion to a structural component of the erythroid cytoskeleton. The SpyTag sequence is not limited to a polypeptide terminus and may be integrated within the interior sequence of an endogenous polypeptide such that polypeptide translation and localization is not perturbed. An exogenous antigen of interest can be fused to SpyCatcher. The nucleic acid sequence encoding the SpyCatcher fusion can be expressed within the same EHC that expresses the SpyTag fusion. Upon reaction of the SpyTag and SpyCatcher polypeptides, a covalent bond will be formed that acts to anchor the antigen of interest in the intracellular space of the EHC.

In one embodiment, an EHC may express SpyTag fused to hemoglobin beta intracellularly. The EHC may be genetically modified with a gene sequence that includes a hemoglobin promoter, beta globin gene and a SpyTag sequence such that upon translation, intracellular beta globin is fused to SpyTag at is C terminus. In addition, the EHC expresses a Gata1 promoter-led gene that codes for SpyCatcher driving phenylalanine hydroxylase (PAH) expression such that upon translation, intracellular PAH is fused to SpyCatcher at its N terminus. Upon expression of both fusion proteins the SpyTag bound beta globin is linked through an isopeptide bond to the SpyCatcher bound PAH in the intracellular space, allowing PAH to be anchored to beta globin and retained during maturation.

In another embodiment, the SpyTag polypeptide can be expressed as a fusion to the exogenous antigen of interest within an EHC. The SpyCatcher polypeptide can be expressed as a fusion to the C terminus (intracellular) of glycophorin A within the same EHC. Upon expression of both fusion polypeptides, an isopeptide bond will be formed between the SpyTag and SpyCatcher polypeptides, forming a covalent bond between the membrane-anchored endogenous erythroid polypeptide and the exogenous antigen of interest.

In another example, the exogenous antigen of interest may be physically loaded into a cultured EHC (as opposed to expressed) by a number of methods, including osmotic loading or hypotonic-hypertonic cycling in which exogenous antigen diffuses through pores introduced into the EHC membrane (see e.g. Cremel and Godfrin, Int J Pharm 2013) and fusion to a cell penetrating peptide, such as one derived from a bacterial toxin, see e.g. Kwon et al., J Contr Rel 2009.

The exogenous antigen of interest may be expressed from a transgene introduced into an EHC by electroporation, chemical or polymeric transfection, viral transduction, mechanical membrane disruption, or other method; an exogenous antigen that is expressed from mRNA that is introduced into a cell by electroporation, chemical or polymeric transfection, viral transduction, mechanical membrane disruption, or other method; an exogenous antigen polypeptide that is over-expressed from the native locus by the introduction of an external factor, e.g. a transcriptional activator, transcriptional repressor, or secretory pathway enhancer; an exogenous antigen that is synthesized, extracted, or produced from a production cell or other external system and incorporated into the EHC.

EHCs of the invention may optionally be loaded with materials (payload) such as peptides, proteins, DNA, RNA, siRNA, and other macromolecules by applying controlled injury to the cell for a predetermined amount of time in order to cause perturbations in the cell membrane such that the materials can be delivered to the inside of the cell (e.g. cytoplasm).

In preferred embodiments, the EHC is a reticulocyte. For example, reticulocytes may be loaded with an mRNA encoding an exogenous antigen by controlled cell injury. The mRNA may be naked or modified, as desired. mRNA modification that improve mRNA stability and/or decrease immunogenicity include, e.g. ARCA: anti-reverse cap analog ($m_2^{7,3'-O}GP_3G$), $GP_3G$ (Unmethylated Cap Analog), $m^7GP_3G$ (Monomethylated Cap Analog), $m_3^{2.2.7}GP_3G$ (Trimethylated Cap Analog), m5CTP (5'-methyl-cytidine triphosphate), m6ATP (N6-methyl-adenosine-5'-triphosphate), s2UTP (2-thio-uridine triphosphate), and Ψ (pseudouridine triphosphate).

In another preferred embodiment, the EHC is an erythrocyte. For example, erythrocytes may be loaded with an exogenous antigen by controlled cell injury. The cell injury can be caused by, for example, pressure induced by mechanical strain or shear forces, subjecting the cell to deformation, constriction, rapid stretching, rapid compression, or pulse of high shear rate. The controlled cell injury leads to uptake of material (payload) into the cytoplasm of the cell from the surrounding cell medium.

Using controlled cell injury based on controlled cell deformation (e.g. mechanical deformation of the cell as it passes through the constriction) leads to uptake of material (payload) by diffusion rather than endocytosis. The material (payload) is present in the cytoplasm rather than in endosomes following cellular uptake upon the controlled injury thereby making the material readily available to the cell. Controlled cell injury, e.g. by controlled deformation, preserves cell viability (e.g. greater than 50%, 70%, or greater than 90%). In certain embodiments, controlled cell injury, e.g. by controlled deformation, preserves the state of cellular differentiation and activity. If desired, a combination treatment is used, e.g., controlled injury by deformation followed by or preceded by, e.g., electroporation or another cell membrane permeability increasing method. Optionally, surfactants may be used.

Mechanical deformation methods are particularly suitable for cells that do not tolerate other membrane permeability increasing methods well, e.g. show decreased viability or a different state of differentiation after performing such methods. Mechanical deformation methods are also suitable for material (payload) that does not tolerate other membrane permeability increasing methods well. Alternatively or in addition, the payload may not be sufficiently introduced into the cell using alternative methods, e.g. because of e.g. charge, hydrophobicity, or size of the payload.

One exemplar method of controlled injury by deformation and devices suitable for such methods is described, e.g. in PCT Publication No. WO2013059343 INTRACELLULAR DELIVERY, incorporated herein by reference.

In a specific embodiment, a population of reticulocytes is provided that has been subjected to controlled cell injury by controlled deformation. The cells can, e.g., be compressed and deformed by passage through a micro-channel having a diameter less than that of an individual reticulocyte, thereby causing perturbations in the cell membrane such that the membrane becomes porous. Cells are moved, e.g., pushed, through the channels or conduits by application of pressure. The compression and deformation occurs in a delivery medium comprising a payload, e.g. an exogenous polypeptide or oligonucleotide (e.g. DNA, RNA, such as mRNA). For example, the delivery medium may comprise an exogenous antigen listed in Table F, Table G, Table H, Table I and Table J or coding mRNA thereof. Upon deformation the reticulocyte takes up and retains the exogenous material. Following controlled injury to the cell by constriction, stretching, and/or a pulse of high shear rate, the cells are optionally incubated in a delivery medium that contains the material (payload). The cells may be maintained in the delivery medium for a few minutes to recover, e.g. to close the injury caused by passing through the constriction. This may occur at room temperature.

Controlled cell injury as used herein includes: i) virus-mediated transfection (e.g. Herpes simplex virus, Adeno virus, Adeno-associated virus, Vaccinia virus, or Sindbis virus), ii) chemically-mediated transfection, e.g. cationic polymer, calcium phosphate, cationic lipid, polymers, and nanoparticles, such as cyclodextrin, liposomes, cationic liposomes, DEAE-dextran, polyethyleneimine, dendrimer, polybrene, calcium phosphate, lipofectin, DOTAP, lipofectamine, CTAB/DOPE, DOTMA; and iii) physically-mediated transfection, including direct injection, biolistic particle delivery, electroporation, laser-irradiation, sonoporation, magnetic nanoparticles, and controlled deformation (e.g. cell squeezing), as exemplified by microneedle, nano-needle, femtosyringe, atomic-force microscopy (AFM) tip, gene gun (e.g. gold nanoparticles), Amaxa Nucleofector, phototransfection (multi-photon laser), impalefection, and magnetofection, and other suitable methods known in the art. Any suitable method may be used to obtain the EHCs described herein comprising one or more desired DNA, RNA (e.g. mRNA), or polypeptides comprising antigen.

Exogenous antigen of interest can be detected on the EHC of the invention. The presence of the exogenous antigen can be validated and quantified using standard molecular biology methods, e.g. Western blotting or FACS analysis. Exogenous antigens present in the intracellular environment may be quantified upon cell lysis or using fluorescent detection.
Manufacturing In some embodiments, the EHC is generated using a precursor hematopoietic cell, e.g., a CD34+ cell, an erythrocyte, a platelet, a megakaryocyte, or a neutrophil as a source. In some embodiments, the precursor hematopoietic cell is isolated from a human donor by a GMP-compliant process. In some embodiments, the starting cells are sourced from an autologous donor. In some embodiments, the starting cells are sourced from an allogeneic donor. The donor may be typed for blood cell antigen polymorphisms and/or the donor is genotyped for blood cell antigens. The donor can be a universal blood donor. In some embodiments, the donor has the Bombay phenotype, i.e. does not express the H antigen. In some embodiments, the donor has ABO blood type O and is Rh-negative.

In some embodiments, the EHC is generated using CD34+ hematopoietic progenitor cells, mobilized peripheral CD34+ cells, or bone marrow-derived CD34+ cells as a source for the starting material. In some embodiments, the starting cells are derived from umbilical cord blood, are induced pluripotent stem cells or are embryonic stem cells.

The exogenous antigen-expressing EHC may be cultured. Cultured EHCs can be scaled up from bench-top scale to bioreactor scale. For example, the EHCs are cultured until they reach saturation density, e.g., $1\times10^5$, $1\times10^6$, $1\times10^7$, or greater than $1\times10^7$ EHCs per ml. Optionally, upon reaching saturation density, the EHCs can be transferred to a larger volume of fresh medium. The exogenous antigen-expressing EHCs may be cultured in a bioreactor, such as, e.g., a Wave-type bioreactor, a stirred-tank bioreactor. Various configurations of bioreactors are known in the art and a suitable configuration may be chosen as desired. Configurations suitable for culturing and/or expanding populations of exogenous antigen-expressing EHCs can easily be determined by one of skill in the art without undue experimentation. The bioreactor can be oxygenated. The bioreactor may optionally contain one or more impellers, a recycle stream, a media inlet stream, and control components to regulate the influx of media and nutrients or to regulate the outflux of media, nutrients, and waste products.

In some embodiments, the bioreactor may contain a population of human EHCs comprising an exogenous antigen that shed their intracellular DNA over the course of the culture process. For example, the bioreactor may contain a population of human EHCs, enucleated EHCs, and pyrenocytes after culture. In a specific embodiment, the human EHCs and enucleated EHCs comprise an exogenous antigen and the exogenous antigen is retained by the enucleated EHC, whereas the recombinant nucleic acid encoding the exogenous antigen is not retained by the enucleated cell. In certain embodiments, the enucleated EHC comprising the exogenous antigen exhibits substantially the same osmotic membrane fragility as a corresponding isolated unmodified, uncultured EHC.

In one embodiment. The population of exogenous antigen-expressing EHCs generated from EHCs or EHC precursors in the bioreactor undergo a total expansion of greater than 20,000-fold in 14 days or greater. In some embodiments, the exogenous antigen is introduced into a cultured or freshly isolated EHC precursor and after introduction of a recombinant nucleic acid encoding the exogenous antigen the population of exogenous antigen-expressing EHCs generated from the EHC precursors in the bioreactor expands in the bioreactor from the precursor cells by more than 20,000-fold.

In some embodiments, the bioreactor is a Wave bioreactor or a impeller-driven agitator. The bioreactor may be aerated by means of a sparger. In one embodiment, the bioreactor is disposable. In one embodiment, the bioreactor is CIP (cleaned in place). The final number of exogenous antigen-expressing EHCs that may be obtained in a bioreactor setting as described herein can be greater than $10^9$, $10^{10}$, $10^{11}$, $10^{12}$, $10^{13}$ or greater than $10^{13}$ EHCs. The density of exogenous antigen-expressing EHCs may be monitored during culture by measuring cell density by hemacytometer counting or by optical density reading at 600 nm. Optionally, the culture process is monitored for pH levels, oxygenation, agitation rate, and/or recycle rate.
Processes and Properties The identity of the exogenous antigen-expressing EHCs can be assessed by in vitro assays. For example, the identity of the exogenous antigen-expressing EHCs is assessed by counting the number of EHCs in a population, e.g., by microscopy, by flow cytometry, or by hemacytometry. Alternatively or in addition, the identity of the exogenous antigen-expressing EHCs is assessed by analysis of protein content of the EHCs, e.g., by flow cytometry, Western blot, immunoprecipitation, fluorescence spectroscopy, chemiluminescence, mass spectrometry, or absorbance spectroscopy. In one embodiment, the protein content assayed is a non-surface protein, e.g., an integral membrane protein, hemoglobin, adult hemoglobin, fetal hemoglobin, embryonic hemoglobin, a cytoskeletal protein. In one embodiment, the protein content assayed is a surface protein, e.g., a differentiation marker, a receptor, a co-receptor, a transporter, a glycoprotein. In one embodiment, the surface protein is selected from the list including, but not limited to, glycophorin A, CKIT, transferrin receptor, Band3, Kell, CD45, CD46, CD47, CD55, CD59, CR1. In some embodiments, the identity of the exogenous antigen-expressing EHCs is assessed by analysis of the exogenous antigen content of the EHCs, e.g., by flow cytometry, Western blot, immunoprecipitation, fluorescence spectroscopy, chemiluminescence, mass spectrometry, or absorbance spectroscopy. For example, the identity of the exogenous antigen-expressing EHCs can be assessed by the mRNA content of the EHCs, e.g., by RT-PCR, flow cytometry, or northern blot. The identity of the exogenous antigen-expressing EHCs can be assessed by nuclear material content, e.g., by flow cytometry, microscopy, or southern blot, using, e.g., a nuclear stain or a nucleic acid probe. Alternatively or in addition, the identity of the exogenous antigen-expressing EHCs is assessed by lipid content of the EHCs, e.g by flow cytometry, liquid chromatography, or by mass spectrometry.

In some embodiments, the identity of the exogenous antigen-expressing EHCs is assessed by metabolic activity of the EHCs, e.g by mass spectrometry, chemiluminescence, fluorescence spectroscopy, absorbance spectroscopy. Metabolic activity can be assessed by ATP consumption rate and/or the metabolic activity is assessed measuring 2,3-diphosphoglycerate (2,3-DPG) level in the exogenous antigen-expressing EHC. The metabolic activity can be assessed as the rate of metabolism of one of the following, including but not limited to, Acetylsalicylic acid, N-Acetylcystein, 4-Aminophenol, Azathioprine, Bunolol, Captopril, Chlorpromazine, Dapsone, Daunorubicin, Dehydroepiandrosterone, Didanosin, Dopamine, Epinephrine, Esmolol, Estradiol, Estrone, Etoposide, Haloperidol, Heroin, Insulin, Isoproterenol, Isosorbide dinitrate, LY 217896, 6-mercaptopurine, Misonidazole, Nitroglycerin, Norepinephrine, Para-aminobenzoic acid. In some embodiments, the identity of the exogenous antigen-expressing EHCs is assessed by partitioning of a substrate by the EHCs, e.g by mass spectrometry, chemiluminescence, fluorescence spectroscopy, or absorbance spectroscopy. The substrate can be one of the following, including but not limited to, Acetazolamide, Arbutine, Bumetamide, Creatinine, Darstine, Desethyldorzolamide, Digoxigenin digitoxoside, Digoxin-16'-glucuronide, Epinephrine, Gentamycin, Hippuric acid, Metformin, Norepinephrine, p-Aminohippuric acid, Papaverine, Penicillin G, Phenol red, Serotonin, Sulfosalicylic acid, Tacrolimus, Tetracycline, Tucaresol, and Vancomycin.

In one embodiment, the population of exogenous antigen-expressing EHCs is differentiated from a precursor cell. In this embodiment, the differentiation state of the population of exogenous antigen-expressing EHCs is assessed by an in vitro assay. The in vitro assays include those described herein for assessing the identity of the EHCs, including but not limited to expansion rate, number, protein content or expression level, mRNA content or expression level, lipid content, partition of a substrate, catalytic activity, or metabolic activity.

In some embodiments, the exogenous antigen-expressing EHCs are cultured and the differentiation state of the EHCs is assessed at multiple time points over the course of the culture process.

Exogenous antigen-expressing EHCs may be generated using reticulocytes as a source for starting material. The purity of isolated reticulocytes may be assessed using microscopy in that reticulocytes are characterized by a reticular (mesh-like) network of ribosomal RNA that becomes visible under a microscope with certain stains such as new methylene blue or brilliant cresyl blue. Surface expression of transferrin receptor (CD71) is also higher on reticulocytes and decreases and they mature to erythrocytes, allowing for enrichment and analysis of reticulocyte populations using anti-CD71 antibodies (See, e.g., Miltenyi CD71 microbeads product insert No. 130-046-201). Alternatively, analysis of creatine and hemoglobin A1C content and pyruvate kinase, aspartate aminotransferase, and porphobilinogen deaminase enzyme activity may be used to assess properties of the isolated reticulocytes relative to mature erythrocytes (See, e.g., Brun et al., Blood 76:2397-2403 (1990)). For example, the activity of porphobilinogen deaminase is nearly 9 fold higher whereas the hemoglobin A1C content is nearly 10 fold less in reticulocytes relative to mature erythrocytes.

In some embodiments, cells suitable for generating exogenous antigen-expressing EHCs are differentiated ex vivo and/or in vivo from one or more stem cells. In one embodiment, the one or more stem cells are one or more hematopoietic stem cells. Various assays may be performed to confirm the ex vivo differentiation of cultured hematopoietic stem cells into reticulocytes and erythrocytes, including, for example, microscopy, hematology, flow cytometry, deformability measurements, enzyme activities, and hemoglobin analysis and functional properties (Giarratana et al., Nature Biotech. 23:69-74 (2005)). The phenotype of cultured hematopoietic stem cells may be assessed using microscopy of cells stained, for example, with Cresyl Brilliant blue. Reticulocytes, for example, exhibit a reticular network of ribosomal RNA under these staining conditions whereas erythrocytes are devoid of staining. Enucleated cells may also be monitored for standard hematological variables including mean corpuscular volume (MCV; femtoliters (fL)), mean corpuscular hemoglobin concentration (MCHC; %) and mean corpuscular hemoglobin (MCH; pg/cell) using, for example, an XE2100 automat (Sysmex, Roche Diagnostics).

In some embodiments, the exogenous antigen-expressing EHCs are assessed for their basic physical properties, e.g., size, mass, volume, diameter, buoyancy, density, and membrane properties, e.g., viscosity, deformability fluctuation, and fluidity.

In one embodiment, the diameter of the exogenous antigen-expressing EHCs is measured by microscopy or by automated instrumentation, e.g., a hematological analysis instrument. In one embodiment the diameter of the exogenous antigen-expressing EHCs is between about 1-20 microns. In one embodiment, the diameter of the exogenous antigen-expressing EHCs is at least in one dimension between about 1-20 microns. In one embodiment, the diameter of the exogenous antigen-expressing EHCs is less than about 1 micron. In one embodiment, the diameter of the EHCs in one dimension is larger than about 20 microns. In one embodiment, the diameter of the exogenous antigen-expressing EHCs is between about 1 micron and about 20 microns, between about 2 microns and about 20 microns between about 3 microns and about 20 microns between about 4 microns and about 20 microns between about 5 microns and about 20 microns between about 6 microns and about 20 microns, between about 5 microns and about 15 microns or between about 10 microns and about 30 microns.

In one embodiment, the mean corpuscular volume of the exogenous antigen-expressing EHCs is measured using a hematological analysis instrument. In one embodiment the volume of the mean corpuscular volume of the EHCs is greater than 10 fL, 20 fL, 30 fL, 40 fL, 50 fL, 60 fL, 70 fL, 80 fL, 90 fL, 100 fL, 110 fL, 120 fL, 130 fL, 140 fL, 150 fL, or greater than 150 fL. In one embodiment the mean corpuscular volume of the EHCs is less than 30 fL, 40 fL, 50 fL, 60 fL, 70 fL, 80 fL, 90 fL, 100 fL, 110 fL, 120 fL, 130 fL, 140 fL, 150 fL, 160 fL, 170 fL, 180 fL, 190 fL, 200 fL, or less than 200 fL. In one embodiment the mean corpuscular volume of the EHCs is between 80-100 femtoliters (fL).

In one embodiment the average buoyant mass of the exogenous antigen-expressing EHCs (pg/cell) is measured using a suspended microchannel resonatory or a double suspended microchannel resonatory (see e.g., Byun et al PNAS 2013 110(19):7580 and Bryan et al. Lab Chip 2014 14(3):569).

In one embodiment the dry density of the exogenous antigen-expressing EHCs is measured by buoyant mass in an H2O-D2O exchange assay (see e.g., Feijo Delgado et al., PLOS One 2013 8(7):e67590).

In some embodiments, the exogenous antigen-expressing EHCs have an average membrane deformability fluctuation of standard deviation greater than 10, 20, 30, 40, 50, 60, 70, 80, 90, 100 or greater than 100 mrad as measured by spatial light interference microscopy (SLIM) (see e.g., Bhaduri et al., Sci Reports 2014, 4:6211).

In one embodiment, the average membrane viscosity of a population of exogenous antigen-expressing EHCs is measured by detecting the average fluorescence upon incubation with viscosity-dependent quantum yield fluorophores (see e.g., Haidekker et al. Chem & Biol 2001 8(2):123).

In one embodiment, the membrane fluidity of the exogenous antigen-expressing EHCs is measured by fluorescence polarization, e.g., with BMG Labtech POLARstar Omega microplate reader.

For example, to measure deformability reticulocytes may be separated from nucleated cells on day 15 of culture, for example, by passage through a deleukocyting filter (e.g., Leucolab LCG2, Macopharma) and subsequently assayed using ektacytometry. The enucleated cells are suspended in 4% polyvinylpyrrolidone solution and then exposed to an increasing osmotic gradient from 60 to 450 mosM. Changes in the laser diffraction pattern (deformability index) of the cells are recorded as a function of osmolarity, to assess the dynamic deformability of the cell membrane. The maximum deformability index achieved at a physiologically relevant osmolarity is related to the mean surface area of erythrocytes.

In some embodiments, the exogenous antigen-expressing EHCs are analyzed for hemoglobin contents. Assays of hemoglobin may be used to assess the phenotype of differentiated cells (Giarratana et al., Nature Biotech. 23:69-74 (2005)). For example, high performance liquid chromatography (HPLC) using a Bio-Rad Variant II Hb analyzer (Bio-Rad Laboratories) may be used to assess the percentage of various hemoglobin fractions. Oxygen equilibrium may be measured using a continuous method with a double-wavelength spectrophotometer (e.g., Hemox analyzer, TCS). The binding properties of hemoglobin may be assessed using flash photolysis. In this method, the rebinding of CO to intracellular hemoglobin tetramers are analyzed at 436 nm after photolysis with a 10 nanosecond pulse at 532 nm.

The exogenous antigen-expressing EHCs described herein can be purified following manufacture if desired. Many suitable methods of purification are known in the art. For example, the exogenous antigen-expressing EHCs are purified by centrifugation, magnetophoresis, irradiation, acoustophoresis, and chemical or physical enucleation. In one embodiment exogenous antigen-expressing EHCs are purified by ex vivo maturation with, e.g., a stromal cell co-culture. In one embodiment, exogenous antigen-expressing EHCs are purified by chemical or enzymatic treatment of EHCs, e.g by treatment with a deglycosylation enzyme.

In one embodiment the exogenous antigen-expressing EHCs are purified by disabling any residual replicative potential of the exogenous antigen-expressing EHCs. In one embodiment the exogenous antigen-expressing EHCs are subjected to radiation, e.g., X rays, gamma rays, beta particles, alpha particles, neutrons, protons, elemental nuclei, UV rays in order to damage residual replication-competent nucleic acids.

Ionizing radiation is energy transmitted via X rays, gamma rays, beta particles (high-speed electrons), alpha particles (the nucleus of the helium atom), neutrons, protons, and other heavy ions such as the nuclei of argon, nitrogen, carbon, and other elements. X rays and gamma rays are electromagnetic waves like light, but their energy is much higher than that of light (their wavelengths are much shorter). Ultraviolet (UV) light is a radiation of intermediate energy that can damage cells but UV light differs from the forms of electromagnetic radiation mentioned above in that it does not cause ionization (loss of an electron) in atoms or molecules, but rather excitation (change in energy level of an electron). The other forms of radiation—particles—are either negatively charged (electrons), positively charged (protons, alpha rays, and other heavy ions), or electrically neutral (neutrons).

Radiation-induced ionizations may act directly on the cellular component molecules or indirectly on water molecules, causing water-derived radicals. Radicals react with nearby molecules in a very short time, resulting in breakage of chemical bonds or oxidation (addition of oxygen atoms) of the affected molecules. The major effect in cells is DNA breaks. Since DNA consists of a pair of complementary double strands, breaks of either a single strand or both strands can occur. However, the latter is believed to be much more important biologically. Most single-strand breaks can be repaired normally thanks to the double-stranded nature of the DNA molecule (the two strands complement each other, so that an intact strand can serve as a template for repair of its damaged, opposite strand). In the case of double-strand breaks, however, repair is more difficult and erroneous rejoining of broken ends may occur. These so-called misrepairs result in induction of mutations, chromosome aberrations, or cell death.

Deletion of DNA segments is the predominant form of radiation damage in cells that survive irradiation. It may be caused by (1) misrepair of two separate double-strand breaks in a DNA molecule with joining of the two outer ends and loss of the fragment between the breaks or (2) the process of cleaning (enzyme digestion of nucleotides—the component molecules of DNA) of the broken ends before rejoining to repair one double-strand break.

Radiations differ not only by their constituents (electrons, protons, neutrons, etc.) but also by their energy. Radiations that cause dense ionization along their track (such as neutrons) are called high-linear-energy-transfer (high-LET) radiation, a physical parameter to describe average energy released per unit length of the track. (See the accompanying figure.) Low-LET radiations produce ionizations only sparsely along their track and, hence, almost homogeneously within a cell. Radiation dose is the amount of energy per unit of biological material (e.g., number of ionizations per cell).

Thus, high-LET radiations are more destructive to biological material than low-LET radiations—such as X and gamma rays—because at the same dose, the low-LET radiations induce the same number of radicals more sparsely within a cell, whereas the high-LET radiations—such as neutrons and alpha particles—transfer most of their energy to a small region of the cell. The localized DNA damage caused by dense ionizations from high-LET radiations is more difficult to repair than the diffuse DNA damage caused by the sparse ionizations from low-LET radiations.

In one embodiment, a population of exogenous antigen-expressing EHCs are subjected to gamma irradiation using an irradiation dose of more than 1, 5, 10, 15, 20, 25, 30, 35, 40, 50, 60, 70, 80, 90, 100, or more than 100 kGy.

In one embodiment, a population of exogenous antigen-expressing EHCs are subjected to X-ray irradiation using an irradiation dose of more than 0.1, 0.5, 1, 5, 10, 15, 20, 25, 30, 35, 40, 50, 60, 70, 80, 90, 100, 200, 300, 400, 500, 600, 700, 800, 900, 1000, 2000, 3000, 4000, 5000, 6000, 7000, 8000, 9000, 10000, or greater than 10000 mSv.

The purity of a population of exogenous antigen-expressing EHCs can be assessed by measuring the homogeneity of the population. In one embodiment, the average distribution width of the exogenous antigen-expressing EHCs is measured by a hematological analysis instrument. In one embodiment, the population of exogenous antigen-expressing EHCs has a reticulocyte to non-reticulocyte ratio greater than 10, 100, 1000, $10^4$, $10^5$, $10^6$, or greater than $10^6$. The homogeneity of the population of exogenous antigen-expressing EHCs may be assessed by measuring the stromal cell content of the population. In one embodiment, the population of exogenous antigen-expressing EHCs has less than 1 ppb of stromal cells. Alternatively or in addition, the homogeneity of the population of exogenous antigen-expressing EHCs is assessed by measuring the viral titer and/or a bacterial colony forming potential of the population.

In one embodiment the homogeneity of a population of exogenous antigen-expressing EHCs is assessed by an in vitro assay. The in vitro assays include those described herein for assessing the identity of the EHCs, including but not limited to expansion rate, number, protein content or expression level, mRNA content or expression level, lipid content, partition of a substrate, catalytic activity, or metabolic activity.

Mature erythrocytes for use in generating the exogenous antigen-expressing EHCs may be isolated using various methods such as, for example, a cell washer, a continuous flow cell separator, density gradient separation, fluorescence-activated cell sorting (FACS), Miltenyi immunomagnetic depletion (MACS), or a combination of these methods (See, e.g., van der Berg et al., Clin. Chem. 33:1081-1082 (1987); Bar-Zvi et al., J. Biol. Chem. 262:17719-17723 (1987); Goodman et al., Exp. Biol. Med. 232:1470-1476 (2007)).

Erythrocytes may be isolated from whole blood by simple centrifugation (See, e.g., van der Berg et al., Clin. Chem. 33:1081-1082 (1987)). For example, EDTA-anticoagulated whole blood may be centrifuged at 800×g for 10 min at 4° C. The platelet-rich plasma and buffy coat are removed and the red blood cells are washed three times with isotonic saline solution (NaCl, 9 g/L).

Alternatively, erythrocytes may be isolated using density gradient centrifugation with various separation mediums such as, for example, Ficoll, Hypaque, Histopaque, Percoll, Sigmacell, or combinations thereof. For example, a volume of Histopaque-1077 is layered on top of an equal volume of Histopaque-1119. EDTA-anticoagulated whole blood diluted 1:1 in an equal volume of isotonic saline solution (NaCl, 9 g/L) is layered on top of the Histopaque and the sample is centrifuged at 700×g for 30 min at room temperature. Under these conditions, granulocytes migrate to the 1077/1119 interface, lymphocytes, other mononuclear cells and platelets remain at the plasma/1077 interface, and the red blood cells are pelleted. The red blood cells are washed twice with isotonic saline solution.

Alternatively, erythrocytes may be isolated by centrifugation using a Percoll step gradient (See, e.g., Bar-Zvi et al., J. Biol. Chem. 262:17719-17723 (1987)). For example, fresh blood is mixed with an anticoagulant solution containing 75 mM sodium citrate and 38 mM citric acid and the cells washed briefly in Hepes-buffered saline. Leukocytes and platelets are removed by adsorption with a mixture of α-cellulose and Sigmacell (1:1). The erythrocytes are further isolated from reticulocytes and residual white blood cells by centrifugation through a 45/75% Percoll step gradient for 10 min at 2500 rpm in a Sorvall SS34 rotor. The erythrocytes are recovered in the pellet while reticulocytes band at the 45/75% interface and the remaining white blood cells band at the 0/45% interface. The Percoll is removed from the erythrocytes by several washes in Hepes-buffered saline. Other materials that may be used to generate density gradients for isolation of erythrocytes include OptiPrep™, a 60% solution of iodixanol in water (from Axis-Shield, Dundee, Scotland).

Erythrocytes may be separated from reticulocytes, for example, using flow cytometry (See, e.g., Goodman el al., Exp. Biol. Med. 232:1470-1476 (2007)). In this instance, whole blood is centrifuged (550×g, 20 min, 25° C.) to separate cells from plasma. The cell pellet is resuspended in phosphate buffered saline solution and further fractionated on Ficoll-Paque (1.077 density), for example, by centrifugation (400×g, 30 min, 25° C.) to separate the erythrocytes from the white blood cells. The resulting cell pellet is resuspended in RPMI supplemented with 10% fetal bovine serum and sorted on a FACS instrument such as, for example, a Becton Dickinson FACSCalibur (BD Biosciences, Franklin Lakes, N.J., USA) based on size and granularity.

Erythrocytes may be isolated by immunomagnetic depletion (See, e.g., Goodman, el al., (2007) Exp. Biol. Med. 232:1470-1476). In this instance, magnetic beads with cell-type specific antibodies are used to eliminate non-erythrocytes. For example, erythrocytes are isolated from the majority of other blood components using a density gradient as described herein followed by immunomagnetic depletion of any residual reticulocytes. The cells are pre-treated with human antibody serum for 20 min at 25° C. and then treated with antibodies against reticulocyte specific antigens such as, for example, CD71 and CD36. The antibodies may be directly attached to magnetic beads or conjugated to PE, for example, to which magnetic beads with anti-PE antibody will react. The antibody-magnetic bead complex is able to selectively extract residual reticulocytes, for example, from the erythrocyte population.

Erythrocytes may also be isolated using apheresis. The process of apheresis involves removal of whole blood from a patient or donor, separation of blood components using centrifugation or cell sorting, withdrawal of one or more of the separated portions, and transfusion of remaining components back into the patient or donor. A number of instruments are currently in use for this purpose such as for example the Amicus and Alyx instruments from Baxter (Deerfield, Ill., USA), the Trima Accel instrument from Gambro BCT (Lakewood, Colo., USA), and the MCS+9000 instrument from Haemonetics (Braintree, Mass., USA). Additional purification methods may be necessary to achieve the appropriate degree of cell purity.

In some embodiments, the exogenous antigen-expressing EHCs are differentiated ex vivo and/or in vivo from one or more reticulocytes. Reticulocytes may be used to generate exogenous antigen-expressing EHCs. Reticulocytes are immature red blood cells and compose approximately 1% of the red blood cells in the human body. Reticulocytes develop and mature in the bone marrow. Once released into circulation, reticulocytes rapidly undergo terminal differentiation to mature erythrocytes. Like mature erythrocytes, reticulocytes do not have a cell nucleus. Unlike mature erythrocytes, reticulocytes maintain the ability to perform protein synthesis. In some embodiments, recombinant nucleic acid (such as mRNA) encoding an exogenous antigen is introduced into reticulocytes to generate exogenous antigen-expressing EHCs.

Reticulocytes of varying age may be isolated from peripheral blood based on the differences in cell density as the reticulocytes mature. Reticulocytes may be isolated from peripheral blood using differential centrifugation through various density gradients. For example, Percoll gradients may be used to isolate reticulocytes (See, e.g., Noble el al., Blood 74:475-481 (1989)). Sterile isotonic Percoll solutions of density 1.096 and 1.058 g/ml are made by diluting Percoll (Sigma-Aldrich, Saint Louis, Mo., USA) to a final concentration of 10 mM triethanolamine, 117 mM NaCl, 5 mM glucose, and 1.5 mg/ml bovine serum albumin (BSA). These solutions have an osmolarity between 295 and 310 mOsm. Five milliliters, for example, of the first Percoll solution (density 1.096) is added to a sterile 15 ml conical centrifuge tube. Two milliliters, for example, of the second Percoll solution (density 1.058) is layered over the higher density first Percoll solution. Two to four milliliters of whole blood are layered on top of the tube. The tube is centrifuged at 250×g for 30 min in a refrigerated centrifuge with swing-out tube holders. Reticulocytes and some white cells migrate to the interface between the two Percoll layers. The cells at the interface are transferred to a new tube and washed twice with phosphate buffered saline (PBS) with 5 mM glucose, 0.03 mM sodium azide and 1 mg/ml BSA. Residual white blood cells are removed by chromatography in PBS over a size exclusion column.

Alternatively, reticulocytes may be isolated by positive selection using an immunomagnetic separation approach (See, e.g., Brun et al., Blood 76:2397-2403 (1990)). This approach takes advantage of the large number of transferrin receptors that are expressed on the surface of reticulocytes relative to erythrocytes prior to maturation. Magnetic beads coated with an antibody to the transferrin receptor may be used to selectively isolate reticulocytes from a mixed blood cell population. Antibodies to the transferrin receptor of a variety of mammalian species, including human, are available from commercial sources (e.g., Affinity BioReagents, Golden, Colo., USA; Sigma-Aldrich, Saint Louis, Mo., USA). The transferrin antibody may be directly linked to the magnetic beads. Alternatively, the transferrin antibody may be indirectly linked to the magnetic beads via a secondary antibody. For example, mouse monoclonal antibody 10D2 (Affinity BioReagents, Golden, Colo., USA) against human transferrin may be mixed with immunomagnetic beads coated with a sheep anti-mouse immunoglobulin G (Dynal/Invitrogen, Carlsbad, Calif., USA). The immunomagnetic beads are then incubated with a leukocyte-depleted red blood cell fraction. The beads and red blood cells are incubated at 22° C. with gentle mixing for 60-90 min followed by isolation of the beads with attached reticulocytes using a magnetic field. The isolated reticulocytes may be removed from the magnetic beads using, for example, DETACHaBEAD® solution (from Invitrogen, Carlsbad, Calif., USA). Alternatively, reticulocytes may be isolated from in vitro growth and maturation of CD34+ hematopoietic stem cells using the methods described herein.

Terminally-differentiated, enucleated erythrocytes can be separated from other cells based on their DNA content. In a non-limiting example, cells are first labeled with a vital DNA dye, such as Hoechst 33342 (Invitrogen Corp.). Hoechst 33342 is a cell-permeant nuclear counterstain that emits blue fluorescence when bound to double-stranded DNA. Undifferentiated precursor cells, macrophages or other nucleated cells in the culture are stained by Hoechst 33342, while enucleated erythrocytes are Hoechst-negative. The Hoechst-positive cells can be separated from enucleated erythrocytes by using fluorescence activated cell sorters or other cell sorting techniques. The Hoechst dye can be removed from the isolated erythrocytes by dialysis or other suitable methods.

A population of exogenous antigen-expressing EHCs can be purified by reducing the nuclear material content of the population of EHCs. For example, the enucleation rate of the population of EHCs is increased, and/or the number of enucleated exogenous antigen-expressing EHCs is increased or enriched.

Populations of exogenous antigen-expressing EHCs can be incubated with a small molecule, e.g., an actin inhibitor, e.g., cytochalasin A, B, C, D, E, F, H, J, and then centrifuged to remove nuclear material. Alternatively or in addition, a population of exogenous antigen-expressing EHCs can be mechanically manipulated by passing through progressively smaller size-restrictive filters to remove nuclear material. The population of exogenous antigen-expressing EHCs may also be incubated on a fibronectin-coated plastic surface to increase the removal of nuclear material. In one embodiment, the population of exogenous antigen-expressing EHCs is incubated in co-culture with stromal cells, e.g., macrophages, to increase the removal of nuclear material.

In some embodiments, the population of exogenous antigen-expressing EHCs is greater than 5%, 10%, 15%, 20%, 25%, 30%, 35%, 40%, 45%, 50%, 55%, 60%, 65%, 70%, 75%, 80%, 85%, 90%, 95%, 99%, 99.5%, 99.9%, or greater than 99.9% enucleated.

In some embodiments, the exogenous antigen-expressing EHCs are not co-cultured with support cells, e.g., with an adherent stromal layer. In some embodiments, the population of exogenous antigen-expressing EHCs is generated by contacting EHCs with an exogenous antigen and differentiating the EHCs to obtain a population of enucleated cells comprising the exogenous antigen. The population of exogenous antigen-expressing EHCs is obtained without an enrichment step, such as gravitational separation, magnetic or fluorescent sorting, irradiation, poisoning of nucleated cells, and the like to select for enucleated cells.

In some embodiments, the population of exogenous antigen-expressing EHCs is comprised of greater than 5%, 10%, 15%, 20%, 25%, 30%, 35%, 40%, 45%, 50%, 55%, 60%, 65%, 70%, 75%, 80%, 85%, 90%, 95%, 99%, 99.5%, 99.9%, or greater than 99.9% of exogenous antigen-expressing EHCs that lack nuclear material as assessed by an assay to detect nuclear material such as those described herein.

In some embodiments, the presence, biological activity and/or function of an exogenous antigen, such as an exogenous antigen polypeptide exhibited by exogenous antigen-expressing EHCs is assessed. Many suitable assays are available and known in the art.

In one embodiment, the exogenous antigen is a polypeptide on the surface of the exogenous antigen-expressing EHC. The presence of the exogenous antigen can be assessed by assays including but not limited to flow cytometry, western blotting, RT-PCR, Northern blotting, Coombs rosetting, mass spectrometry. In one embodiment, the exogenous antigen is a polypeptide in the interior of the exogenous antigen-expressing EHC. The presence of the exogenous antigen can be assessed by assays including but not limited to Western blotting, RT-PCR, Norther blotting, PCR, Southern blotting, mass spectrometry.

In one embodiment, the exogenous antigen is a nucleic acid on the surface of the exogenous antigen-expressing EHC. The presence of the exogenous antigen can be assessed by assays including but not limited to flow cytometry, flow cytometry with a homologous fluorescent probe, southern blotting, northern blotting, PCR. In one embodiment, the exogenous antigen is a nucleic acid in the interior of the exogenous antigen-expressing EHC. The presence of the exogenous antigen can be assessed by assays including but not limited to southern blotting, northern blotting, PCR.

In one embodiment, the exogenous antigen is a small molecule on the surface of the exogenous antigen-expressing EHC. The presence of the exogenous antigen can be assessed by assays including but not limited to flow cytometry, mass spectrometry. In one embodiment, the exogenous antigen is a small molecule in the interior of the exogenous antigen-expressing EHC. The presence of the exogenous antigen can be assessed by assays including but not limited to nass spectrometry, fluorescence spectroscopy.

In one embodiment, the exogenous antigen is a lipid in the membrane of the exogenous antigen-expressing EHC. The presence of the exogenous antigen can be assessed by assays including but not limited to mass spectrometry, flow cytometry, membrane solubility, fluorescence polarization, spatial light interferences microscopy.

In one embodiment, the exogenous antigen is fluorescent or is fused to a fluoresecent molecule or is co-expressed from a recombinant nucleic acid (e.g., in a vector) with a fluorescent reporter protein like GFP. The presence of the exogenous antigen in or on the exogenous antigen-expressing EHC can be assessed by assays including but not limited to flow cytometry, fluorescence spectroscopy, absorbance spectroscopy.

In one embodiment, the exogenous antigen is a gaseous molecule. The presence of the exogenous antigen in or on the exogenous antigen-expressing EHC can be assessed by assays including but not limited to chemiluminescence assays, mass spectroscopy.

The presence of the exogenous antigen in or on the exogenous antigen-expressing EHC can be assessed by flow cytometry in a quantitative fashion using calibration beads such as commercially available cytometry calibration beads to quantify the number of exogenous antigens on an individual EHC. Alternatively or in addition, the presence of the exogenous antigen in or on the exogenous antigen-expressing EHC can be assessed by Western blot in a quantitative fashion using a standard of known concentration that is detectable using the same detection reagents as the exogenous antigen, and in this way the number of exogenous antigens on an individual EHC can be quantified.

In some embodiments, the presence of two or more different exogenous antigens can be assessed by the same or different methods, either simultaneously, in sequential fashion, or in parallel. For example, in one embodiment an exogenous antigen on the surface can be assessed by flow cytometry using an antibody specific to the exogenous antigen and a different exogenous antigen not on the surface that is fluoresecent can be assessed by fluorescent signal using a different channel in flow cytometry. In a different example, an exogenous antigen on the surface can be assessed by flow cytometry and a different exogenous antigen not on the surface can be assessed by Western blot.

In a specific embodiment, the exogenous antigen is retained on the exogenous antigen-expressing EHC following terminal differentiation of the cell source. For example, the exogenous antigen-expressing EHC is generated from a cultured EHC and the expression or presence of the exogenous antigen is assessed following terminal differentiation of the cell by a suitable method, e.g., by flow cytometry, Western blot, immunoprecipitation, fluorescence spectroscopy, chemiluminescence, Southern blot, Northern blot, or absorbance spectroscopy.

In a specific embodiment, the exogenous antigen is retained on the exogenous antigen-expressing EHC following circulation in vivo after administration of the exogenous antigen-expressing EHC to a subject. The exogenous antigen-expressing EHC can be injected into a laboratory animal or animal model, such as a mouse intravenously, e.g., via the tail vein, or is injected into a human intravenously. Then blood is drawn and the presence of the exogenous antigen on the exogenous antigen-expressing EHC is assessed by suitable assay, e.g., by flow cytometry, Western blot, immunoprecipitation, fluorescence spectroscopy, chemiluminescence, Southern blot, Northern blot, or absorbance spectroscopy.

In some embodiments, the biological activity of the exogenous antigen in or on the exogenous antigen-expressing EHC, the overall biological activity of the EHC, and the overall activity of a population of EHCs can be assessed by in vitro assays.

In some embodiments, the activity of the exogenous antigen-expressing EHC is rapidly iterated using a model cell line. For example, a library of suitable exogenous antigens is expressed in a model cell line, e.g., HEK293T or K562, and the activity is assessed via a suitable assay; then the best exogenous antigen candidate, e.g., the one that is expressed at the highest level or one that demonstrates the highest activity in the suitable assay, is expressed, e.g., in cultured EHCs to generate exogenous antigen-expressing EHCs.

In one embodiment, the activity of the exogenous antigen-expressing EHC is rapidly iterated using a cultured mouse model. For example, a library of suitable exogenous antigens is expressed in cultured mouse EHCs; activity is assessed in a suitable mouse model of disease or a suitable mouse model system for assessing activity; the best exogenous antigen candidate, e.g., the one that is expressed at the highest level or the one that demonstrates the highest activity in the suitable assay, is then expressed, e.g., in cultured EHCs to generate exogenous antigen-expressing EHC.

In some instances, the exogenous antigen is an enzyme and the activity of the exogenous antigen can be assessed by an enzymatic assay in which the disappearance of a specific substrate molecule is detected or the appearance of a specific product molecule is detected. Such assays include but are not limited to, colorimetric assays, mass spectrometry, HPLC, fluorescent assays.

For example, a) the exogenous antigen is adenosine deaminase (ADA) and the enzymatic assay detects the conversion of adenosine to inosine; b) the exogenous antigen is phenylalanine hydroxylase (PAH) and the assay detects the conversion of phenylalanine to tyrosine; c) the exogenous antigen is phenylalanine ammonia lyase (PAL) and the assay detects the conversion of phenylalanine to trans-cinnamic acid; d) the exogenous antigen is thymidine phosphorylase (TP) and the assay detects the conversion of thymidine to thymine and 2-deoxy-ribose; e) the exogenous antigen is Purine nucleoside phosphorylase (PNP) and the assay detects the conversion of inosine to hypoxanthine, adenosine into adenine, and guanosine into guanine; f) the exogenous antigen is homogentisate 1,2-dioxygenase (HDG) and the assay detects the conversion of homogentisate to maleylacetoacetate; g) the exogenous antigen is cystathionine beta synthase and the assay detects the conversion of serine and homocysteine to cystathionine; h) the exogenous antigen is oxalate oxidase and the assay detects the oxidation of oxalate.

In some embodiments, activity of the exogenous antigen-expressing EHC is assessed in an animal model, for example a mouse model, and immunodeficient mouse, or an NSG mouse, of a disease, for example a metabolic disease or an enzyme deficiency, or that can demonstrate the effect of the exogenous antigen-expressing EHC, for example a mouse into which a substrate is injected and the product of the exogenous antigen-mediated conversion measured.

In one embodiment, the exogenous antigen is complement receptor 1 (CR1) polypeptide, a derivative or functional fragment thereof. The activity of the CR1 exogenous antigen can be assessed in several ways including, for example, the specific capture of immune complexes by the CR1 exogenous antigen, the efficient transfer of the immune complexes to macrophages, or the in vivo clearance of immune complexes from a mouse.

Functionality of EHCs overexpressing CR1 exogenous antigen may be assessed by one or more processes: capture of immune complexes on the EHC surface comprising CR1 exogenous antigen, release of the immune complexes to macrophages while sparing the EHC comprising CR1 exogenous antigen, and proper circulation of the EHCs comprising CR1 exogenous antigen. These three parameters can be assayed in vitro. Immune complex capture assays are described in the art, e.g., Oudin et al., J Immunol 2000 and Schifferli et al., J Immunol 1991. For example, labeled immune complexes are incubated with EHCs expressing native CR1 or CR1 exogenous antigen polypeptide or a fragment thereof and the number of immune complexes captured by the EHCs is assayed by flow cytometry. Macrophage transfer assays are described in the art, e.g., Kuhn et al., J Immunol 1998. For example, labeled immune complexes loaded onto erythrocytes expressing native CR1 or CR1 exogenous antigen polypeptide or a fragment thereof are incubated with macrophages. The transfer of immune complex from erythrocyte surface to macrophage, and the consumption or sparing of erythrocytes by macrophages, can be measured by flow cytometry. Proper circulation can be predicted by analyzing EHC morphology and deformability. Morphology of EHCs expressing native CR1 or CR1 exogenous antigen polypeptide or a fragment thereof can be assessed by eye using standard microscopy techniques, as described e.g., by Giarratana et al., Blood 2011 and Repik et al., Clin Exp Immunol 2005. Deformability of EHCs expressing native CR1 or CR1 exogenous antigen polypeptide or a fragment thereof can be assessed by ektacytometry, also known as laser-assisted optical rotational cell analysis (LORCA), as described e.g., Giarratana et al., Blood 2011.

For example, an exogenous CR1 antigen-expressing EHC (the EHC comprises a CR1 polypeptide exogenous antigen) is incubated with immune complexes, such as in vivtro generated immune complexes or patient-derived immune complexes. The capture of the immune complexes by the CR1 exogenous antigen is assessed by, for example, flow cytometry using a fluorescent marker in the immune complex or by flow cytometry using a secondary detection agent against an element of the immune complex.

In one embodiment, the exogenous CR1 antigen-expressing EHC is first incubated with immune complexes and then incubated with macrophages, such as primary macrophages, primary monocytes, cultured macrophages, cultured monocytpes, U937 cells, PMA-activated U937 cells, AA9 cells, RAW 264.7 cells, J774 Cells, THP1 cells, KG-1 cells, NR8383 cells, MV-4-11 cells, 3D4/31 cells, MD cells, Fcwf-4 cells, DH82 cells. The macrophages are assayed by, for example, flow cytometry or radiography, for the presence of immune complexes transferred by the exogenous CR1 antigen-expressing EHC. The transfer of captured immune complexes from cultured EHCs to macrophages is a standard assay in the art, see for example: Repik et al. 2005 Clin Exp Immunol. 140:230; Li et al. 2010 Infection Immunity 78(7):3129.

In one embodiment, activity of the exogenous CR1 antigen-expressing EHC is assessed in an animal model. For example, a suitable mouse model may be used, such as an immunodeficient mouse, or an NSG mouse. The mouse disease model can be for example an immune complex disease, such as lupus. Mouse models include NZBWF1/J, MRL/MpJ, MRL/MpJ-Fas(lpr), Smn.C3-Fasl/J, NZM2410/Aeg, 129S4-Cd48, Cg-Sle1, NZM-Sle1 Sle2 Sle3/LmoJ, and BXSB. 129P2. Alternatively or in addition, a disease phenotype may be introduced into a mouse, e.g., by injection of immune complexes. The exogenous CR1 antigen-expressing EHCs may be injected into any suitable mouse (or other animal model) to test one or more biological effects of the EHC, e.g., the clearance of the injected immune complexes by the exogenous CR1 antigen-expressing EHC.

In one embodiment, the exogenous antigen is a complement regulatory molecule or has complement regulatory activity. This activity of the exogenous antigen can be assessed by both in vitro and in vivo assays. For instance, the activity of the exogenous antigen can be assessed by measuring the reduction in an in vitro complement activation assay, e.g., CH50 assay that measures complement-mediated lysis of sensitized sheep erythroctyes, or AH50 assay that measured alternate pathway complement-mediated lysis of non-sensitized rabbit erythrocytes. Alternatively, the activity of the exogenous antigen can be assessed by detecting the cleavage or absence of cleavage, which may or may not expose a neoepitope, of a recombinant complement component that has been incubated with the exogenous antigen, including but not limited to e.g., the cleavage of recombinant C2 into C2a and C2b, the cleavage of factor B into factor Ba and factor Bb, the cleavage of factor C3b into iC3bH and iC3bL, the cleavage of C3bBb into C3b and Bb, the cleavage of C4bBb into C4b and Bb, or the cleavage of factor C4b into iC4bH and iC4bL. The cleavage or absence of cleavage of a suitable recombinant complement component can be assessed by protein analysis methods known in the art including, but not limited to, e.g., chromatography, gel electrophoresis, ELISA, and western blotting. Suitable in vivo assays for exogenous antigen activity include injection of the exogenous antigen-expressing EHC into animal, for example a mouse, and examining the deposition of complement factors, for example membrane attack complex, by histological staining.

In one embodiment, the exogenous antigen is capable of binding or capturing a target and the activity of the exogenous antigen can be assessed by detecting the captured target on the exogenous antigen in vitro or in vivo.

In one embodiment, the exogenous antigen-expressing EHC is incubated with the target in vitro, and the capture of the target by the exogenous antigen is detected using an in vitro assay including but not limited to, for example, flow cytometry, immunohistochemistry, magnetic separation, radiography, colony-forming assays, microscopy.

In one embodiment, the exogenous antigen-expressing EHC is incubated with the target in vitro, and the capture of the target by the exogenous antigen is detected using an in vitro co-culture assay including but not limited to for example a macrophage consumption assay of opsonized exogenous antigen-expressing EHC, a T cell activation assay, a B cell stimulation assay, a mast cell degranulation assay, an infectious potential assay.

In an embodiment, the exogenous antigen-expressing EHC is incubated with the target in vitro, and the release or off-rate of the captured target is measured using an in vitro assay including but not limited to, for example, flow cytometry, immunohistochemistry, magnetic separation, radiography, colony-forming assays, microscopy.

The capture of the target by the exogenous antigen-expressing EHC can be assayed in an in vivo assay, for example in an animal, including a mouse model of diseases in which the target is naturally present in the mouse. Suitable diseases include bacterial infections, viral infections, fungal infections, immune complex diseases, self-antibody diseases, hyperlipidemia, hyperglycemia. In other mouse models, the target is administered to the mouse externally, e.g., by injection or by feeding. In these assays, the capture of the target by the exogenous antigen-expressing EHC is assayed either by examining the animal, e.g the plasma, the tissue, for reduction or retention of the target, or by isolating or collecting the exogenous antigen-expressing EHC from the animal, e.g., from the blood, from the plasma, from a tissue, and assaying the presence of the target on the exogenous antigen using an in vitro assay including, but not limited to, for example, flow cytometry, immunohistochemistry, magnetic separation, radiography, colony-forming assays, microscopy.

In some embodiments, the exogenous antigen is capable of binding or capturing a target and substantially increasing the clearance of the target in vivo, or substantially reducing the concentration of the target in circulation. The activity of the exogenous antigen on the exogenous antigen-expressing EHC can be assessed by detecting the enhanced clearance of the target in vitro or in vivo.

In one embodiment, the exogenous antigen-expressing EHC is incubated with the target in vitro, and the capture of the target by the exogenous antigen is detected using an in vitro assay including but not limited to, for example, flow cytometry, immunohistochemistry, magnetic separation, radiography, colony-forming assays, microscopy. Subsequently, the exogenous antigen-expressing EHC is incubated in a co-culture assay with a cell known to promote clearance, for example a macrophage or a monocyte, and the clearance of the target and exogenous antigen-expressing EHC is assessed by, for example, flow cytometry, immunohistochemistry, magnetic separation, radiography, colony-forming assays, microscopy.

In one embodiment, the exogenous antigen-expressing EHC is incubated with the target in vitro, and the capture of the target by the exogenous antigen is detected using an in vitro assay including but not limited to, for example, flow cytometry, immunohistochemistry, magnetic separation, radiography, colony-forming assays, microscopy. Subsequently, the exogenous antigen-expressing EHC is incubated in a physical system that mimics the clearance mechanism of the EHC in vivo, for example an artificial spleen, a microchannel, a packed column, a resin, a tissue explant, a centrifuge, and the clearance of the target and exogenous antigen-expressing EHC is assessed by, for example, flow cytometry, immunohistochemistry, magnetic separation, radiography, colony-forming assays, microscopy.

In one embodiment, the clearance of the target by the exogenous antigen-expressing EHC is assayed in an in vivo assay, for example in an animal, including, for example, a mouse model of diseases in which the target is naturally present in the mouse, for example bacterial infection, viral infection, fungal infection, immune complex disease, self-antibody disease, hyperlipidemia, hyperglycemia, or for example, a mouse model in which the target is administered to the mouse externally, e.g., by injection or by feeding. In these assays, the clearance of the target by the exogenous antigen-expressing EHC is assayed either by examining the animal, e.g the plasma, the tissue, for reduction of the target, or by isolating or collecting the exogenous antigen-expressing EHC from the animal, e.g., from the blood, from the plasma, from a tissue, and assaying the presence of the target on the exogenous antigen using an in vitro assay including, but not limited to, for example, flow cytometry, immunohistochemistry, magnetic separation, radiography, colony-forming assays, microscopy.

In some embodiments, the exogenous antigen-expressing EHC is capable of delivering a suitable exogenous antigen to a specific subcellular compartment, for example a lysosome.

For example, an exogenous antigen may be delivered to the lysosomal compartment of a target cell, e.g., a macrophage. The successful delivery of the exogenous antigen to the lysosomal compartment of a target cell is assessed by microscopy and the detection of punctate spots corresponding to a fluorescent exogenous antigen or fluorescent exogenous antigen detection agent. Alternatively or in addition, the successful delivery of the exogenous antigen to the lysosomal compartment of a target cell is assessed by microscopy and the colocalization of a fluorescent exogenous antigen detection agent with a fluorescent detection agent for a known lysosomal marker, e.g., lysotracker, LAMP-1.

In some embodiments, the exogenous antigen is an enzyme that can degrade toxic components that have built up in the lysosome of a cell exhibiting the genotype or phenotype of, or derived from a patient with, a lysosomal storage disease. For example, the exogenous antigen is capable of degrading the toxic material built up in the cell and rescue the cell phenotype, e.g., preventing cell death.

The population of exogenous antigen-expressing EHCs can be assessed for the inability of the EHCs to replicate, the ability of the EHCs to circulate safely through the vasculature, and the lack of immunogenicity of the EHCs.

In some embodiments, the safety of the population of exogenous antigen-expressing EHCs is assessed by measuring the replication potential of the population of EHCs using a suitable in vitro or in vivo assay. For example, tests for a substantial inability of the exogenous antigen-expressing EHCs to self-replicate include: a) a susbstanital inability to form a tumor when injected into an immunocompromised mouse; b) a substantial inability to form a colony when cultured in soft agar; c) a substantial inability to incorporate thymidine in a thymidine incorporation assay; d) a substantial lack of positive signal upon transfection with DNA encoding a fluorescent reporter, e.g., less than 10%, 1%, 0.1%, 0.01%, 0.001%, 1 ppm, 100 ppb, 10 ppb, 1 ppb, 100 ppt, 10 ppt, 1 ppt, or less than 1 ppt positive signal; e) a substantial lack of positive signal upon staining with a nuclear dye, e.g., less than 10%, 1%, 0.1%, 0.01%; and 0.001%, 1 ppm, 100 ppb, 10 ppb, 1 ppb, 100 ppt, 10 ppt, 1 ppt, or less than 1 ppt positive signal; f) a substantial lack of positive signal upon staining with cell markers of hematological malignancy, e.g., CKIT, CD34, EpCam, e.g., less than 10%, 1%, 0.1%, 0.01%, 0.001%, 1 ppm, 100 ppb, 10 ppb, 1 ppb, 100 ppt, 10 ppt, 1 ppt, or less than 1 ppt positive signal. In certain embodiments, exogenous antigen-expressing EHCs are provided that do not contain a substantial amount of a replicating nucleic acid.

In some embodiments, the safety of the population of exogenous antigen-expressing EHCs is assessed by measuring the ability of an administered EHC to circulate in vivo (in the circulatory system of a subject) without causing substantial vascular occlusion or induction of the clotting cascade. Optionally, the circulation pharmacokinetics of the exogenous antigen-expressing EHCs may be assessed.

In one embodiment, the circulation pharmacokinetics of the exogenous antigen-expressing EHCs is assessed by injecting the EHC into an animal intravenously, such as a mouse. The mouse can be an NSG (nod-SCID-gamma) immunodeficient mouse. The mouse is depleted of macrophages prior to injection with the EHC, e.g., by intraperitoneal injection of human red blood cells, or by intravenous injection with clodronate liposomes. The exogenous antigen-expressing EHCs can be labeled with a fluoresecent dye, e.g., CFSE. After injection of the EHCs, blood is drawn and the number of exogenous antigen-expressing EHCs remaining is assessed by, e.g., flow cytometry, western blot, and the clearance rate of the exogenous antigen-expressing EHCs is deduced from these data. Human red blood cells can be injected into the same animal model as the exogenous antigen-expressing EHCs and the clearance rates of the EHCs and human red blood cells are compared.

In one embodiment, the risk of activation of the clotting cascade by the exogenous antigen-expressing EHC is assessed with an in vitro assay. In one embodiment, the exogenous antigen-expressing EHC is incubated with human blood and clotting cascade activation is assessed by measuring the time required for coagulation in the presence of kaolin, negatively-charged phospholipids, and calcium (activated partial thromboplastn time (aPTT) test), see e.g., Exner and Rickard, Biomedicine 1977 27(2):62, or by measuring the time required for coagulation in the presence of thromboplastin and calcium (prothrombin time (PT) test), see e.g., Jaques and Dunlop 1945, Am J Physiol 145:67. The normal range for the aPTT test is approximately 25-38 seconds. The normal range for the PT test is approximately 10-12 seconds.

In one embodiment, any adverse events induced by the exogenous antigen-expressing EHCs are assessed by injecting the EHCs into an animal intravenously and assessing the activation of the clotting cascade. The level of clotting cascade induction is assessed by drawing blood and assessing the levels of clotting cascade components in the plasma by, e.g., Western Blot or ELISA. The clotting cascade components are typically fibrinogen breakdown products, e.g., fibrinopeptide A and fibrinopeptide B. For example, the level of clotting cascade induction is assessed by drawing blood and assessing the levels of clotting activity in the plasma by platelet activation assay, e.g., incubating the plasma with platelets and assessing the activation of the platelets by flow cytometry, e.g., by staining for markers of activation, e.g., by staining for PAC-1, CD62p, or CD40L.

In one embodiment, any adverse events induced by the exogenous antigen-expressing EHCs are assessed by injecting the EHCs into an animal intravenously and assessing the activation of inflammatory pathways. The level of inflammation can be assessed by drawing blood and assessing the levels of inflammatory cytokines in the plasma by, e.g., Western Blot or ELISA. In one embodiment, the inflammatory citokines are interferon gamma, tumor necrosis factor alpha, or IL-12 fragment p70.

In one embodiment, any adverse events induced by the exogenous antigen-expressing EHCs are assessed by injecting the EHCs into an animal intravenously and assessing the status of tissues, e.g., liver, spleen, heart, lungs, brain, skin, kidneys. The status of tissue can be assessed by gross necropsy, dissection of the tissue, histological staining, and imaging by microscopy.

In one embodiment, the ability of the exogenous antigen-expressing EHC to circulate in vivo without causing substantial vascular occlusion or activation of the clotting cascade is assessed by measuring the deformability of the EHCs. The deformability of the exogenous antigen-expressing EHC is assessed using an in vitro assay. For example, the assay is an osmotic fragility assay. Mechanical fragility of the exogenous antigen-expressing EHC can be assessed by measuring the structural integrity in response to shear stress in a Couett-type shearing system. In one embodiment, the deformability of the exogenous antigen-expressing EHC is assessed using an Ektacytometer. In one embodiment, the deformability of the exogenous antigen-expressing EHC is assessed by measuring the elongation index at a defined pressure by laser diffraction using a laser-assisted optical rotational cell analyzer (LORCA) instrument. In one embodiment, the deformability of the exogenous antigen-expressing EHC is assessed by measuring the transit time through a series of micron-scale constrictions of defined dimensions at a fixed pressure in a microfluidic device. In one embodiment, the deformability of the exogenous antigen-expressing EHC is assessed by measuring the survival rate through a series of micron-scale constrictions of defined dimensions at a fixed pressure in a microfluidic device. The microfluidic device can be selected from one of the following, including but not limited to, a poly dimethyl siloxane (PDMS) chip with micron-scale constrictions (e.g., Hoelzle et al. J Vis Exp 2014 91:e51474); a chip with funnel-shaped constrictions (e.g., Guo et al. Lab Chip 2012 12:1143); a PDMS chip with pillars (e.g., Zhang et al. PNAS 2012 109(46):18707); or an in vitro artificial spleen microbead packed column (Guillaume DePlaine et al., Blood 2011, 117(8)).

In one embodiment, the ability of the exogenous antigen-expressing EHC to circulate in vivo without causing substantial vascular occlusion or activation of the clotting cascade is assessed by measuring the vascular occlusion of the EHCs. Vascular occlusion of the exogenous antigen-expressing EHC can be assessed using an in vitro assay. For example, the vascular occlusion of the exogenous antigen-expressing EHC is assessed using an ex vivo assay. The exogenous antigen-expressing EHC is incubated at a 1:1 ratio with reference human red blood cells and induction of multi-cell rosettes are assessed by light microscopy in comparison to a reference assay with Rh-mismatched blood. The vascular occlusion of the exogenous antigen-expressing EHC is assessed by measuring the adhesion of the EHCs to human vascular endothelial cells under flow conditions, see e.g., Kaul D K, Finnegan E, and Barabino G A (2009)

Microcirculation 16(1):97-111. Alternatively or in addition, vascular occlusion is assessed by measuring the peripheral resistance unit (PRU) increase in an ex vivo perfusion assay of rat vascular endothelium, see e.g., Kaul, Fabry and Nagel, PNAS 1989, 86:3356. Further, vascular occlusion is assessed by intravital microscopy, see e.g., Zennadi et al. 2007 Blood 110(7):2708. Vascular occlusion may also be assessed by measuring flow rates and adhesion of the EHCs in vitro graduated height flow chambers, see e.g., Zennadi et al 2004, Blood 104(12):3774.

In some embodiments, the safety of the population of exogenous antigen-expressing EHCs is assessed by measuring the immunogenicity of the population of EHCs using a suitable in vitro or in vivo assay.

For example, the population of exogenous antigen-expressing EHCs a) does not induce agglutination in a Coombs test using serum from the intended recipient subject or b) does not induce agglutination in a Coombs test using pooled human serum.

In one embodiment, the population of exogenous antigen-expressing EHCs is derived from a progenitor cell that has been genotyped for the predominant blood group antigens and matched to the blood group antigen genotype of the recipient.

In one embodiment, the population of exogenous antigen-expressing EHCs comprises an exogenous antigen or other exogenous protein that has less than 10%, 1%, 0.1%, 0.01%, 0.001%, or less than 0.001% predicted T cell reactivity by an in silico T cell epitope prediction algorithm.

In one embodiment, the population of exogenous antigen-expressing EHCs comprises an exogenous antigen or other exogenous protein that has less than 10%, 1%, 0.1%, 0.01%, 0.001%, or less than 0.001% reactivity in an in vitro T cell activation assay, e.g., Antitope Inc. EpiScreen assay.

For example, exogenous antigen-expressing EHCs derived from erythrocytes can be centrifuged and resuspended in appropriate solution (e.g., standard AS-3 solution) for infusion into subjects in need thereof. In some embodiments, the exogenous antigen-expressing EHCs to be infused have the same ABO type as that of the recipient to minimize the risk of infusion-associated immune reactions. The exogenous antigen-expressing EHCs can also be pre-treated to remove blood type-specific antigens or otherwise reduce antigenicities. Methods suitable for this purpose include, but are not limited to, those described in U.S. Patent Application Publication Nos. 20010006772 and 20030207247.

Therapeutic Compositions

Provided are compositions containing EHCs having effective levels of exogenous antigen of interest. Such compositions contain a plurality of EHCs, e.g., $1\times10^3$ cells, or $1\times10^4$, $1\times10^5$, $1\times10^6$, $1\times10^7$, $1\times10^8$, $1\times10^9$, $1\times10^{10}$, $1\times10^{11}$, $1\times10^{12}$, or greater than $1\times10^{12}$ cells. EHCs of the invention can, for example, be administered as packed red blood cells in a saline solution at a concentration of 10%, 20%, 30%, 40%, 50%, 60%, 70%, 80%, 90%, or greater than 90% mass to volume ratio (% m/v). The time of administration to a patient may range from 10 minutes to four hours, or more.

The cultured EHCs of the invention can be stored in an appropriate buffer, e.g. an FDA-approved anticoagulant preservative solution such as anticoagulant citrate-dextrose A (ACD-A), citrate-phosphate dextrose (CPD), Citratephosphate-dextrose-dextrose (CP2D), or citrate-phosphate-dextrose-adenine (CPDA-1). The compositions may be stored for up to 21 days.

Alternatively, the cultured EHCs of the invention can be stored in an approved additive solution, e.g. AS-1 (Adsol), AS-3 (Nutricel), AS-5 (Optisol), or AS-7 (SOLX).

Alternatively, the cultured EHCs of the invention can be stored in a glycerol cryoprotective solution. The compositions may be frozen and stored for up to 10 years. Frozen cells may be thawed and deglycerolized by successive washing steps, for example with 0.9% sodium chloride before use.

Considering the life span of human and murine erythrocytes (120 and 50 days, respectively (see, e.g. Khandelwal et al., Transfusion 2007), it may be advantageous to stimulate artificial erythrocyte aging to increase phagocytosis by antigen presenting cells. The most important and physiological mechanism of erythrocyte removal from the circulation is immune-mediated (Singer et al., PNAS 1986) after exposure of new antigenic sites on RBC cell surface such as phosphatidylserine externalization (Schroit et al., J Biol Chem 1985) or Band 3 protein clustering (Kay, PNAS 1975; Turrini et al., J Biol Chem 1991) induced artificially with calcium ionophore or BS3 chemical treatments, respectively.

The cultured EHCs of the invention may be treated with a phagocytosis-inducing agent such as, e.g. calcium ionophore or BS3. The plurality of cultured EHCs of the invention may comprise EHCs that have been treated with a phagocytosis-inducing agent, such as, e.g. calcium ionophore or BS3, for differing lengths of time, such that upon administration to a subject, the plurality of cultured EHCs of the invention are phagocytosed at different rates, e.g. continuously over the course of one day or several days rather than as a bolus.

Provided herein are compositions and pharmaceutical compositions comprising a plurality of cultured EHCs that comprise an exogenous antigen of interest. The compositions and pharmaceutical compositions may comprise a solution of appropriate storage buffer such as, e.g. anticoagulant citrate-dextrose A. The compositions and pharmaceutical compositions comprising the plurality of cultured EHCs that comprise an exogenous antigen of interest may additionally comprise an approved additive such as, e.g. Adsol. The compositions and pharmaceutical compositions comprising the plurality of cultured EHCs that comprise an exogenous antigen of interest may additionally comprise a glycerol cryoprotective solution for frozen storage.

Provided herein are EHCs comprising an exogenous antigen of interest selected from one or more of the antigens of Table F, Table G, Table H, Table I and Table J, such as e.g. myelin basic protein, proteolipid protein, myelin oligodendrocyte glycoprotein, pancreatic beta cell antigen, insulin, flagellin, gluten, 2S albumin, hyalauronidase, factor VIII, factor IX, and anti-TNFa, adenosine deaminase, L-asparaginase, rasburicase, antithymocyte globulin, L-arginase, L-methionase, preproinsulin, proinsulin, insulin, GAD65, GAD67, IA-2, IA-2β, thyroglobulin, thyroid peroxidase, thyrotropin receptor, myelin oligodendrocyte glycoprotein, proteolipid protein, collagen II, collagen IV, acetylcholine receptor, matrix metalloprotein 1 and 3, molecular chaperone heat-shock protein 47, fibrillin-1, PDGF receptor a, PDGF receptor β, nuclear protein SS-A, conarachin (Ara h 1), allergen II (Ara h 2), arachis agglutinin (Ara h 6), a-lactalbumin (ALA), lactotransferrin, glutein, low molecular weight glutein, a-gliadin, γ-gliadin, hordein, secalin, avenin and combinations thereof. A plurality of EHCs comprising an exogenous antigen of interest may be provided as a composition or pharmaceutical composition.

Provided herein are expression vectors encoding one or more antigens of Table F, Table G, Table H, Table I and Table J, such as e.g. myelin basic protein, proteolipid protein, myelin oligodendrocyte glycoprotein, pancreatic beta cell antigen, insulin, flagellin, gluten, Ara h2, 2S albumin, hyaluronidase, factor VIII, factor IX, and anti-TNFa, optionally fused to one of the endogenous erythroid proteins of Table C.

Provided herein are pharmaceutical compositions comprising exogenous antigen-expressing EHCs that are suitable for administration to a subject. The pharmaceutical compositions generally comprise a population of exogenous antigen-expressing EHCs and a pharmaceutically-acceptable carrier in a form suitable for administration to a subject. Pharmaceutically-acceptable carriers are determined in part by the particular composition being administered, as well as by the particular method used to administer the composition. Accordingly, there is a wide variety of suitable formulations of pharmaceutical compositions comprising a population of exogenous antigen-expressing EHCs. (See, e.g., Remington's Pharmaceutical Sciences, Mack Publishing Co., Easton, Pa. 18th ed. (1990)). The pharmaceutical compositions are generally formulated as sterile, substantially isotonic and in full compliance with all Good Manufacturing Practice (GMP) regulations of the U.S. Food and Drug Administration.

Pharmaceutically-acceptable excipients include excipients that are generally safe, non-toxic, and desirable, including excipients that are acceptable for veterinary use as well as for human pharmaceutical use. Such excipients can be solid, liquid, semisolid, or, in the case of an aerosol composition, gaseous.

Examples of carriers or diluents include, but are not limited to, water, saline, Ringer's solutions, dextrose solution, and 5% human serum albumin. The use of such media and compounds for pharmaceutically active substances is well known in the art. Except insofar as any conventional media or compound is incompatible with the exogenous antigen-expressing EHCs described herein, use thereof in the compositions is contemplated. Supplementary therapeutic agents may also be incorporated into the compositions. Typically, a pharmaceutical composition is formulated to be compatible with its intended route of administration. The exogenous antigen-expressing EHCs can be administered by parenteral, topical, intravenous, oral, subcutaneous, intraarterial, intradermal, transdermal, rectal, intracranial, intraperitoneal, intranasal; intramuscular route or as inhalants. The exogenous antigen-expressing EHCs can optionally be administered in combination with other therapeutic agents that are at least partly effective in treating the disease, disorder or condition for which the exogenous antigen-expressing EHCs are intended.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be preferable to include isotonic compounds, e.g., sugars, polyalcohols such as manitol, sorbitol, sodium chloride in the composition. Prolonged absorption of the injectable compositions can be brought about by including in the composition a compound which delays absorption, e.g., aluminum monostearate and gelatin.

Sterile injectable solutions can be prepared by incorporating the exogenous antigen-expressing EHCs in an effective amount and in an appropriate solvent with one or a combination of ingredients enumerated herein, as desired. Generally, dispersions are prepared by incorporating the exogenous antigen-expressing EHCs into a sterile vehicle that contains a basic dispersion medium and any desired other ingredients. In the case of sterile powders for the preparation of sterile injectable solutions, methods of preparation are vacuum drying and freeze-drying that yields a powder of the active ingredient plus any additional desired ingredient from a previously sterile-filtered solution thereof. The exogenous antigen-expressing EHCs can be administered in the form of a depot injection or implant preparation which can be formulated in such a manner to permit a sustained or pulsatile release of the exogenous antigen-expressing EHCs, their exogenous antigen(s) and/or their optional payload(s).

Oral compositions generally include an inert diluent or an edible carrier. They can be enclosed in gelatin capsules or compressed into tablets. For the purpose of oral therapeutic administration, the exogenous antigen-expressing EHCs can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

For administration by inhalation, the exogenous antigen-expressing EHCs are delivered in the form of an aerosol spray from pressured container or dispenser which contains a suitable propellant, e.g., a gas such as carbon dioxide, or a nebulizer.

Systemic administration of compositions comprising exogenous antigen-expressing EHCs can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the modified red blood cells are formulated into ointments, salves, gels, or creams as generally known in the art.

The exogenous antigen-expressing EHCs can also be prepared as pharmaceutical compositions in the form of suppositories (e.g., with conventional suppository bases such as cocoa butter and other glycerides) or retention enemas for rectal delivery.

In some embodiments, the exogenous antigen-expressing EHCs are prepared with carriers that will decrease the rate with which exogenous antigen-expressing EHCs are eliminated from the body of a subject. For example, controlled release formulation are suitable, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

In one embodiment the pharmaceutical composition comprising exogenous antigen-expressing EHCs is administered intravenously into a subject that would benefit from the pharmaceutical composition. In other embodiments, the composition is administered to the lymphatic system, e.g., by intralymphatic injection or by intranodal injection (see e.g., Senti et al., 2008 PNAS 105(46): 17908), or by intramuscular injection, by subcutaneous administration, by direct injection into the thymus, or into the liver.

In one embodiment, the pharmaceutical composition comprising exogenous antigen-expressing EHCs is administered as a liquid suspension. In one embodiment the pharmaceutical composition is administered as a coagulated formulation that is capable of forming a depot following administration, and in a preferred embodiment slowly release exogenous antigen-expressing EHCs into circulation, or in a preferred embodiment remain in depot form.

In one embodiment, the pharmaceutical composition comprising exogenous antigen-expressing EHCs is stored using methods and buffer compositions that are capable of maintaining viability of the exogenous antigen-expressing EHCs. For example, deoxygenation prior to storage to maintain an anaerobic state, manipulation of pH, supplementation of metabolic precursors, manipulation of osmotic balance, increasing of the volume of the suspending medium, and/or reduction of oxidative stress by adding protective molecules can be used to maintain the viability of the exogenous antigen-expressing EHCs. Several studies employing a combination of these strategies have reported maintenance of viability of erythrocytes allowing an extension of storage beyond 6 weeks (see e.g., Yoshida and Shevkoplyas, Blood Transfus 2010 8:220).

Pharmaceutically acceptable carriers or excipients may be used to deliver the exogenous antigen-expressing EHCs described herein. Excipient refers to an inert substance used as a diluent or vehicle. Pharmaceutically acceptable carriers are used, in general, with a compound so as to make the compound useful for a therapy or as a product. In general, for any substance, a pharmaceutically acceptable carrier is a material that is combined with the substance for delivery to a subject. Conventional pharmaceutical carriers, aqueous, powder or oily bases, thickeners and the like may be necessary or desirable. In some cases the carrier is essential for delivery, e.g., to solubilize an insoluble compound for liquid delivery; a buffer for control of the pH of the substance to preserve its activity; or a diluent to prevent loss of the substance in the storage vessel. In other cases, however, the carrier is for convenience, e.g., a liquid for more convenient administration. Pharmaceutically acceptable salts of the compounds described herein may be synthesized according to methods known to those skilled in the arts.

Typically, pharmaceutically acceptable compositions are highly purified to be free of contaminants, are biocompatible and not toxic, and are suited to administration to a subject. If water is a constituent of the carrier, the water is highly purified and processed to be free of contaminants, e.g., endotoxins.

The pharmaceutically acceptable carrier may be lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and/or mineral oil, but is not limited thereto. The pharmaceutical composition may further include a lubricant, a wetting agent, a sweetener, a flavor enhancer, an emulsifying agent, a suspension agent, and/or a preservative.

Provided are pharmaceutical compositions containing exogenous antigen-expressing EHCs having effective levels of exogenous antigens. Such compositions contain a plurality of exogenous antigen-expressing EHCs, e.g., $1\times10^3$ EHCs, or $1\times10^4$, $1\times10^5$, $1\times10^6$, $1\times10^7$, $1\times10^8$, $1\times10^9$, $1\times10^{10}$, $1\times10^{11}$, $1\times10^{12}$, or greater than $1\times10^{12}$ EHCs. In specific examples, exogenous antigen-expressing EHCs generated from EHCs may be administered as packed red blood cells in a saline solution at a concentration of 10%, 20%, 30%, 40%, 50%, 60%, 70%, 80%, 90%, or greater than 90% mass to volume ratio (% m/v). The time of administration to a patient may range from 10 minutes to four hours, or more.

In specific examples, exogenous antigen-expressing EHCs generated from EHCs can be stored in an appropriate buffer, e.g., an FDA-approved anticoagulant preservative solution such as anticoagulant citrate-dextrose A (ACD-A), citrate-phosphate dextrose (CPD), Citratephosphate-dextrose-dextrose (CP2D), or citrate-phosphate-dextrose-adenine (CPDA-1). The compositions may be stored for up to 21 days.

Alternatively, exogenous antigen-expressing EHCs generated from EHCs can be stored in an approved additive solution, e.g., AS-1 (Adsol), AS-3 (Nutricel), AS-5 (Optisol), or AS-7 (SOLX).

Alternatively, exogenous antigen-expressing EHCs generated from EHCs can stored in a glycerol cryoprotective solution. The compositions may be frozen and stored for up to 10 years. Frozen cells may be thawed and deglycerolized by successive washing steps, for example with 0.9% sodium chloride before use.

Provided herein are compositions and pharmaceutical compositions comprising a plurality of cultured EHCs that comprise an exogenous antigen. The compositions and pharmaceutical compositions may comprise a solution of appropriate storage buffer such as, e.g., anticoagulant citrate-dextrose A. The compositions and pharmaceutical compositions comprising the plurality of cultured EHCs that comprise an exogenous antigen may additionally comprise an approved additive such as, e.g., Adsol. The compositions and pharmaceutical compositions comprising the plurality of cultured EHCs that comprise exogenous antigen may additionally comprise a glycerol cryoprotective solution for frozen storage.

In one embodiment, the exogenous antigen-expressing EHC is able to form a multi-complex aggregate, e.g., a dimer, a trimer, a multimer, with another exogenous antigen-expressing EHC.

In one embodiment the exogenous antigen-expressing EHC is able to form a multi-complex aggregate, e.g., a dimer, a trimer, a multimer, with component of the circulatory system, e.g an erythrocyte, a reticulocyte, a platelet, a macrophage, a T cell, a B cell, a mast cell.

The dosage and frequency of the administration of the exogenous antigen-expressing EHCs and pharmaceutical compositions thereof can be determined by the attending physician based on various factors such as the severity of disease, the patient's age, sex and diet, the severity of any inflammation, time of administration, and other clinical factors. In one example, an intravenous administration is initiated at a dose which is minimally effective, and the dose is increased over a pre-selected time course until a positive effect is observed. Subsequently, incremental increases in dosage are made limiting to levels that produce a corresponding increase in effect while taking into account any adverse affects that may appear.

Non-limited examples of suitable dosages can range, for example, from $1\times10^3$ to $1\times10^{14}$, from $1\times10^3$ to $1\times10^7$, from $1\times10^5$ to $1\times10^6$, from $1\times10^7$ to $1\times10^{11}$, from $1\times0$ to $1\times10^9$, from $1\times10^{10}$ to $1\times10^{14}$, from $1\times10^{11}$ to $1\times10^{13}$, or from $5\times10^{11}$ to $5\times10^{12}$ exogenous antigen-expressing EHCs. Specific examples include about $1\times10^3$, $2\times10^3$, $3\times10^3$, $4\times10^3$, $5\times10^3$, $6\times10^3$, $7\times10^3$, $8\times10^3$, $9\times10^3$, $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, or more exogenous antigen-expressing EHCs. Each dose of exogenous antigen-expressing EHCs can be administered at intervals such as once daily, once weekly, twice weekly, once monthly, or twice monthly. Each EHC may express a range of antigen molecules, for example, from about 100 to $10^7$, or from about $10^3$ to $10^6$. Specific examples include about 1000, 3000, 5000, $1\times10^4$, $3\times10^4$, $5\times10^4$, $1\times10^5$, $3\times10^5$, $5\times10^5$, $1\times10^6$, $3\times10^6$, $5\times10^6$, $1\times10^7$, or more exogenous antigen molecules per EHC.

"EHC-based proportional dosage" is the number of exogenous antigen-expressing EHCs administered as a dose relative to a naturally occurring quantity of circulating entities. The circulating entities may be cells, e.g., erythrocytes, reticulocytes, or lymphocytes, or targets, e.g., antigens, antibodies, viruses, toxins, cytokines, etc. The units are defined as exogenous antigen-expressing EHC per circulating entity, ie SCMRC/CE. This dosage unit may include $10^{-7}$, $10^{-6}$, $10^{-5}$, $10^{-4}$, $10^{-3}$, $10^{-2}$, $10^{-1}$, 1, 10, $10^2$, $10^3$, $10^4$, $10^5$, $10^6$, $10^7$, $10^8$, $10^9$.

The pharmaceutical compositions described herein comprise an exogenous antigen-expressing EHC and optionally a pharmaceutically active or therapeutic agent. The therapeutic agent can be a biological agent, a small molecule agent, or a nucleic acid agent.

Dosage forms are provided that comprise a pharmaceutical composition comprising an exogenous antigen-expressing EHC described herein. In some embodiments, the dosage form is formulated as a liquid suspension for intravenous injection.

Medical devices are provided that comprise a container holding a pharmaceutical composition comprising an exogenous antigen-expressing EHC described herein and an applicator for intravenous injection of the pharmaceutical composition to a subject.

Medical kits are provided that comprise a pharmaceutical composition comprising an exogenous antigen-expressing EHC described herein and a medical device for intravenous injection of the pharmaceutical composition to a subject.

A pharmaceutically acceptable suspension of exogenous antigen-expressing EHCs is preferably packaged in a volume of approximately 10 to approximately 250 ml. The packaging can be a syringe or an IV bag suitable for transfusions. Administration of the suspension is carried out, e.g., by intravenous or intra-arterial injection, optionally using a drip from an IV bag or the like. The administration is typically carried out intravenously in the arm or via a central catheter. For administrations exceeding 50 ml use of a drip is preferred.

Treatment of Diseases

Provided are methods of inducing immune tolerance. The methods include administering to a subject in need of induction of immune tolerance a pharmaceutical composition of the erythrocyte cells that comprise an exogenous antigen of interest provided herein in an amount and/or a dosing frequency sufficient to induce immune tolerance in the subject.

The pharmaceutical compositions of the invention provide erythrocyte cells that comprise an exogenous antigen of interest that are useful to promote or enhance immune tolerance. Immune tolerance may be used to treat, prevent, or reduce the severity of a disease, disorder, or condition associated with immune activation.

Diseases of immune activation include autoimmune diseases, such as, e.g. multiple sclerosis, type 1 diabetes, rheumatoid arthritis, and membranous nephritis, and those listed in Table F. Diseases of immune activation also include inflammatory diseases, such as, e.g. Crohn's disease, ulcerative colitis, celiac disease, or other idiopathic inflammatory bowl diseases, and those listed in Table G. Diseases of immune activation also include allergic diseases, such as, e.g. asthma, peanut allergy, shellfish allergy, pollen allergy, milk protein allergy, insect sting allergy, and latex allergy, and those listed in Table H. Diseases of immune activation also include immune activation in response to a therapeutic protein, administered to treat a primary condition, that lessens the efficacy of the therapeutic protein, such as, e.g., clotting factor VIII in hemophilia A, clotting factor IX in hemophilia B, anti-tumor necrosis factor alpha (TNFa) antibodies in rheumatoid arthritis and other inflammatory diseases, glucocerebrosidase in Gaucher's disease, or asparaginase in acute lymphoblastic leukemia (ALL), and those listed in Table I, Table J, Table 5, and Table 7.

Further provided are methods for treating an immune activation disease. The methods include administering to a subject in need of induction of treatment a pharmaceutical composition of the erythrocyte cells that comprise an exogenous antigen of interest provided herein in an amount sufficient to treat the immune activation disease. For example, a subject that has or is suspected of having an immune activation disease such as autoimmune disease, inflammatory disease or allergic disease would benefit from the treatment methods provided.

In some embodiments a patient is suffering from an autoimmune disease or condition or a self-antibody mediated disease or condition, in which the patient's immune system is active against an endogenous molecule, for example a protein antigen, such that the immune system attacks the endogenous molecule, induces inflammation, damages tissue, and otherwise causes the symptoms of the autoimmune or self-antibody disease or conditions. The immune response might be driven by antibodies that bind to the endogenous molecule, or it may be driven by overactive T cells that attack cells expressing the endogenous molecule, or it may be driven by other immune cells such as regulatory T cells, NK cells, NKT cells, or B cells. In these embodiments, the antigenic protein or a fragment thereof may be expressed on an enucleated hematopoietic cell of the invention. A population of these cells, when administered once or more to the patient suffering from the disease or condition, would be sufficient to induce tolerance to the antigenic protein such that it no longer induced activation of the immune system, and thus would treat or ameliorate the symptoms of the underlying disease or condition.

For example, a patient suffering from acquired thrombotic thrombocytopenic purpura (TTP) has an aberrant self-antibody mediated disease in which antibodies are generated against endogenous ADAMTS13 protein rendering it ineffective at performing its von Willebrand Factor-cleaving activities, which results in microthrombi forming throughout the vasculature and consequent thrombocytopenia. In this embodiment, the ADAMTS13 antigen is expressed on an eucleated hematopoietic cell and administered to a patient suffering from TTP in an amount effective to induce tolerance to ADAMTS13, thus reducing the quantity of inhibitory anti-ADAMTS13 self-antibodies in circulation and restoring the ability of the body to cleave von Willebrand Factor thus reducing the symptoms of the disease. In a preferred embodiment, only the antigenic fragment of ADAMTS13 is expressed on the enucleated hematopoietic cell. In a preferred embodiment, the full-length ADAMTS13 is expressed on the enucleated hematopoietic cell. In a preferred embodiment, the full-length ADAMTS13 is expressed on the enucleated hematopoietic cell and is enzymatically active, such that the administered cell product is able to both induce tolerance and also therapeutically cleave von Willebrand Factor.

In another example, a patient suffering from atypical hemolytic anemic syndrome (aHUS) has an aberrant self-antibody response to the endogenous protein Complement Factor H (CFH), preventing CFH from performing it's complement regulatory function. As a result, complement overactivation occurs in the vasculature leading to intravascular hemolysis. In this embodiment, the CFH antigen is expressed on an enucleated hematopoietic cell and administered to a patient suffering from aHUS in an amount effective to induce tolerance to CFH, thus reducing the quantity of inhibitory anti-CFH self-antibodies in circulation and restoring the ability of the body to inhibit complement thus reducing the symptoms of the disease. In a preferred embodiment, only the antigenic fragment of CFH is expressed on the enucleated hematopoietic cell. In a preferred embodiment, the full-length CFH is expressed on the enucleated hematopoietic cell. In a preferred embodiment, the full-length CFH is expressed on the enucleated hematopoietic cell and is therapeutically active, such that the administered cell product is able to both induce tolerance and also therapeutically promote complement regulation.

In another example, a patient suffering from multiple sclerosis (MS) has an autoimmune response to the polypeptide myelin that sheathes neurons. As a result, T cells attack the myelin and the resultant inflammation causes demyelination of the nerve fibers and impairs the ability for electrical signals to be sent along the nerves leading to the symptoms of multiple sclerosis. In this embodiment, the myelin antigen is expressed on an enucleated hematopoietic cell and administered to a patient suffering from MS in an amount effective to induce tolerance to myelin antigen, thus reducing the anti-myelin immune response and restoring the ability of the body to send electrical impulses down myelinated nerve fibers, thus reducing the symptoms of the disease. In a preferred embodiment, only one or more antigenic fragments of myelin are expressed on the enucleated hematopoietic cell. In a preferred embodiment, the full-length myelin protein is expressed on the enucleated hematopoietic cell.

In another example, a patient suffering from type 1 diabetes (T1D) has an autoimmune response to the beta islet cells of the pancreas. As a result, T cells kill the beta islet cells reducing or eliminating the pancreas' ability to produce and secrete insulin, which leads to the symptoms and pathology of T1D. In this embodiment, the beta cell antigen is expressed on an enucleated hematopoietic cell and administered to a patient suffering from T1D in an amount effective to induce tolerance to beta cell antigen, thus reducing the anti-beta cell immune response and restoring the ability of the pancreas to produce and secrete insulin, thus reducing the symptoms of the disease. In a preferred embodiment, only one or more antigenic fragments of beta cell antigen are expressed on the enucleated hematopoietic cell. In a preferred embodiment, the full-length beta cell protein is expressed on the enucleated hematopoietic cell.

Further provided are methods of reducing or alleviating an immune activation in response to a therapeutic protein treatment regimen. The methods include administering to a subject in need of reducing or alleviating an immune activation in response to a therapeutic protein treatment regimen a pharmaceutical composition of the erythrocyte cells that comprise an exogenous antigen of interest provided herein in an amount sufficient to reduce or alleviate the immune activation in response to a therapeutic protein treatment regimen.

In some embodiments a patient is suffering from a disease or condition for which a therapeutic protein can be administered to treat or ameliorate the symptoms of the disease or condition, but the therapeutic protein is immunogenic such that the patient elicits an immune response against the therapeutic protein such that it is no longer effective at treating or ameliorating the original disease. For example, the immunogenic therapeutic protein might be derived from a non-human source, e.g. bovine, porcine, or non-human primate, or from a non-mammalian source, e.g. bacterial, fungal, or plat-derived, or the immunogenic therapeutic protein may be derived from a human source but the repetitive exposure and dosing might be sufficient to induce immunogenicity. The immune response might be driven by antibodies that bind to the immunogenic therapeutic protein and inhibit its function (neutralizing antibodies) or that bind to the immunogenic therapeutic protein and trigger its clearance by other immune cells (opsonizing antibodies). In these embodiments, the immunogenic therapeutic protein or an antigenic fragment thereof may be expressed on an enucleated hematopoietic cell of the invention. A population of these cells, when administered once or more to the patient suffering from the disease, would be sufficient to induce tolerance to the immunogenic therapeutic protein such that it was no longer neutralized or opsonized by the immune system. In one preferred embodiment, the immunogenic therapeutic protein expressed on the surface of the enucleated hematopoietic cell of the invention is therapeutically active on the cell in circulation, such that the composition of cell and protein is able to both induce tolerance and treat or ameliorate the symptoms of the underlying disease or condition when administered to the patient. In another preferred embodiment the antigenic fragment of the immunogenic therapeutic protein expressed on the surface of the enucleated hematopoietic cell of the invention is not therapeutically active on the cell in circulation, such that the composition of cell and protein is able to induce tolerance when administered to the patient but a separate formulation of immunogenic therapeutic protein is administered to treat or ameliorate the symptoms of the underlying disease or condition.

For example, a patient suffering from hemophilia A requires infusions of clotting factor VIII (FVIII) to restore proper coagulation. However many patients develop neutralizing antibodies to FVIII despite it being human derived, which render the therapeutic ineffective and lead to a life-threatening risk of bleeding. In one embodiment, an exogenous FVIII expressing enucleated hematopoietic cell is administered to the patient suffering from hemophilia A such that (1) the levels of circulating active FVIII are restored to a level necessary to ameliorate the symptoms and prevent severe uncontrolled bleeding, and such that (2) tolerance is induced to FVIII.

In another example, a patient suffering from rheumatoid arthritis requires injections of anti-TNFa antibody to reduce the inflammation associated with that disease. However may patients develop neutralizing antibodies against the anti-TNFa antibody that render the therapeutic antibody ineffective. In this instance, the patient typically suffers a worsening of symptoms and either has to increase the dose of the anti-TNFa antibody or switch to a different anti-TNFa antibody with a different coding sequence of amino acids. In this embodiment, an enucleated hematopoietic cell expressing an antigenic fragment of anti-TNFa is administered to a patient with rheumatoid arthritis who has developed neutralizing antibodies against the anti-TNFa antibody. The composition is administered at a dose sufficient to induce tolerance to the anti-TNFa antibody, allowing effective administration of anti-TNFa to reduce the circulating TNFa levels and thus reduce the symptoms of rheumatoid arthritis in the patient.

In another example, a patient suffering from phenylketonuria (PKU) is treated with pegylated phenylalanine ammonia lyase (PAL), a non-human enzyme. The patient develops opsonizing and neutralizing antibodies against PAL that also elicit an allergic reaction upon administration of the therapeutic protein. This immune response not only renders the PAL ineffective, it also threatens the health of the patient. In one embodiment, enucleated hematopoietic cells expressing exogenous PAL are administered to a patient suffering from PKU in an amount sufficient to induce tolerance to PAL. In a preferred embodiment, the cell-expressed PAL is active on the cell, and the composition is able to reduce the circulating levels of phenylalanine and treat or ameliorate the symptoms of phenylketonuria in addition to preventing a dangerous immune reaction against PAL. In another preferred embodiment, an antigenic fragment of PAL is expressed on the enucleated hematopoietic cell, and this cell-expressed fragment is not therapeutically active, so a separate formulation of PAL is administered to the patient to treat or ameliorate the symptoms of phenylketonuria. The tolerance-inducing cell composition can be administered prior to administering the therapeutic formulation of PAL, or the tolerance-inducing cell composition can be administered concurrent to the administration of the therapeutic formulation of PAL.

In some embodiments a patient is suffering from an allergic disease, for example an allergy to animal dander, black walnut, brazil nut, cashew nut, chestnut, dust mites, egg, english walnut, fish, hazelnut, insect venom, latex, milk, mold, peanuts, pollen, grass, shellfish, soy, tree nuts, or wheat. A patient suffering from an allergy may mount an immune response upon contact with the antigenic fragment of the allergen, for example through diet, skin contact, injection, or environmental exposure. The immune response may involve IgE antibody, sensitized mast cells, degranulation, histamine release, and anaphylaxis, as well as canonical immune cells like T cells, B cells, dendritic cells, T regulatory cells, NK cells, neutrophils, and NKT cells. The allergic reaction may cause discomfort or it may be severe enough to cause death, and thus requires constant vigilance on the part of the sufferer as well as his or her family and caretakers. In these embodiments, the antigenic protein or a fragment thereof may be expressed on an enucleated hematopoietic cell of the invention. A population of these cells, when administered once or more to the patient suffering from the allergic disease or condition, would be sufficient to induce tolerance to the antigenic protein such that it no longer induced activation of the immune system upon exposure, and thus would treat or ameliorate the symptoms of the underlying allergic disease or condition.

In one example a patient suffering from peanut allergy has an immune response following exposure to peanut antigen AraH1. In this embodiment, AraH1 is expressed on an enucleated hematopoietic cell and administered to a patient suffering from peanut allergy in an amount effective to induce tolerance to AraH1 antigen, thus reducing the allergic immune response and restoring the ability of the individual to safely consume peanuts, thus reducing the symptoms of the disease. In a preferred embodiment, only one or more antigenic fragments of AraH1 are expressed on the enucleated hematopoietic cell. In a preferred embodiment, the full-length AraH1 protein is expressed on the enucleated hematopoietic cell.

Certain aspects of the invention relate to EHCs that comprise antigen that is recognized by immune cells in human leukocyte antigen (HLA) mismatch-mediated diseases, such as, e.g. graft-versus-host disease or organ transplant rejection.

In some embodiments, a patient is suffering from a disease or condition of human leukocyte antigen (HLA)-mismatch in which immune cells are activated against HLA antigens on a tissue and attack the tissue. This commonly occurs following allogeneic transplantation of an organ or tissue from a donor who is not a perfect match and leads to the medical condition of transplant rejection, in which the patient's immune system attacks the foreign tissue or organ and causes the transplanted organ or tissue to die. Another common HLA-mismatch condition is Graft-versus-Host Disease (GVHD) in which a patient has received an allogeneic bone marrow transplantation from a donor who is not a perfect match and in which the transplanted immune cells (graft) become activated and attack the recipients organs (host), which are recognized as foreign, causing the damage of host tissues and organs and leading to severe consequences including death. HLA-mismatch immune activation is typically mediated by T cells, but can also involve T regulatory cells, NK cells, NKT cells, B cells, antibodies, dendritic cells, monocytes, macrophages, and neutrophils. In these embodiments, the antigenic HLA molecule or a fragment thereof may be expressed on an enucleated hematopoietic cell of the invention. A population of these cells, when administered once or more to the patient suffering from the HLA-mismatch disease or condition, would be sufficient to induce tolerance to the antigenic HLA molecule such that it no longer induced activation of the immune system and thus would treat or ameliorate the symptoms of the underlying HLA-mismatch disease or condition, for example the survival of the transplanted organ or the survival of the patient. In a preferred embodiment, the HLA molecule expressed on the surface of the cell also contains a peptide loaded into the HLA molecule.

The erythrocyte cells that comprise an exogenous antigen that are used for the methods described herein can be derived autologously, i.e. from the same subject, or may be allogeneically derived, i.e. from a different cell donor.

The pharmaceutical compositions may be administered to the subject for example by intravenous transfusion or intramuscular injection.

OTHER EMBODIMENTS

It is to be understood that this invention is not limited to particular methods, reagents, compounds, compositions or biological systems, which can, of course, vary. It is also to be understood that the terminology used herein is for the purpose of describing particular aspects only, and is not intended to be limiting.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

In some embodiments, the exogenous antigen-expressing EHC comprising a CR1 exogenous antigen is not generated in a mouse and/or is not generated from mouse erythroid cells. In some embodiments, the exogenous antigen-expressing EHC comprising a CR1 exogenous antigen is not generated in a laboratory animal and/or is not generated from an erythroid cells derived from a laboratory animal. In some embodiments, the exogenous antigen-expressing EHC is generated from megakaryocytes or platelets. In some embodiments, the exogenous antigen-expressing EHC is generated from an erythroid cell, such as, e.g. an erythrocyte or a reticulocyte. In some embodiments, the exogenous antigen-expressing EHC is not generated from a neutrophil, an eosinophil, or a basophil. In some embodiments, the exogenous antigen-expressing EHC is not generated from a monocyte or a macrophage. In some embodiments, the exogenous antigen-expressing EHC is not generated from a CD34$^+$Thy-1$^+$ hematopoietic stem cell or cell populations enriched in CD34$^+$Lin$^-$ or CD34$^+$Thy-1$^+$Lin$^-$ cells. In some embodiments, the exogenous antigen-expressing EHC does not comprise an exogenous antigen comprising an extracellular domain of an HIV coreceptor. In some embodiments, the exogenous antigen-expressing EHC does not comprise an exogenous antigen capable of binding to a virus. In some embodiments, the exogenous antigen-expressing EHC does not comprise an exogenous antigen comprising CD4. In some embodiments, the exogenous antigen-expressing EHC does not comprise an exogenous antigen comprising an HIV coreceptor. In some embodiments, the exogenous antigen-expressing EHC does not comprise an exogenous antigen comprising CXCR4, CCR5, CCR1, CCR2, CCR3, CCR4, CCR8, CXCR1, CXCR2, CXCR3, CXCR6, GPR15, APJ, CMKLR1, or CX3CR1 or any combination thereof. In some embodiments, the exogenous antigen-expressing EHC does not contain an exogenous nucleic acid encoding an adenosine deaminase antigen. In some embodiments, the exogenous antigen-expressing EHC does not comprise an exogenous antigen comprising adenosine deaminase (ADA). In some embodiments, the exogenous antigen-expressing EHC does not comprise an exogenous nucleic acid encoding an oncogene. In some embodiments, the exogenous antigen-expressing EHC does not comprise an exogenous antigen comprising oncogene. In some embodiments, the exogenous antigen-expressing EHC does not contain an exogenous nucleic acid encoding cdx1, cdx2, or cdx4. In some embodiments, the exogenous antigen-expressing EHC does not comprise an exogenous antigen comprising cdx1, cdx2, or cdx4, or any combination thereof. In some embodiments, the exogenous antigen-expressing EHC does not comprise an exogenous antigen comprising a chimeric polypeptide comprising a ligand binding domain. In some embodiments, the exogenous antigen-expressing EHC does not comprise an exogenous antigen comprising an S domain that is capable of binding a ligand. In some embodiments, the exogenous antigen-expressing EHC does not comprise an exogenous antigen comprising CD3ζ, CD3η, an IL-2 receptor, an IL-3 receptor, an IL-4 receptor, an IL-7 receptor, an IL-11 receptor, an IL-13 receptor, a GM-CSF receptor, a LIF receptor, a CNTF receptor, an oncostatin M receptor, a TGF-β receptor, an EGF receptor, ATR2/neu, a HER2/neu, a HER3/c-erbB-3, Xmrk, an insulin receptor, an IGF-1 receptor, IRR, PDGF receptor, a CSF-1 receptor, c-kit, STK-1/flk-2, an FGF receptor, fig, bek, an NGF receptor, Ror1 and Ror2 or any combination thereof. In some embodiments, the exogenous antigen-expressing EHC does not comprise an exogenous antigen comprising E6 or E7 genes of human papillomavirus. In some embodiments, the exogenous antigen-expressing EHC does not comprise an exogenous antigen comprising a tumor antigen. In some embodiments, the exogenous antigen-expressing EHC does not comprise an exogenous antigen comprising glucocerebrosidase. In some embodiments, the exogenous antigen-expressing EHC does not comprise an exogenous antigen comprising asparaginase. In some embodiments, the exogenous antigen-expressing EHC does not comprise an exogenous antigen comprising arginine deiminase. In some embodiments, the exogenous antigen-expressing EHC does not comprise a fusion molecule capable of promoting fusion of the exogenous antigen-expressing EHC to a target cell that is i) different from and/or ii) acts independent of the exogenous antigen, wherein the exogenous antigen is capable of interacting with a target. In some embodiments, the exogenous antigen-expressing EHC does not comprise an exogenous antigen comprising Syncytin-1. In some embodiments, the exogenous antigen-expressing EHC does not comprise a photosensitive synthetic compound, such as, e.g. a compound that can be activated by photons or quenchable compounds. In some embodiments, the exogenous antigen-expressing EHC does not comprise an activatable molecular detection agent capable of producing a detectable response. In some embodiments, the exogenous antigen-expressing EHC does not comprise a diagnostic compound. In some embodiments, the exogenous antigen-expressing EHC does not comprise a virus or bacterium. In some embodiments, the exogenous antigen-expressing EHC is not generated from or does not comprise an autologous CD34+ cell. In some embodiments, methods of treatment and prevention using exogenous antigen-expressing EHCs generated from erythroid cells described herein do not comprise the step of detecting the erythroid cell in vivo, e.g., through a detection agent that is associated with the erythroid cell. In some embodiments, the exogenous antigen-expressing EHC is not generated from a human donor pluripotent hematopoietic stem cell. In some embodiments, a population of exogenous antigen-expressing EHCs is not expanded in a bioreactor. In some embodiments, the population of exogenous antigen-expressing EHCs after expansion and/or differentiation does not comprise a single species of differentiated human blood cells. In some embodiments, the exogenous antigen-expressing EHC is not a differentiated, mature human blood cell. In some embodiments, the exogenous antigen-expressing EHC is not generated from a blood cell derived from a universal donor, e.g. blood type O, Rh factor negative. In some embodiments, an exogenous ADA polypeptide antigen-expressing EHC is not used to treat severe combined immune deficiency (ADA-SCID). In some embodiments, methods of expansion and differentiation of the exogenous antigen-expressing EHCs do not include culturing the exogenous antigen-expressing EHCs in a medium comprising a myeloproliferative receptor (mpl) ligand. In some embodiments, the exogenous antigen-expressing EHC does not comprise a payload comprising a synthetic triphosphorylated nucleoside analog. In some embodiments, the exogenous antigen-expressing EHC does not comprise a payload comprising 2',3'-dideoxycytidine-5'-triphosphate (ddCTP) and/or 3'-azido-3'-deoxythymidine-5'-triphosphate (AZT-TP). In some embodiments, the exogenous antigen-expressing EHC does not comprise a payload comprising a bisphosphonate. In some embodiments, the exogenous antigen-expressing EHC is generated by contacting an erythroid cell with an exogenous antigen and optionally a payload without lysing and resealing the cells to incorporate the exogenous antigen and/or payload. In some embodiments, the exogenous antigen-expressing EHC is generated by contacting an erythroid cell with an exogenous antigen and optionally a payload, wherein contacting does not comprise hypotonic dialysis. In some embodiments, the exogenous antigen-expressing EHC is generated by contacting an erythroid cell with an exogenous antigen and optionally a payload, wherein contacting does not include loading the exogenous antigen and/or payload into or onto the erythroid cell. In some embodiments, the exogenous antigen is generated in an entity that is not the erythroid cell to be contacted and/or the exogenous antigen is isolated from a sample that does not comprise the erythroid cell to be contacted. For example, for a polypeptide exogenous antigen suitable entities include a cell line, an in vitro expression system, a bacterial expression system, etc.

In some embodiments, the exogenous antigen polypeptide expressed by the EHC is present on the surface of the EHC but is not non-covalently bound to the surface of the EHC. In some embodiments, the non-covalent attachment of the antigen to the surface of the EHC is not mediated by an antibody, an antibody-fragment, an antibody-like polypeptide, or a non-antibody polypeptide binding scaffold. In some embodiments, the non-covalent attachment of the exogenous antigen to the surface of the EHC is not directed against an erythroid cell antigen such as Band 3 (CD233), aquaporin-1, Glut-1, Kidd antigen, RhAg/Rh50 (CD241), Rh (CD240), Rh30 CE (CD240CE), Rh30D (CD240D), Kx, glycophorin B (CD235b), glycophorin C (CD235c), glycophorin D (CD235d), Kell (CD238), Duffy/DARCi (CD234), CR1 (CD35), DAF (CD55), globoside, CD44, ICAM-4 (CD242), Lu/B-CAM (CD239), XG1/XG2 (CD99), EMMPRIN/neur. thelin (CD147), JMH, glycosyltransferase, Cartwright, Dombrock, C4A/CAB, Scianna, MER2, s tomatin, BA-1 (CD24), GPIV (CD36), CD108, CD139, and H antigen (CD173), or another erythrocyte-binding moiety.

In some embodiments, the exogenous antigen polypeptide is not generated apart from the EHC and then conjugated to the EHC. In some embodiments, the exogenous antigen polypeptide is not enzymatically conjugated, e.g. through an autocatalytic isopeptide bond-forming reaction such as carried out, e.g. by a transpeptidase, a sortase, and/or isopeptidase. In one embodiment, the exogenous antigen polypeptide is not enzymatically conjugated using a sortase.

In some embodiments, the exogenous antigen polypeptide is not chemically conjugated, e.g. through a cross-linking agent such as a carbodiimide (including sortase 1-Ethyl-3-(3-dimethylaminopropyl)carbodiimide (EDC)).

In one embodiment, the exogenous antigen is not generated apart from the EHC and then encapsulated by the EHC. In one embodiment, the encapsulation of the exogenous antigen is not mediated by hypotonic dialysis of the EHC in the presence of exogenous antigen.

Many modifications and other embodiments of the inventions set forth herein will easily come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

As used in this specification and the appended claims, the singular forms "a", "an" and "the" include plural references unless the content clearly dictates otherwise.

The use of the alternative (e.g., "or") should be understood to mean either one, both, or any combination thereof of the alternatives.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, any concentration range, percentage range, ratio range, or integer range is to be understood to include the value of any integer within the recited range and, when appropriate, fractions thereof (such as one tenth and one hundredth of an integer), unless otherwise indicated.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

As used herein, the terms "such as", "for example" and the like are intended to refer to exemplary embodiments and not to limit the scope of the present disclosure.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, preferred materials and methods are described herein.

All publications and patent applications cited in this specification are herein incorporated by reference in their entirety for all purposes as if each individual publication or patent application were specifically and individually indicated to be incorporated by reference for all purposes. The publications discussed herein are provided solely for their disclosure prior to the filing date of the present application. Nothing herein is to be construed as an admission that the inventors described herein are not entitled to antedate such disclosure by virtue of prior invention or for any other reason.

Definitions

"Administration," "administering" and variants thereof means introducing a composition, such as an exogenous antigen-expressing EHC, or agent into a subject and includes concurrent and sequential introduction of a composition or agent. The introduction of a composition or agent into a subject is by any suitable route, including orally, pulmonarily, intranasally, parenterally (intravenously, intramuscularly, intraperitoneally, or subcutaneously), rectally, intralymphatically, or topically. Administration includes self-administration and the administration by another. A suitable route of administration allows the composition or the agent to perform its intended function. For example, if a suitable route is intravenous, the composition is administered by introducing the composition or agent into a vein of the subject. Administration can be carried out by any suitable route, "Anchor" or "anchor domain" or "A domain" is used to refer to the portion of an exogenous antigen polypeptide, including a fusion or chimeric exogenous antigen polypeptide that is in contact with the cell membrane of an EHC. The exogenous antigen polypeptide may interact with the lipid cell membrane layer via a phospholipid tail insertion, covalent binding to a lipid layer constituent, an ionic bond, hydrogen bond, or via a single or multi-pass transmembrane polypeptide domain that cross one or more of the lipid cell membrane layers.

As used herein, the term "antibody" encompasses an immunoglobulin whether natural or partly or wholly synthetically produced, and fragments thereof. The term also covers any protein having a binding domain which is homologous to an immunoglobulin binding domain. These proteins can be derived from natural sources, or partly or wholly synthetically produced. "Antibody" further includes a polypeptide comprising a framework region from an immunoglobulin gene or fragments thereof that specifically binds and recognizes an antigen. Use of the term antibody is meant to include whole antibodies, polyclonal, monoclonal and recombinant antibodies, fragments thereof, and further includes single-chain antibodies, humanized antibodies; murine antibodies; chimeric, mouse-human, mouse-primate, primate-human monoclonal antibodies, anti-idiotype antibodies, antibody fragments, such as, e.g., scFv, (scFv)2, Fab, Fab', and F(ab')2, F(ab1)2, Fv, dAb, and Fd fragments, diabodies, and antibody-related polypeptides. Antibody includes bispecific antibodies and multispecific antibodies so long as they exhibit the desired biological activity or function.

The term "antigen binding fragment" used herein refers to fragments of an intact immunoglobulin, and any part of a polypeptide including antigen binding regions having the ability to specifically bind to the antigen. For example, the antigen binding fragment may be a F(ab')2 fragment, a Fab' fragment, a Fab fragment, a Fv fragment, or a scFv fragment, but is not limited thereto. A Fab fragment has one antigen binding site and contains the variable regions of a light chain and a heavy chain, the constant region of the light chain, and the first constant region CH1 of the heavy chain. A Fab' fragment differs from a Fab fragment in that the Fab' fragment additionally includes the hinge region of the heavy chain, including at least one cysteine residue at the C-terminal of the heavy chain CH1 region. The F(ab')2 fragment is produced whereby cysteine residues of the Fab' fragment are joined by a disulfide bond at the hinge region. A Fv fragment is the minimal antibody fragment having only heavy chain variable regions and light chain variable regions, and a recombinant technique for producing the Fv fragment is well known in the art. Two-chain Fv fragments may have a structure in which heavy chain variable regions are linked to light chain variable regions by a non-covalent bond. Single-chain Fv (scFv) fragments generally may have a dimer structure as in the two-chain Fv fragments in which heavy chain variable regions are covalently bound to light chain variable regions via a peptide linker or heavy and light chain variable regions are directly linked to each other at the C-terminal thereof. The antigen binding fragment may be obtained using a protease (for example, a whole antibody is digested with papain to obtain Fab fragments, and is digested with pepsin to obtain F(ab')2 fragments), and may be prepared by a genetic recombinant technique. A dAb fragment consists of a VH domain. Single-chain antibody molecules may comprise a polymer with a number of individual molecules, for example, dimmer, trimer or other polymers.

"Applicator" refers to any device used to connect to a subject. This includes, e.g., needles, cannulae, catheters, and tubing.

"Associated with" when used to describe the relationships among multiple compounds or molecules encompasses such as, e.g., any interaction between an exogenous antigen and a target or between an exogenous antigen-expressing EHC and a target. This includes enzymatic interaction, ionic binding, covalent binding, non-covalent binding, hydrogen bonding, London forces, van der Waals forces, hydrophobic interaction, lipophilic interactions, magnetic interactions, electrostatic interactions, and the like.

"Associated with" when used to describe the relationships among a target, entity, compound, agent, or molecule and a disease, disorder, condition, symptom or phenotype is any link that may reasonably be made between them, including a causal link, or a statistical significant link, an empirically established link, a suggested link, whether or not causative of the disease, disorder, condition, symptom or phenotype.

"Autoimmune disorders" generally are conditions in which a subject's immune system attacks the body's own cells, causing tissue destruction. Autoimmune disorders may be diagnosed using blood tests, cerebrospinal fluid analysis, electromyogram (measures muscle function), and magnetic resonance imaging of the brain, but antibody testing in the blood, for self-antibodies (or auto-antibodies) is particularly useful. Usually, IgG class antibodies are associated with autoimmune diseases.

"Binding" describes an interaction among compounds or molecules, e.g., between an exogenous antigen and a target or between an exogenous antigen-expressing EHC and a target, that comes about by covalent binding or non-covalent binding, including ionic binding, electrostatic interactions, hydrogen bonding, London forces, van der Waals forces, hydrophobic interaction, lipophilic interactions, and similar.

The "biological activity of a polypeptide" refers to any molecular activity or phenotype (such as, e.g., binding, signal transduction, catalytic, etc.) that is caused by the polypeptide, such as an exogenous antigen polypeptide.

As used herein, the term "biological sample" refers to any type of material of biological origin isolated from a subject, including, for example, DNA, RNA, lipids, carbohydrates, and protein. The term "biological sample" includes tissues, cells and biological fluids isolated from a subject. Biological samples include, e.g., but are not limited to, whole blood, plasma, serum, semen, saliva, tears, urine, fecal material, sweat, buccal, skin, cerebrospinal fluid, bone marrow, bile, hair, muscle biopsy, organ tissue or other material of biological origin known by those of ordinary skill in the art. Biological samples can be obtained from, e.g., biopsies of internal organs or from cancers. Biological samples can be obtained from subjects for diagnosis or research or can be obtained from healthy subjects, as controls or for basic research.

The "clearance rate" as used herein is calculated by measuring the amount or concentration of, e.g., exogenous antigen, target-exogenous antigen, or exogenous antigen-expressing EHCs remaining in the circulatory system of a subject over time. For example, 1%, 2%, 3%, 4%, 5%, 10%, 15%, 20%, 30%, 40%, 50%, 60%, 70%, 80%, 90%, 95%, or 99% of target detected in a first sample may still be detected in a second sample that is taken 1 hour, 5 hours, 10 hours, 24 hours, 2 days, 3 days, 4 days, 5 days, 6 days, 7 days, 2 weeks, 3 weeks, 4 weeks, 2 months, 3 months, 4 months, 5 months, 6 months, 7 months, 8 months, 9 months, 10 months, 11 months, 12 months, 2 years, 3 years, 4 years, or 5 years later. The clearance rate may alternatively be expressed as: number of entities (e.g., target/exogenous antigen) per unit of time (e.g., per day). An increase in clearance rate is a rate greater than that exhibited in an untreated or healthy suitable control subject. A decrease in clearance rate is a rate less than that exhibited in an untreated or healthy suitable control subject. The increase or decrease may be 1%, 2%, 3%, 4%, 5%, 10%, 15%, 20%, 30%, 40%, 50%, 60%, 70%, 80%, 90%, 100%, 150%, 200%, 500%, 1000% or may be 1.1-fold, 1.2-fold, 1.3 fold, 1.4-fold, 1.5-fold, 2-fold, 3-fold, 4-fold, 5-fold, 10-fold, 20-fold, 50-fold, 100-fold, 500-fold, or 1000-fold.

"Cleaving" as used herein is a process that disrupts a bonding interaction present in a target, such as a polypeptide or nucleic e.g., to produce two or more entities that after cleaving can be separated from one another. The separation can involve, e.g., disrupt an ionic bond, a covalent bond, a polar covalent bond, a non-polar covalent bond, or a metallic bond. As cleaving applies to polypeptide targets, cleavage can involve breaking one or more peptide bonds. As cleaving applies to small molecule targets, cleavage can involve breaking one or more carbon or sulfide bonds. As cleaving applies to nucleotide sequences, cleavage can involve breaking one or more phosphodiester bonds. As cleaving applies to microbes such as bacteria, fungi, or viruses, cleavage can involve lysis of a membrane or capsid structure. Cleaving can be carried out by an enzyme, e.g., a catalytically active exogenous antigen polypeptide. Exogenous antigens can comprise, e.g., exonuclease, endonuclease, or protease activity.

The "circulatory system of a subject," as used herein, encompasses the space occupied by whole blood and optionally the lymphatic system in a human, inclusive of plasma and all circulating cells and molecules, and distributed throughout arteries, veins, capillaries, and lymphatic vessels of all tissues. The "circulatory concentration" is the concentration of a target, e.g., a cell, polypeptide (such as an antibody, pathogenic antigen, etc.), therapeutic agent, small molecule, metabolite or other entity, an exogenous antigen or an exogenous antigen-expressing EHC in the space defined as the circulatory system. In certain embodiments, the concentration may be defined as the number of free (unbound) entities in a given volume. In other embodiments, the concentration may be defined as the total number of entities in a given volume.

The term "complementarity determining region (CDR)" used herein refers to an amino acid sequence found in the variable region of a heavy chain or a light chain of an immunoglobulin. The CDRs determine the specificity of an antibody and may provide a contact residue for binding to a specific epitope of an antigen. The heavy chain and the light chain may respectively include three CDRs (CDRH1, CDRH2, and CDRH3, and CDRL1, CDRL2, and CDRL3). Four framework regions, which have more highly conserved amino acid sequences than the CDRs, separate the CDR regions in the VH or VL.

A "complex" as used herein comprises an association of two or more entities. A complex may comprise one or more polypeptides, nucleic acid, lipids, carbohydrates, inorganic compounds, organic compounds, and the like. A complex can be functional (multiunit polypeptides) or non-functional (e.g., aggregates or precipitates) and may have beneficial or detrimental properties (e.g., immune complexes). Complexes may be naturally occurring or may be man-made or synthetic. Synthetic complexes include higher order entities, e.g., subcellular structures and cells if they comprise a synthetic compound or molecule.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. As used herein the term "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

"Decrease," in the context of a symptom of a treated disease, disorder or condition, refers to a reduction in measurable or conveyable parameters associated with the disease or condition that manifest as symptoms. Examples of measurable parameters are a reduction in the subject's body temperature, a reduction in the concentration of targets in a sample taken from the subject, reduction in the intensity of inflammation or size of an inflamed area, reduction in the number of infiltrating cells, reduction in the number of episodes associated with the disease, disorder or condition, increase/decrease in organ size, weight gain/loss, etc. Examples of conveyable parameters are, e.g., the subject's own assessment of well being and quality of life. For example, for self-antibody mediated diseases, the decrease may be quantified as one, or a combination of, the following parameters: reduced inflammation, reduced flare-ups, reduced fatigue, reduced blood clotting, reduced swelling, increased energy, or increased hair growth, etc. The parameters that may be quantified are those appropriate for assessing the specific disease, disorder or condition that is being treated. Delay, in the context of symptoms of a treated disease, disorder or condition, refers to the significant extension of a manageable health condition that would otherwise become exacerbated, using a treatment.

"Degrading" is defined as the process in which a target is either directly, or indirectly, reduced, inactivated, decomposed, deconstructed, lysed, dissolved, broken, lessened, impaired, weakened, deteriorated, diminished, or partitioned.

"Different polypeptide origin" refers to the organism or species from which a genetic sequence encoding the polypeptide, the polypeptide, or portion thereof, is sourced. In certain embodiments, a fusion comprising polypeptides of different polypeptide origin may include an exogenous antigen polypeptide that is encoded by the genetic sequence for human adenosine deaminase and the genetic sequence for phenylalanine hydroxylase from chromobacterium violaceum.

A "domain" is a part of a polypeptide, such as an exogenous antigen polypeptide that is generally having a 3-dimensional structure and may exhibit a distinct activity, function, such as, e.g., a catalytic, an enzymatic, a structural role, or a binding function.

By an "enriched population of cells" it is meant a population of cells that is substantially comprised of a particular cell of interest. In an enriched population, 50% or more of the cells in the population are the cells of interest, e.g., 50%, 60%, 70%, usually 80%, 85%, 90%, more usually 92%, 95%, 96%, 97%, 98%, or 99%, sometimes as much as 100% of the cells in the population. The separation of cells of interest from a complex mixture or heterogeneous culture of cells may be performed by any convenient means known in the art, for example, by affinity separation techniques such as magnetic separation using magnetic beads coated with an affinity reagent, affinity chromatography, or "panning" with an affinity reagent attached to a solid matrix, e.g., plate, or other convenient technique. Other techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells. Any technique may be employed which is not unduly detrimental to the viability of the desired cells.

"Enucleation" is the rendering of a cell to a non-replicative state, either through inactivation or removal of the nucleus.

An "epitope" includes any segment on an antigen to which an antibody or other ligand or binding molecule binds. An epitope may consist of chemically active surface groupings of molecules such as amino acids or sugar side chains and usually have specific three dimensional structural characteristics, as well as specific charge characteristics. In some embodiments, exogenous antigens comprise specific epitopes. In some embodiments, targets comprise specific epitopes.

"Erythroid cells" as used herein, include nucleated red blood cells, red blood cell precursors, and enucleated red blood cells and those listed in Table A1. For example, the erythroid cells are a cord blood stem cell, a CD34+ cell, a hematopoietic stem cell (HSC), a spleen colony forming (CFU-S) cell, a common myeloid progenitor (CMP) cell, a blastocyte colony-forming cell, a burst forming unit-erythroid (BFU-E), a megakaryocyte-erythroid progenitor (MEP) cell, an erythroid colony-forming unit (CFU-E), a reticulocyte, an erythrocyte, an induced pluripotent stem cell (iPSC), a mesenchymal stem cell (MSC), a polychromatic normoblast, an orthochromatic normoblast, or a combination thereof. In some embodiments, the erythroid cells are immortal or immortalized cells. For example, immortalized erythroblast cells can be generated by retroviral transduction of CD34+ hematopoietic progenitor cells to express Oct4, Sox2, Klf4, cMyc, and suppress TP53 (e.g., as described in Huang et al., Mol Ther 2013, epub ahead of print September 3). In addition, the cells may be intended for autologous use or provide a source for allogeneic transfusion. Erythroid cells can be contacted with an exogenous antigen to generate an exogenous antigen-expressing EHC. Erythroid cells comprising an exogenous antigen are one example of an exogenous antigen-expressing EHC. In some embodiments, erythroid cells are cultured. In some embodiments, erythroid progenitor cells are contacted with an exogenous antigen to generate an exogenous antigen-expressing EHC.

As used herein, the term "thromboid cell" refers to a cell of the stem cell-megakaryocyte-platelet lineage, including for example megakayrocytes and platelets, or cells that are induced to differentiate by thrombopoietin, or cells that express surface markers associated with this lineage, for example CD41 (GP IIb/IIIa), CD42a (GPIX), CD42b (GPIb), and CD61 (avb3, vitronectin receptor), PAC-1 (activated IIb/IIIa), CD62P (P-selectin), CD31 (PECAM) and CD63.

As used herein, the term "enucleated hematopoietic cell" (EHC) refers to a hematopoietic cell, human or non-human, that is or has been rendered enucleated as defined herein. This definition encompasses the both "erythroid cells" and "thromboid cells" as defined herein.

As used herein, the term "excipient" refers to an inert substance added to a pharmaceutical composition to further facilitate administration of a compound. Examples of excipients include, but are not limited to, calcium carbonate, calcium phosphate, various sugars and types of starch, cellulose derivatives, gelatin, vegetable oils, anti-coagulants, and polyethylene glycols.

The term "exogenous" as used herein means a cellular component or function that is generated by a carbohydrate, polysaccharide, lipid, oligonucleotide or polypeptide not found naturally within a cell or the enhancement or manipulation of a cellular component or function that is endogenous to a cell, including, e.g., a fusion protein comprising an exogenous polypeptide antigen and an endogenous protein or a functional fragment thereof. The exogenous antigen, including an exogenous antigen polypeptide is "exogenous" or "heterologous", thus it may either not naturally exist, such as a fusion or chimera comprising domains of different polypeptide or species origin, it may not naturally occur in a naturally occurring cell, such as an unmodified erythrocyte or platelet, it may not function in the same way as a naturally occurring polypeptide would, or it may not naturally occur in the quantity that the exogenous antigen polypeptide occurs, e.g., in embodiments in which the exogenous antigen is overexpressed as compared to the expression of a naturally occurring polypeptide in an unmodified cell. In some embodiments, the polypeptide exogenous antigen is expressed from an exogenous nucleic acid. In some embodiments, the exogenous antigen is isolated from a source and loaded into or conjugated to an exogenous antigen-expressing EHC. The term "exogenous" when used in the context of nucleic acid includes a transgene and recombinant nucleic acids.

As used herein, the term "expression" or "expressing" refers to the process to produce a polypeptide, such as an exogenous antigen polypeptide including transcription and translation. Expression may be, e.g., increased by a number of approaches, including: increasing the number of genes encoding the polypeptide, increasing the transcription of the gene (such as by placing the gene under the control of a constitutive promoter), increasing the translation of the gene, knocking out of a competitive gene, or a combination of these and/or other approaches. The term "expression" or "expressing" also include EHCs that comprise an exogenous polypeptide that was at one time actively expressed by the EHC but active expression (defined as transcription and translation) since has ceased. For example, the exogenous antigen polypeptide was actively expressed (i.e. transcribed and translated) by an EHC prior to the enucleation event and the antigen polypeptide is retained by the EHC after enucleation but no longer actively expressed, e.g. for lack of encoding nucleic acid. For example, the EHC may comprise an exogenous antigen polypeptide encoded by an exogenous nucleic acid. During enucleation the exogenous antigen polypeptide is retained by the EHC whereas the exogenous nucleic acid is not retained, such EHC is said to be "antigen-expressing" or "expressing antigen" even in the event that the active expression (transcription and translation) of the antigen polypeptide is effectively terminated and/or the EHC does not contain a substantial amount of a replicating nucleic acid.

A "functional" exogenous antigen or exogenous antigen-expressing EHC exhibits a desired or specified activity or characteristic, including enzymatic, catalytic or metabolic activity, structural integrity, immunogenic complementarity, target binding, and correct localization or is capable of promoting a desired or specified effect or phenotype.

"Fusion or chimera" is a polypeptide sequence, or corresponding encoding nucleotide sequence, that is derived from the combination of two or more sequences that are not found together in nature. This may be a combination of separate sequences derived from separate genes within the same genome, or from heterologous genes derived from distinctly different species' genomes.

"Genetic material" refers to nucleic acid molecules having nucleotide sequences of adenosine, thymine, uracil, cytosine, and guanine capable of encoding a gene.

The term "heavy chain" used herein is understood to include a full-length heavy chain including a variable region (VH) having amino acid sequences that determine specificity for antigens and a constant region having three constant domains (CH1, CH2, and CH3), and fragments thereof. In addition, the term "light chain" used herein is understood to include a full-length light chain including a variable region (VL) having amino acid sequences that determine specificity for antigens and a constant region (CL), and fragments thereof.

The term "homolog" indicates polypeptides, including exogenous antigen polypeptide that have the same or conserved residues at a corresponding position in their primary, secondary or tertiary structure. Functional homologs include exogenous antigens and other polypeptides that exhibit similar function and/or specificity (e.g., for a particular target).

A naturally occurring intact antibody, or immunoglobulin, includes four polypeptides: two full-length light chains and two full-length heavy chains, in which each light chain is linked to a heavy chain by disulfide bonds. Each heavy chain has a constant region and a variable region. Similarly, each light chain has a constant region and a variable region. There are five heavy chain classes (isotypes): gamma ($\gamma$), mu ($\mu$), alpha ($\alpha$), delta ($\delta$), or epsilon ($\varepsilon$), and additionally several subclasses gamma 1 ($\gamma$1), gamma 2($\gamma$2), gamma 3($\gamma$3), gamma 4($\gamma$4), alpha 1($\alpha$1), and alpha 2($\alpha$2). The light chain constant region can be either kappa ($\kappa$) or lambda ($\lambda$) type. The variable regions differ in sequence among antibodies and are used in the binding and specificity of a given antibody to its particular antigen.

As used herein, the term "increase," "enhance," "stimulate," and/or "induce" (and like terms) generally refers to the act of improving or increasing, either directly or indirectly, a concentration, level, function, activity, or behavior relative to the natural, expected, or average, or relative to a control condition.

As used herein, the term "inhibit," "suppress," "decrease," "interfere," and/or "reduce" (and like terms) generally refers to the act of reducing, either directly or indirectly, a concentration, level, function, activity, or behavior relative to the natural, expected, or average, or relative to a control condition.

A "library" as used herein includes a collection of nucleic acid molecules (e.g., DNA, RNA) having diverse nucleic acid sequences, a genetically diverse collection of clones, a collection of diverse polypeptides, a diverse collection of cells, such as EHCs, etc.

As used herein, "a mammalian subject" includes all mammals, including without limitation, humans, domestic animals (e.g., dogs, cats and the like), farm animals (e.g., cows, sheep, pigs, horses and the like) and laboratory animals (e.g., monkey, rats, mice, rabbits, guinea pigs and the like). The terms "individual," "subject," "host," and "patient," are used interchangeably herein and refer to any mammalian subject for whom diagnosis, treatment, or therapy is desired, particularly humans. The methods described herein are applicable to both human therapy and veterinary applications. In some embodiments, the subject is a mammal, and in other embodiments the subject is a human.

"Medical device" refers to any device, apparatus or machine used to deliver a dose of an exogenous antigen-expressing EHC and/or a therapeutic agent. This includes containers, bottles, vials, syringes, bags, cartridges, cassettes, magazines, cylinders, or canisters.

"Medical kit" refers to a packaged unit that includes a medical device or applicator, an appropriate dosage of exogenous antigen-expressing EHC, optionally including a therapeutic agent, and relevant labeling and instructions.

As used herein, the term "modulate," "modulating", "modify," and/or "modulator" generally refers to the ability to alter, by increase or decrease, e.g., directly or indirectly promoting/stimulating/upregulating or interfering with/inhibiting/downregulating a specific concentration, level, expression, function or behavior, such as, e.g., to act as an antagonist or agonist. In some instances a modulator may increase and/or decrease a certain concentration, level, activity or function relative to a control, or relative to the average level of activity that would generally be expected or relative to a control level of activity.

"Membrane" as used herein is a boundary layer that separates an interior space from an exterior space comprising one or more biological compounds, typically lipids, and optionally polypeptides. Membranes can be lipid bilayers. In certain embodiments, membranes comprise one or more of phosphatidylcholine, sphingomyelin, lysophosphatidylcholine, phosphatidylethanolamine, phosphatidylserine, phosphatidylinositol, or phosphatidic acid. In some embodiments, membranes comprise one or more polypeptides such as ankyrin and coenzyme Q10. Included in the definition of membrane are cell membranes comprising, e.g., a phospholipid bilayer and cell membrane associated polypeptides.

The phrase "nucleic acid molecule" refers to a single or double-stranded polymer of deoxyribonucleotide or ribonucleotide bases. It includes chromosomal DNA and self-replicating plasmids, vectors, mRNA, tRNA, siRNA, etc. which may be recombinant and from which exogenous polypeptides may be expressed when the nucleic acid is introduced into a cell.

Orthologs are defined as genes in different species that evolved from a common ancestral gene by speciation.

The term "pharmaceutically-acceptable" and grammatical variations thereof, refers to compositions, carriers, diluents and reagents capable of administration to or upon a subject without the production of undesirable physiological effects to a degree that would prohibit administration of the composition. For example, "pharmaceutically-acceptable excipient" includes an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

As used herein, the term "pharmaceutically acceptable carrier" includes any of the standard pharmaceutical carriers, such as a phosphate buffered saline solution, water, emulsions such as an oil/water or water/oil, and various types of wetting agents. The term also encompasses any of the agents approved by a regulatory agency of the US Federal government or listed in the US Pharmacopeia for use in animals, including humans, as well as any carrier or diluent that does not cause significant irritation to a subject and does not abrogate the biological activity and properties of the administered compound.

Some agents may be administered as "pharmaceutically acceptable salt", e.g., prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Salts can also be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines. Any ordinary skilled person in the art will know how to select a proper pharmaceutically acceptable carrier, a pharmaceutically acceptable salt thereof for implementing this invention without undue experimentation.

As used herein, the term "pharmaceutical composition" refers to one or more of the compounds described herein, such as, e.g., an exogenous antigen-expressing EHC mixed or intermingled with, or suspended in one or more other chemical components, such as physiologically acceptable carriers and excipients. One purpose of a pharmaceutical composition is to facilitate administration of a compound to a subject.

Certain embodiments provide various polypeptide molecules having sequences associated with a desired function or activity, such as exogenous antigen polypeptides. A polypeptide is a term that refers to a chain of amino acid residues, regardless of post-translational modification (e.g., phosphorylation or glycosylation) and/or complexation with additional polypeptides, synthesis into multisubunit complexes, with nucleic acids and/or carbohydrates, or other molecules. Proteoglycans therefore also are referred to herein as polypeptides. In certain embodiments, the exogenous antigen-expressing EHC comprises a polypeptide exogenous antigen. In certain embodiments, the exogenous antigen-expressing EHC comprises one or more non-exogenous antigen polypeptides that are optionally membrane-associated.

The term "pharmaceutically active agent" or "pharmaceutical agent" is defined as any compound, e.g., a small molecule drug, or a biologic (e.g., a polypeptide drug or a nucleic acid drug) that when administered to a subject has a measurable or conveyable effect on the subject, e.g., it alleviates or decreases a symptom of a disease, disorder or condition. In some embodiments, the pharmaceutical agent may be administered prior to, in combination with, or following the delivery of an exogenous antigen-expressing EHC. In some embodiments, the pharmaceutically active agent exerts a synergistic treatment effect with the exogenous antigen-expressing EHC. In some embodiments, the pharmaceutically active agent exerts an additive treatment effect with the exogenous antigen-expressing EHC.

A "promoter" is defined as an array of nucleic acid control sequences that direct transcription of an operably linked nucleic acid. Promoters include necessary nucleic acid sequences near the start site of transcription. A promoter also optionally includes distal enhancer or repressor elements. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

A "exogenous antigen," as used herein, is an entity capable of interacting with a target, e.g., to associate with or bind to a target. An exogenous antigen can comprise or can consist essentially of a polypeptide. In some embodiments, the exogenous antigen comprises a polypeptide, a carbohydrate, a nucleic acid, a lipid, a small molecule, or a combination thereof. In embodiments in which an exogenous antigen is a naturally occurring compound or molecule, the antigen is "exogenous" in the sense that it is an exogenous or heterologous compound or molecule with regard to its presence in the EHC. In other embodiments the antigen is "exogenous" in the sense that it is a man-made compound or molecule, such as a fusion or chimera, a non-naturally occurring polypeptide, carbohydrate, nucleic acid, lipid, or combination thereof, or a man-made small molecule or other therapeutic agent. For example, the exogenous antigen may comprise a fusion or chimera comprising one or more of an S domain, an A domain and a U domain. The S domain is a surface domain exposed to the environment around the EHC, such as the circulatory system of a subject. The A domain is an anchor domain that attaches the S domain to the cell membrane of the EHC. The U domain faces the unexposed side of or is located within (i.e. in the intracellular space of) the EHC. Irrespective of any domains, an exogenous antigen may be located on the surface of the exogenous antigen-expressing EHC or may be located within the EHC. The exogenous antigen may be associated with the membrane of the exogenous antigen-expressing EHC, e.g., the exogenous antigen is anchored in, conjugated to or otherwise bound to the membrane. In some embodiments, the exogenous antigen may be conjugated to the membrane of the exogenous antigen-expressing EHC by chemical or enzymatic conjugation. In other embodiments, the exogenous antigen is not conjugated to the membrane. In some embodiments, the exogenous antigen is not associated with the membrane of the exogenous antigen-expressing EHC and is located within the membrane-encapsulated intracellular space of the EHC. In some embodiments, an exogenous antigen located within the intracellular space of the EHC does not substantially diffuse out of the EHC and/or may not permeate the membrane. In other embodiments, the exogenous antigen may substantially diffuse out of the EHC and/or may permeate the membrane. In some embodiments, the exogenous antigen is loaded, e.g., introduced into or put onto the EHC. An exogenous antigen that is loaded is not biologically synthesized by the exogenous antigen-expressing EHC. An exogenous antigen suitable for loading may be e.g., produced in a cell-based expression system, isolated from a biological sample, chemically or enzymatically synthesized, and then loaded into or onto the EHC. In some embodiments, the exogenous antigen may be further modified by the exogenous antigen-expressing EHC after loading. In other embodiments, the exogenous antigen is not modified after loading. In some embodiments, the exogenous antigen polypeptide is not loaded onto or into the EHC. In some embodiments, the exogenous antigen is made, e.g., biologically synthesized by the exogenous antigen-expressing EHC. Typically an exogenous antigen polypeptide is expressed by the exogenous antigen-expressing EHC from an exogenous nucleic acid molecule (e.g., a DNA or mRNA) that was introduced into the EHC. The exogenous antigen may have a biological function that is retained when the antigen is expressed on the EHC. The exogenous antigen may bind to and/or sequester a target. Alternatively or in addition the exogenous antigen may exhibit a catalytic activity toward the target, e.g., the exogenous antigen may convert or modify the target, or may degrade the target. A product may then optionally be released from the exogenous antigen.

"Residency" of an exogenous antigen-expressing EHC refers to the period of time it spends in a physiological location. The specific location of the exogenous antigen-expressing EHC may change during its lifetime and "residency" applies to the period of time spent in various environments, including vascular circulation, peripheral tissues, capillaries, digestive system, pulmonary system, nasal tissues, epidermal surface, and interstitial tissue. In specific embodiments, the exogenous antigen-expressing EHC resides in the circulatory system of a subject.

"Replicating nucleic acid" refers to deoxyribonucleic acid (DNA) that is capable of being copied by enzymes dedicated to the increasing the number of copies of the DNA. Usually, DNA replication leads to the production of two identical replicas from one original DNA molecule. DNA replication comprises the incorporation of nucleotides into a growing DNA strand by DNA polymerase matched to the template strand one at a time via the creation of phosphodiester bonds.

"Sequestering" is defined as cloistering, occluding, separating, segregating, hiding, insulating, or isolating of a target and preventing it from freely interacting with its environment.

"Specifically binding" or "specifically interacting", as used herein, describes any interaction between two entities (e.g., a target with an exogenous antigen, such as an antibody with an antigen, a receptor with a ligand, an enzyme with a substrate, biotin with avidin, etc.) that is saturable, often reversible and so competitive, as these terms are understood by those of ordinary skill in the chemical and biochemical arts. e.g., Specific binding involving biological molecules such as, e.g., proteins, peptides and nucleic acid occurs when one member of the binding pair has a site with a shape and distribution of charged, polar, or hydrophobic moieties such that the interaction of the cognate ligand with that site is characterized by favorable energetics (i.e., a negative free energy of binding). The specificity of the interaction may be measured or expressed as a binding constant (Kd). The Kd may range from a mM range to a fM range, including pM ranges, µM ranges and nM ranges. Typical Kd values are below about $10^{-6}$ M, below about $10^{-7}$ M, below about $10^{-8}$ M, and in some embodiments below about $10^{-9}$ M.

As used herein, the term "substantially" or "substantial" refers, e.g., to the presence, level, or concentration of an entity in a particular space, the effect of one entity on another entity, or the effect of a treatment. For example, an activity, level or concentration of an entity is substantially increased if the increase is 2-fold, 3-fold, 4-fold, 5-fold, 10-fold, 50-fold, 100-fold, or 1000-fold relative to a baseline. An activity, level or concentration of an entity is also substantially increased if the increase is 5%, 10%, 20%, 30%, 40%, 50%, 60%, 70%, 80%, 90%, 100%, 200%, or 500% relative to a baseline. An entity may be substantially present in a particular space if it can be detected by methods known in the art. An entity may not be substantially present in a particular space if it is present at levels below the limit of detection for assays and methods known in the art. In some embodiments, an entity may not be substantially present in a particular space if it is barely detectable but only in non-functional quantities or minute quantities that do not cause or change a phenotype. In other embodiments, an entity may not be substantially present in a particular population if it is present and can be detected only in a small number of constituents making up the population, e.g., less than 10%, 9%, 8%, 7%, 6%, 5%, 4%, 3% 2% or less than 1%, 0.5%, 0.1% of constituents of the population. For example, an exogenous nucleic acid may not be retained upon enucleation, the cell is rendered non-replicative, and the enucleated cell is incapable of continued expression of the exogenous antigen polypeptide encoded by the exogenous nucleic acid. The loss of the ability of the cell to continue to significantly translate the exogenous polypeptide "effectively terminates" protein expression. In certain embodiments, the exogenous antigen-expressing EHC is substantially incapable of self-replication, e.g., the replication of nucleic acids. For example, the exogenous antigen-expressing EHC does not substantially incorporate a nucleoside if contacted with labeled nucleoside, such as thymidine, in an incorporation assay. In some embodiments, the exogenous antigen-expressing EHC does not contain a substantial amount of self-replicating nucleic acids. The term "substantial identity" of polynucleotide or nucleic acid sequences means that a polynucleotide comprises a sequence that has at least 25% sequence identity. Alternatively, percent identity can be any integer from 25% to 100%. More preferred embodiments include at least: 25%, 30%, 35%, 40%, 45%, 50%, 55%, 60%, 65%, 70%, 75%, 80%, 85%, 90%, 95%, or 99% compared to a reference sequence using the programs described herein; preferably BLAST using standard parameters.

"Synthetic" refers to a compound or molecule that is either man-made and non-naturally occurring, or if it is naturally occurring is placed in a context or location that it would not naturally exist, or if it naturally exists in the context or location is in a state of purity, or is present in an amount, concentration or number that it would not naturally be present in the context or location. Synthetic entities can be isolated or purified compounds that are optionally chemically or enzymatically modified from their natural state, exogenous nucleic acids, exogenous (heterologous) exogenous antigens, and the like. The presence of a synthetic compound or molecule, as defined herein, in any entity renders the entire entity "synthetic". For example, a cell comprising an exogenous antigen is a synthetic cell.

A "target," as used herein, is an entity capable of interacting with an exogenous antigen, e.g., to associate with or bind to an exogenous antigen. A "target" includes, but is not limited to a polypeptide (e.g., an antibody or antibody-related polypeptide, a complement constituent, an amyloid protein, a pathogen, a toxin, a prion), a molecule (e.g., a metabolite, a steroid, a hormone, a carbohydrate; an oligosaccharide; a chemical; a polysaccharide, a DNA; an RNA; a lipid, an amino acid, an element, a toxin or pathogen), a complex (e.g., an immune complex), or a cell (e.g., a cancer cell, a macrophage, a bacterium, a fungus, a virus, or a parasite). A target is intended to be detected, diagnosed, impaired, destroyed or altered (e.g., functionally complemented) by the methods provided herein. The specific target may occur free or is associated with other entities in the circulatory system of a subject.

A "target self-antibody," as used herein, is a self-antibody associated with an autoimmune disease. Such self-antibodies may be detected and analyzed using antibody binding tests involving contacting the subject's antibodies to samples of the subject's own tissue, usually thyroid, stomach, liver, and kidney tissue. Antibodies binding to the "self" tissue (comprising self-antigens) indicate an autoimmune disorder.

"Transgene" or "exogenous nucleic acid" refers to a foreign or native nucleotide sequence that is introduced into an EHC. Transgene and exogenous nucleic acid are used interchangeably herein and encompass recombinant nucleic acids.

As used herein, "treat," "treating," and/or "treatment" are an approach for obtaining beneficial or desired clinical results, pharmacologic and/or physiologic effect, e.g., alleviation of the symptoms, preventing or eliminating said symptoms, and refer to both therapeutic treatment and prophylactic or preventative treatment of the specific disease, disorder or condition. Beneficial or desired clinical results, pharmacologic and/or physiologic effect include, but are not limited to, preventing the disease, disorder or condition from occurring in a subject that may be predisposed to the disease, disorder or condition but does not yet experience or exhibit symptoms of the disease (prophylactic treatment), alleviation of symptoms of the disease, disorder or condition, diminishment of extent of the disease, disorder or condition, stabilization (i.e., not worsening) of the disease, disorder or condition, preventing spread of the disease, disorder or condition, delaying or slowing of the disease, disorder or condition progression, amelioration or palliation of the disease, disorder or condition, and combinations thereof, as well as prolonging survival as compared to expected survival if not receiving treatment.

A "therapeutic agent" or "therapeutic molecule" includes a compound or molecule that, when present in an effective amount, produces a desired therapeutic effect, pharmacologic and/or physiologic effect on a subject in need thereof.

The term "therapeutically effective amount" or "effective amount" is an amount of an agent being administered to a subject sufficient to effect beneficial or desired clinical results, pharmacologic and/or physiologic effects. An effective amount can be administered in one or more administrations. An effective amount is typically sufficient to palliate, ameliorate, stabilize, reverse, slow or delay the progression of the disease state. The effective amount thus refers to a quantity of an agent or frequency of administration of a specific quantity of an agent sufficient to reasonably achieve a desired therapeutic and/or prophylactic effect. For example, it may include an amount that results in the prevention of, treatment of, or a decrease in, the symptoms associated with a disease or condition that is being treated, e.g., the disease or medical conditions associated with autoimmune response, overactive immune activation, or inhibitory antibody generation for which immune tolerance is desired, or the diseases or medical conditions associated with a target polypeptide. The amount of a therapeutic composition administered to the subject will depend on the type and severity of the disease and on the characteristics of the individual, such as general health, pathologic conditions, diets, age, sex, body weight and tolerance to drugs. It will also depend on the degree, severity and type of disease. Further, the effective amount will depend on the methods of formulation and administration used, e.g., administration time, administration route, excretion speed, and reaction sensitivity. The skilled artisan will be able to determine appropriate dosages depending on these and other factors. The compositions can also be administered in combination with one or more additional therapeutic compounds. A desirable dosage of the pharmaceutical composition may be in the range of about 0.001 to 100 mg/kg for an adult. In one example, an intravenous administration is initiated at a dose which is minimally effective, and the dose is increased over a pre-selected time course until a positive effect is observed. Subsequently, incremental increases in dosage are made limiting to levels that produce a corresponding increase in effect while taking into account any adverse affects that may appear. Non-limited examples of suitable dosages can range, for example, from $1\times10^{10}$ to $1\times10^{14}$, from $1\times10^{11}$ to $1\times10^{13}$, or from $5\times10^{11}$ to $5\times10^{12}$ exogenous antigen-expressing EHCs of the present invention. Specific examples include about $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, or more exogenous antigen-expressing EHCs of the present invention. Each dose of exogenous antigen-expressing EHCs can be administered at intervals such as once daily, once weekly, twice weekly, once monthly, or twice monthly.

"Unbound" refers to the state of a target with which the exogenous antigen is capable of interacting. An unbound target is not associated with another entity or an exogenous antigen. An unbound exogenous antigen is not associated with another entity or a target. A target is considered "bound" once it is associated with the exogenous antigen or another entity. Unbound targets include soluble forms of the target in circulation. Bound targets include targets that are embedded, associated with, linked to, or otherwise interacting with entities in circulation or peripheral tissue. Entities with which a target may interact include circulating cells, peripheral endothelial tissue, immune complexes, glycolipids, microbes, immunoglobulins, serum albumin, clotting factors, lipoproteins, and electrolytes.

A "variant" is a polypeptide which differs from the original protein by one or more amino acid substitutions, deletions, insertions, or other modifications. These modifications do not significantly change the biological activity of the original protein. In many cases, a variant retains at least 10%, 20%, 30%, 40%, 50%, 60%, 70%, 80%, 90%, 95%, or 100% of the biological activity of original protein. The biological activity of a variant can also be higher than that of the original protein. A variant can be naturally-occurring, such as by allelic variation or polymorphism, or be deliberately engineered.

The amino acid sequence of a variant is substantially identical to that of the original protein. In many embodiments, a variant shares at least 50%, 60%, 70%, 80%, 85%, 90%, 95%, 99%, or more global sequence identity or similarity with the original protein. Sequence identity or similarity can be determined using various methods known in the art, such as Basic Local Alignment Tool (BLAST), dot matrix analysis, or the dynamic programming method. In one example, the sequence identity or similarity is determined by using the Genetics Computer Group (GCG) programs GAP (Needleman-Wunsch algorithm). The amino acid sequences of a variant and the original protein can be substantially identical in one or more regions, but divergent in other regions.

As used herein, the term "vector" is a nucleic acid molecule, preferably self-replicating, which transfers and/or replicates an inserted nucleic acid molecule, such as a transgene or exogenous nucleic acid into and/or between host cells. It includes a plasmid or viral chromosome into whose genome a fragment of recombinant DNA is inserted and used to introduce recombinant DNA, or a transgene, into an EHC.

EXAMPLES

The following examples are offered by way of illustration and not by way of limitation.

Example 1: Culture of Erythroid Cells with Heterologous Gene Expression

CD34 cells are isolated from peripheral blood by supermagnetic microbead selection by the use of Mini-MACS columns (Miltenyi Biotec; 94%+/−3% purity). The cells are cultured in erythroid differentiation medium (EDM) on the basis of IMDM supplemented with stabilized glutamine, 330 ug/mL holo-human transferrin, 10 ug/mL recombinant human insulin, 2 IU/mL heparin, and 5% solvent/detergent virus-inactivated plasma. The expansion procedure comprises 3 steps. In the first step (day 0 to day 7), $10^4$/mL CD34 cells are cultured in EDM in the presence of 1 uM hydrocortisone, 100 ng/mL SCF, 5 ng/mL IL-3, and 3 IU/mL Epo. On day 4, 1 volume of cell culture is diluted in 4 volumes of fresh medium containing SCF, IL-3, Epo, and hydrocortisone. In the second step (day 7 to day 11), the cells are resuspended at $10^5$/mL in EDM supplemented with SCF and Epo. In the third step (day 11 to day 18), the cells are cultured in EDM supplemented with Epo alone. Cell counts are adjusted to $7.5 \times 10^5$ to $1 \times 10^6$ and $5$-$10 \times 10^6$ cells/mL on days 11 and 15, respectively. Beyond day 18, the culture medium containing Epo is renewed twice a week. The cultures are maintained at 37° C. in 5% CO2 in air.

The coding sequence of the antigen of interest is placed under the control of an erythroid-specific promoter, e.g. GATA-1, and terminated with a poly-A tail, see e.g. Repik et al., Clin Exp Immunol 2005, 140:230. This sequence is encoded in a lentiviral vector (e.g. EFI, System Biosciences, Inc.). The vector is produced by standard methods from 293T cells. The lentiviral vector is transduced into human hematopoietic progenitor cell, e.g. CD34+ cell or immortalized erythroblast or iPS cell, for example as described by Chang et al., Nat Biotechnol 2006, 24:1017, during days 1-4 of culturing. Subsequent expansion and differentiation stages are performed as described above.

Example 2: Loading of Protein into Erythroid Cell by Hypotonic/Hypertonic Cycling Antigen, in this case OVA, is added to a RBC suspension at a final concentration of 0.5 or 5 mg/ml with a hematocrit (Hct) of 70%. After a hypotonic dialysis process (50 mOsmol/kg), RBC are resealed by adding a hypertonic solution (1900 mOsmol/kg) at 37 C for 30 min. OVA-loaded RBC are washed four times with a 0.9% NaCl+0.2% glucose solution, centrifuged at 1000×g for 10 min at 4 C and adjusted to a Hct of 50% with plasma or buffer.

Example 3: Cell Surface Labeling with Heterobifunctional Crosslinker

Antigen with exposed, reduced thiol group (antigen-SH) is prepared by incubation with 5 mM TCEP. The reducing agent is removed by size exclusion chromatography prior to conjugation. Cells are incubated with maleimide-PEG-NHS crosslinker, e.g. SM(PEG)$_x$ (Thermo Scientific) for 30 minutes. The NHS group reacts with free amine groups on cell surface antigens. Reacted cells are washed in PBS to remove excess crosslinker. Antigen-SH solution is introduced to the cells-plus-crosslinker solution, and the maleimide-SH reaction is allowed to proceed for 30 minutes. Cells are pelleted and washed to remove unbound antigen.

Example 4: Cell Surface Labeling with Sortase

Cells expressing surface proteinst that contain the Sortase A acceptor sequence, LPXTG (Seq. ID No. 24), are incubated with 100 uM sortase A in a reaction buffer consisting of 50 mM Tris-C1, pH 7.5, 150 mM NaCl, 1 mM CaCl$_2$, for 4 h at 37° C. 10× molar excess of nucleophile, GGG-antigen, is introduced and the reaction is allowed to proceed at room temperature overnight. Following the reaction, excess sortase and unreacted nucleophile is removed by pelleting and washing the cells.

Example 5: Cell Surface Labeling with Click Chemistry

Cells are reacted with Alkyne-NHS Ester to conjugate the alkyne group to exposed primary amines on the cell surface, per manufacturer's instructions (e.g. Glen Research). Excess alkyne-NHS ester is removed by pelleting and washing the cells. Antigen is reacted with Azide-NHS ester to conjugate the azide group to exposed primary amines on the antigen, per manufacturer's instructions (e.g. Thermo Scientific). Excess azide-NHS ester is removed by size exclusion chromatography. Alkyne-cells and azide-antigen are reacted by copper-catalyzed cycloaddition at room temperature.

Example 6: Measurement of T Cell Proliferation in a Mouse

CD8$^+$ T cells from OTI (CD45.2$^+$) mouse spleens are isolated using a CD8 magnetic bead negative selection kit (Miltenyi Biotec) as per the manufacturer's instructions. Freshly isolated CD8$^+$ OTI cells are resuspended in PBS and labeled with 1 μM CFSE (Invitrogen) for 6 min at room temperature, and the reaction is quenched for 1 min with an equal volume of Iscove's modified Dulbecco's medium (IMDM) with 10% (vol/vol) FBS (Gibco). Cells are washed, counted, and resuspended in pure IMDM before injection. A total of 3×10$^6$ CFSE-labeled CD8$^+$ OTI cells are injected i.v. into the tail vein of recipient CD45.1$^+$ mice. For short-term proliferation studies, OVA-comprising erythroid cells are injected 24 h following adoptive transfer. Splenocytes are harvested 5 d following antigen administration and stained for analysis by flow cytometry.

Example 7: OVA Antigen Challenge Model in a Mouse

A total of 3×10$^5$ CFSE-labeled OTI CD8$^+$ T cells are injected into CD45.1$^+$ recipient mice as described above. At 1 and 6 d following adoptive transfer, mice are i.v. administered 100 μL of OVA-comprising erythroid cells into the tail vein. At 15 d following adoptive transfer, mice are challenged with 5 μg of OVA and 25 ng of ultrapure E. coli LPS (InvivoGen) in 25 μL of saline injected intradermally into each rear leg pad (Hock method: total dose of 10 μg of OVA and 50 ng of LPS). Quantification of antigen specific B and T cells and serum antibody titer is described below.

Example 8: Quantification of Antigen Specific B and T Cells in a Mouse

Mice are killed 4 d following OVA challenge, described above, and spleen and draining lymph node cells are isolated for restimulation. For flow cytometry analysis of intracellular cytokines, cells are restimulated in the presence of 1 mg/mL OVA or 1 μg/mL SIINFEKL peptide (Seq. ID No. 26) (Genscript) for 3 h. Brefeldin-A (5 μg/mL; Sigma) is added, and restimulation is resumed for an additional 3 h before staining and flow cytometry analysis. For ELISA measurements of secreted factors, cells are restimulated in the presence of 100 μg/mL OVA or 1 μg/mL SIINFEKL peptide (Seq. ID No. 26) for 4 d. Cells are spun, and the media are collected for ELISA analysis using IFN-γ and IL-10 Ready-Set-Go kits (eBioscience) as per the manufacturer's instructions.

Example 9: Quantification of Circulating Antibody Titer

OVA-specific serum IgG is detected by incubating mouse serum at varying dilutions on OVA-coated plates, followed by a final incubation with goat anti-mouse IgG-HRP (Southern Biotech).

Example 10: Extracellular SpyTag-SpyCatcher Tolerance Induction

An expression cassette containing the coding sequence of Kell and SpyTag is synthesized and inserted in the lentiviral vector EF1. A population of CD34+ cells is transformed with the vector. The expression of Kell-SpyTag fusion protein is quantified by FACS. Cells that express Kell-SpyTag extracellularly are then placed in a solution of Ara h(1-6) peptides fused to the SpyCatcher sequence and a cMyc tag. Following incubation, the cells are sorted using FACs to quantify covalent isopeptide conjugation of Kell-SpyTag to SpyCatcher-ArahX-cMyc. The cells are also hypotonically lysed and the presence of Kell-SpyTag-SpyCatcher-ArahX-cMyc is quantified by Western blot.

Example 11: Gene Assembly

DNA encoding the following genes—glycophorin A (Uniprot ID P02724), Kell (Uniprot ID P23276), antibody scFv against hepatitis B surface antigen (Bose et al. 2003 Mol Immunol 40(9):617, GenBank ID AJ549501.1), adenosine deaminase (Uniprot ID P00813), phenylalanine hydroxylase from Chromobacterium violaceum (GenBank ID AF146711.1), complement receptor 1 (Uniprot ID P17927), CD46 (GenBank: BAA12224.1), CD55 (Uniprot ID P08174), CD59 (Uniprot ID P13987), green fluorescent protein (Uniprot ID P42212), thymidine phosphorylase (Uniprot ID P19971), glucocerebrosidase (Uniprot ID P04062), beta2 glycoprotein 1 (Uniprot ID P02749), phospholipase a2 receptor (Uniprot ID Q13018), collagen alpha-3(IV) (Uniprot ID Q01955), serum amyloid P (Uniprot ID P02743), lipoprotein lipase (Uniprot ID P06858), asparaginase (Uniprot ID P00805), factor IX (Uniprot ID F2RM35), ADAMTS13 (Uniprot ID Q76LX8) —were purchased as cDNA from Dharmacon (GE Life Sciences) or synthesized de novo by DNA2.0 and Genscript.

1. Single Gene Cloning (CR1)

Genes were assembled into expression vectors by standard molecular biology methods known in the art. The gene for complement receptor 1 (CR1) was synthesized by a commercial vendor (DNA2.0) and supplied in a standard cloning vector (pJ series). The gene was amplified out of the pJ vector by polymerase chain reaction (PCR) using oligos with non-homologous terminal sequences to prepare for insertion into the mammalian expression vector (System Biosciences, pM series): the upstream oligo consisted of 25 nt homologous to the upstream pM insertion site and 25 nt homologous to the start of CR1; the downstream oligo consisted of 25 nt homologous to the downstream pM insertion site and 25 nt homologous to the end of CR1. The amplified product was purified by gel electrophoresis (Qiagen). The pM vector was linearized by PCR with tail-to-tail oligos homologous to the upstream and downstream insertion sites and purified by PCR purification (Qiagen). The CR1 amplicon was ligated into the linearized pM vector by Gibson assembly, described in detail in Gibson 2011, Methods Enzymology Vol 498, p. 394. Sequences were confirmed by Sanger sequencing.

2. Fusion of Two Genes (Membrane Kell-scFv)

The gene for Kell was purchased as cDNA and supplied in a standard cloning vector (pJ series). The gene for an antibody scFv specific to hepatitis B surface antigen (scFv, described in Bose 2003, Molecular Immunology 40:617) was synthesized by a commercial vendor (DNA2.0) and supplied in a standard cloning vector (pJ series). The genes was amplified out of the pJ vectors by polymerase chain reaction (PCR) using oligos with non-homologous terminal sequences to prepare for insertion into the mammalian expression vector (System Biosciences, pM series). Kell was amplified with an upstream oligo consisting of 25 nt homologous to the upstream pM insertion site and 25 nt homologous to the 5' terminus of Kell, and a downstream oligo consisting of 25 nt homologous to the 5' terminus of scFv and 25 nt homologous to the 3' terminus of Kell. scFv was amplified with an upstream oligo consisting of 25 nt homologous to the 3' terminus of Kell insertion site and 25 nt homologous to the 5' terminus of scFv, and a downstream oligo consisting of 25 nt homologous to the downstream pM insertion site and 25 nt homologous to the 3' terminus of scFv. The amplified products were purified by gel electrophoresis (Qiagen). The pM vector was linearized by PCR with tail-to-tail oligos homologous to the upstream and downstream insertion sites and purified by PCR purification (Qiagen). The Kell and scFv amplicons were ligated into the linearized pM vector by one-pot Gibson assembly, described in detail in Gibson 2011, Methods Enzymology Vol 498, p. 394. Sequences were confirmed by Sanger sequencing.

3. Linker-Assembly Between Genes (Kell-scfv)

The gene for Kell was purchased as cDNA and supplied in a standard cloning vector (pJ series). The gene for an antibody scFv specific to hepatitis B surface antigen (scFv, described in Bose 2003, Molecular Immunology 40:617) was synthesized by a commercial vendor (DNA2.0) and supplied in a standard cloning vector (pJ series). The genes was amplified out of the pJ vectors by polymerase chain reaction (PCR) using oligos with non-homologous terminal sequences to prepare for insertion into the mammalian expression vector (System Biosciences, pM series). Kell was amplified with an upstream oligo consisting of 25 nt homologous to the upstream pM insertion site and 25 nt homologous to the 5' terminus of Kell; and a downstream oligo consisting of 25 nt homologous to the 5' terminus of scFv, 24 nt encoding a (GlyGlyGlySer)×2 spacer (Seq. ID No. 23), and 25 nt homologous to the 3' terminus of Kell. scFv was amplified with an upstream oligo consisting of 25 nt homologous to the 3' terminus of Kell insertion site, 24 nt encoding a (GlyGlyGlySer)×2 spacer (Seq. ID No. 23), and 25 nt homologous to the 5' terminus of scFv; and a downstream oligo consisting of 25 nt homologous to the downstream pM insertion site and 25 nt homologous to the 3' terminus of scFv. The amplified products were purified by gel electrophoresis (Qiagen). The pM vector was linearized by PCR with tail-to-tail oligos homologous to the upstream and downstream insertion sites and purified by PCR purification (Qiagen). The Kell and scFv amplicons were ligated into the linearized pM vector by one-pot Gibson assembly, described in detail in Gibson 2011, Methods Enzymology Vol 498, p. 394. Sequences were confirmed by Sanger sequencing.

4. Epitope Tag Attachment (Kell-scFv)

The gene for Kell was purchased as cDNA and supplied in a standard cloning vector (pJ series). The gene for an antibody scFv specific to hepatitis B surface antigen (scFv, described in Bose 2003, Molecular Immunology 40:617) was synthesized by a commercial vendor (DNA2.0) and supplied in a standard cloning vector (pJ series). The genes was amplified out of the pJ vectors by polymerase chain reaction (PCR) using oligos with non-homologous terminal sequences to prepare for insertion into the mammalian expression vector (System Biosciences, pM series). Kell was amplified with an upstream oligo consisting of 25 nt homologous to the upstream pM insertion site and 25 nt homologous to the 5' terminus of Kell; and a downstream oligo consisting of 25 nt homologous to the 5' terminus of scFv, 24 nt encoding a (GlyGlyGlySer)×2 spacer (Seq. ID No. 23), and 25 nt homologous to the 3' terminus of Kell. scFv was amplified with an upstream oligo consisting of 25 nt homologous to the 3' terminus of Kell insertion site, 24 nt encoding a (GlyGlyGlySer)×2 spacer (Seq. ID No. 23), and 25 nt homologous to the 5' terminus of scFv; and a downstream oligo consisting of 25 nt homologous to the downstream pM insertion site, the 27 nt sequence tacccctatgacgtgcccgactatgcc (Seq. ID No. 8) encoding an HA epitope tag, and 25 nt homologous to the 3' terminus of scFv. The amplified products were purified by gel electrophoresis (Qiagen). The pM vector was linearized by PCR with tail-to-tail oligos homologous to the upstream and downstream insertion sites. The downstream primer additionally contained the 27 nt sequence tacccctatgacgtgcccgactatgcc (Seq. ID No. 8) encoding an HA epitope tag. The linearized vector was purified by PCR purification (Qiagen). The Kell and scFv amplicons were ligated into the linearized pM vector by one-pot Gibson assembly, described in detail in Gibson 2011, Methods Enzymology Vol 498, p. 394. Sequences were confirmed by Sanger sequencing. 5. Fusion of Two Genes (Reporter Assembly) (GPA-HA) The genes for complement receptor 1 (CR1) and green fluorescent protein (GFP) were synthesized by a commercial vendor (DNA2.0) and supplied in standard cloning vectors (pJ series). The CR1 gene was amplified out of the pJ vector by polymerase chain reaction (PCR) using oligos with non-homologous terminal sequences to prepare for insertion into the mammalian expression vector (System Biosciences, pM series): the upstream oligo consisted of 25 nt homologous to the upstream pM insertion site and 25 nt homologous to the start of CR1; the downstream oligo consisted of 54 nt homologous to the viral-derived T2A sequence gagggcagaggaagtcttctaacatgcggtgacgtggaggsgsstcccggccct (Seq. ID No. 7). The GFP gene was amplified out of the pJ vector by polymerase chain reaction (PCR) using oligos with non-homologous terminal sequences to prepare for insertion into the mammalian expression vector (System Biosciences, pM series): the upstream oligo consisted of 54 nt homologous to the viral-derived T2A sequence gagggcagaggaagtcttctaacatgcggtgacgtggaggsgsstcccggccct (Seq. ID No. 7) and 25 nt homologous to the start of GFP; the downstream oligo consisted of 25 nt homologous to the downstream pM insertion site and 25 nt homologous to the end of GFP. The amplified products were purified by gel electrophoresis (Qiagen). The pM vector was linearized by PCR with tail-to-tail oligos homologous to the upstream and downstream insertion sites and purified by PCR purification (Qiagen). The CR1 and GFP amplicons were ligated together and into the linearized pM vector by Gibson assembly, described in detail in Gibson 2011, Methods Enzymology Vol 498, p. 394. Sequences were confirmed by Sanger sequencing.

Example 12: mRNA Assembly

A gene of interest is cloned into the multiple cloning site of the pSP64 vector (Promega) using standard molecular biology methods. The vector is digested with EcoRI (NEB) to generate a linearized dsDNA vector containing the SP6 promoter, gene of interest, and 30 nucleotide long poly-A tail. mRNA is synthesized by reaction with SP6 RNA polymerase (Promega) according to manufacturer's instructions, including recommended concentrations of 5' cap analog (ARCA) to synthesize capped mRNA transcript. The reaction mixture is then treated with DNAse to digest the template vector (Riboprobe from Promega) and the mRNA is purified using the EZNA MicroElute RNA Clean-Up kit (Omega).

Example 13: Cell Culture

1. Human Red Blood Cells (RBCs)

CD34 cells are isolated from peripheral blood by supermagnetic microbead selection by the use of Mini-MACS columns (Miltenyi Biotec; 94%+/−3% purity). The cells are cultured in erythroid differentiation medium (EDM) on the basis of IMDM supplemented with stabilized glutamine, 330 µg/mL holo-human transferrin, 10 µg/mL recombinant human insulin, 2 IU/mL heparin, and 5% solvent/detergent virus-inactivated plasma. The expansion procedure comprises 3 steps. In the first step (day 0 to day 7), $10^4$/mL CD34+ cells are cultured in EDM in the presence of 1 µM hydrocortisone, 100 ng/mL SCF, 5 ng/mL IL-3, and 3 IU/mL EPO. On day 4, 1 volume of cell culture is diluted in 4 volumes of fresh medium containing SCF, IL-3, EPO, and hydrocortisone. In the second step (day 7 to day 11), the cells are resuspended at $10^5$/mL in EDM supplemented with SCF and EPO. In the third step (day 11 to day 18), the cells are cultured in EDM supplemented with EPO alone. Cell counts are adjusted to $7.5 \times 10^5$ to $1 \times 10^6$ and $5\text{-}10 \times 10^6$ cells/mL on days 11 and 15, respectively. Beyond day 18, the culture medium containing EPO is renewed twice a week. The cultures are maintained at 37° C. in 5% CO2 in air.

2. Mouse Red Blood Cells

Methods of culturing mouse erythroid cells from mouse fetal liver erythroid progenitors are known in the art, see e.g., Shi et al. 2014, PNAS 2014 111(28):10131.

Mouse erythroid progenitors are isolated from fetal livers. Fetal livers are purchased from Charles River Labs. Livers are put in 1 ml PBS on ice. Pipette up and down to get a single-cell suspension solution and pass by a 70 um strainer (BD Falcon 35-2235). Rinse the mesh with 1 ml PBS. Combine the flow through (1 ml per embryo). Pellet the cells at 1.5 k RPM for 5 min, re-suspend with red cell lysis buffer (Ammonium Chloride Solution from Stemcell), and incubate on ice for 10 mins. Pellet the cells at 1.5 k RPM for 5 min, remove the lysis buffer, and re-suspend with 10 ml PBS-2% FBS. Add chromPure Rat IgG (Jackson ImmunoResearch, #012-000-003) at 50 ul/mouse and incubate at 4 C for 5 min. Add Biotinylated anti-mouse TER119 (BD Pharmingen, #553672) at (at 1 ul/$1 \times 10^6$ cells) and incubate at 4 C for 15 min. Add Ms Lineage Panel (Fisher Scientific (Thermo Fisher Scientific) #BDB559971) to the cells at (2 ul/$1 \times 10^6$ cells) and incubate at 4 C for 15 min. Washing once with 10× volume of PBS/ and Spin the cells with 1.5 k RPM for 5 min at 4 degree. Add Streptavidin Particles Plus—DM (magnetic beads) (BD Pharmigen, #557812) (5 ul/$1 \times 10^6$ cells) and incubate at 4 C for 30 min. Prepare 2-4 FACS tubes on a magnetic holder. Aliquot 2 ml cells into each tube (4 ml in total), and carefully take the cells out of the tube and put into the other tube on the other side avoiding the disruption of the magnetic stick beads. Repeat the same procedure and take the Ter119 negative and linkage negative cells to a new tube. Concentrate the cells, and resuspend the cells with 50-100 ul PBS (2% FBS).

Purified erythroid progenitors are cultured in differentiation medium comprising (for 40 mL): IMDM: 29 ml, FBS (Stem Cell): 6 ml (Final 15%), 10% BSA in IMDM (Stem Cell): 4 ml (Final 1%), 10 mg/ml Holo-transferrin: 2000 ul (Final: 500 ug/ml), 100*L-Glutamine: 400 ul, 100* penicillin streptomycin: 400 ul, 10 U/ul Epo: 2 ul (Final: 0.5 U/ml), 10 mg/ml Insulin: 40 ul (Final: 10 ug/ml). Culture $2 \times 10^5$ cells/ml in the differentiation medium in 24 wells plate at 37 C. After a total culture of 44-48 hours, analyses are performed, for example by flow cytometry as performed herein. Enucleated red blood cells are gated out using (Hoechst stain) for differentiation profile analysis. A successful culture will yield 16 fold increase.

3. Platelets

Donated CD34+ cells are acquired from the Fred Hutchinson Cancer Research Center. The CD34+ enriched cells are plated in a serum-free medium at $2\text{-}4 \times 10^4$ cells/mL and medium refreshment is done on day 4 by adding an equal volume of media. On day 6, cells are counted and analyzed: $1.5 \times 10^5$ cells are washed and placed in 1 mL of the same medium supplemented with a cytokine cocktail consisting of TPO 30 ng/mL, SCF 1 ng/mL, interleukin (IL)-6 7.5 ng/mL and IL-9 13.5 ng/mL] to induce megakaryocyte differentiation. At day 10, ½-¼ of the suspension culture is replaced with fresh medium. All cytokines are purchased from Peprotech. The cultures are incubated in a humidified atmosphere (10% CO2) at 39° C. for the first 6 days of culture and 37° C. for the last 8 days. Viable nucleated cells are counted with a hemocytometer (0.4% trypan blue; Invitrogen, Burlington, ON, Canada).

Clonogenic progenitor cells (CPC) are assayed using MethoCult H4436 for myeloid CPC, and MegaCult-C for colony-forming unit-megakaryocyte (CFU-Mk), according to manufacturer's instructions (StemCell Technologies, Vancouver, BC, Canada). To assess differentiation, cells are stained with antibodies against CD61m CD42b, CD41, CD61, and CD49b by flow cytometry using a FACS-Calibur (Becton Dickinson). For cell cycle analysis, cells are rinsed with phosphate-buffered saline (PBS), fixed with formaldehyde 2% (Sigma, St Louis, Mo., USA) for 5 min and permeabilized with 0.1% of Triton X-100 (Bio-Rad, Hercules, Calif., USA). Cells are then marked with mAb-Ki-67-FITC (BD Bioscience, San Jose, Calif., USA), washed and resuspended in 0.5 mL PBS-1% fetal bovine serum (FBS)-0.01% azide 7-amino-actinomycin D (7-AAD) following the manufacturer's instructions (BD Biosciences).

Example 14: Cell Isolation

1. Primary RBCs

Whole blood is collected using aseptic techniques in tubes containing low molecular weight heparin, dalteparin sodium (9 units/mL blood). Blood is centrifuged at 5000×g for 5 minutes and after removal of plasma and buffy coat (both can be retained for later use), the erythrocytes are washed twice in cold (4 C) phosphate buffered saline (PBS) with centrifugation. The resultant red blood cell population is stored at 4 C in CPDA-1 anticoagulant or a glycerol solution for long-term preservation.

2. Primary Platelets

Whole blood (40 ml) is collected in 3.8% sodium citrate (1:9 citrate to blood vol/vol) from healthy individuals under an appropriate IRB protocol. Blood is centrifuged at 200 g for 15 minutes to isolate platelet-rich plasma (PRP). Platelets are then washed in modified Tyrode's buffer (containing 138 mM NaCl, 5.5 mM dextrose, 12 mM NaHCO3, 0.8 mM CaCl2, 0.4 mM MgCl2, 2.9 mM KCl2, 0.36 mM Na2HPO4 and 20 mM Hepes, pH 7.4) in presence of 1 µM prostaglandin 12, and resuspended in the same buffer.

Example 15: Irradiation of Primary or Cultured Cells

Irradiation of a population of exogenous antigen-expressing EHCs can be performed to ensure that they are incapable of replication. Such protocols are similar to those known in the art for irradiating cells, e.g., primary red blood cells. Briefly, one unit (350 ml) of whole blood is taken and divided into two aliquots of 175 ml each, 10 such units are thus divided into 20 aliquots. One aliquot (175 ml) from each unit of blood is subjected to gamma irradiation of 25 Gy, and not exceeding 50 Gy, by a self-contained gamma cell irradiator (GammaCell 1000, Theratronics). The blood is then stored at 4 C under conventional blood banking conditions. Sampling is done from these 10 irradiated and 10 non-irradiated blood bags on days 0, 7, 14, and 21 with the help of sampling site coupler (Fenwal, USA). Tests for cell proliferation are conducted, including a thymidine incorporation assay to quantify any mitotic potential. Supernatant is assayed for free hemoglobin by absorbance spectroscopy, and for free lactate dehydrogenase by colorimetric assay (Pierce) to evaluate levels of cell lysis.

Example 16: Enucleation of Erythroid Cells

Erythroid cells are grown to semiconfluence (1 to $4\times10^4$ cells per cm2) on 12-mm diameter coverslips coated with collagen in IMDM medium supplemented with 100 units/ml of penicillin and 100 units/ml of streptomycin. The collagen is necessary to prevent all the cells from falling off the coverslip during centrifugation. Cells are grown to monolayers (5×104 cells per cm2) on coverslips either in the same medium or in Dulbecco's modified Eagle's medium with 10% calf serum. It is not necessary to coat the cell coverslips with collagen. In order to enucleate the cells, the coverslips are inverted (cell side down) and placed into the bottom of 15-ml Corex centrifuge tubes containing 2-5 ml of medium with 10 g of cytochalasin B per ml. The centrifuge tubes with the coverslips are placed immediately into a Sorvall RC-2 centrifuge that has been warmed to 37 C by spinning the (SS 34) rotor with the head in place for about 1 hr at 10,000 rpm (with the temperature regulator set at 37-39°). The length of time and speed of centrifugation are crucial factors for successful enucleation. Cells are spun at 9000 rpm for 1 hr at 37±20 and cells are spun at 6500 rpm for 50 min at 37±–20. After centrifugation, the coverslips are removed from the centrifuge and placed cell side up into 35-mm (Falcon) tissue culture dishes (Biolquest) containing 3 ml of medium without cytochalasin B. Within 30-60 min at 370, the cells are morphologically normal and 90-99% lacked nuclei. Enucleated cells are removed from the coverslips by treatment with trypsin-EDTA (Grand Island Biological Co.) and the cells are suspended in normal medium. The enucleated cells are then replated in small drops on 22-mm2 coverslips kept in 35-mm tissue culture dishes and placed in an incubator. At time intervals after replating, the coverslips are mounted on slides (12) and observations on the enucleates are made with Zeiss phase contrast, polarized light, and Nomarski optics.

Example 17: Contacting of Cells

1. Nucleic Acid—Transfection

The nucleic acid of interest is scaled up to provide approximately 5 ug nucleic acid per $10^5$ EHCs to be loaded, e.g., a cell, such as an erythroid cell, a platelet, or a hematopoietic precursor cell. The nucleic acid is diluted in Opti-MEM Medium (Life Technologies) at a ratio of 1 ug to 50 uL medium. The diluted nucleic is then combined with a transfection reagent (Trans-IT for DNA, Trans-IT mRNA for mRNA, Trans-IT siRNA for siRNA, Mirus Bio) at a 1:1 volume ratio and allowed to form complexes for 5 minutes at room temperature. The nucleic acid complex is added to cells for 12-24 hours. Optionally, after this period of time, the media can be exchanged with fresh media such that the transfection reagents are no longer present.

2. Nucleic Acid—Viral Transduction

The gene of interest is cloned into the multiple cloning site of lentivirus vector pCDH with the MSCV promoter sequence from System Biosciences.

Lentivirus is produced in 293T cells by transfecting the cells with lipofectamine. $5\times10^6$ 293T cells (Lenti-X 293T Cell Line, Clontech catalog #632180) are plated in a P10 petri dish the day before transfection. Cell confluency should be around 70%. One plate is transfected per construct. 20 μl (10 μg) pPACKH1 (System Biosciences) plasmid mix+2 μg lenti construct+20 μl Plus reagent (LifeTechnologies, Catalog #11514-015) are combined in 400 μl Optimem and incubated 15 min at RT. 30 μl of LF2000 (LifeTechnologies, Catalog #11668-019) is diluted into 400 μl Optimem, added dropwise to DNA mix, and incubated for 15 min RT. DNA mix is added to cells (cells are in 9 ml of Optimem). Cells are incubated for 6 hours and then the medium is changed to DMEM/10% FBS. The virus supernatant is collected 48 hours post-transfection by centrifugation at 1,500 rpm for 5 minutes. The supernatant is collected and frozen in 1 ml aliquots at −80° C.

Target cells are transduced at day 3-7 of the culture process described herein. $5\times10^5$ cultured cells are plated in 500 μL of medium containing 20 μg/mL polybrene in a 24-well plate. For each virus, cells are transduced in triplicate wells. Virus supernatant is added in another 500 μL of medium and the sample is mixed by pipetting. Infection is achieved by spinoculation, spinning the plate at 2000 rpm for 90 minutes at room temperature. After spinoculation, the cells are incubated at 37 C overnight, and the next day 1 mL of fresh IMDM medium with appropriate cytokines is added.

3. Nucleic Acid—Cationic Polymer

An mRNA ecoding the transgene of interest, and including an upstream promoter sequence and a downstream poly A tail, can be purchased from multiple commercial vendors (e.g., IDT-DNA, Coralville Iowa). RNA transfections are carried out using RNAIMax (Invitrogen, Carlsbad, Calif.) or TRANSIT-mRNA (Mims Bio, Madison, Wis.) cationic lipid delivery vehicles. RNA and reagent are first diluted in Opti-MEM basal media (Invitrogen, Carlsbad, Calif.). 100 ng/uL RNA is diluted 5× and 5 μL, of RNAIMax per μg of RNA is diluted 10×. The diluted components are pooled and incubated 15 minutes at room temperature before they are dispensed to culture media. For TRANSIT-mRNA transfections, 100 ng/uL RNA is diluted 10× in Opti-MEM and BOOST reagent is added (at a concentration of 2 μL, per μg of RNA), TRANSIT-mRNA is added (at a concentration of 2 μL, per μg of RNA), and then the RNA-lipid complexes are delivered to the culture media after a 2-minute incubation at room temperature. RNA transfections are performed in Nutristem xenofree hES media (STEMGENT®, Cambridge, Mass.) or Opti-MEM plus 2% FBS. Successful introduction of the mRNA transcript into host cells can be monitored using various known methods, such as a fluorescent label or reporter protein, such as Green Fluorescent Protein (GFP). Successful transfection of a modified mRNA can also be determined by measuring the protein expression level of the target polypeptide by e.g., Western Blotting or immunocytochemistry. Similar methods may be followed for large volume scale-up to multi-liter (5-10,000 L) culture format following similar RNA-lipid complex ratios.

4. Nucleic Acid—Electroporation mRNA ecoding the transgene of interest, and including an upstream promoter sequence and a downstream poly A tail, can be purchased from multiple commercial vendors (e.g., IDT-DNA, Coralville Iowa). Electroporation parameters are optimized by transfecting erythroid lineage cells with mRNA transcripts and measuring transfection efficiency by quantitative RT-PCR with primers designed to specifically detect the exogenous transcripts. For certain cells preparations, discharging a 150 uF capacitor into 2.5×10^6 cells suspended in 50 µl of Opti-MEM (Invitrogen, Carlsbad, Calif.) in a standard electroporation cuvette with a 2 mm gap is sufficient for repeated delivery in excess of 10,000 copies of modified mRNA transcripts per cell, as determined using the standard curve method, while maintaining high viability (>70%). Cell density may vary from 1×10^6 cell/50 µl to a density of 2.5×10^6 cells/500 and require from 110V to 145V to transfect cells with similar efficiencies measured in transcript copies per cell. Large multi-liter (5-10,000 L) electroporation may be performed similar to large volume flow electroporation strategies similar to methods described with the above described constraints (Li et al., 2002; Geng et al., 2010).

5. Polypeptide—Liposome

Cells, including primary terminally-differentiated cells e.g., erythrocytes, can be loaded with exogenous protein on their surface and in their cytoplasm. The loading of proteins can be performed using liposomes.

Lipids (Pro-Ject reagent, Pierce) in organic solvent were dried under nitrogen into a thin film in glass scintillation vial. Approximately 2 uL lipids were used per 10^5 cells. Polyclonal mouse IgG (Abcam) was labeled with Dylight-650 (Pierce) per manufacturer's instructions. Protein solution at 0.1 mg/mL in PBS was added to the dried lipid mixture. The solution was pipetted several times, incubated for 5 minutes at room temperature, then vortexed vigorously to generate encapsulating liposomes. Serum-free medium was added to bring the total volume to 500 uL per 10^5 cells. The liposomal mixture was then incubated with the cells for 3-4 hours at 37 C.

FIG. 1 shows the loading of an exogenous protein, in this case fluorescently-labeled IgG, into primary erythrocytes with liposomes. The loading is measured by flow cytometry. The loading is dose-dependent, as 0.06% of cells are fluorescent without liposomes, ~60% of cells are fluorescent at a low liposome dose, and ~85% of cells are fluorescent at a high liposome dose. The data in FIG. 1 is strong proof that exogenous proteins can be loaded into erythroid cells with liposomes.

6. Polypeptide—Mechanical Disruption

Cells may be loaded using a microfluidic device containing 1 µm, 2 µm, 3 µm, 4 µm, 5 µm, 10 µm wide channels that transiently porate the cells, allowing a payload to enter when the cells are pressured through the system.

The silicon-based devices are fabricated at the Massachusetts Institute of Technology microfabrication facility using photolithography and deep reactive ion etching techniques. In this process, 6" silicon wafers with a 450-µm thickness are treated with hexamethyldisilazane, spin coated with photoresist (OCG934; FujiFilm) for 60 s at 3,000 rpm, exposed to UV light (EV1; EVG) through a chrome mask with the constriction channel design, and developed in AZ405 (AZ Electronic Materials) solution for 100 s. After 20 min of baking at 90° C., the wafer is etched by deep reactive ion etching (SPTS Technologies) to the desired depth (typically 15 µm). The process is repeated on the opposite side of the wafer (i.e., the one not containing the etched channels) using a different mask, which contains the access hole patterns, and using a thicker photoresist AZ9260 (AZ Electronic Materials). Wet oxidation is then used to grow 100-200 nm of silicon oxide before the wafer is anodically bonded to a Pyrex wafer and diced into individual devices. Before each experiment, devices are visually inspected and mounted onto a holder with inlet and outlet reservoirs (all designed in-house and produced by Firstcut). These reservoirs interface with the device using Buna-N O-rings (McMaster-Carr) to provide proper sealing. The inlet reservoir is connected to a home-made pressure regulator system using Teflon tubing to provide the necessary driving force to push material through the device. A population of erythroid cells is first suspended in the desired delivery buffer [growth medium, PBS, or PBS supplemented with 3% FBS and 1% F-68 Pluronics (Sigma)], mixed with the desired delivery material, and placed in the device's inlet reservoir. This reservoir is connected to a compressed air line controlled by a regulator, and the selected pressure (0-70 psi) is used to drive the fluid through the device. Treated cells are then collected from the outlet reservoir. Cells are incubated at room temperature in the delivery solution for 5-20 min after treatment to ensure hole closure before being subjected to any further treatment. To deliver fluorescently labeled phenylalanine ammonia hydroxylase (PAH), the experiments are conducted as described above such that the delivery buffer contained 0.1-0.3 mg/mL PAH. GFP knockdown is measured as the percentage reduction in a cell population's average fluorescence intensity relative to untreated controls.

7. Polypeptide—Surface Conjugation

The cell surface is treated with Traut's reagent (2-iminothiolane HCl, Pierce) to thiolate primary amines. Traut's reagent is dissolved in Tris buffer pH 8 with EDTA to prevent oxidation of sulfhydryls. Approximately 1 pmol Traut's reagent is used to treat 10^6 cells. Incubate Traut's reagent with cells for 1 hour at room temperature. Remove excess or unreacted reagent by centrifugation and washing the cells. The number of available sulfhydryl groups can be measured using Ellman's Reagent. In the meantime, treat suitable exogenous antigen polypeptide with amine-to-sulfhydryl crosslinker, such as SMCC (Pierce) according to manufacturer's instructions. Excess crosslinking reagent is removed by desalting. The maleimide-functionalized protein is then incubated with the thiolated cells for several hours. Unreacted protein is separated from the conjugated cells by centrifugation and washing.

8. Polypeptide—Non-Covalent Surface Attachment

The gene for an antibody scFv against hepatitis B surface antigen (scFv, described in Bose 2003, Molecular Immunology 40:617) is fused to a 6-histidine affinity tag (Seq. ID No. 27) and to the gene encoding the polypeptide sequence that binds mouse glycophorin A, HWMVLPWLPGTLDGGSGCRG (Seq. ID No. 28), in a mammalian expression vector (Genlantis). The full fusion protein is produced by transient transfection of HEK-293T cells using standard methods and purified on a Ni-NTA affinity resin (Pierce) according to manufacturer's instructions. The purified fusion protein is incubated with mouse erythrocytes at >100 nM concentration to allow for rapid equilibration and binding of the peptide to glycophorin A.

9. Polypeptide—Lipid Insertion into Membrane

Traut's reagent (Thermo Fisher) is used to generate sulfhydryl groups on an amine-containing suitable exogenous antigen polypeptide molecule following manufacturer's protocol. The reaction mixture is incubated for 1 h at room temperature (RT) on a shaker and washed through a spin desalting column (Zeba, MWCO 7K, Thermo Scientific) following the manufacturer's instructions to remove the unreacted Traut's reagent. The generation of sulfhydryl groups on the modified polypeptide is quantified using Ellman's Reagent (Pierce) based on the manufacturer's protocol.

DSPE-PEG$_{3400}$-mal (1×10^−3M in PBS, 4 µL, molar ratio lipid:Polypeptide=1:1) (all lipids purchased from Avanti Polar Lipids and stored as chloroform solution under argon at −20 C) are added to the desalted polypeptide solution and incubated at RT on a shaker. After 1 h, the sample solution is filtered using a centrifugal filter device (Microcon, Millipore Co.) at 14 000 g for 15 min at 4° C. to remove the small molecules and suspended in 600 µL PBS (1 mg/mL polypeptide).

200 µL of whole blood is suspended in 1000 µL PBS and spun at 1500 g for 30 s, repeated four times. Finally, the RBCs are suspended in 800 µL PBS. The conjugation of RBC/DSPE-PEG-Polypeptide is prepared by mixing the above RBCs suspensions and various amounts of DSPE-PEG-Polypeptide solution (1 mg per mL) followed by incubation for 15-30 min at 37° C. The mixture is kept for 5 min at room temperature, then washed three times in PBS and resuspended to a final RBC concentration of 5×10^8 per mL. An automated cell counter (Countess, Invitrogen) is used to measure the cell concentration.

10. Polypeptide—Hypotonic Loading

A suitable exogenous antigen polypeptide, in this instance mouse IgG, was purchased from Abcam and was added at 0.25 mg/mL to a RBC suspension in isotonic solution at a hematocrit (Hct) of 70%. The suspension was dialyzed in 250 mL of a hypotonic solution containing 10 mM sodium phosphate pH 7.4, 10 mM sodium bicarbonate, and 20 mM glucose, stirred at 15 rpm for 1 hour at 4 C. The cells were then isotonically resealed by adding 1/10 volume of resealing solution comprising 5 mM adenine, 100 mM inosine, 100 mM sodium pyruvate, 100 mM sodium phosphate, 100 mM glucose, 12% (w/v) NaCl at pH 7.4. Cells were then incubated at 37 C for 30 minutes.

11. Polypeptide—Cell-Penetrating Peptide

The manufacture of protamine-conjugated polypeptide is known in the art, see e.g., Kwon et al. 2009 J Contr Rel 139(3):182. 5 mg/ml of Low Molecular Weight Protamine (LMWP) in 50 mM HEPES buffer (pH 8) is mixed with the heterobifunctional cross-linker 3-(2-pyridyldithio)propionic acid N-hydroxysuccinimide (SPDP, Sigma-Aldrich) at a 1:10 molar ratio in DMSO and shaken for 1 h at room temperature. The reaction mixture is then treated with 50 mM dithiothreitol (DTT, Sigma-Aldrich) and the thiolated LMWP is purified by HPLC on a heparin affinity column. The product is collected by ultrafiltration, lyophilized, and stored at −20° C. until further use.

For conjugation, 5 mg/ml suitable exogenous antigen polypeptide is mixed with SPDP (40 µl of 0.1M SPDP in ethanol to 1 ml protein solution) in phosphate buffer, and stirred at room temperature for 1 h. Unreacted SPDP is removed by rapid desalting and buffer exchange by FPLC with 0.1M phosphate buffer (pH 7.4). Activated polypeptide is then conjugated with a 10-fold molar excess of the above-prepared LMWP-SH for 24 h at 4° C. The LMWP-polypeptide conjugates are isolated by ion-exchange chromatography using a heparin affinity column followed by five rounds of centrifugal filtration (molecular weight cut-off: 5,000 Da). Pooled LMWP-polypeptide conjugates are concentrated, and the degree of conjugation determined by MALDI-TOF mass spectroscopy.

For uptake experiments, fresh sheep erythrocytes (MP Biomedicals, Solon, Ohio) are suspended in Hank's balanced salt solution (HBSS) at a density of 5×10^8 cells/ml, and are then incubated with a 0.5 mg/ml solution of the LMWP-polypeptide conjugates for 30 min at room temperature under gentle shaking. RBCs are then washed with HBSS and stored at 2-8 C.

12. Polypeptide—Chemical Permeability

3×10^8 RBCs were preincubated for 30 min with chlorpromazine (Sigma Aldrich) at 200 µM in Ringer's solution. Afterwards, the suitable exogenous antigen polypeptide was added in Ringer's solution (1 to 4 µM) to a final volume of 400 µl and incubated for 30 min at room temperature under mild agitation. After incubation, cells were washed twice, resuspended in Ringer and collected for analysis.

13. Polypeptide—Enzymatic Conjugation

Cell surface enzymatic conjugations with sortase are known in the art, see e.g., Shi et al PNAS 2014 111(28): 10131. To label the GPA N terminus with polypeptide, 30 uL of 500 uM *S aureus* sortase and 1 mM polypeptide with LPETGG (Seq. ID No. 29) at the C terminus is preincubated in 50 mM Tris pH 7.5, 150 mM NaCl, on ice for 15 minutes and added to 5×10^7 RBCs in DMEM. The sortase and cell mixture is incubated on ice for 30 min with occasional gentle mixing, then spun at 500×g for 2 min at 4 C to remove buffer/DMEM, then washed three times with 1 mL of ice-cold PBS.

Example 18: Assessment of Polypeptide Presence

1. Fluorescent Transgene

Erythroid cells were cultured as described herein. A transgene encoding glycophorin A with an HA tag on the C-terminus fused to GFP with an intervening viral T2A peptide was constructed by Gibson assembly as described herein. The transgene was introduced into the erythroid cells by lentiviral transduction as described herein. Two days after transduction, cells were collected, washed in PBS buffer, and analyzed on a flow cytometer (Attune, Life Technologies). Transduction efficiency was assessed as the percentage of GFP-positive cells in the population.

2. Cell Surface Proteins

For cell surface proteins, the level of protein expression can be detected as early as 2 days after transfection by flow cytometry with antibodies specific for the protein or for a co-expressed epitope tag. Erythroid cells were cultured as described herein. A transgene encoding glycophorin A with an HA tag at the N-terminus was constructed by Gibson assembly as described herein. The transgene was introduced into the erythroid cells by lentiviral transduction as described herein. Two days after transduction, cells were collected, washed in PBS buffer, and stained with 1:50 dilution of mouse anti-HA antibody (Abcam) for 1 hr. Cells were washed and then stained with a 1:100 dilution of alexa 488-labeled goat anti-mouse secondary antibody (Life Technologies) for 30 minutes on ice. Cells were washed and analyzed on a flow cytometer (Attune, Life Technologies). Transduction efficiency was assessed as the percentage of alexa 488-positive cells in the population.

3. Intracellular Proteins

For intracellular proteins, the level of protein expression can be detected as early as 8-12 hours after transfection by Western Blot. Erythroid cells were cultured as described herein. A transgene encoding adenosine deaminase with an HA tag at the C-terminus was constructed by Gibson assembly as described herein. The transgene was introduced into the erythroid cells by lentiviral transduction as described herein. Two days after transduction, cells were collected, washed in PBS buffer, and lysed in RIPA cell lysis buffer (Pierce). Cell lysate was denatured by boiling in 100 mM DTT, then loaded onto a NuPage SDS-PAGE pre-cast gel.

After electrophoresis and transfer to nitrocellulose membrane, protein bands were developed by staining with 1:5000 dilution of mouse anti-HA antibody (Abcam) followed by 1:5000 dilution of goat anti-mouse HRP (Pierce), and subsequent treatment with HRP substrate (SuperSignal, Pierce). Images were captured using an Amersham imager (GE healthcare).

Example 19: Contacting Cells with Chemical Modifying Agent

To increase antigen-presenting cell phagocytosis and to promote liver targeting, the cell compositions described herein are treated for 30 min with 0.15 microM of calcium ionophore A23187 (Sigma Aldrich, Saint Quentin Fallavier, France) at 37 C or with 5 mM of BS3 (Fischer Bioblock Scientific, Illkirch, France) at room temperature (RT). After processing, the final products are stored at 2-8 C in suitable buffer.

Example 20: Assessment of Expression and Activity

The expression of exogenous proteins in and on cultured cells can be assessed quantitatively by flow cytometry (if the protein is expressed on the surface) or by Western blot (for proteins expressed in the cytoplasm).

1. Quantitative Flow Cytometry

Anti-mouse Fc-binding quantitative flow cytometry beads (Simply Cellular Calibration) were purchased from Bangs Labs. Fluorescently labeled mouse antibodies against relevant cell surface receptors—glycophorin A, Ckit, and transferrin receptor—were purchased from BioLegend. Fluorescently labeled mouse antibody against the HA epitope tag was purchased from Life Technologies. Erythroid cells were cultured as described herein. A transgene encoding glycophorin A with an HA tag at the N-terminus was constructed by Gibson assembly as described herein. The transgene was introduced into the erythroid cells by lentiviral transduction as described herein. At least two days after transduction, $2 \times 10^5$ cells were collected, washed in PBS buffer, and stained with 1:100 dilution of one of the above-listed antibodies for 1 hr. Cells were washed and analyzed on a flow cytometer (Attune, Life Technologies). The protocol was repeated for each of the four antibodies listed above. Quantification was performed according to manufacturer's instructions. Briefly, one drop of each of the five bead samples was incubated with 1:100 dilution of an above-listed antibody. The beads were incubated for 1 hr, washed in PBS, and analyzed on a flow cytometer (Attune, Life Technologies). The protocol was repeated for each of the four antibodies listed above. Calibration curves were fit using the manufacturer's provided excel spreadsheets, from which quantification of fluorescence intensity for the cell-based signals was derived.

2. Quantitative Western Blot

Erythroid cells were cultured as described herein. A transgene encoding adenosine deaminase with an HA tag at the C-terminus was constructed by Gibson assembly as described herein. The transgene was introduced into the erythroid cells by lentiviral transduction as described herein. Two days after transduction, cells were collected, washed in PBS buffer, and lysed in RIPA cell lysis buffer (Pierce).

The transgene was introduced into HEK293T cells by transient transfection using lipofectamine 2000 (Life technologies). Cells were cultured for one week and the supernatant was harvested. Recombinant protein was purified on an HA affinity column (Pierce) according to manufacturer's instructions. Protein concentration was assessed by absorbance at 280 nm.

Western blotting was performed as described herein. In addition to the cell lysate samples, known amounts of the recombinant adenosine deaminase were run on the same gel. Following image collection, the intensity of the recombinant bands were used to generate a standard curve to quantify the amount of protein present in the cell samples.

Figure 2:
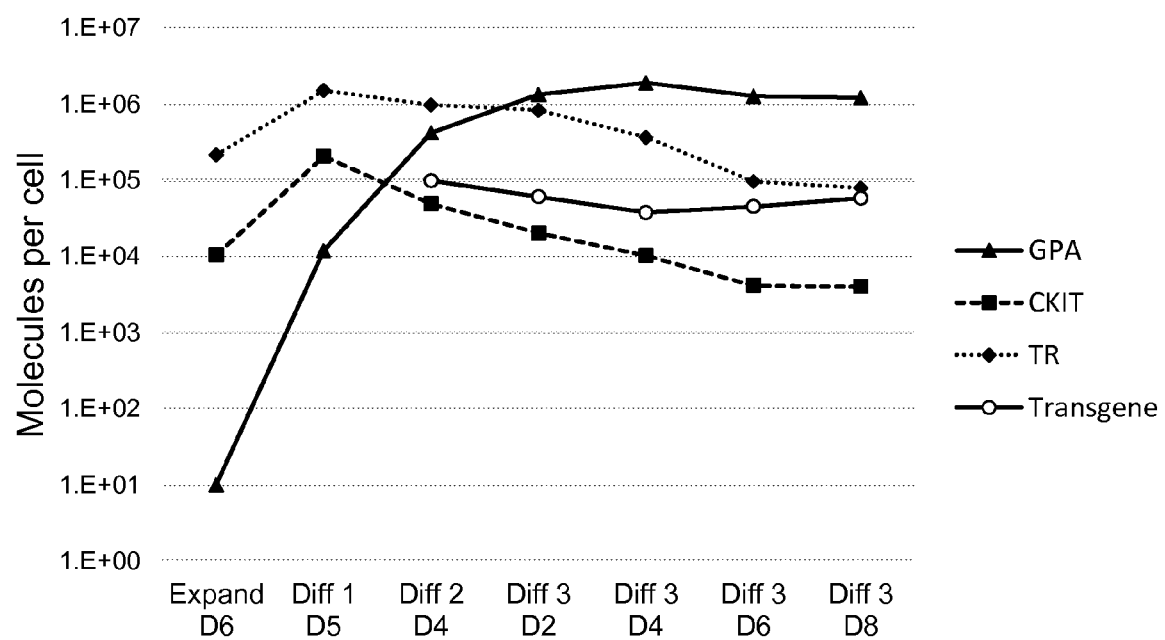
FIG. 2 is a plot of cell surface expression levels assessed by quantitative flow cytometry. The plot shows of various cell surface receptors—glycophorin A (solid triangles), cKIT (dashed squares), transferrin receptor (dotted diamonds)—and an exogenous surface transgene (open circles) during the course of erythroid cell differentiation.
Figure 3J:
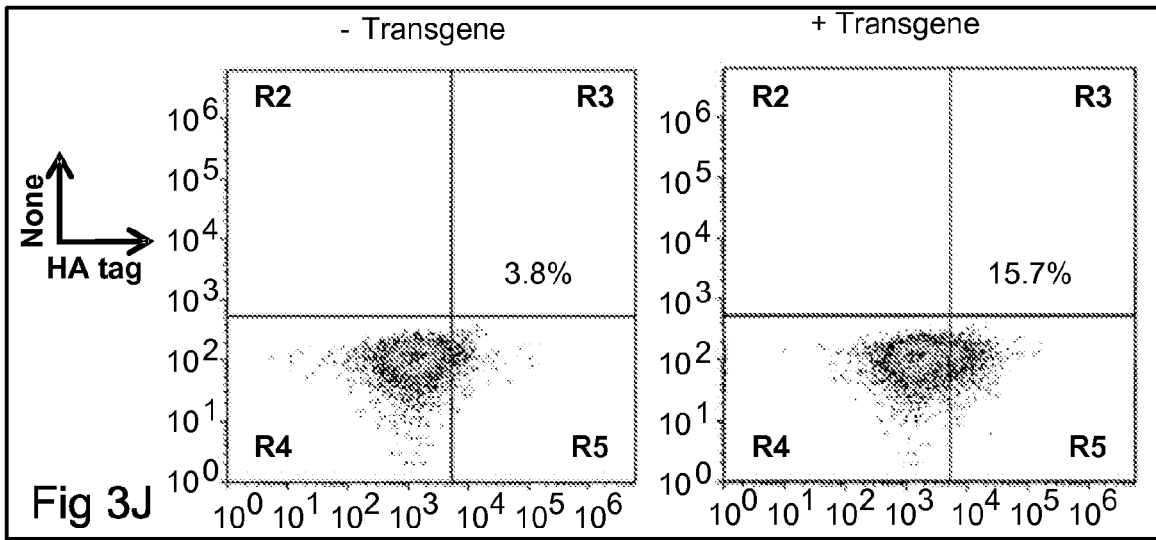
FIG. 3J—Expression of antibody scFv fused to C terminus of Kell-derived fragment of 79 amino acids assessed by anti-HA staining.
Figure 3K:
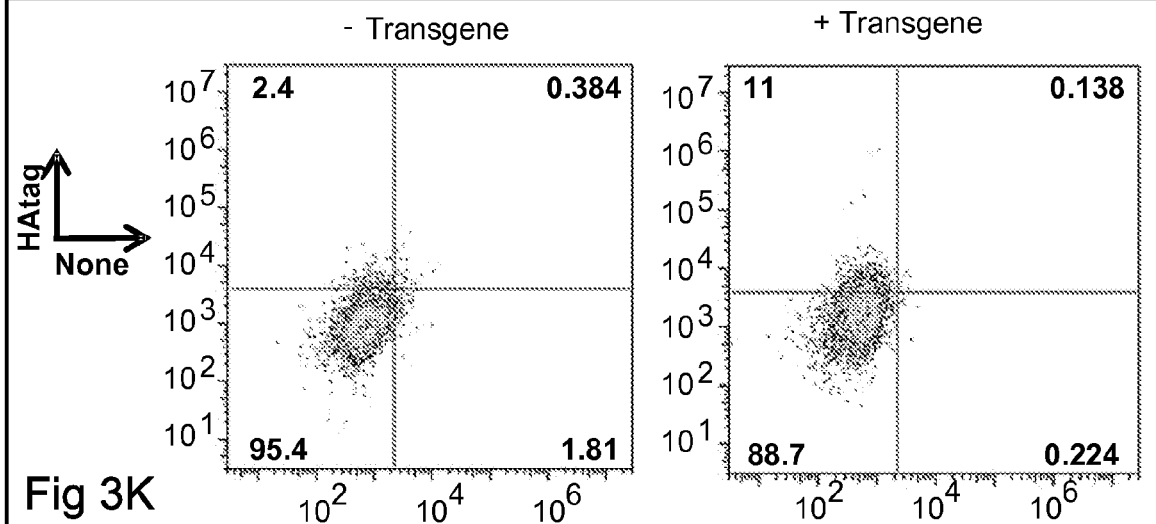
FIG. 3K—Expression of CD55 with HA epitope tag at the extracellular N terminus after the leader sequence assessed by anti-HA staining.
Figure 3L:
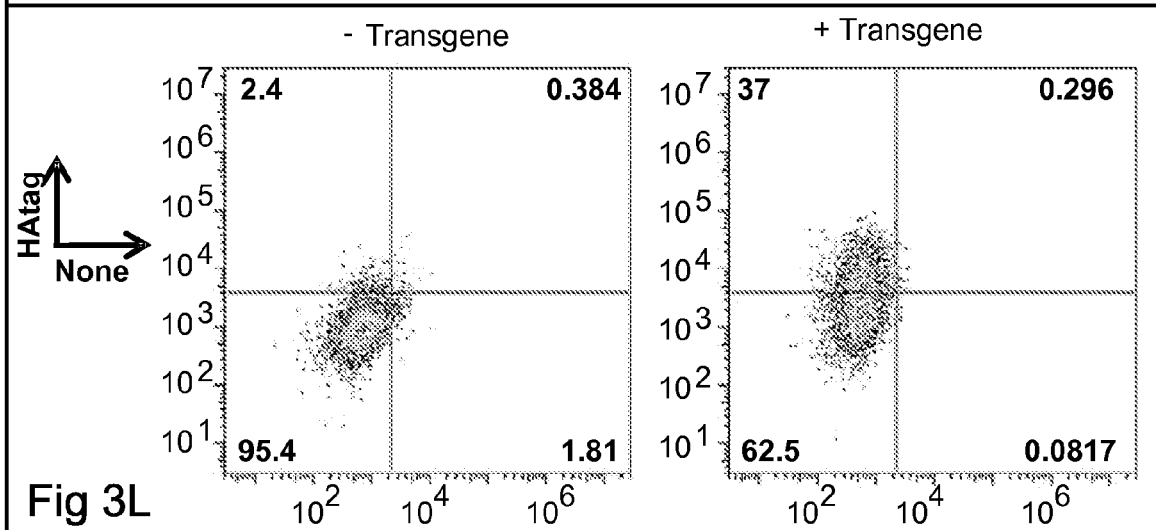
FIG. 3L—Expression of CD59 with HA epitope tag at the extracellular N terminus after the leader sequences assessed by anti-HA staining.
Figure 3Z:
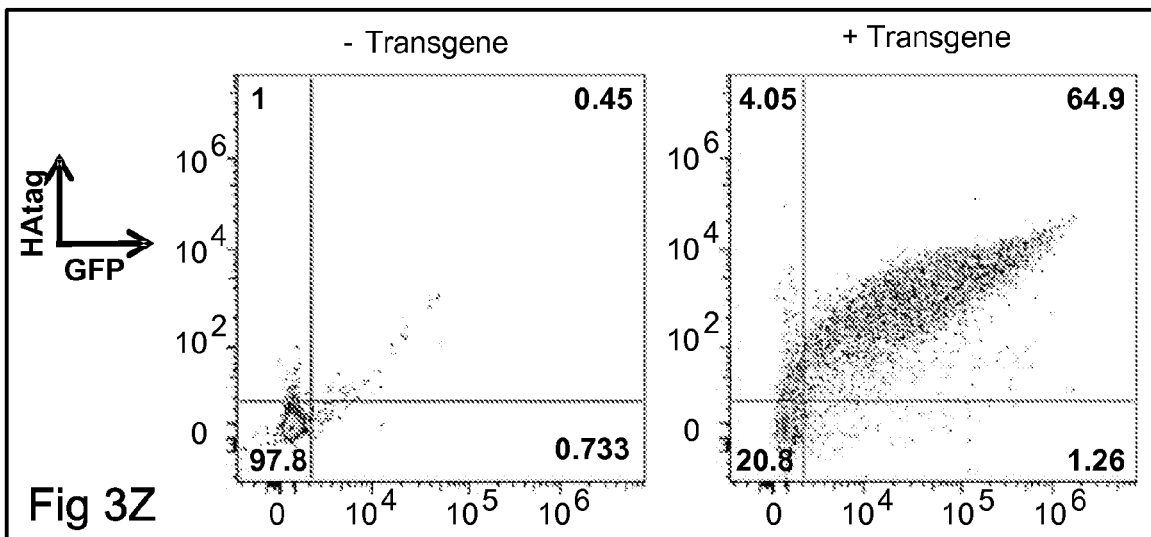
FIG. 3Z—Expression of antibody scFv as N terminal fusion to glycophorin A assessed by anti-HA staining.
Figure 3A:
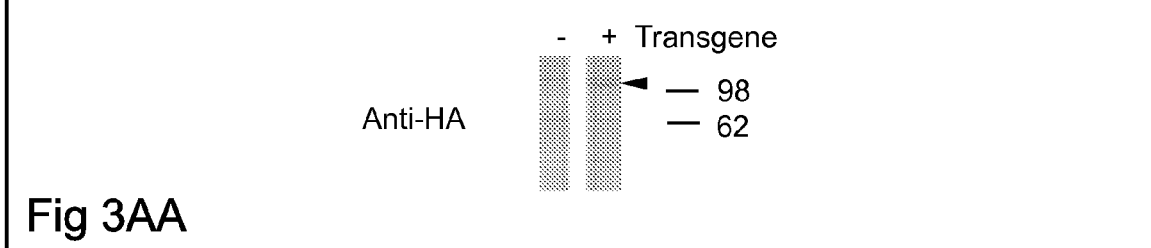
FIG. 3A—Expression of glycophorin A with an HA epitope tag at the cytoplasmic C terminus assessed by expression of co-translated GFP.
Figure 3A:
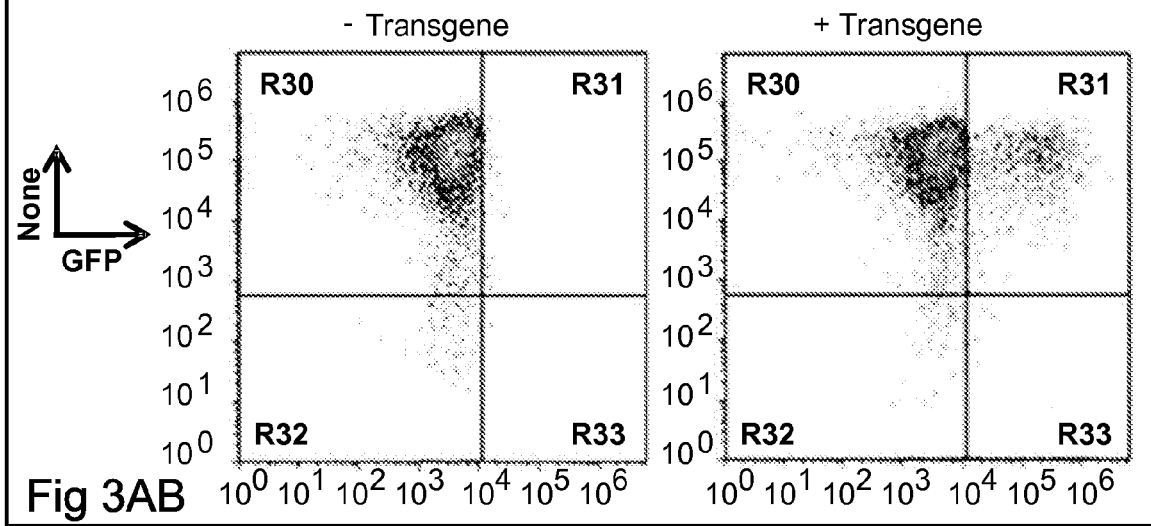
Figure 3A:
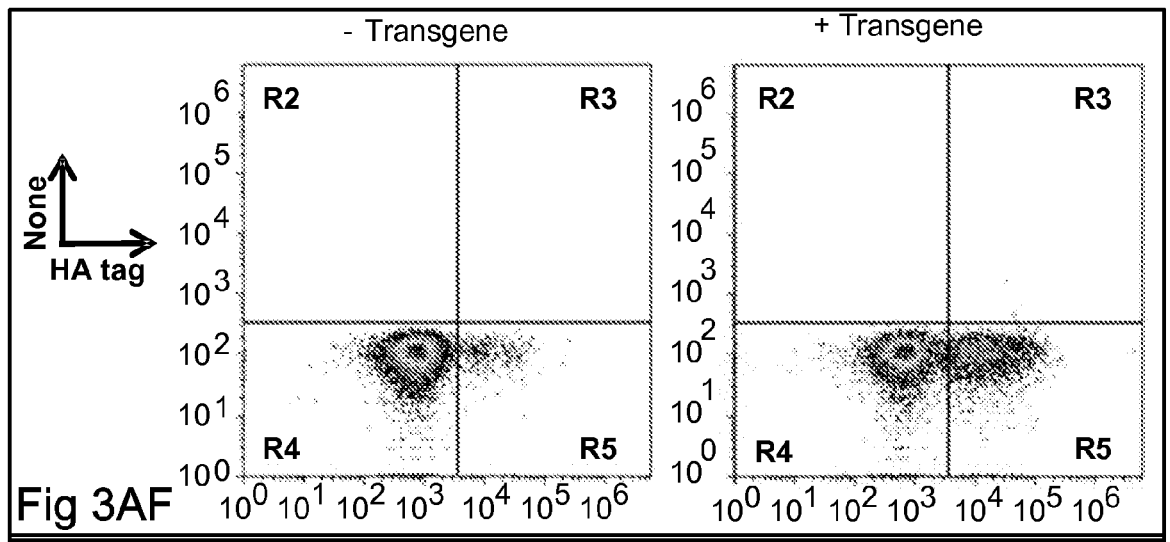
Figure 3A:
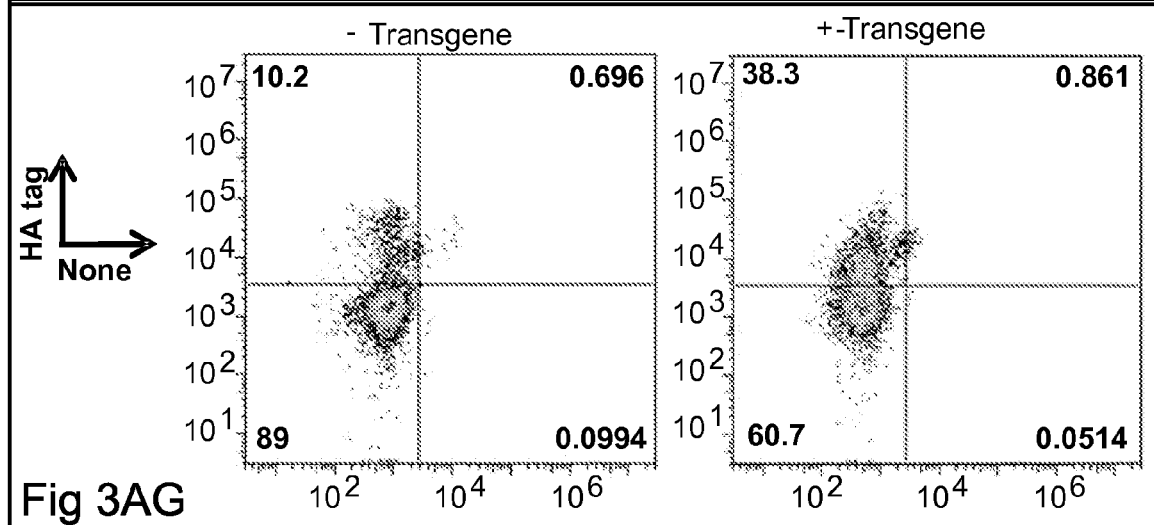
Figure 3A:
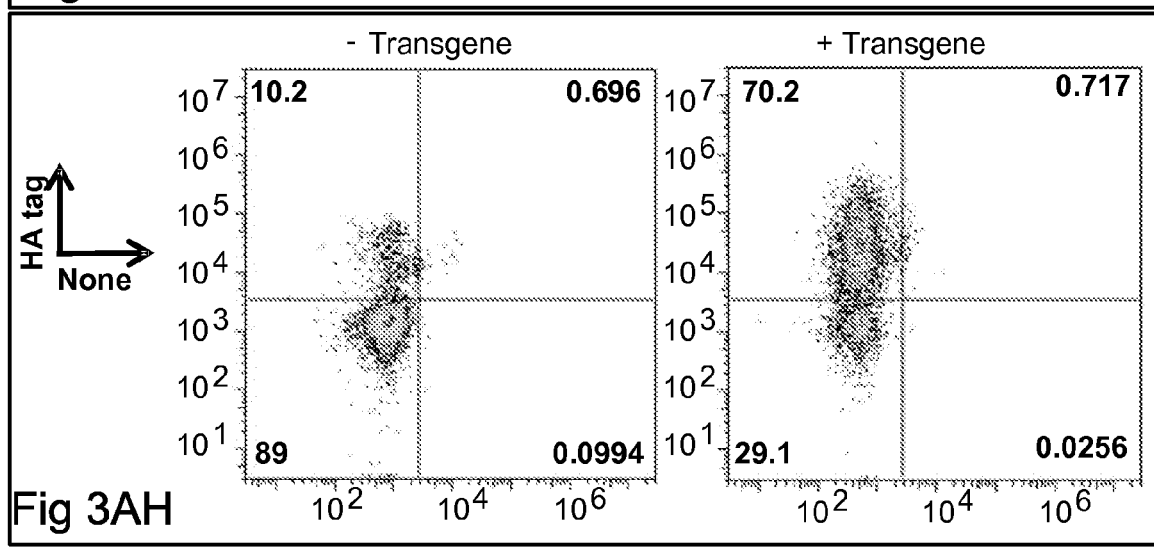
Figure 3A:
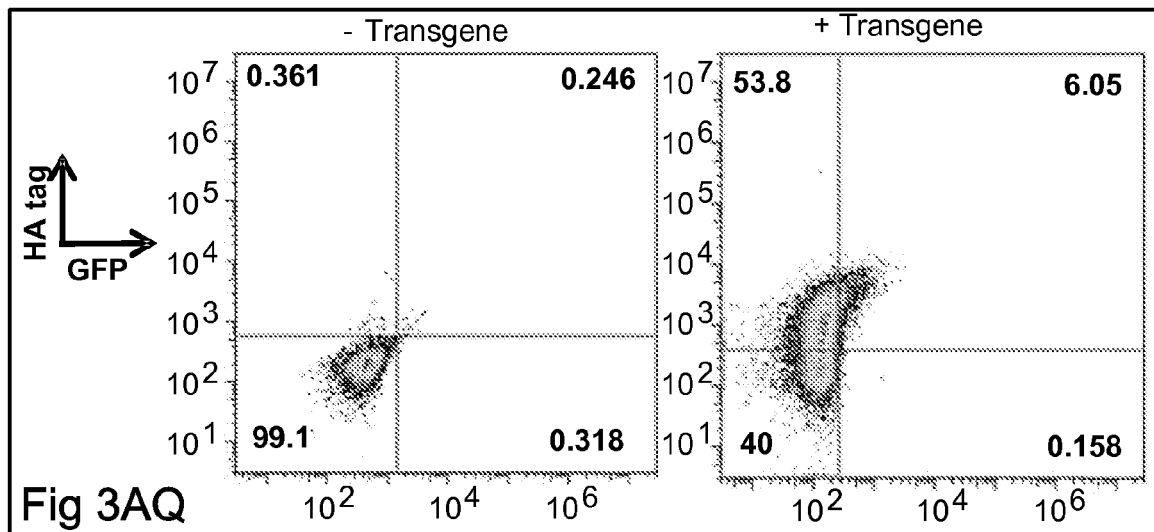
Figure 3A:
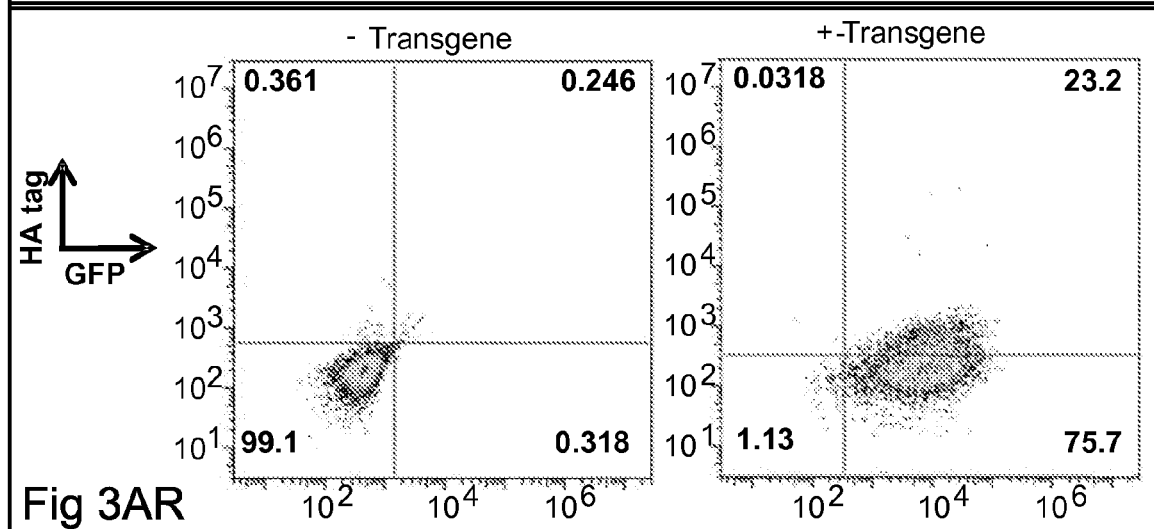
Figure 3A:
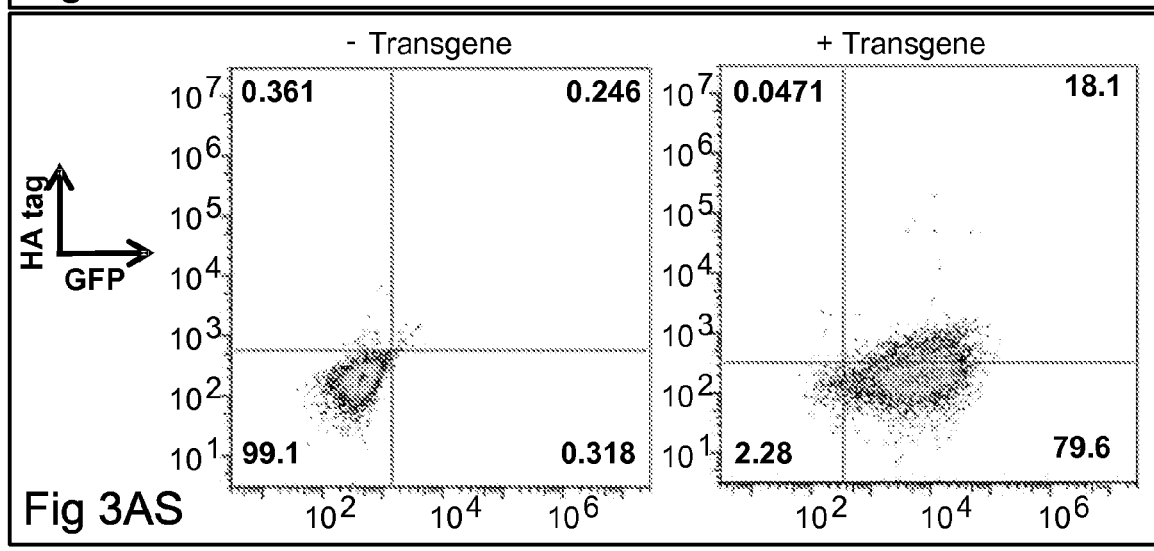

The robust expression of transgenes at high levels has important implications for the therapeutic capacity of the final cell population. FIG. 2 quantifies the expression of three surface proteins indicative of differentiation and one exogenous transgene by quantitative flow cytometry, and demonstrates that the transgene is robustly expressed at a high level.

Erythroid cells in culture were collected at seven time points during a four-stage in vitro differentiation process. At the first time point ("Expand D6") the cells are nucleated hematopoietic precursors. By the final time point ("Diff 3 D8") the cells are predominantly enucleated erythroid cells. GPA (solid triangles), a canonical marker of erythroid cells, starts low in the precursor cells and rapidly reaches $>1 \times 10^6$ copies per cell. CKIT (dashed squares), a receptor for stem cell factor, starts high then decreases to $<1 \times 10^4$ copies per cell as differentiation ensues. TR (dotted diamonds), necessary for the transport of iron into erythroid cells, increases initially then gradually declines to $<1 \times 10^5$ copies per cell. The transgene (open circles) is introduced at the end of the second differentiation stage ("Diff 1") and is steadily expressed at approximately $1 \times 10^5$ copies per cell throughout differentiation. The above data demonstrate that transgenes are robustly expressed in cultured cells.

The expression of exogenous proteins in and on cultured cells can be assessed by flow cytometry (if the protein is expressed on the surface) as described herein, or by Western blot (for proteins expressed in the cytoplasm) as described herein. In instances where an exogenous gene is in a single-transcript construct that contains a downstream fluorescent reporter protein, the fluorescence of the reporter protein can be used as a proxy for expression of the upstream gene, and assessed by flow cytometry as described herein.

FIGS. 3 A-S shows the exogenous expression of surface and cytoplasmic proteins on enucleated cultured erythroid cells. The above data conclusively demonstrate that multiple protein classes—including cytoplasmic, surface, intact, fusions to type I membrane proteins, fusions to type II membrane proteins, fusions to GPI-linked membrane proteins, intracellular fusions, overexpressed, and de novo expressed—can be expressed on multiple cell types including cultured enucleated erythroid cells, cultured nucleated erthyroid precursor cells, and K562 erythroleukemia cells.

FIGS. 3 B and 3 F demonstrate the simultaneous expression of two exogenous proteins in an enucleated cultured cell.

In FIG. 3 B, Erythroid cells were cultured as described herein. A transgene construct encoding glycophorin A signal sequence, an HA epitope tag, glycophorin A coding sequence, viral T2A cleavable sequence and GFP was assembled by Gibson assembly as described herein. The transgene was introduced into the erythroid cells by lentiviral transduction as described herein. The cells were cultured to terminal differentiation as described herein. Cells were analyzed by flow cytometry as described herein, using a fluorescent anti-HA antibody and GFP fluorescence to detect expression of both transgenes.

In FIG. 3 F, Erythroid cells were cultured as described herein. A transgene construct encoding glycophorin A signal sequence, antibody scFv specific to hepatitis B surface antigen, HA epitope tag, glycophorin A coding sequence, viral T2A cleavable sequence and GFP was assembled by Gibson assembly as described herein. The transgene was introduced into the erythroid cells by lentiviral transduction as described herein. The cells were cultured to terminal differentiation as described herein. Cells were analyzed by flow cytometry as described herein, using a fluorescent anti-HA antibody and GFP fluorescence to detect expression of both transgenes.

Example 21: Expression of Protein from mRNA in Platelets

The expression in platelets of exogenous proteins translated from exogenous transfected mRNA was measured by flow cytometry. In brief, platelet-enriched serum was centrifuged at 190 g for 15 minutes to remove erythrocytes and leukocytes. The supernatant was then spun for an additional 5 minutes at 2500 g to pellet platelets. Platelets were resuspended in 5 mL of Tyrode's buffer with 1 uM prostaglandin, washed, and resuspended in 750 uL of Tyrode's buffer with 1 uM prostaglandin. mRNA encoding the gene of interest, in this example GFP, was mixed with lipofectamine at a 1:1 mg/mL ratio. The mixture was incubated for 5 minutes, then added to the washed platelet population. The combination was incubated for 24 hours at room temperature with slow rocking. Platelet expression of the transgene was assayed by flow cytometry measuring GFP fluorescence. Surface proteins can also be assayed by flow cytometry. Cytoplasmic or other intracellularly-expressed proteins can also be assayed by Western blot.

There is therapeutic relevance to introducing exogenous proteins into and onto platelets. Since platelets do not possess a nucleus or RNA transcription machinery, DNA transfection is not a viable means of inducing exogenous protein expression in platelets. However, mRNA transfection and translation is a way of introducing exogenous proteins into cells. It is thought that platelets contain mRNA translation machinery, but until now it was not known whether they are able to accept and translate exogenous mRNA into protein.

Figure 4C:
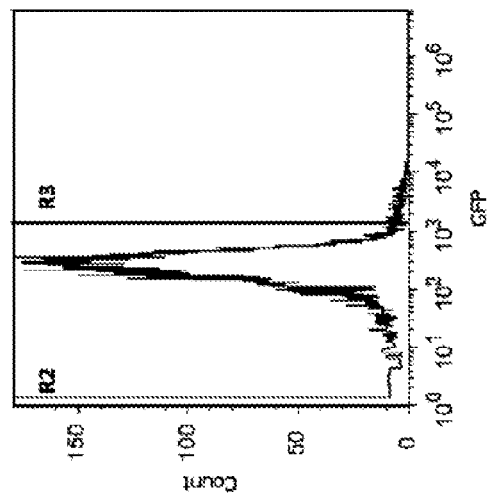
FIGS. 4A-4C are a collection of flow cytometry histograms that measure fluorescence in primary platelets that have been transfected with mRNA encoding a fluorescent protein (GFP).
Figure 4B:
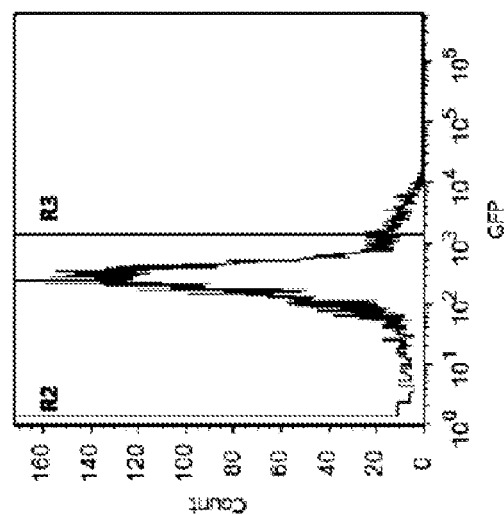
Figure 4A:
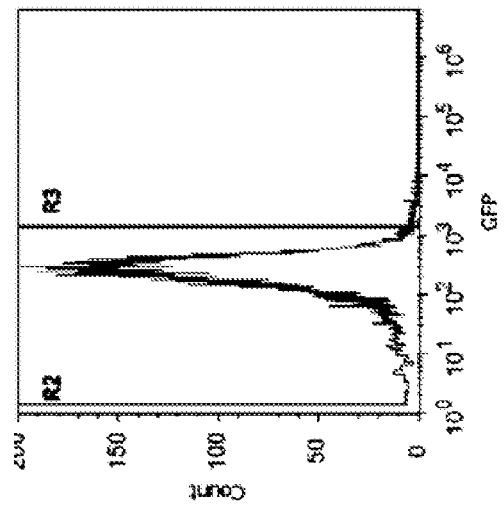

FIGS. 4A-4C are a collection of flow cytometry plots that demonstrate the translation of exogenous mRNA encoding a transgene, in this case GFP, by platelets. The GFP is detected by fluorescence in the FL1 channel after excitation with a 488 nm laser. (4A) Untransfected platelets (1.7% GFP+). (4B) Platelets transfected with 3 ug GFP mRNA (8.6% GFP+). (4C) Platelets transfected with 6.8 ug GFP mRNA (3.3% GFP+).

The data conclusively demonstrate, for the first time, the translation of exogenous mRNA into exogenous protein by platelets.

Example 22: Activity of Enzymes

FIGS. 5A-5D demonstrate the activity for enzymes contained on erythroid cells. Biochemical activity of cytoplasmic enzymes was assessed by Western blot for retention of a protein over the course of differentiation. Biological activity of cytoplasmic enzymes was assessed by in vitro enzymatic activity assay.

FIGS. 5A-5D show the activity of two different intracellular enzymes expressed in cultured erythroid cells.

1. Adenosine Deaminase.

A transgene encoding adenosine deaminase with an HA tag at the C-terminus was constructed by Gibson assembly as described herein. The transgene was introduced into HEK-293T cells by lipofectamine transfection (Life Technologies) as described herein. Enzymatic activity is assayed using a protocol derived from Helenius 2012, Biochim Biophys Acta 1823(10):1967, in which a specific mixture of enzymes convert purines into uric acid and H2O2 followed by fluorometric detection of the generated H2O2. In brief, two days after transfection, cells were collected, media aspirated, and Krebs Ringer phosphate glucose (KRPG; comprising: 145 mM NaCl, 5.7 mM sodium phosphate, 4.86 mM KCl, 0.54 mM CaCl2, 1.22 mM MgSO4, and 5.5 mM glucose; pH 7.35) added to the cells at 2×10^5 cells/mL. Adenosine was added at 50 uM. After reaction for 6 hours, supernatant was collected and heat inactivated for 5 minutes at 60 C. Aliquots of supernatant were transferred to wells in a white 96-well microplate containing 0.25 U/ml bacterial purine nucleoside phosphorylase (PNP) and 0.15 U/ml microbial xanthine oxidase (XO), both from Sigma. After 20 min incubation at RT, 30 µl of H2O2-detecting mixture containing HRP (final concentration 1 U/ml, Sigma) and Amplex Red reagent (60 µM, Invitrogen, Molecular Probes) was added to the microwells, followed by measurement of the fluorescence intensity at the emission and excitation wavelengths of 545 and 590 nm, respectively (Tecan Infinite M200).

2. Phenylalanine Hydroxylase

Erythroid cells were cultured as described herein. A transgene encoding phenylalanine hydroxylase with an HA tag at the C-terminus was constructed by Gibson assembly as described herein. The transgene was introduced into the erythroid cells by lentiviral transduction as described herein. Two days after transduction, cells were collected, washed in PBS buffer, and lysed in RIPA cell lysis buffer (Pierce). Cell lysates (64 ug total protein) were added to 1 mL reaction buffer containing 100 mM Tris-HCl, pH 7.5, 4 mM DTT, 4 mM Phenylalanine, 33 µg catalase, and 0.4 mM DMPH4 (all from Sigma). Reactions were run overnight at 37 C. After incubation, samples were de-proteinized by centrifugal filtration in an Amicon Ultra-4 Centrifugal Filter 10 KD (Millipore UFC801024) spinning at 3700 rpm for 10 min. Samples were collected and assayed for tyrosine concentration by absorbance at 540 nm.

Figure 5A:
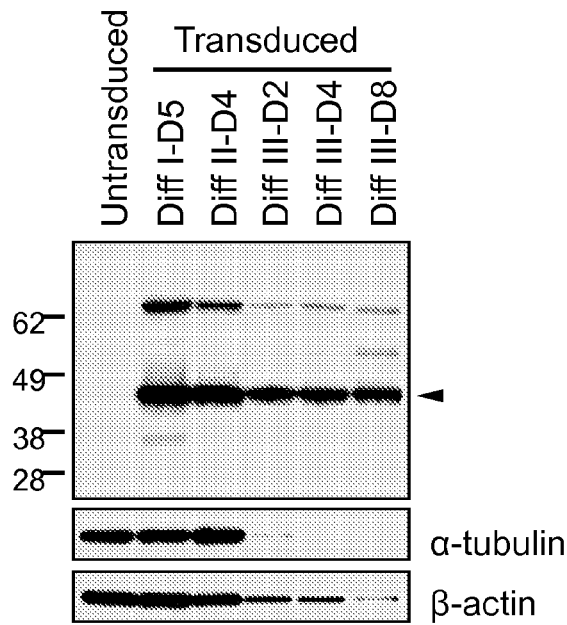
FIGS. 5A-5D show protein expression and enzymatic activity of transgenic erythroid cells in culture.
Figure 5B:
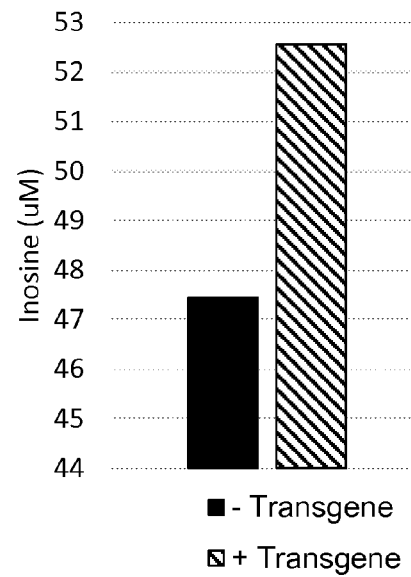
Figure 5C:
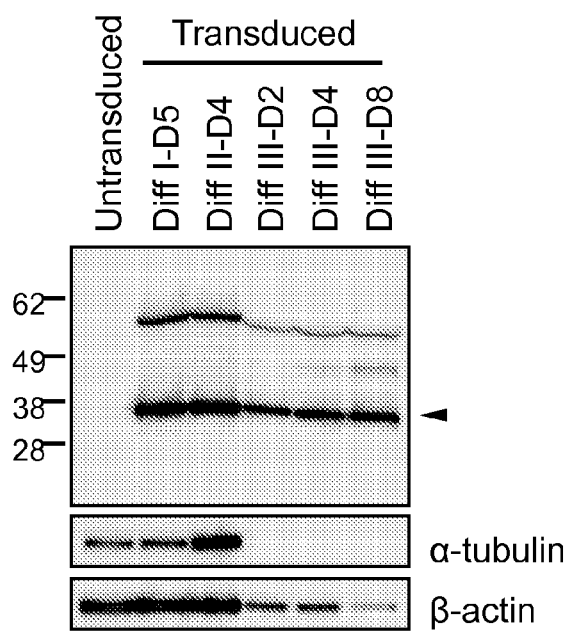

Both of these exogenous proteins were retained through the end of terminal differentiation, a non-trivial feat given that it is well-known in the field that erythroid cells undergo a rigorous program of elimination of proteins unnecessary for basic function (Liu J et al. (2010) Blood 115(10):2021-2027, Lodish H F et al. (1975) Developmental Biology 47(1):59). In FIG. 5A, the exogenously over-expressed protein adenosine deaminase is detected by anti-HA Western blot at various time points over the course of differentiation, from nucleated precursor cells ("Diff I D5") through to enucleated erythroid cells ("Diff III D8"). In FIG. 5C, the exogenously expressed microbial protein phenylalanine hydroxylase is detected by anti-HA Western blot at various time points over the course of differentiation, from nucleated precursor cells ("Diff I D5") through to enucleated erythroid cells ("Diff III D8").

Figure 5D:
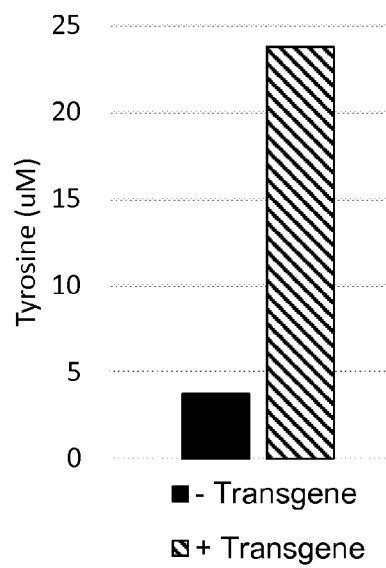

Additionally, both of these enzymes maintained their ability to enzymatically convert substrate into product. FIG. 5B shows the enzymatic conversion of adenosine to inosine by intact adenosine deaminase-expressing 293T cells. FIG. 5D shows the enzymatic conversion of phenylalanine to tyrosine by lysates of cultured phenylalanine hydroxylase-expressing enucleated erythroid cells.

These data conclusively demonstrate that exogenous enzymes are retained on erythroid cells throughout the culture process and that they are enzymatically active in erythroid cells, which has profound therapeutic implications.

Example 23: Activity of CR1

Figure 6A:
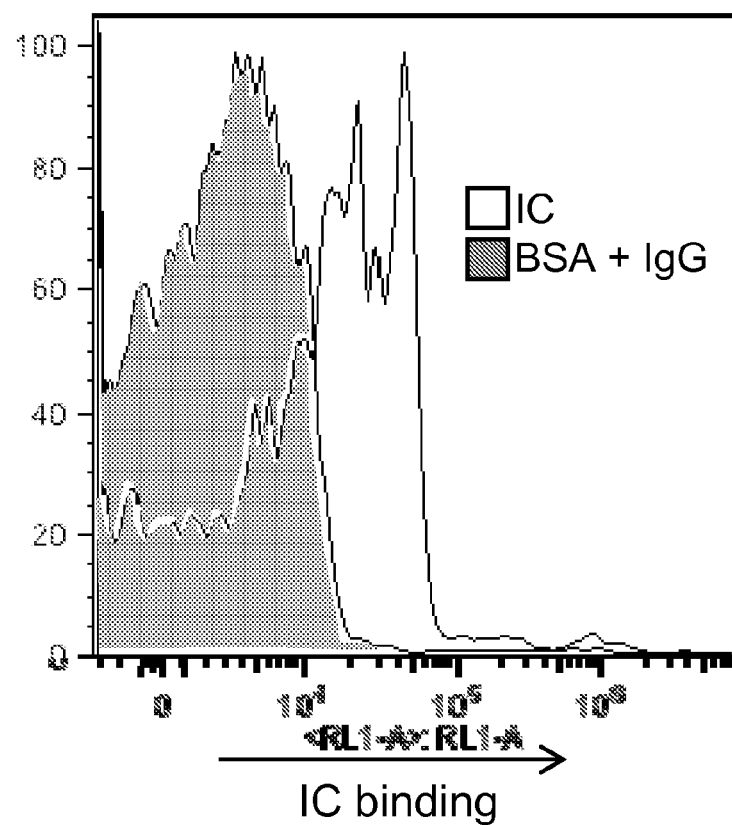
FIGS. 6A-6B show immune complex capture and transfer to macrophages by cultured erythroid cells that overexpress complement receptor 1 (CR1).
Figure 6B:
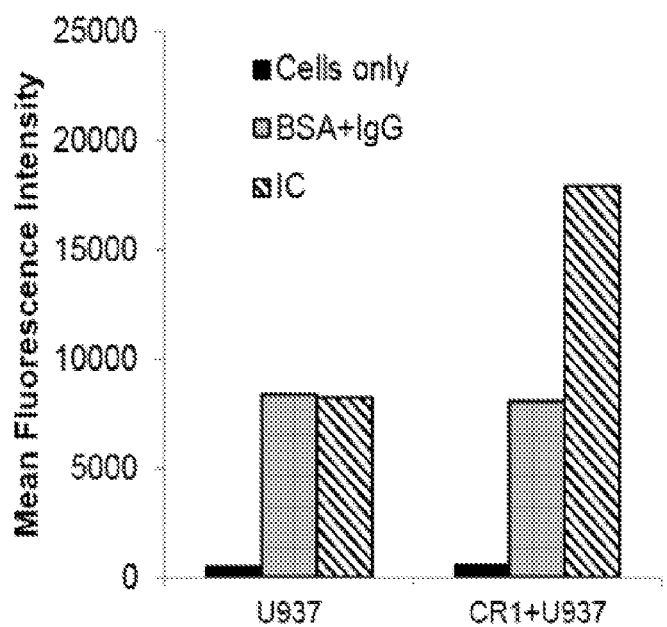

FIGS. 6A-6B show both biochemical and biological activity for complement receptor 1 (CR1) over-expressed on the surface of cultured erythroid cells. Biochemical activity of CR1 was assessed by flow cytometry for binding to an immune complex. Biological activity of CR1 was assessed by transfer of immune complexes to macrophages in a co-culture assay.

1. Immune Complex Binding of CR1-Expressing Cells.

Erythroid cells were cultured as described herein. A transgene construct encoding complement receptor 1 (CR1) was constructed by Gibson assembly as described herein. The transgene was introduced into the erythroid cells by lentiviral transduction as described herein. Transgene expression levels were assessed by flow cytometry as described herein using an anti-CR1 antibody (Abcam). The cells were cultured to terminal differentiation as described herein.

Dylight 650-labeled bovine serum albumin (BSA-650) was incubated with polyclonal rabbit anti-BSA (Abcam) in an excess of antibody for 30 minutes at room temp. The complexes were then mixed with human serum at a 1:1 volume ratio for 30 minutes at 37 C. Control complexes were either not mixed with human serum or mixed with heat-inactivated human serum.

Complexes were incubated with the CR1-expressing cells for 30 minutes at 37 C. Cells were washed and analyzed by flow cytometry for capture of immune complexes by detecting Dylight 650 fluorescence.

2. Immune Complex Transfer to Macrophages

Cultured U937 monocytes were activated by incubation with 100 nM phorbol myristate acetate (PMA) for 24 hours at 37 C. Cells coated with immune complexes (see above) were incubated with activated U937 macrophages for 30 minutes at 37 C. The co-culture was analyzed by flow cytometry. Macrophages were identified by FSC/SSC gating. Presence of immune complex on macrophages was analyzed by detecting Dylight 650 fluorescence in the macrophage population.

FIGS. 6A-6B show the biochemical and biological activity of complement receptor 1 (CR1) exogenously over-expressed on cultured erythroid cells.

FIG. 6A shows the biochemical activity of CR1, defined as the capture of immune complexes in vitro. The black histogram shows the capture of BSA-based immune complexes by CR1 over-expressed on cultured erythroid cells. The shaded histogram shows the minimal background binding to complexes of BSA and IgG that lack human complement, demonstrating that the binding event is CR1-mediated.

FIG. 6B shows the biological activity of CR1, defined as the transfer of captured immune complexes from cultured erythroid cells to macrophages. This is a standard assay in the field, see: Repik et al. 2005 Clin Exp Immunol. 140:230; Li et al. 2010 Infection Immunity 78(7):3129. Transfer is assessed by flow cytometry and measured as the intensity of labeled immune complex-derived fluorescence on macrophages. In this assay, macrophages that are incubated with no immune complexes (black bars) do not become fluorescent. Macrophages that are incubated with complexes of BSA and IgG that lack complement (and therefore do not bind CR1) take up only a small amount of immune complex (solid gray bars), independent of the presence of cultured CR1-overexpressing erythroid cells. This uptake is likely due to Fc-gamma receptors on the U937 cells interacting with the Fc regions of the IgG molecules. Macrophages that are incubated with immune complexes (BSA+IgG+complement) in the absence of CR1-overexpressing cells (hashed bar, left) take up the same amount of immune complex as in the absence of complement, likely by the same Fc-gamma mediated method. However, the macrophages that are incubated with immune complexes in the presence of CR1-overexpressing cells (hashed bar, right) take up nearly double the number of immune complexes as measured by fluorescence.

These data conclusively demonstrate that CR1 overexpression on cultured erythroid cells enables the capture of immune complexes on said erythroid cells, facilitates the transfer of immune complexes from erythoroid cells to macrophages, and significantly increases the rate and number of immune complexes taken up by macrophages.

Example 24: Activity of scFv

FIGS. 7A-7D show the biochemical and biological activity of antibody scFv exogenously expressed on the surface of cultured erythroid cells as a fusion to the transmembrane protein GPA.

Erythroid cells were cultured as described herein. A transgene construct encoding the leader sequence of glycophorin A, an antibody scFv specific to hepatitis B surface antigen (scFv, described in Bose 2003, Molecular Immunology 40:617), an HA epitope tag, a [Gly-3-Ser]2 flexible linker (Seq. ID No. 23), and the body of glycophorin A was assembled by Gibson assembly as described herein. The transgene was introduced into the erythroid cells by lentiviral transduction as described herein. Transgene expression was assessed by flow cytometry as described herein using an anti-HA antibody (Abcam). The cells were cultured to terminal differentiation as described herein. Biochemical activity of the antibody scFv was assessed by flow cytometry for binding to the target protein, in this case hepatitis B surface antigen (HBsAg). Recombinant HBsAg protein (Abcam) was labeled with Dylight-650 fluorophore (Pierce). scFv-expressing cells were incubated with 100 nM labeled protein, washed in PBS, and analyzed for Dylight 650 fluorescence by flow cytometry as described herein.

Biological activity of the antibody scFv was assessed by in vivo capture of HBsAg detected by flow cytometry. Recombinant HBsAg protein (Abcam) was labeled with Dylight-650 fluorophore (Pierce). scFv-expressing cells were fluorescently labeled with CFSE (Sigma). Immunocompromised NSG mice (Jackson labs) were injected with ~400 pmol of the labeled HBsAg into the tail vein. A few minutes later, the same mice were injected with $2 \times 10^7$ scFv-expressing cells. Blood was collected by submandibular puncture at regular intervals in an EDTA-containing tube. Collected blood cells were washed and analyzed by flow cytometry as described herein. Human cells were identified as those that were CFSE positive. Capture of HBsAg was detected as Dylight 650 fluorescence on the human cells.

FIG. 7A-7B show the biochemical activity of antibody scFv, defined as the binding of its cognate antigen, hepatitis B surface antigen (HBsAg). In FIG. 7A, cells that express (black) or do not express (gray shaded) the antibody scFv are incubated with 450 nM HBsAg and stained with biotinylated anti-HBsAg antibody and fluorescent streptavidin. Cells that express the antibody scFv (~45% of the cells in this culture) bind to the antigen. In FIG. 7B, cells that express the antibody scFv are incubated with various concentrations of HBsAg and stained as above, showing that the binding event is dose-dependent with an affinity of approximately 10 nM.

FIG. 7C-7D show the biological activity of antibody scFv, defined as the capture of cognate antigen HBsAg while in circulation in a mouse. In this experiment, immunocompromised NSG mice were injected with ~400 pmol fluorescently-labeled HBsAg via the tail vein. Five minutes later, cultured enucleated erythroid cells (7C) or cultured enucleated erythroid cells that expressed exogenous antibody scFv (7D) were injected via the tail vein. Prior to injection, all cultured cells were labeled with CFSE fluorescent dye. Blood was collected 6 hours later, analyzed on a flow cytometer, and gated on CFSE+ human cells. Bare cultured cells did not bind to HBsAg (7C), whereas antibody scFv-expressing cells do bind to HBsAg (7D). Consistently with the biochemical activity experiment, approximately 45% of the cells in this culture express antibody-scFv.

These data demonstrate that the antibody scFv is biochemically active when expressed on the surface of cultured erythroid cells and that the antibody scFv on the erythroid cell is able to bind its target in vivo when in circulation. This has profound implications for therapeutic approaches in which the capture, sequestration, and clearance of a substance in circulation is desired.

Example 25: Activity—Circulating Clearance

FIGS. 8A-8D show both biochemical and biological activity for surface molecule capture agents used for circulating clearance of a target.

Biochemical activity of the capture agents, in this case HA polypeptide and biotin, was assessed by flow cytometry for binding to the target protein, in this case anti-HA antibody and anti-biotin antibody. Biological activity of the capture agents was assessed by in vivo capture and clearance of target protein as detected by flow cytometry and plasma protein quantification.

1. Capture of Anti-Biotin Antibody by Chemically-Modified Cells

Eyrthrocytes from a normal human donor were purchased (Research Blood Components). Cells were labeled with CFSE (Sigma) per manufacturer's instructions for 20 minutes at 37 C. Cells were then biotinylated with NHS-biotin (Sigma) per manufacturer's instructions using 0.02 volumes of 2 mM stock biotin reagent for 30 minutes at room temperature. Anti-biotin antibody (Abcam) was fluorescently labeled with Dylight 650 (Pierce). Labeling efficiency of the cells was assessed by flow cytometry using the labeled anti-biotin antibody and CFSE fluorescence as detection markers. 250 ug labeled antibody was injected into an NSG mouse (Jackson Labs) intravenously via the tail vein. Four hours later $1\times10^8$ biotinylated cells were injected intravenously via the tail vein. Blood was collected by submandibular puncture at regular intervals in an EDTA-containing tube. Collected blood cells were washed and analyzed by flow cytometry as described herein. Human cells were identified as those that were CFSE positive. Capture of anti-biotin antibody was detected as Dylight 650 fluorescence on the human cells. Plasma from the blood draw was analyzed by ELISA using a biotin-coated microplate (Pierce) per manufacturer's instructions to detect the level of antibody in circulation.

2. Capture of Anti-HA Antibody by Transgenic Cultured Cells

Erythroid cells were cultured as described herein. A transgene construct encoding glycophorin A signal sequence, an HA epitope tag, glycophorin A coding sequence, viral T2A cleavable sequence and GFP was assembled by Gibson assembly as described herein. The transgene was introduced into the erythroid cells by lentiviral transduction as described herein. The cells were cultured to terminal differentiation as described herein. Cells were analyzed by flow cytometry as described herein, using an anti-HA antibody (Life Technologies) fluorescently labeled with Dylight 650 (Pierce) and GFP fluorescence to detect expression of both transgenes. 250 ug labeled anti-HA antibody was injected into an NSG mouse (Jackson Labs) intravenously via the tail vein. Four hours later $1\times10^8$ cultured cells were injected intravenously via the tail vein. Blood was collected by submandibular puncture at regular intervals in an EDTA-containing tube. Collected blood cells were washed and analyzed by flow cytometry as described herein. Human cells were identified as those that were CFSE positive. Capture of anti-HA antibody was detected as Dylight 650 fluorescence on the human cells. Plasma from the blood draw was analyzed by ELISA using an HA peptide-coated microplate (Pierce) per manufacturer's instructions to detect the level of antibody in circulation.

FIGS. 8A-8D show biochemical and biological activity of (8A-8B) the polypeptide HA expressed on the surface of cultured erythroid cells as a fusion to GPA and of (8C-8D) biotin chemically conjugated to the surface of primary erythrocytes. Biochemical activity is defined as the capture of a target protein in vitro. Biological activity is defined as the enhanced clearance of a target protein in vitro.

Figure 8A:
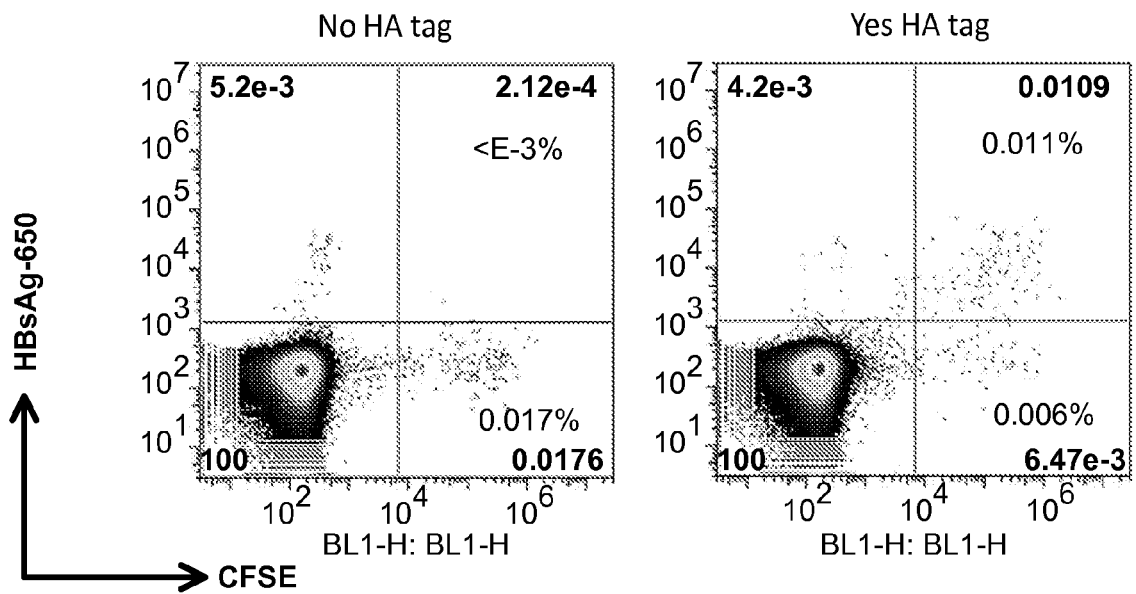
FIGS. 8A-8D show the specific clearance of circulating antibodies mediated by exogenous antigen-expressing EHCs in vivo.

In FIG. 8A, the HA polypeptide, expressed as a fusion to the N terminus of GPA, captures a mouse anti-HA antibody in vivo. NSG mice were injected with fluorescently-labeled mouse anti-HA antibody, followed by injection of cultured human erythroid cells that either do not (top) or do (bottom) express HA epitope tag on their surface as a fusion to GPA. Blood was drawn and cells analyzed on the flow cytometer. The x-axis measures CFSE fluorescence. The y-axis measures anti-HA antibody Dylight 650 fluorescence. CFSE-positive cultured human erythrocytes are observed in both samples, but only the cells expressing the HA epitope tag are able to capture circulating anti-HA antibody.

Figure 8B:
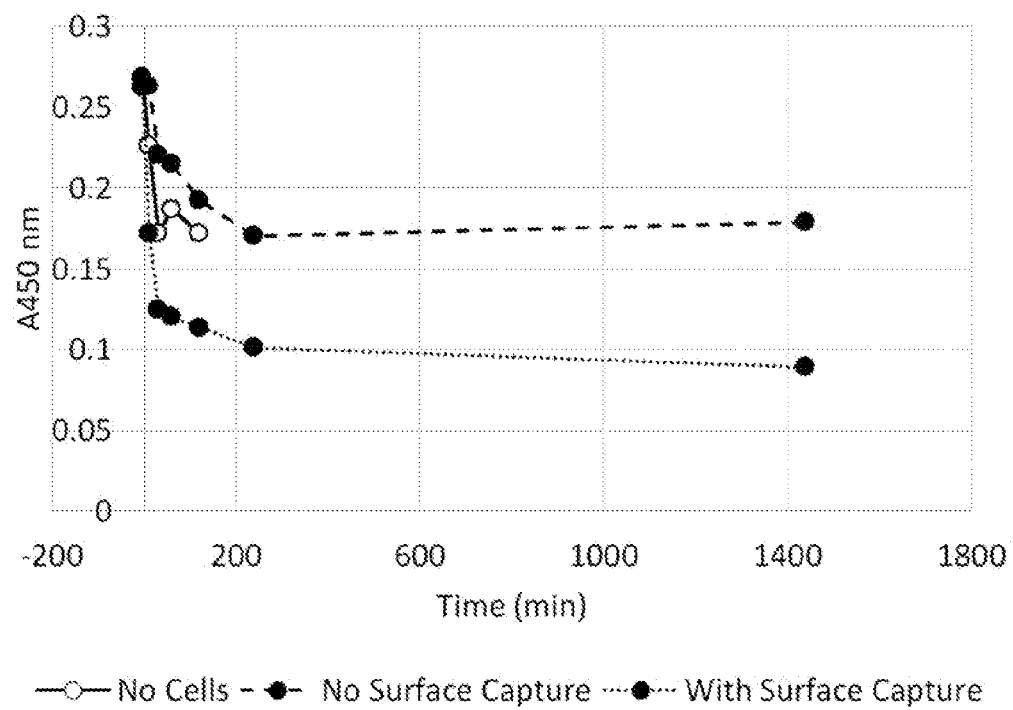

In FIG. 8B, mice were injected with anti-HA antibody then then optionally with cultured human erythrocyte cells that either do not or do express HA peptide on their surface as a fusion to GPA. Plasma was collected at multiple time points and the level of anti-HA antibody in plasma was assessed by ELISA using an HA peptide-coated plate as a substrate. Mice injected with anti-HA antibody alone (open circles, solid line—this mouse died after 120 minutes of causes unrelated to treatment) or with anti-HA antibody followed by cells that do not express HA peptide on their surface (dashed line) have significant antibody in circulation out to 24 hours post injection of cells. In contrast, mice injected with anti-HA antibody followed by cells that express HA peptide on their surface are depleted of target antibody within minutes. This data conclusively demonstrates that the target antibody is rapidly and specifically cleared from circulation by cultured erythroid cells that express exogenous antigen polypeptide on their surface.

Figure 8C:
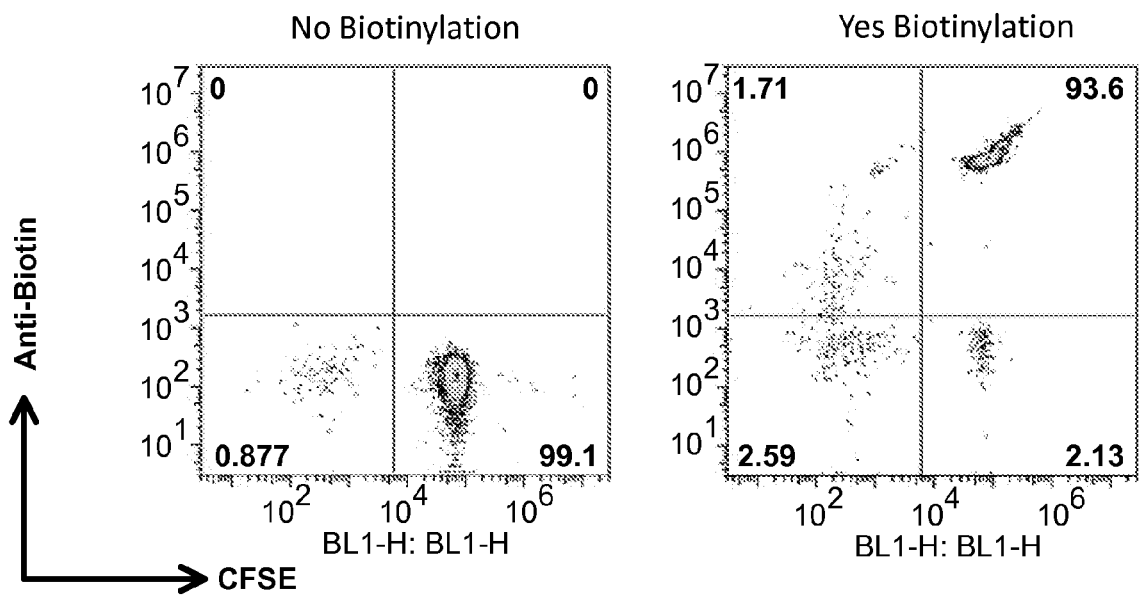

In FIG. 8C, the biotin molecule, conjugated to the surface of erythroid cells by amine functionalization chemistry, captures a mouse anti-biotin antibody. In both of these cases capture was assessed by flow cytometry. Cells that are CFSE labeled and biotinylated show up as double positive when stained with a fluorescent anti-biotin antibody (lower dot plot), whereas CFSE-labeled cells that are not biotinylated only show up as single positive (upper dot plot).

Figure 8D:
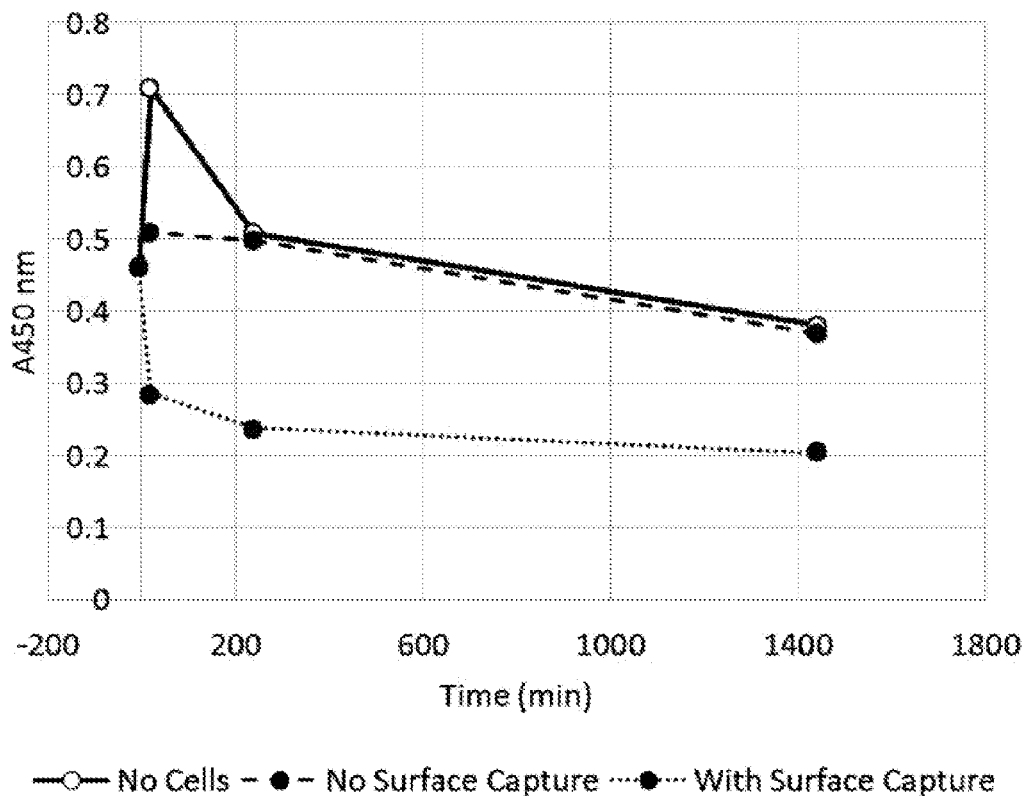

In FIG. 8D, mice were injected with anti-biotin antibody then then optionally with cultured human erythroid cells that either are not or are conjugated to biotin on their surface. Plasma was collected at multiple time points and the level of anti-biotin antibody in plasma was assessed by ELISA using a biotin-coated plate as a substrate. Mice injected with anti-biotin antibody alone (open circles, solid line) or with anti-biotin antibody followed by cells that are not conjugated to biotin on their surface (dashed line) have significant antibody in circulation out to 24 hours post injection of cells. In contrast, mice injected with anti-biotin antibody followed by cells that are conjugated to biotin on their surface are depleted of target antibody within minutes. This data conclusively demonstrates that target antibodies are rapidly and specifically cleared from circulation by cultured erythroid cells that contain exogenous antigen polypeptide on their surface.

Together the data conclusively demonstrate that suitable exogenous antigens on exogenous antigen-expressing EHCs are able to bind their target molecules in vivo and mediate rapid circulating clearance of target molecules when in circulation, which has profound therapeutic implications.

Example 26: Activity of Complement Regulators

The complement regulatory activity of the exogenous antigen-expressing EHCs is assessed by standard CH50 and AH50 assays known in the art (see e.g., Kabat et al. 1961 Exp Immunochem pp. 133-239 and Platts-Mills et al. 1974 J Immunol 113:348).

Briefly, the CH50 assay utilizes sheep erythrocytes (SRBC) as target cells. Briefly, a suspension containing $1\times10^9$ SRBC/ml is prepared in the GVB(2+) buffer (gelatin/Veronal-buffered saline with Ca2+ and Mg2+), pH 7.35. Hemolysin (rabbit anti-sheep antiserum) is titrated to determine the optimal dilution to sensitize SRBC. Diluted hemolysin (1:800) is mixed with an equal volume of SRBC (1×109 SRBC/ml), and the whole is incubated at 37° C. for 15 minutes. This results in $5\times10^8$/ml antibody-coated erythrocytes (EA). EA (100 µl) are incubated with 100 µl of five serial twofold dilutions (1:20, 1:40, 1:80, 1:160, and 1:320) of the normal human serum (NHS) or similar dilution of the mixture of NHS and the exogenous antigen-expressing EHC at 37° C. for 1 hour. NHS incubated with GVB2+ buffer is used as the control. Background control is obtained by incubating EA with buffer alone (serum is not added), and total lysis (100% hemolysis) is determined by adding distilled water to EA. The reaction is stopped using 1.2 ml of ice-cold 0.15M NaCl, the mixture is spun to pellet the unlysed cells, and the optical density of the supernatant is determined spectrophotometrically (412 nm). The percentage of hemolysis is determined relative to the 100% lysis control. Complement activity is quantitated by determining the serum dilution required to lyse 50% of cells in the assay mixture. The results are expressed as the reciprocal of this dilution in CH50 units/ml of serum.

Briefly, the AH50 assay depends on lysis of unsensitized rabbit erythrocytes (Erab) by human serum by activation of the alternative pathway. Activation of the calcium-dependent classical pathway is prevented by addition of the calcium chelator ethylene glycol tetraacetic acid (EGTA) to the assay buffer, and magnesium, necessary for both pathways, is added to the buffer. Briefly, a cell suspension of rabbit RBC ($2\times10^8$ cell/ml) is prepared in the GVB-Mg2+-EGTA buffer. A serial 1.5-fold dilution (1:4, 1:6, 1:9, 1:13.5, and 1:20.25) of normal human serum (NHS) or similar dilution of the mixture of NHS and the exogenous antigen-expressing EHC are prepared in GVB-Mg2+-EGTA buffer, and 100 µl of each serum dilution is added to 50 µl of standardized Erab. NHS incubated with GVB-Mg2+-EGTA buffer is used as the control. The mixture is then incubated at 60 minutes at 37° C. in a shaking water bath to keep cells in suspension, and 1.2 ml of ice-cold NaCl (0.15 M) is used to stop the reaction. The tubes are spun at 1250 g, at 4° C., for 10 minutes to pellet the cells, and the optical density of the supernatant is determined spectrophotometrically (412 nm). Background control has 100 µl GVB-Mg2+-EGTA buffer, and 50 µl Erab and does not exceed 10% of the total lysis. In the total lysis control tube 100 µl of distilled water is added to 50 µl Erab suspension, and the percentage of hemolysis is determined relative to 100% lysis control. The results of the assay are calculated and complement activity is quantitated by determining the serum dilution required to lyse 50% of cells in the assay mixture. The results are expressed as the reciprocal of this dilution in AH50 units/ml of serum.

Example 27: Activity of Platelet-Loaded Thymidine Phosphorylase

A transgene encoding thymidine phosphorylase with an HA tag at the C-terminus is constructed by Gibson assembly as described herein. Platelets are cultured from precursor cells as described herein. The transgene is introduced into the cultured platelet precursor cells by lentiviral transduction as described herein. Expression of thymidine phosphorylase within the cultured platelets is assessed by Western blotting using an anti-HA detection antibody, as described herein.

Thymidine phosphorylase activity is determined in platelet samples by quantifying the rate of conversion of thymidine to thymine. Preliminary experiments are conducted to determine the linear metabolite formation kinetics with respect to time and enzyme dilution; the method is shown to be linear for up to 16 min, over a thymine phosphorylase range of 4.0-719 nmol/min/ml (corresponding to a sample dilution range of 10-9088). Lysates of pre-dialysis samples cultured platelet and control platelet samples are prepared by diluting thawed samples 1:710 with 125 mM Tris-HCl, pH 7.4. Twenty-five ul of the platelet lysate is then added to 100 ul sodium phosphate buffer (100 mM, pH 6.5) and 25 ul thymidine standard (10 mM), mixed and incubated at 37 C for 10 min. The reaction is terminated with 25 ul of 40% TCA. Assay blanks are prepared by adding TCA to the sodium phosphate buffer/thymidine incubation mixture prior to adding the platelet lysate. Samples are centrifuged at 13,400×g for 2 min, and the supernatant washed twice with water-saturated diethyl ether with 2 min on a shaker to extract the TCA. To avoid ether interfering with HPLC separation, effective removal is achieved by exposing the matrix to the air for 5 min to allow evaporation of the ether. A sample volume of 10 ul is injected into the HPLC.

Chromatographic separation of substrate and product is achieved using reversed phase chromatography with isocratic elution using a Waters Alliance HPLC 2795 system. A pre-packed C18column (Spherisorb ODS 125 mm×4.6 mm ID, 5 um particle size, Waters) is used as the stationary stage. Analytes are eluted using a mobile phase of ammonium acetate (40 mM) with the ion-pairing agent tetrabutyl ammonium hydrogen sulphate (5 mM) adjusted to pH 2.70 with HCl, delivered at a flow rate of 1.0 ml/min, with a run time of 8 min. UV detection is at 254 nm and 0.1 absorbance units full scale. Metabolites are identified by comparing spectra with pure standards.

Example 28: Activity of Platelet-Displayed Goodpasture Antigen

A transgene encoding collagen alpha-3(IV) (COL4A3) NCI domain antigen fused to the N terminus of CD42b (GP1B, genbank AAH27955.1) with an intervening HA tag is constructed by Gibson assembly as described herein. Platelets are cultured from precursor cells as described herein. The transgene is introduced into the cultured platelet precursor cells by lentiviral transduction as described herein. Expression of the exogenous antigen on the cultured platelets is assessed by flow cytometry using an anti-HA detection antibody as described herein.

Serum is collected from a patient suffering from Goodpasture's syndrome, and the serum is tested for anti-COL4A3 antibodies by commercial ELISA (MyBioSource COL4A3 ELISA Kit). The binding capacity of the antigen-expressing platelets is assessed by flow cytometry as described herein, using this anti-COL4A3 serum as the primary detection antibody and fluorescent anti-human IgG as the secondary detection antibody.

Platelet-facilitated clearance of a circulating antigen in vivo is modeled in a mouse using the antigen-expressing platelets. NSG mice are injected with 100 uL of mouse anti-human COL4A3 antibody (Creative BioMart) fluorescently labeled with Dylight 650 dye. CFSE-labeled cultured platelets (10^8 per mouse) that express the exogenous antigen are then injected via the tail vein. Blood is drawn from a submandibular location at 10 min, 30 min, 2 h, 12 h, and 24 h. Blood is centrifuged to collect the platelet-rich fraction, which is then stained and analyzed by flow cytometry as described herein. Antibody capture by platelets is determined by tracking the CFSE-Dylight 650 double positive population.

Example 29: Activity In Vivo (Mouse)

Mouse erythroid cells are cultured as described herein. Erythroid precursor cells are transduced with a suitable exogenous antigen polypeptide transgene, e.g., encoding complement receptor 1 (CR1) using a lentivirus as described herein. Cells are cultured to terminal differentiation as described herein. The presence of the exogenous protein in the cells is assessed by flow cytometry as described herein. The cells are labeled with a fluorescent die, e.g., CFSE (Sigma Aldrich) per manufacturer's instructions to aid in their detection. The cells are injected into a NZBWF1/J mouse model of lupus, or other appropriate model of disease or activity corresponding to the suitable exogenous antigen polypeptide, approximately 1×10^8 cells injected via the tail vein. Blood is collected at multiple time points by submandibular puncture. Immune complex levels in the plasma are detected by Raji cell assay, see e.g., Theofilopoulos et al. 976, J Clin Invest 57(1):169. Pharmacokinetics of the cultured cells are assessed by flow cytometry as described herein, by tracking the percentage of CFSE fluorescent cells in the drawn blood sample. Mouse overall health is assessed by gross necropsy, including histology of kidney tissue to track reduction of immune complex deposition and inflammation-mediated damage.

Example 30: Rapid Screening

Cell lines, e.g., 293T and K562, have shorter expression and culturing cycles (~1 day) compared to cultured erythroid cells (days-weeks). These cell lines can be used to rapidly iterate through a gene library encoding suitable exogenous antigen polypeptides to identify the exogenous antigen polypeptide with the highest expression or activity.

A library of suitable exogenous antigen polypeptide transgenes, e.g., full-length and shorter variants of complement receptor 1 (CR1), are constructed by polymerase chain reaction and Gibson assembly as described herein. The library of transgenes is transfected into HEK293T cells in a parallel fashion in a microtiter plate using lipofectamine as described herein and transduced into K562 cells using lentivirus as described herein. The expression of the exogenous antigens is assessed by flow cytometry as described herein after 24-48 hours. The activity of each of the exogenous antigens in the library is assessed by capture of fluorescent immune complex detected with flow cytometry as described herein, and by the transfer of fluorescent immune complexes to cultured monocytes detected with flow cytometry as described herein. The exogenous antigens from the library that are most functional—e.g., are highest expressed, capture most immune complexes, or best transfer immune complexes to monocytes—are then individually transduced into parallel erythroid cell cultures as described herein using lentivirus as described herein. The expression of each exogenous antigen on cultured erythroid cells is assessed by flow cytometry as described herein The activity of each exogenous antigen on cultured erythroid cells is assessed by capture of fluorescent immune complex detected with flow cytometry as described herein, and by the transfer of fluorescent immune complexes to cultured monocytes detected with flow cytometry as described herein.

Example 31: Assessment of Clearance Rate of RBC In Vivo

The clearance rate of erythroid cells was assessed in vivo in an immunocompromised mouse model. NSG mice were treated at day −1 with 100 uL of clordonate liposome (Clodrosomes.com) solution to selectively deplete macrophages. Cells were labeled with the fluorescent tag CFSE and approximately 1×10^8 cells were injected into each mouse via the tail vein. At regular intervals blood was collected by submandibular puncture and blood cells were collected. Cells were co-stained with anti-human GPA antibodies and analyzed by flow cytometry. Human erythroid cells were distinguished from mouse erythroid cells by CFSE signal and by human GPA signal.

Figure 9A:
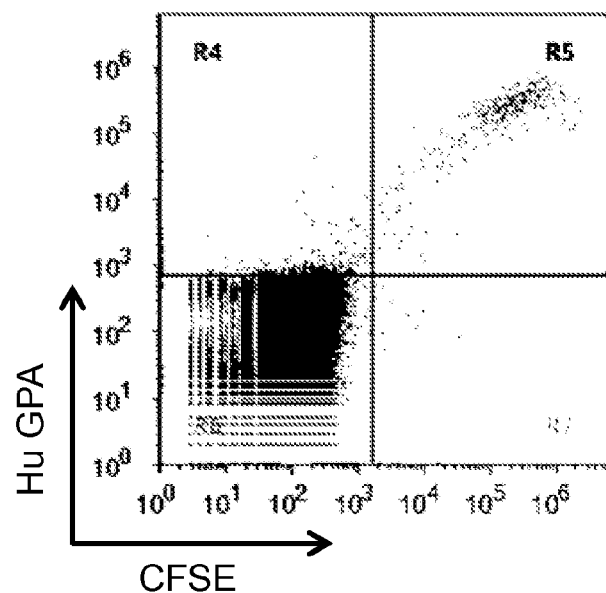
FIGS. 9A-9B show the clearance rate of cultured human eyrthroid cells in a mouse.
Figure 9B:
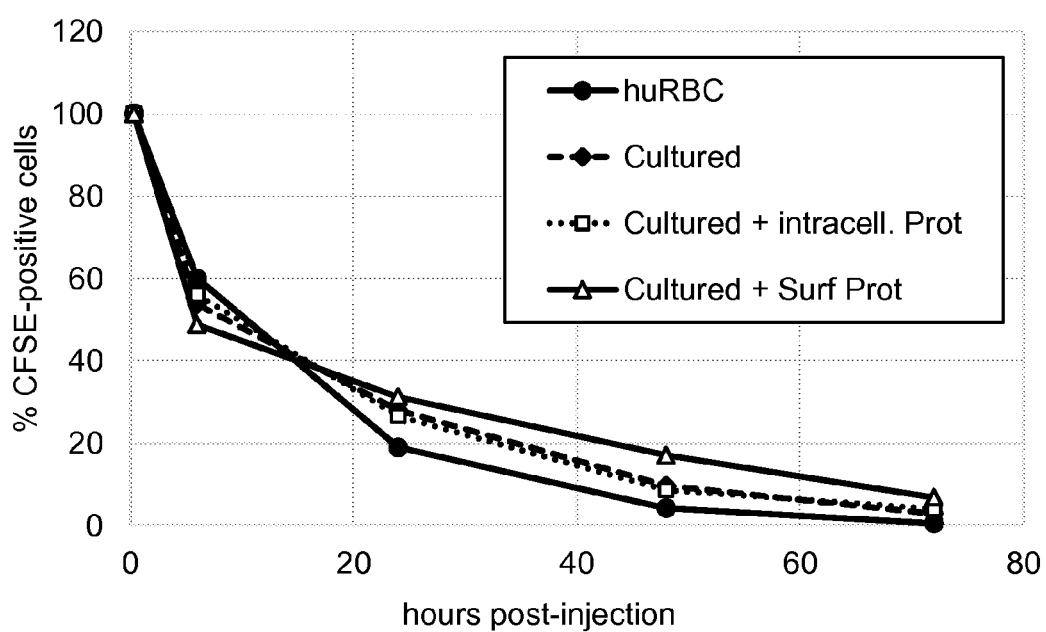

For therapeutic applications, it is important that cultured erythroid cells and cultured erythroid cells containing exogenous protein either intracellularly or on the surface circulate normally in vivo. This is shown in FIGS. 9A-9B using a standard immunocompromised mouse model. In FIG. 9A, blood collected from an injected mouse is analyzed on the flow cytometer. Cultured human erythroid cells are identified in the top right quadrant of the plot, double-positive for CFSE and human-GPA. In FIG. 9B, mice were injected with human red blood cells (solid circles), cultured enucleated erythroid cells (dashed diamonds), cultured enucleated erythroid cells that express an intracellular exogenous protein (dotted squares) and cultured enucleated erythroid cells that express a surface exogenous protein (open triangles). The clearance rate of the human cells is measured as the percentage of CFSE+ cells remaining over time, scaled to the initial time point (20 minutes post injection). There is no significant difference in clearance rate between the four samples.

These data clearly demonstrates that cultured enucleated erythroid cells have substantially similar circulation to normal human red blood cells. Furthermore, exogenous proteins expressed either in the intracellular space or on the surface of the cells do not substantially affect the circulation behavior of these cells. This is an important result for therapeutic translation of the technology.

Example 32: Assessment of Adverse Circulatory Events

The incidence of adverse events caused by cultured eyrthroid cells in circulation were assessed by detection of fibrinogen breakdown products in blood and histology in animals injected with cultured erythroid cells.

Detection of Fibrinogen Breakdown Products. Mice were injected with cultured erythroid cells as described herein. Blood was collected from mice by submandibular puncture in an EDTA-containing tube. Cells were separated by centrifugation and plasma was collected. The levels of fibrinogen breakdown products fibrinopeptide A and fibrinopeptide B were measured in mouse plasma by ELISA (MyBiosource) following manufacturer's instructions.

Histology. Tissue samples from the same mice were collected following necropsy. Tissues were trimmed, embedded in paraffin wax, and sectioned. Tissue sections were stained by H&E staining and trichrome staining. Microscope images were taken at 10× and 20× magnification.

For therapeutic applications, it is important that cultured erythroid cells and cultured erythroid cells that contain exogenous proteins (either intracellularly or on the surface) not induce adverse events, such as activation of the clotting cascade and tissue thrombus formation.

Figure 10A:
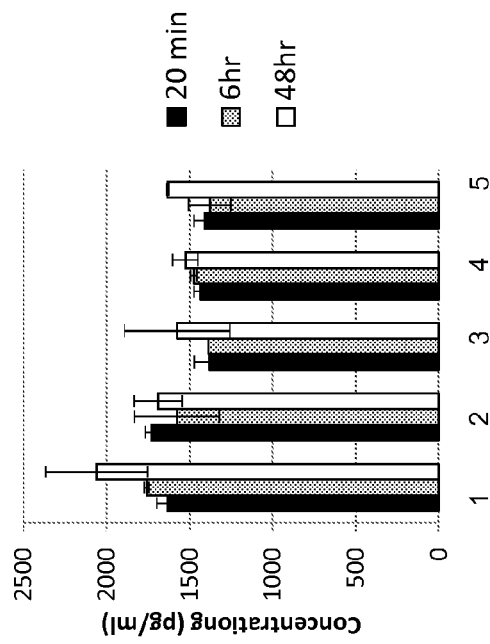
FIGS. 10A-10D are an assessment of adverse events following injection of cultured human erythroid cells into a mouse.
Figure 10B:
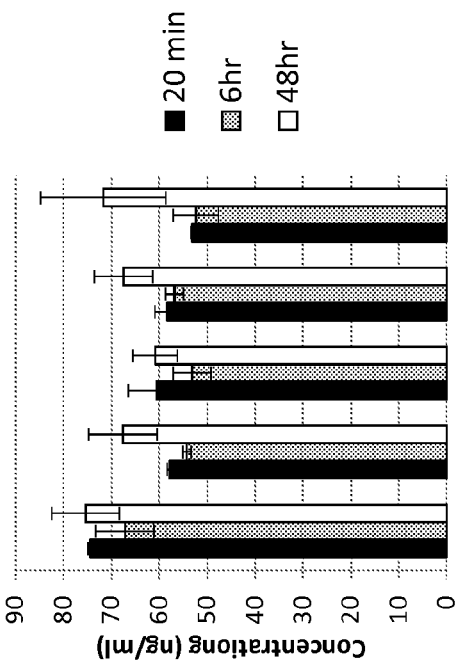

FIGS. 10A and 10B show the levels of fibrinopeptide A and B in mouse plasma for mice injected with (1) human red blood cells, (2) cultured enucleated erythroid cells, (3) cultured enucleated erythroid cells expressing an intracellular exogenous protein, (4) cultured enucleated erythroid cells expressing a surface exogenous protein, and (5) recombinant protein alone. The levels of fibrinopeptide A and B, a marker of fibrinogen breakdown and activation of the clotting cascade, are substantially similar for all samples.

Figure 10C:
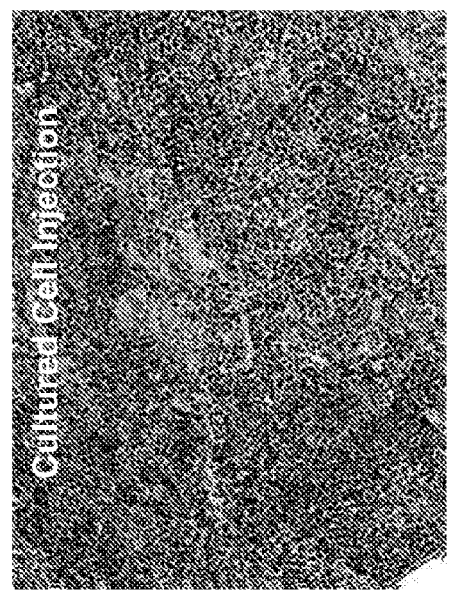
Figure 10D:
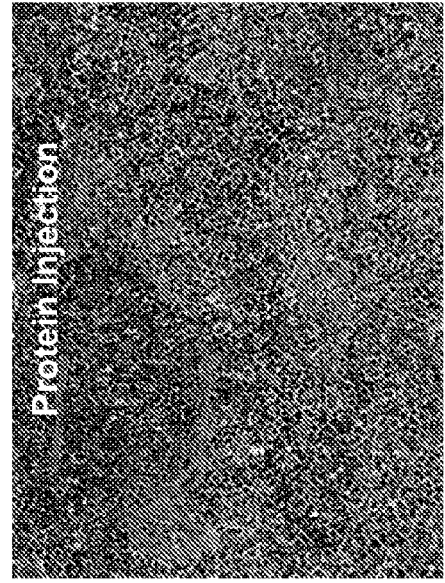

FIGS. 10C and 10D show histologically stained sections of spleen for a mouse injected with cultured enucleated erythroid cells (10C) and recombinant protein (10D). There is no substantial difference between the tissue, and no identifiable tissue damage in spleen, liver, lung, brain, heart, and kidney was observed between any of the samples.

These data conclusively demonstrate that cultured erythroid cells, with or without exogenous protein, do not induce any adverse events while in circulation in mice.

Example 33: Assessment of Exogenous Protein Retention in Circulation

The retention of exogenous proteins in and on cultured enucleated erythroid cells was assessed by flow cytometry and Western blotting.

1. Retention of Exogenous Protein Assessed by Flow Cytometry

Erythroid cells were cultured as described herein. A transgene construct encoding glycophorin A signal sequence, antibody scFv specific to hepatitis B surface antigen, HA epitope tag, and glycophorin A coding sequence was assembled by Gibson assembly as described herein. The transgene was introduced into the erythroid cells by lentiviral transduction as described herein. The cells were cultured to terminal differentiation as described herein. Cells were fluorescently labeled with CFSE and injected into an immunocompromised NSG mouse (Jackson Labs) via the tail vein ($1 \times 10^8$ cells per mouse). At regular intervals blood was collected by submandibular puncture. Collected cells were stained with a fluorescent anti-HA antibody (Abcam), and analyzed by flow cytometry. Human cells were identified as CFSE+ cells, and exogenous protein retention was assessed by the fraction of CFSE+ cells that also stained positive for the epitope tag.

2. Retention of Exogenous Protein Assessed by Western Blot

Erythroid cells were cultured as described herein. A transgene construct encoding adenosine deaminase and an HA epitope tag was assembled by Gibson assembly as described herein. The transgene was introduced into the erythroid cells by lentiviral transduction as described herein. The cells were cultured to terminal differentiation as described herein. Cells were fluorescently labeled with CFSE and injected into an immunocompromised NSG mouse (Jackson Labs) via the tail vein ($1 \times 10^8$ cells per mouse). At regular intervals blood was collected by submandibular puncture. Collected cells were washed, lysed, and analyzed by Western blot as described herein with a detection antibody against the HA epitope tag.

For therapeutic applications, it is important that cultured erythroid cells that contain exogenous proteins either intracellularly or on the surface retain these transgenes when in circulation. This feat is non-trivial given that it is widely hypothesized in the field that erythroid cells undergo a rigorous program of maturation and elimination of proteins unnecessary for basic function when in circulation as they mature (Liu J et al. (2010) Blood 115(10):2021-2027, Lodish H F et al. (1975) Developmental Biology 47(1):59).

Figure 11A:
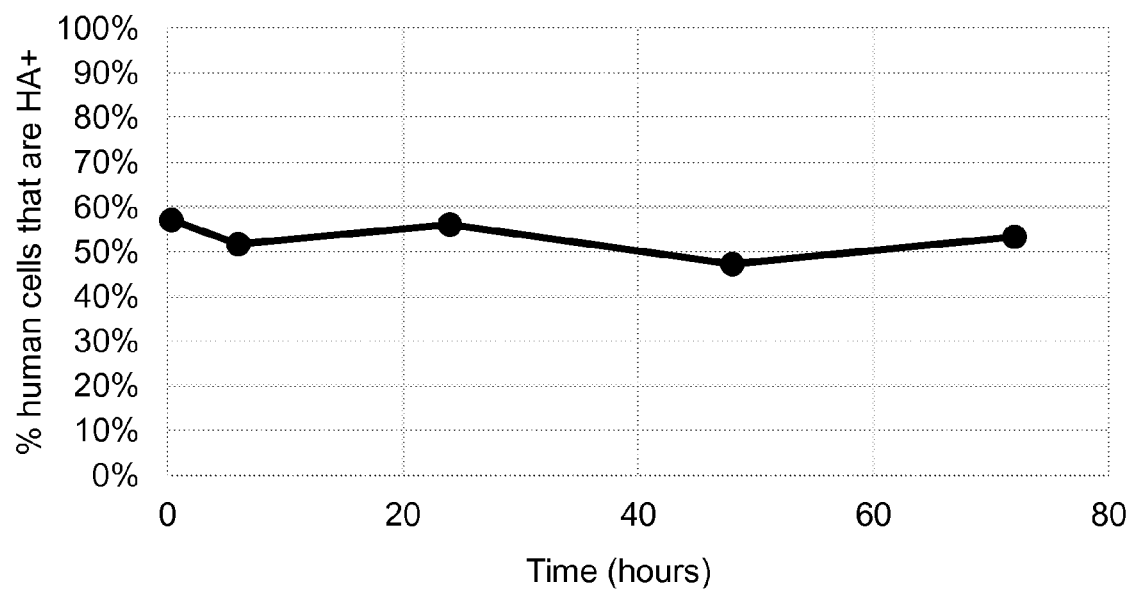
FIGS. 11A-11B track the expression of exogenous protein on cultured erythroid cells in circulation.
Figure 11B:
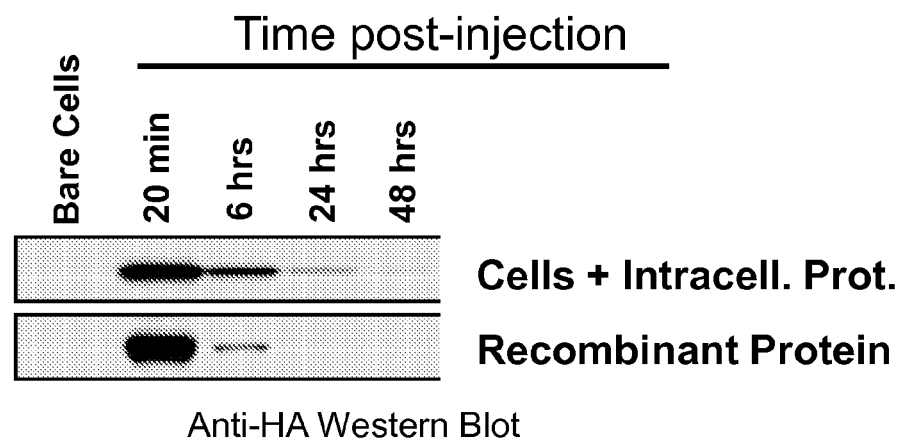

FIGS. 11A-11B show that exogenous proteins expressed in and on cultured enucleated erythroid cells were retained in circulation. In FIG. 11A, mice were injected with cultured enucleated erythroid cells that expressed antibody scFv on their surface. The percentage of antibody scFv-positive cells began and remained steadily at approximately 50% through the duration of the multi-day circulation study. In FIG. 11B, mice were injected either with cultured enucleated erythroid cells that expressed a cytoplasmic enzyme with an HA tag or with recombinant enzyme with an HA tag. When analyzed by Western blot, it is clear that the enzyme retained within the cultured cell for the duration of the experiment. The decrease in band intensity is attributable to the clearance of cells during the experiment, not from the removal of exogenous enzyme from said cells.

The data clearly demonstrate that exogenous proteins expressed in and on culture enucleated erythroid cells are retained in and on the cells in circulation, which has tremendous and unprecedented implications for therapeutic relevance.

Example 34: Assessment of Half-Life Extension In Vivo

Erythroid cells were cultured as described herein. A transgene construct encoding adenosine deaminase and an HA epitope tag was assembled by Gibson assembly as described herein. The transgene was introduced into the erythroid cells by lentiviral transduction as described herein. The cells were cultured to terminal differentiation as described herein. Cells were fluorescently labeled with CFSE and injected into an immunocompromised NSG mouse (Jackson Labs) via the tail vein (1×10^8 cells per mouse). At regular intervals blood was collected by submandibular puncture. Collected cells were washed, lysed, and analyzed by Western blot as described herein with a detection antibody against the HA epitope tag.

A transgene encoding adenosine deaminase with an HA tag at the C-terminus was constructed by Gibson assembly as described herein. The transgene was introduced into HEK-293T cells by lipofectamine transfection (Life Technologies) as described herein. The protein was purified from the cell culture supernatant after 7 days using an HA affinity resin (Pierce) according to manufacturer's instructions. Protein concentration was assessed by absorbance of light at 280 nm. Protein (40 ug) was injected into an immunocompromised NSG mouse (Jackson Labs) via the tail vein. At regular intervals blood was collected by submandibular puncture. Plasma was analyzed by Western blot as described herein with a detection antibody against the HA epitope tag.

In FIG. 11B, mice were injected either with cultured enucleated erythroid cells that expressed a cytoplasmic enzyme with an HA tag or with recombinant enzyme with an HA tag. When analyzed by Western blot, it is clear that the enzyme's circulating half-life is significantly extended when expressed within a circulating cell compared to when injected in soluble form.

Example 35: Assessment of Clearance Rate In Vivo—Platelets

A population of exogenous thymidine phosphorylase expressing platelets is cultured using the herein detailed procedure and is labeled with CFSE and injected into an NSG mouse via the tail vein. A population of native human-sourced platelets is similarly labeled with CFSE and injected into another mouse. Samples are taken from both mice at 10 min, 1 h, 4 h, 8 h, 24 h, and 48 h and flow cytometry is used to quantify platelet circulation levels. The half-life of natural vs cultured platelets is compared.

Example 36: Assessment of Adverse Circulatory Events—Platelets

For therapeutic applications, it is important that cultured platelets and cultured platelets that contain exogenous proteins (either intracellularly or on the surface) not induce adverse events, such as activation of the clotting cascade and tissue thrombus formation. Upon injection of cultured platelets into an NSG mouse via the tail vein, fibrinogen breakdown products fibrinopeptide A and fibrinopeptide B are detected in mouse plasma by ELISA following manufacturer's protocol (MyBiosource). Tissue samples from NSG mice are collected following necropsy. Tissues are trimmed, embedded in paraffin wax, and sectioned. Tissue sections are stained by H&E staining and trichrome staining. Microscope images are taken at 10× and 20× magnification and assessed by a trained pathologist for any pathogenic features.

Example 37: Assessment of Exogenous Protein Retention in Circulation—Platelets The retention of exogenous proteins in and on cultured platelets is assessed by flow cytometry and Western blotting.

CFSE labeled platelets that contain intracellular exogenous protein are injected into a mouse via the tail vein. At regular intervals blood is collected by submandibular puncture. Blood is centrifuged to isolate the platelet-rich plasma, which is then lysed, and analyzed by Western blot with staining for an epitope tag present on the exogenous protein.

Example 38: Acquisition of Donor Cells for Production

After obtaining informed consent, healthy CD34+ stem cell donors receive rhG-CSF (Granocyte or Neupogen), 10 ug/kg/day s.c., for 5 days for peripheral blood stem cell mobilization and then undergo apheresis for 2 consecutive days to collect mobilized CD34+HSC. Mononuclear cells (MNC) are isolated from mobilized peripheral blood by Ficoll density gradient centrifugation and are split in two parts. One part is used to purify CD34+ cells by using anti-CD34-coated magnetic beads (Miltenyi Biotec, Inc., Germany), relative to Miltenyi protocol. The purity of the CD34+ fractions is controlled. CD34+-enriched HSC are then used immediately in the two-step culture method or frozen until use in the one-step culture method.

Complete medium (CM) used is RPMI 1640 (Eurobio, France), supplemented with 2 mM L-glutamine and 100 IU/ml penicillin-streptomycin (Gibco, Grand Island, N.Y., USA) and 10% heat-inactivated FBS (Gibco). IMDM (Gibco), supplemented with 10% heat-inactivated FBS, is used for expansion. Recombinant human stem cell factor (rhSCF), thrombopoietin (TPO), fetal liver tyrosine kinase 3 ligand (Flt-3L), GM-CSF, and TNF-alpha are purchased from R&D Systems (Minneapolis, Minn., USA).

Example 39: Scale-Up for Production

Erythroid cells are scaled up in volume progressively, maintaining the cells at a density of between 1×10^5 and 2×10^6 cells/mL in static culture. Expansion stage is seeded at 10^5/ml and includes 3-7 progressive volume transfers; 100 ml, 500 ml, 1 L, 10 L, 50 L, 100 L, 100 L. During the course of production the cell media includes a combination of IMDM, FBS, BSA, holotransferrin, insulin, glutamine, dexamethasone, beta estradiol, IL-3, SCF, and erythropoietin. When the cells reach a volume appropriate for seeding the production bioreactor, they are transferred to the production bioreactor for final scale-up and differentiation.

Example 40: Culturing Cells in a Bioreactor (Wave)

The WAVE Bioreactor 2/10 system is set up according to the operator manual. In brief, the Cellbag is assembled on the rocking unit, which is placed on the perfusion module. After inflating the bag with air, the weight is set to zero. Subsequently, the bag is filled with the appropriate amount of culturing media and incubated for at least two hours, allowing the media to reach 37 C. The media and cells are transferred to the bag via a transfer flask, a special designed DURAN glass bottle with two ports. In the upper part of the flask, a filter is connected to the port. In the other port, by the bottom of the flask, a tube is assembled. The tube one the transfer flask is coupled with the feed connection on the Cellbag. The transfer flask is maintained in a LAF hood, to decrease the risk of contamination.

Before perfusion is started, tubing and containers for harvest and feed are connected to the Cellbag. Tubing is prepared as follows; a 50 or 70 cm long Saniflex ASTP-ELP silicone tubing (Gore/Saniflex AB), with an inner and outer diameter of 3.2 respectively 6.4 mm, is equipped with male luer lock connections in both ends. The silicone tubing is connected to one end of a C-Flex tube, via a female luer lock. At the other end of the C-Flex tube a male luer lock is assembled and tubings are thereafter autoclaved. Luer locks are held in place with zip-ties on all tubes. Prior to perfusion, the silicone part is connected to the Cellbag and the C-Flex part to a 5 L container (Hyclone Labtainer) for both feed and harvest. All connections are performed in a laminar airflow cabinet.

Control of environmental and metabolic factors can alter the expression or activity of transcription factors and gene regulatory proteins of erythroid cells in culture, see e.g., Csaszar et al., 2009 Biotechnol Bioeng 103(2):402; Csaszar et al. 2012 Cell Stem Cell 10(2):218. To provide control over inputs and outputs in the reactor a micro-volume delivery system is created, a key component of which is a 60-80 cm long fused silica capillary (#TSP100375, Polymicro Technologies) with an internal diameter of 100 um. At the input end, the capillary is fed with a luer-lok tip stock syringe (#309585 BD) connected via a PEEK luer to a MicroTight adapter (#P-662, Upchurch Scientific). The stock syringe is loaded on a Model 33 Twin Syringe Pump (#553333, Harvard Apparatus), kept in a refrigerator at 4 C. At the output end, the capillary enters the bioreactor: a two port FEP cell culture bag (#2PF-0002, VueLife) placed on an orbital shaker in a cell culture incubator at 37 C with 5% $CO_2$. The capillary is fed through a self-sealing rubber septa (#B-IIS, InterLink) with a needle, into the midpoint of the bioreactor. The opposing connector on the bioreactor is replaced with an additional self-sealing rubber septa. Stock syringes and delivery capillaries are blocked overnight before use with a solution of PBS with 10% fetal bovine serum to prevent protein adhesion to syringe and capillary walls.

National Instruments LabVIEW 7.1 is used to create a program to control the syringe pump's injections. The program's basic dosing strategy is an initial injection to concentration L1 followed by wait time t1 and subsequent injections, each to concentration L2 and followed by wait time t2, repeated for n times. The user inputs the flow rate, the stock concentration, the initial culture volume, the desired concentration after injections, the time between injections, and the total number of injections.

Example 41: Assessment of Immunogenicity and Tolerance Induction

1. Tolerance Induction in Mice

In mice, tolerance can be induced by 3 sequential intravenous injections with a cell composition of the invention comprising an antigenic protein, in this example ovalbumin (OVA). Naive mice are injected on days −7, −3 and −1 with either free OVA or OVA expressed within the cell composition of the invention (cell-OVA). Mice are then immunized to OVA by two injections of the antigen mixed with poly I:C adjuvant (Invivogen, San Diego, Calif.) to induce a strong immune response.

2. Assessment of Antibody Titer

IgG levels in mouse serum are evaluated by standard ELISA. Briefly, serum is obtained at various time points from blood samples of mice that have been injected with a cell composition of the invention comprising an antigenic protein, e.g. Ovalbumin (OVA), and from mice that have been injected with free or recombinant OVA. A standard ELISA assay is used, with OVA as the antigen (1 µg/ml in 50 mM carbonate buffer, pH 9.7) adsorbed onto assay plates. Serum samples are serially diluted in the range of 1:50-1:200 for pre-treatment or no-treatment serum, and 1:400-1:500,000 for post-treatment serum and tested in duplicate. The binding of anti-OVA antibodies in serum to the adsorbed recombinant OVA is detected colorimetrically with a secondary anti-mouse immunoglobulin conjugated to horseradish peroxidase, followed by treatment with a chromogenic substrate.

3. Analysis of T Cell Responses

Tolerance is induced to the antigenic protein OVA as described herein. Mice are euthanized 7 days after the 2nd administration of the immunization phase injection of OVA, and their spleens are collected. Spleen cell suspensions are obtained by straining the organs through a 70 micron cell strainer and after RBC lysis with a 0.8% ammonium chloride solution (Stem-Cell Technologies, Grenoble, France). All samples are incubated with anti-Fc receptor antibody (purified anti-CD16/32, Ozyme, San Diego, Calif.) to prevent non-specific binding prior to incubations with antibodies for analysis. The following monoclonal antibodies (Abs) are used for spleen cell staining: PC5-anti-CD62L (MEL14) and PC7-anti-CD8, purchased from Biolegend. OVA peptide-MHC tetramers (PE-Kb-SIINFEKL tetramers (Seq. ID No. 30)) are purchased from Beckmann Coulter. OVA-specific T cells are identified by flow cytometry as cells that are double positive by staining with anti-CD8 and OVA peptide-MCH tetramers. Of this cell population, the percentage of OVA-specific CD8 T cells that are activated is determined by the fraction of cells that are positive by staining anti-CD62L antibody.

4. In Vivo T Cell Lysis Assay

Naive spleen cells are pulsed with 10 micrograms/ml of SIINFEKL peptide (Seq. ID No. 26) (Genscript, Piscataway, N.J.) at 37 C for 1 hour and then labeled with 0.4 microM CFSE (CFSE low). A control population of untreated splenocytes is labeled with 4 microM CFSE (CFSE high). CFSE low and CFSE high cells are combined in a ratio of 1:1 and 1E7 cells per mouse are injected by i.v. route to mice that have previously been tolerized to OVA antigen as described herein or to mice that have been immunized with OVA antigen as described herein. Sixteen hours later, spleen single-cell suspensions are prepared as described herein and analyzed using flow cytometry to determine the CFSE low/CFSE high cell ratio.

Example 42: Assess Expansion and Differentiation of Cultured Erythroid Cells

It is important to assess the expansion, differentiation, and enucleation in vitro differentiated cells to ensure that the introduction of a transgene does not negatively affect the quality of the cells in culture. Expansion is assessed by cell counting. Differentiation is assessed by flow cytometry, Western blot, and RT-PCR. Enucleation is assessed by flow cytometry.

Assessing Expansion Rate by Cell Counting. Erythroid cells are cultured as described herein. At various time points, cells are collected, washed with PBS, and counted using a Countess Automatic Cell Counter instrument (Life Technologies). The expansion rate of the cells is determined by the growth in number of cells over time.

Assessing Differentiation by Flow Cytometry. Erythroid cells are cultured as described herein. At various time points, cells are collected, washed with PBS, and stained with 1:100 dilutions of fluorescent antibodies against the cell surface markers GPA (CD235a), CKIT (CD117), and TR (CD71), purchased from Life Technologies. Labeled cells were analyzed by flow cytometry as described herein.

Assessing Differentiation by Western Blot. Erythroid cells are cultured as described herein. At various time points, cells are collected, washed with PBS, lysed with RIPA buffer, and analyzed by Western Blot as described herein using antibodies for differentiation markers GATA1, GATA2, Band3, CD44, and actin (Abcam).

Assessing Enucleation by Flow Cytometry. Erythroid cells are cultured as described herein. At various time points, cells are collected, washed with PBS, and stained with a fluorescent antibody against glycophorin A (Life Technologies) and the nucleic acid stain DRAQ5 (Pierce) at manufacturer-recommended dilutions, and analyzed on an Attune flow cytometer as described herein.

Assessing Enucleation by Microscopy (Benzidine-Giemsa). Erythroid cells were cultured as described herein. At various time points, cells were collected, washed with PBS, and spun onto slides using a Cytospin (Thermo Scientific). Cells were fixed cells after cytospin with −20 C methanol for 2 min at room temp, rinsed with water, and air-dried. A benzidine tablet (Sigma #D5905) was dissolved with 10 mL PBS, to which 10 VaL of $H_2O_2$ was added. The solution was filtered with a 0.22 um syringe filter. The cell spot on the slide was covered with 300-500 uL of benzidine solution, incubated at room temperature for 1 hr, then washed with water. Giemsa stain was diluted (Sigma #GS500) 1:20 with water. The cell spot on the slide was covered with 300-500 uL Giemsa solution, incubated at room temperature for 40 minutes, washed with water, and air-dried. Slides were then mounted and sealed before imaging on a microscope.

Figure 12A:
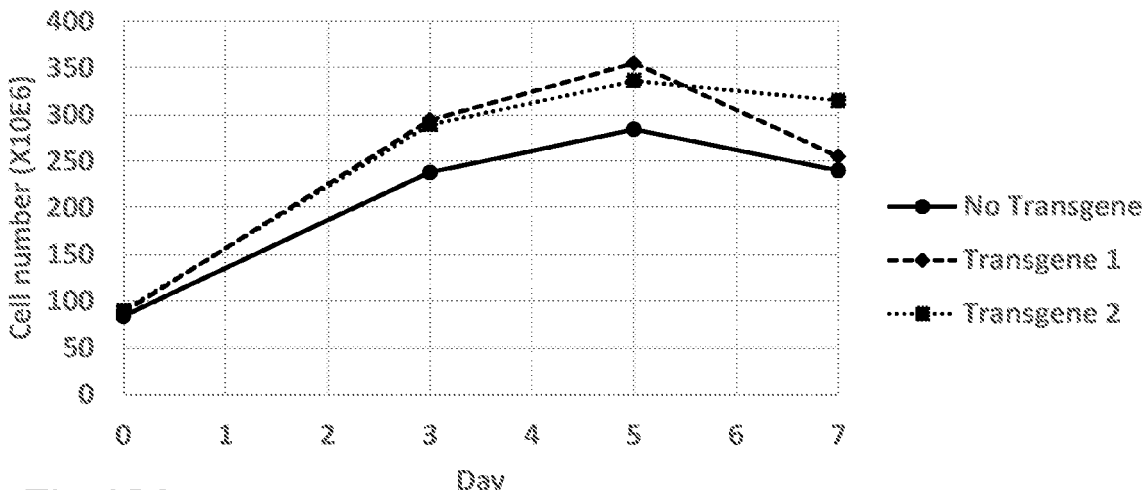
FIGS. 12A-12C are an assessment of expansion and differentiation of cultured human erythroid cells.

FIG. 12A shows the expansion rate of erythroid cells in culture during a seven day window of expansion and differentiation for cells that contain transgenes (dashed line and dotted line) and cells that do not contain a transgene (solid line). Of note, the expansion rate of cultured cells that contain a transgene is indistinguishable from that of cells that do not contain a transgene.

Figure 12B:
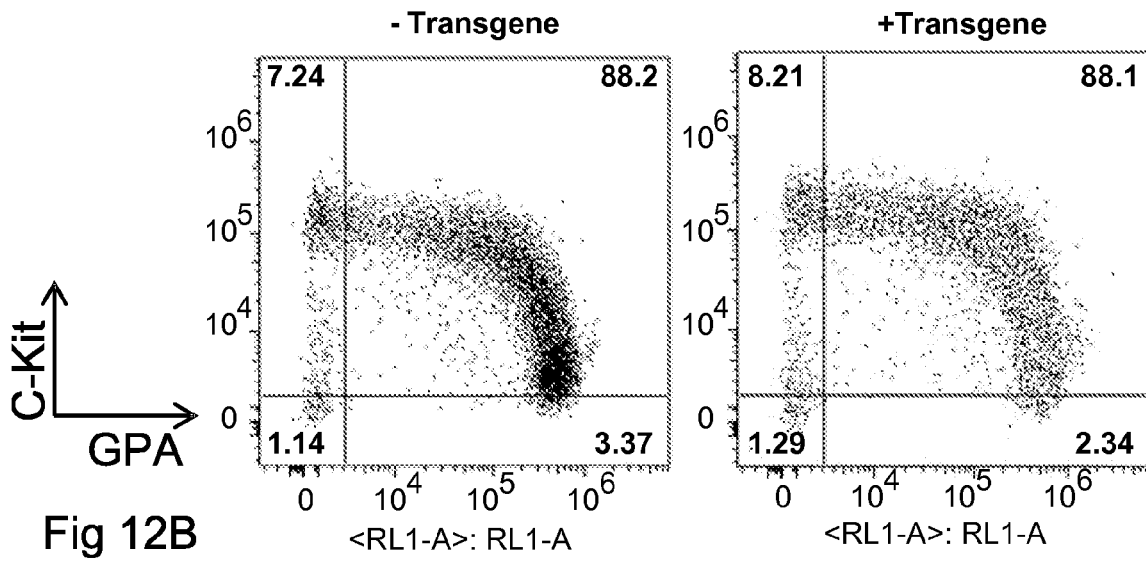

FIG. 12B is a collection of flow cytometry plots for cells stained with antibodies against the cell surface differentiation markers GPA and CKIT. At this particular stage of differentiation, the culture is losing its CKIT expression and increasing its GPA expression as the cells approach terminal maturation. Of note, cultured cells that contain a transgene are indistinguishable from those that do not contain a transgene by this metric of differentiation.

Figure 12C:
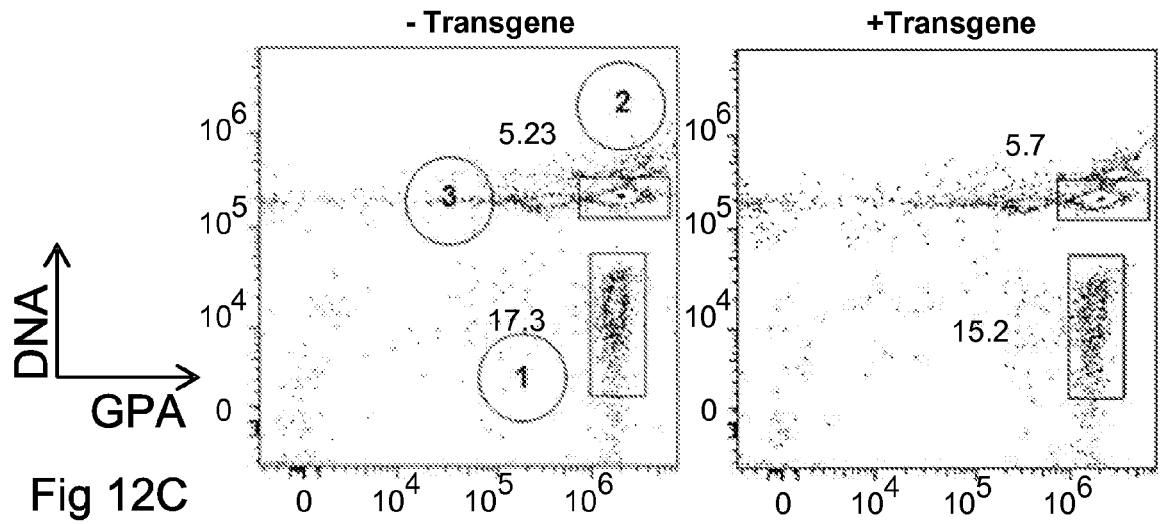

FIG. 12C is a collection of flow cytometry plots for cells stained with an antibody against the surface marker GPA and a fluorescent DNA stain. Three cell populations are evident: (1) cells that are GPA-high and DNA-low, comprising enucleated erythroid cells; (2) cells that are GPA-high and DNA-high, comprising erythroid cells that still contain genetic material; and (3) cells that are GPA-low and DNA-high, comprising pyrenocytes or the membrane-encapsulated ejected nuclei from enucleated cells. Of note, cultured cells that contain a transgene are indistinguishable from those that do not contain a transgene by this metric of enucleation.

The introduction of a transgene into cell culture does not noticeably affect the rate of expansion, the differentiation, or the rate of enucleation of the cells in culture.

Example 43: Assess Hemoglobin Content

1. Total Hemoglobin

Erythrocyte hemoglobin content was determined by Drabkin's reagent (Sigma-Aldrich, product D5941) per manufacturer's instructions. Briefly, blood cells were combined with the reagent in an aqueous buffer, mixed thoroughly, and absorbance of light at a wavelength of 540 nm was measured using a standard spectrophotometer. A soluble hemoglobin standard curve was used to quantify the hemoglobin content in the cells.

2. Hemoglobin Typing by RT-PCR

Cells were lysed and total RNA is collected. Reverse Transcription was carried out with the SuperScript First-Strand Synthesis System for RT-PCR (Life Technologies) according to manufacturer's protocol. Briefly, total RNA (5 ug) was incubated with 150 ng random hexamer primer and 10 nmol dNTP mix in 10 uL H2O for five minutes at 65 C then 1 minute on ice. The reaction master mixture was prepared with 2 uL 10× RT buffer, 4 uL of 25 mM MgCl2, 2 uL of 0.1M DTT, and 1 uL of RNAseOUT. The reaction mixture was added to the RNA/primer mixture, mixed briefly, and then placed at room temperature for 2 min. 1 uL (50 units) of SuperScript II RT was added to each tube, mixed, and incubated at 25° C. for 10 min. The reaction was incubated at 42 C for 50 min, heat inactivated at 70 C for 15 min, then stored on ice. 1 uL RNase H was added and incubated at 37 C for 20 min. This reaction product, the $1^{st}$ strand cDNA, was then stored at −20 C until needed for RT-PCR reaction.

Primers to amplify the different hemoglobin genes and control genes were purchased from IDT-DNA. The primers were as follows: hHBB_F-tcctgaggagaagtctgccgt (Seq. ID No. 9); hHBB_R-ggagtggacagatccccaaag (Seq. ID No. 10); hHBA_F1-tctcctgccgacaagaccaa (Seq. ID No. 11); hHBA_R1-gcagtggcttagcttgaagttg (Seq. ID No. 12); hHBA_F2-caacttcaagctaagccactgc (Seq. ID No. 13); hHBA_R2-cggtgctcacagaagccag (Seq. ID No. 14); hHBD_F-gactgctgtcaatgccctgt (Seq. ID No. 15); hHBD_R-aaaggcacctagcaccttctt (Seq. ID No. 16); hHBG2_F-cactggagctacagacaagaaggtg (Seq. ID No. 17); hHBG2_R-tctcccaccatagaagataccagg (Seq. ID No. 18); hHBE_F-aagagcctcaggatccagcac (Seq. ID No. 19); hHBE_R-tcagcagtgatggatggacac (Seq. ID No. 20); h18S-RNA-F-cgcagctaggaataatggaatagg (Seq. ID No. 21); h18S-RNA-R-catggcctcagttccgaaa (Seq. ID No. 22).

An RT PCR reaction mix was prepared with 25 uL SYBR Green Mix (2×) (Applied Biosystems), 0.5 uL $1^{st}$ strand cDNA, 2 uL forward/reverse primer pair mix (each primer at 5 pmol/uL), in a total volume of 50 uL H2O. Reactions were run in an ABI Prism SDS 7000 instrument (applied biosystems) using the following amplification cycle: 50 C 2 min, 1 cycle; 95 C 10 min, 1 cycle; 95 C 15 s->60 C 30 s->72 C 30 s, 40 cycles; 72 C 10 min, 1 cycle. Dissociation curve analysis and RT-PCR results was performed with the SDS 7000 instrument.

Example 44: Assessment Differentiation of Cultured Platelets—FACS

The differentiation state of platelets in culture can be assessed by flow cytometry. Megakaryocytes (MKs) represent a distinct cellular morphology that precedes terminal platelet differentiation. To determine the extent of maturation toward MKs, 1×10^6 cultured cells (LAMA-84 and CD34+ cells) are washed and then labeled with (a) anti-CD41-FITC (GpIIb/IIIa; BD Bioscience, San Jose, Calif., USA) or anti CD71-FITC or (b) anti-CD33-FITC, anti-CD41-PE, anti-CD45-PerCp and CD34-APC (Beckman Coulter, Fullerton, Calif., USA), and analyzed for the percentage of CD41 cells generated.

To determine the amount of ploidy, differentiated LAMA-84 cells are fixed overnight in 75% ethanol at 4° C. and labeled with propidium iodide (PI, 50 ug/ml) and analyzed using the FACScalibur (Becton Dickinson), whereas day 14 differentiated CD34+ cells are analyzed quantitatively under a microscope after May-Grunwald/Giemsa staining by quantitating the number of nuclei per cell and specific morphology of MKs with this stain. Only cells with MK morphology are analyzed. The presence of multinucleated cells in the cytospin preparation is indicative of the presence of polyploid MKs. Differentiated CD34+ cells are assessed for the presence of multinucleated mature MKs by morphology.

Example 45: Assessment Differentiation of Cultured Platelets—qPCR

The differentiation state of platelets in culture can be assessed by quantitative PCR. Platelet RNA is extracted to further characterize the cultured cells. Total RNA is extracted using TRIzol reagent (Invitrogen). The purity of each platelet preparation is assessed by PCR analysis of platelet (GPIIIa) and leukocyte (CD45) markers. The integrity of platelet RNA is assessed using Bioanalyzer 2100 (Agilent) prior to further analyses.

Total RNA is collected from cell lysate and a cDNA library is generated using a commercial synthesis kit (Clontech). The labeled cDNAs are quantified with the Quant-iT PicoGreen dsDNA Kit (Invitrogen) and diluted to 3 pM for loading into a single lane and sequencing on an Illumina 1G Genome Analyzer (Solexa).

Raw sequences are filtered through serial quality control criteria. First, the presence of at least 6 nt of the 3' Solexa adapter is verified. The sequence reads that did not comply with this criterion are discarded, whereas the others are trimmed to remove the adapter sequence harbored at the 3' end. The remaining tags are further filtered regarding their length (>10 nt), copy number (>4 reads) and readability (<9 non-identified nucleotides, annotated N). Reads complying with all those criteria are subsequently defined as usable reads.

All the usable reads are aligned to pre-microRNAs extracted from miRBase database. Sequence tags that matched perfectly to more than one precursor are distributed equally among them. In order to account for Drosha and Dicer imperfect cleavage, any sequence tag that perfectly matched the pre-microRNA in the mature microRNA region, allowing up to 4 nt shift as compared to the reference mature microRNA position, is considered as a mature microRNA. The microRNA expression level is defined as the number of reads mapping each mature microRNA normalized to the total number of usable reads, considering that the overall number of small RNAs is invariant. The relative abundance of each microRNA is defined as the number of reads mapping each microRNA compared to the total number of reads mapping mature microRNAs.

Example 46: Purification by Centrifugation

Cultured cell fractions can be purified and separated from nuclei and contaminating alternate-density cell types via centrifugation. Cells are centrifuged at 200 g for 15 minutes to isolate an erythrocyte and reticulocyte rich fraction. The supernatant is pipetted off and the desirable cell fraction is then washed in modified Tyrode's buffer (containing 138 mM NaCl, 5.5 mM dextrose, 12 mM NaHCO3, 0.8 mM CaCl2, 0.4 mM MgCl2, 2.9 mM KCl2, 0.36 mM Na2HPO4 and 20 mM Hepes, pH 7.4) in presence of 1 μM prostaglandin 12, and resuspended in the same buffer.

Example 47: Purification by Chemical Enucleation

Enucleation of cultured cells can be stimulated by chemical additives to the culture, which can help increase the enucleated fraction of cells prior to purification. Erythroid cells are cultured as described herein. 48 hours prior to collection, cells are incubated with 210 mM Me2SO. Cells are then collected by centrifugation at 350×g for 5 min at room temperature, resuspended at a level of 3×105 cells per ml in fresh medium containing 210 mM Me2SO and 5 ug/mL of cytochalasin B (or other actin or nucleus manipulating molecule, ie. p38 MAPK, psoralens) and incubated at 37 C. The proportion of cells without nuclei is assessed by flow cytometry as described herein, using DRAQ5 as a nucleic acid stain and antibodies against glycophorin A as an erythroid surface marker of differentiation.

Example 48: Purification by Acoustophoresis

Several mechanical separation systems may be used to obtain a uniform cell population. Free flow acoustophoresis represents one mechanical separation method (Petersson 2007, American Chemical Society). While suspended in saline solution (0.9 mg/mL) with nutrient additives, including CsCl (0.22 g/mL), is added to the saline solution. A sample suspension containing cultured erythroid cells is processed using an acoustophoresis chip (Cell-Care) with two active outlets (flow rate 0.10 mL/min per outlet).

Syringe pumps (WPI SP260P, World Precision Instruments Inc., Sarasota, Fla.) are used to control the flow rates in the chip. All outlets are individually connected to high-precision glass syringes (1005 TLL and 1010 TLL, Hamilton Bonaduz AG, Bonaduz, Switzerland) via the injectors using Teflon tubing, allowing independent control of the outlet flow rates. The clean fluid inlet is connected to a syringe pump and the cell suspension inlet to a 50-mm-long piece of Teflon tubing (0.3-mm i.d.) with its other end submerged in a beaker from which the sample suspension is aspirated at a rate defined by the difference between the net outlet flow and the clean fluid inlet flow.

The ultrasound used to induce the standing wave between the walls of the separation channel is generated using a 20×20 mm piezoelectric ceramic (Pz26, Ferroperm Piezoceramics AS, Kvistgard, Denmark) attached to the back side of the chip. Ultrasonic gel (Aquasonic Clear, Parker Laboratories Inc., Fairfield, N.J.) ensures a good acoustic coupling between the two. The piezoelectric ceramic is actuated via a power amplifier (model 75A250, Amplifier Research, Souderton, Pa.) connected to a function generator (HP 3325A, Hewlett-Packard Inc., Palo Alto, Calif.). Even though the acoustic waves enter the chip from the back side, a standing wave is induced between the side walls of the separation channel as a result of the coupling of the mechanical vibrations along the three axes of the crystal structure.

The separation process is monitored using a standard microscope and a wattmeter (43 Thruline Wattmeter, Bird Electronic Corp., Cleveland, Ohio). The process can subsequently be controlled by tuning the signal frequency, the actuation power, and the flow rates.

The cell size distributions in the samples are analyzed using a Coulter counter (Multisizer 3, Beckman Coulter Inc., Fullerton, Calif.). Each sample is mixed with an electrolyte (Isoton II, Beckman Coulter Inc.) and analyzed using a 100-um aperture. The level of hemolysis, i.e., the concentration of free hemoglobin from damaged red cells, is measured using a photometer (Plasma/low HB Photometer, HemoCue AB, Angelholm, Sweden).

Example 49: Purification by Ex Vivo Maturation

Erythroid cells that are not fully mature can be driven to maturity by ex vivo incubation in a system that mimics the natural in vivo maturation triggers.

1. Co-Culture with Stromal Cells

In the final stage of culture, erythroid cells are cultured on an adherent stromal layer in fresh medium without cytokines. The cultures are maintained at 37 C in 5% CO2 in air. The adherent cell layer consists of either the MS-5 stromal cell line or mesenchymal stromal cells (MSCs) established from whole normal adult bone marrow (see Prockop, D J (1997) Science 276:71) in RPMI (Invitrogen) supplemented with 10% fetal calf serum. Adherent MSCs are expanded and purified through at least two successive passages prior to use in co-culture.

2. Culture in Fibronectin-Coated Plates

In the final stage of culture, erythroid cells are cultured in plates adsorbed with human fibronectin. To produce these plates, fibronectin (Sigma Aldrich) is reconstituted with 1 mL sterile H2O/mg of protein and allowed to dissolve for at least 30 minutes at 37° C. A small amount of undissolved material may remain. This will not affect product performance. The fibronectin solution is diluted 100× in sterile balanced salt solution and added to the culture surface with a minimal volume. The culture surface is allowed to air dry for at least 45 minutes at room temperature. Excess fibronectin is removed by aspiration.

Example 50: Purification by Magnetophoresis

Strategies for separating, enriching, and/or purifying erythroid cells by magnetophoresis are known in the art, see e.g., Zborowski et al., 2003, Biophys J 84(4) 2638 and Jin & Chalmers 2012, PLOS One 2012 7(8):e39491. A commercial magnetic separation system (QuadroMACS™ Separator combining four MidiMACS™ separation units and LD columns, Miltenyi Biotec, Auburn, Calif.) is used for magnetic erythrocyte enrichment from HSC-derived erythrocyte cultures. Cells are deoxygenated in a Glove-Bag™ inflatable glove chamber (Cole Parmer, Vernon Hills, Ill.), filled with nitrogen (Medipure™ nitrogen, concentration >99%, Praxair, Inc., Danbury, Conn.). Before deoxygenation, all materials and equipment including the separation system, degassed sterile buffer (PBS +2 mM EDTA +0.5% BSA), and sterile collection tubes are placed in the glove bag, which is then tightly sealed. Deoxygenated cultures are loaded directly into a MACS® LD column which was placed in the QuadroMACS™ separator kept under anoxic conditions inside an inflatable glove chamber filled with N2 gas. Cells which pass through the column contained within the magnet are labeled as negative fraction and they are expected to be "non-magnetic", including HSCs and erythroid cells before final maturation. The cells retained in the separation column are labeled as positive fraction, which is "magnetic" and consist of maturing RBC-like cells nearly full of functional hemoglobin. They are eluted from LD column after its removal from the magnet. Once separation is finished, oxygenated cells are reversibly recovered by exposing the collected cells to air.

Example 51: Purification by FACS

A population of erythroid cultured cells is sorted using a Becton-Dickinson Aria IIu cell sorter. Prior to sorting, cells are collected, washed with PBS, and stained with a fluorescent antibody against glycophorin A (Life Technologies) and the nucleic acid stain DRAQ5 (Pierce) at manufacturer-recommended dilutions. A 100 m nozzle is used with a drop drive frequency of 28,000 drops/second. The sample threshold rate is approximately 4000 events/second. The temperature control option is used to maintain sample and collection tubes at 4° C. the entire duration of sorting. Additionally, the sample agitation feature is used at 200 rpm to prevent the sample from sedimenting throughout the sort. The sample is sorted in aliquots of approximately 750 µl dispensed from the syringe. Meanwhile, during these pauses the collection tubes are kept at 4° C., protected from the light, and gently mixed prior to resuming sort. The sorted samples are collected into a 12×75 mm borosilicate glass collection tube containing 250 µl DMEM supplemented with 10% FCS.

Example 51: Purification by Enzymatic Treatment of Cells

Allogeneic erythrocyte sourcing may benefit from A and B antigen removal to generate a universally compatible product. This may be facilitated by a set of enzymes capable of selectively cleaving the galactose groups, rendering the erythroid cells more immunogenically favorable.

Two types of recombinant proteins of endo-ß-galactosidase, which are originally identified from *Clostridium perfringens*, are produced in *E. coli* BL-21 using standard cloning methods. ABase is prepared for releasing A/B Ag and endo-ß-galactosidase C (EndoGalC) for releasing Galα1-3Galß1-4GlcNAc (Gal Ag), which is known to be highly immunogenic in xenotransplantation, and has a carbohydrate structure resembling the A/B Ag. ABase cleaves Galß1-4GlcNAc linkage in blood type A [GalNAcα1-3 (Fucα1-2) Galß1-4GlcNAc] and in blood type B [Galα1-3 (Fucα1-2) Galß1-4GlcNAc].

Briefly, after cloning of ABase, an expression plasmid with a C-terminal His tag is constructed in the pET-15b vector eabC without signal peptide. This exogenous gene is transformed into *E. coli* BL-21 cells. The enzyme produced in the cells as a soluble protein fraction is purified over a nickel-nitrilotriacetic acid column (QIAGEN GmbH, Hilden, Germany). Finally, 5 mL of purified recombinant ABase is obtained at the concentration of 3.6 mg/mL with the specific activity of 1500 U/mg. One unit of the enzymatic activity is defined as the amount of the enzyme required to hydrolyze 1 µmol of the substrate per min.

The effect of ABase treatment on Ag presence, Ab binding and complement activation is examined. Human A/B RBC are digested with ABase and subjected to flow cytometric analysis after incubation with cross-reactive (anti-A or anti-B or anti-A and B containing; type B, type A or type O respectively) human sera. The mean fluorescence intensity (MFI) is used to quantitate the expression level of blood type A, B and Gal Ag. Digestion level is expressed as a percentage of blood type A or B Ag expressed on RBC after incubation in the absence of ABase.

Fresh blood type O sera are pooled from three healthy human volunteers and frozen at −80° C. to preserve endogenous complement activity until used. Heat-inactivated (for 30 min at 56° C.) sera are used for analysis of Ab binding. RBC with and without enzyme (ABase) digestion are incubated with 50% blood type O sera (100 µL) diluted with phosphate-buffered saline containing 0.2% bovine serum albumin (PBS/BSA) for 30 min at 37° C. After washing, RBC are reacted with FITC-labeled anti-human IgG/IgM (DAKO, Glostrup, Denmark) (×30, 100 µL) for 30 min at 4° C. and then subjected to flow cytometric analysis.

The inhibitory effect of enzyme treatment on complement activation is also evaluated by the change of C3d deposition. After RBC are incubated with 50% human sera in the presence of complement activity for 15 min at 37° C., RBC are reacted with FITC-labeled rabbit anti-human C3d Ab (DAKO, Glostrup, Denmark) (×100, 100 µL) for 30 min at 4° C. and then applied to flow cytometric analysis. The percentage of the control level (in the absence of enzyme) is calculated based on MFI to evaluate the inhibitory effect of enzyme treatment on Ab binding and C3d deposition.

Example 52: Purification of Platelets by Centrifugation

Platelets can be purified from mixed cell suspensions by centrifugation. Some 40 ml of whole blood is distributed in blood collection tubes with sodium citrate at 3.2% used as an anticoagulant. The tubes are centrifuged at 400×g for 10 min. After this stage, three layers are clearly demarcated: plasma, red blood cells, and an intermediate zone. The plasma is at the top with the platelets, the red blood cells are at the bottom because of their heavier density; and the fine, whitish intermediate zone consists of larger platelets and leukocytes and is called the buffy coat. Using a Jelco 18G needle, the upper portion of plasma with platelets is drawn off, and the buffy coat is placed into two other tubes, this time with no additives: one tube to produce plasma (P tube) and the other to produce thrombin (T tube). Only 1.5 ml of plasma is used to produce thrombin, to which 0.5 ml of calcium gluconate at 10% is added, with 15 min in a double boiler at 37° C. The two tubes are then centrifuged again, this time at 800×g, for the same length of time (T=10 min). After this final centrifugation, the T tube contains a thrombin-rich liquid while the P tube contains the platelet sedimentation and some red blood cells (erythrocyte-platelet clump). The volume is reduced at this stage by removing two-thirds of the total plasma volume. The portion removed is platelet poor, while the remaining portion with the sedimented platelets (that are easily dispersible by stirring) is platelet rich.

Example 53: Thymidine Incorporation

Self-replication potential of a cell population can be assessed using a thymidine incorporation assay known in the art, see e.g., Harkonen et al. 1991 Exp Cell Res 186L288 and Tanaka et al. 1992 PNAS 89:8928.

Briefly, uniformly 13C- and 15N-enriched thymidine [U-13C, 15N-TdR] is obtained from Martek Biosciences (Columbia, Md.), and 3 H-TdR (80 Ci/mmol) is purchased from ICN Radiochemicals (Irvine, Calif.). Media and buffers are obtained from Fisher Scientific (Pittsburgh, Pa.). All enzymes except phosphodiesterase are from Boehinger Mannheim (Indianapolis, Ind.). Phosphodiesterase II is obtained from Worthington Biochemical Corporation (Lakewood, N.J.). High-performance liquid chomatography (HPLC) solvents are from EM Science (Gibbstown, N.J.) and contained <0.1 ppm evaporation residue.

Erythroid cells are cultured as described herein. Following the culture, cells are collected for use in the thymidine incorporation assay.

Cells are labeled with [U-13C, 15N]-TdR at 1.6 µg/ml for 18 h, with the addition of unenriched thymidine to achieve a final thymidine concentration of 1 µM. After they are washed with phosphate-buffered saline, the cells are cultured in supplemented DMEM for 6 h more before 3 H-TdR is added at the indicated concentrations (0.1-10 µCi/ml) for another 18-h incubation. Unlabeled thymidine is added to the samples to bring the final thymidine concentration to 0.13 µM, which is equivalent to the concentration of 3 H-TdR in the samples receiving 10 µCi radiolabel/ml. After removal of 3 H-TdR, the cells are incubated in supplemented DMEM for an additional 6-54 h before isolation of DNA.

DNA is extracted using the modified Puregene DNA isolation kit (Gentra Systems, Minneapolis, Minn.). Based on the number of cells in the sample, a scale-up/scale-down procedure is used to determine the added reagent volumes. For example, when 1×10^7 cells are used, 21 µl containing 328 µg of proteinase K is added to 3 ml of cell lysis solution. After mixing, the sample is left overnight at room temperature. The following day, 10 µg of RNase is added and the sample is mixed and incubated for 2 h at 37 C. Protein precipitation solution (1 ml) is added, and the sample is incubated on ice for 5 min. After centrifugation for 10 min at 2000 g, the supernatant containing DNA is mixed with 3 ml 100% 2-propanol and gently inverted 50 times or until white threads of DNA became visible. The sample is then centrifuged at 2000 g for 5 min. The resultant DNA pellet is dried for 5 min before washing in 3 ml of 70% ethanol and recentrifugation for 5 min at 2000 g. The final pellet is air-dried and then rehydrated in deionized H2O and quantitated by absorption at 260 nm. The same procedure is applied to CD34+ stem cells as a control for replicative ability.

Any DNA is denatured by boiling for 3 min, then chilled rapidly on ice. The enzymatic hydrolysis procedure is carried out with a DNA concentration of 0.5 mg/ml. The following protocol describes volume of reagent added per milliliter of DNA solution. DNA is hydrolyzed with 10 µl of nuclease P1 (0.5 U/µl) and 5 µl of DNase I (4 U/µl) in 10 µl of buffer containing 200 mM MgCl2, 100 mM ZnCl2, and 1M Tris, pH 7.2, for 2 h at 45° C., followed by addition of 20 µl phosphodiesterase (4 mU/µl) and further incubation for 2 h at 37° C. Finally, 5 µl of 10M ammonium acetate (pH 9.0) and 10 µl of alkaline phosphatase (1 U/µl) are added, and the samples incubated for another 2 h at 37° C.

The digested DNA sample is filtered with a 0.22-µm nylon filter. This sample is analyzed with the HPLC/CRI/IRMS system, using a 4.6×250 mm Supelcosil LC-18-S HPLC column (Supelco, Bellefonte, Pa.). The same solvent system is used at 1 ml/min and a linear gradient of 5% to 25% B in 15 min.

After separation by HPLC, the deoxynucleosides are analyzed using chemical reaction interface mass spectrometry (CRIMS). In this process, the deoxynucleosides flow into a nebulization and desolvation system driven by a stream of helium, where they emerge as a dry particle beam. The 13CO2/12CO2 abundances from this in-line generated CO2 are determined with a Finnigan/MAT Delta S isotope ratio mass spectrometer (ThermoFinnigan, San Jose, Calif.) and its accompanying Isodat data system. 5-Fluorodeoxyuridine (Sigma) is used as an internal isotope ratio standard.

Isotope ratios (IR in equation that follows) for three nucleosides are obtained from each sample: T, dA, and dG. The enrichment of CO2 evolved from each DNA-derived deoxynucleoside is computed by the equation (13)CO2 (per mil)=1000×(IR experimental−IR std)/IRstd. To maintain the highest level of internal consistency and avoid any interexperimental drift, the isotope ratio for dG is subtracted across all experiments from the isotope ratio for T. The data from the end of the stable-isotope labeling period (day 0) to the end of the washout (day 3) are evaluated.

Example 54: Quantification of Nuclear Material

The number of cells in a mixed population that contain DNA is assessed by flow cytometry using the DNA stain DRAQ5 (Pierce). Cells are incubated with the stain per manufacturer's instructions and analyzed on a flow cytometer, e.g., an Attune cytometer (Life Technologies). The percentage of cells above a predefined threshold of nuclear material content is quantified.

Example 55: Tumorigenicity Assay In Vitro

To assess the replication potential of cells, a soft agar colony formation assay can be performed. In brief, a base agar layer is made by making a 0.5% Agar+1×RPMI+10% FCS solution, all components warmed to 40 C, and adding 1.5 mL of the solution to a 35 mm petri dish. The agar is allowed to solidify for 30 min at room temp before use.

The top agarose layer is prepared by melting 0.7% agarose in a microwave and cooling to 40 C. A 2×RPMI+20% FCS solution is heated to 40 C. Cells are counted and prepared for plating at 5000 cells per plate at a density of 200,000 cells per mL. 0.1 mL of cell suspension is added to 10 mL tubes, followed by 3 mL of the warm 0.7% Agarose and 3 mL of the warm RPMI/FCS solution. The solution is mixed gently by swirling and added (1.5 mL) to each of three or four replicate base agar plates.

Plates are incubated at 37 C in a humidified incubator for 10-30 days. Cells are fed 1-2 times per week with cell culture media, 0.75 mL/plate.

To assess colony formation, plates are stained with 0.5 mL of 0.005% Crystal Violet for >1 hr. Colonies are counted using a dissecting microscope.

Example 56: Tumorigenicity Assay In Vivo

Terminally-differentiated cultured erythroid cells are implanted in various animal models to evaluate the potential for tumorigenicity. Several tissues are collected from the various models and analyzed with histological, immunochemical, and fluorescent assays to quantify tumorigenicity.

Animals receive daily intraperitoneal injections of CsA (10 mg/kg, Sandimmune, Novartis Pharma, Nürnberg) starting two days before grafting. For the depletion of NK cells, some rats receive, in addition to CsA intraperitoneal injections of the monoclonal antibody (mAb), anti-NKR-P1A (clone 10/78, mouse IgG$_1$, BD Biosciences, Heidelberg, Germany) or the respective isotype control (clone PPV-06, mouse IgG$_1$, Exbio, Prague, Czech Republic). The anti-NKR-P1A mAb (clone 10/78) is directed against the same epitope as the mAb (clone 3.2.3). One mg of the respective antibodies are given one day before the injection of erythroid cells followed by 0.5 mg at day 4 after cell transplantation.

Blood samples are taken before starting these experiments, at day 0 and 4 days after erythroid cell transplantation, and at autopsy (day 92) in order to determine the proportion of NK cells in the blood by flow cytometry. For the analysis of subcutaneous tumor growth erythroid cells are injected in 100 µl phosphate-buffered saline (PBS) into the flank of the animals. Tumor growth is monitored every second day by palpation and size is recorded using linear calipers. Animals are sacrificed before day 100 when a tumor volume of 1 cm$^3$ in mice and 5 cm$^3$ in rats is reached, when a weight loss of more than 10% occurs, or when any behavioral signs of pain or suffering are observable. Autopsies of all animals are performed.

Murine tissue near the site of injection is immediately frozen in liquid nitrogen or placed in phosphate-buffered 4% formalin for 16 h and then embedded in paraffin. Spleens and lymph nodes are removed for subsequent immunological analyses. The transplantation of erythroid cells into the striatum of unilaterally 6-OHDA-lesioned rats is performed. These animals are sacrificed 6 weeks after transplantation.

Animal tissue is analyzed by flow cytometry. Appropriate fluorescent and PE-conjugated antibodies against established cancer cell biomarkers of CD133, CD3, CD, CD16, CD19, CD20, CD56, CD44, CD24, and CD133 are added to the excised tissues samples and analyzed to quantify tumorigenic potential.

Example 57: Deformability by EKTA

Erythroid cells cultured as described herein are assessed for deformability characteristics relative to natural erythrocyte samples via ektacytometry.

The ektacytometer consists of a Couette-type viscometer combined with a helium-neon laser used to produce a diffraction image of red cells suspended in a viscous fluid between the two cylinders. When the viscometer rotates, normal red cells elongate in the shear field, causing the diffraction image to become elliptical. The ellipticity of the image is measured by quantifying the light intensity along the major (A) and minor (B) axes of the diffraction pattern and expressing this as a ratio (A−B)/(A+B), the deformability index (DI) or elongation index (EI). The viscosity of the medium is chosen to be greater than the internal viscosity of the densest erythroid cells. A 31 g/liter solution of polyvinylpyrrolidone (PVP), mw=360,000, in a phosphate buffer of 0.04M composed of K2HP04 and KH2P04 in distilled water yields a viscosity of 0.20 poise at 25° C. and 12 poise at 37 C.

Osmolarity is adjusted with NaCl to the desired level and measured in a Roebling freezing-point osmometer. The final pH is varied by using small additions of 1-M solutions of NaOH and HCl and is measured in a Technicon BG II blood gas analyzer. Sodium azide is added as a preservative to stock solutions to obtain 0.4 g/l.

The ektacytometer collects three primary metrics from the erythroid cell samples and compares them to native erythrocytes; Osmolality minimum ($O_{min}$), deformability index ($Di_{max}$), and the osmolality at which the DI reaches half of its maximum value ($O_{hyp}$).

$O_{min}$ is related to the surface area to volume ratio of the cell and has been found to equal the 50% hemolysis point in the classical osmotic fragility test.

$Di_{max}$ is the maximum value of the deformability index, normally reached at 290 mosmol (the physiologic osmolality value). This indicates the maximum deformability of the cell under shear stress and is related to a number of factors, such as surface area, volume, internal viscosity, and mechanical properties of the cell membrane.

$O_{hyp}$ is the osmolality at which the DI reaches half of its maximum value. This gives an indication of the position of the hypertonic part of the curve, which is related to the internal viscosity of the cell as well as mechanical properties of the membrane, such as how it will bend under force (stiffness).

The parameters obtained for the cultured erythroid cells are compared to the same values for primary erythroid cells.

Example 58: Deformability by LORCA

The deformability of purified cRBC populations is measured by a laser diffraction technique (LORCA, laser-assisted optical rotational cell analyzer, R&R Mechanotrics). In brief, a highly diluted suspension of cells is sheared in a Couette system with a gap of 0.3 mm between 2 cylinders, one of which is able to rotate to induce shear stresses. A laser beam is passed through the suspension, and the diffraction pattern is measured at 37° C. At low shear stress, the cells are circular disks, whereas at high shear stress, the cells become elliptical. The cell deformability is expressed in terms of the elongation index (EI), which depends on the ellipticity of the deforming cells. Aliquots containing 12.5 uL of pelleted RBC pellets are diluted in 5 mL of polyvinylpyrrolidone solution (molecular weight 360 000). The EI values at 30 Pa (referred to as EImax) and 3 Pa are selected as representative values of the deformability for easy comparison between samples at various shear stresses.

Example 59: Assessment of Vascular Occlusion—Ex Vivo Rat Vasculature

The potential for vascular occlusion of erythroid cells can be assessed with isolated artificially perfused rat vasculature using methods known in the art, see e.g., Kaul et al. 1983, J Clin Invest 72:22. Briefly, in anesthetized (sodium pentabarbitol 30 mg/kg) rats of the Wistar strain, 120-150 g, the right ileocolic artery and vein are cannulated with heparinized (100 uL/mL) silastic tubing at a site 3 cm distant from the ileocolic junction. Under a steady-state perfusion with Ringer's containing 1% bovine serum albumin, the ascending colon and terminal ileum (3 cm each) are sectioned between ties. After hemostatic ties of all vascular connections is achieved, the tissue is isolated. The isolated mesoappendix is gently spread on an optically clear Lucite block on a microscope stage. The entire preparation is covered with a plastic saran wrap except for outlets of cannulas and the microscope objective.

The control arterial perfusion pressure (Ppa) and venous outflow pressures (Pv) are kept constant at 80 and 3.8 mmHg, respectively, and monitored via Statham-Gould P-50 pressure transducers (Stathan Instruments Inc, Oxnard Calif.). The venous outflow (Fv) rate is monitored using a photoelectric dropcounter and expressed in mL/min. A lapse of 10-12 min is allowed for tissue equilibration and stabilization of Fv. Only preparations exhibiting mesoappendix microvasculature free of host blood cells and with a steady Fv of 4.6+/−0.5 (mean+/−SD) are used. The experiments are done at 37 C.

Erythroid cells are isolated as described herein. After control measurements of Ppa and Fv, erythroid cells (0.2 mL, Hct 30%) are gently delivered via an injection port 15 cm distal to site of arterial cannulation, and the changes in Ppa and Fv are recorded on the strip chart of a Grass polygraph (Grass Instrument Co, Quincy Mass.). The tissue preparations are perfused for 10-15 min before the infusion of samples with Ringer's solution to allow stabilization of the tissue and clear the vasculature of the remaining blood cells of the host animal. The resulting obstruction after the infusion of cells can be cleared and the flow restored by briefly (2-3 min) perfusing the vasculature with fully-oxygenated Ringer's solution at high pressure (100 mmHg).

At the end of each experiment the entire tissue preparation (free of cannulas and luminal content) is weighed. Peripheral resistance units (PRU) are calculated and expressed as $PRU=\Delta P/Q=mmHg/mL/(min-g)$ where $\Delta P$ (mmHg) is the arteriovenous pressure difference and Q (mL/min−g) is the rate of venous outflow per gram of tissue.

In each experiment, pressure-flow recovery time (Tpf) is determined following the bolus infusion of samples. Tpf is defined as the time (seconds) required for Ppa and Fv to return to their base-line levels following the delivery of a given sample, and it represents total transit time throughout the mesoappendix vasculature. The parameter values obtained for cultured erythroid cells are compared to the values obtained for primary erythroid cells.

Example 60: Assessment of Vascular Occlusion—In Vitro Flow Chamber

Methods to assess vascular occlusion of erythroid cells using in vitro graduated height flow chambers are known in the art, see e.g., Zennadi et al 2004, Blood 104(12):3774.

Briefly, graduated height flow chambers are used to quantitate the adhesion of erythroid cells to endothelial cells (ECs). Slides coated with ECs are washed with Hanks balanced saline solution (HBSS) with 1.26 mM Ca2+, 0.9 mM Mg2+ (Gibco, Grand Island, N.Y.) warmed previously to 37° C. and then fit into a variable height flow chamber. The flow chamber is mounted on the stage of an inverted phase contrast microscope (Diaphot; Nikon, Melville, N.Y.) connected to a thermoplate (Tokai Hit, Fujinomiya-shi, Japan) set at 37° C. Cells are observed using a video camera (RS Photometrics, Tucson, Ariz.) attached to the microscope and connected to a Macintosh G4 computer (Apple, Cupertino, Calif.). Erythroid cells are cultured as described herein, and labeled with fluorescent dye PKH 26 red fluorescent cell linker kit (Sigma) following the manufacturer's instructions. Cells (3 mL) suspended at 0.2% (vol/vol) in HBSS with Ca2+, Mg2+ are infused into the flow chamber and allowed to adhere to the slide for 15 minutes without flow. Before exposure to flow, a minimum of 3 fields at each of 7 different locations along a line oriented normal to future flow are examined for the total number of fluorescent cells. Fluid flow (HBSS with Ca2+, Mg2+) is then started using a calibrated syringe pump. After exposure to flow, the fields are again examined and the number of adherent cells counted. The fraction of adherent cells is presented as follows: Number of cells attached after exposure to flow/ Cells present per field before flow. The wall shear stress is calculated as follows: $\tau w=(6 \mu Q)/(wH[x]2)$, in which $\tau w$ indicates wall shear stress (dyne/cm2); Q, volumetric flow rate (cm3/s); $\mu$, media viscosity; w, width of the flow channel; and H(x), height of the flow chamber as a function of position along the microscope slide.

Example 61: Assessment of Vascular Occlusion—Intravital Microscopy

Methods to assess vascular occlusion of erythroid cells using intravital microscopy are known in the art, see e.g., Zennadi et al. 2007 Blood 110(7):2708.

Briefly, general anesthesia of a test animal is achieved by intraperitoneal injection of 100 mg/kg ketamine (Abbott Laboratory, Chicago, Ill.) and 10 mg/kg xylazine (Bayer, Shawnee Mission, Kans.). A double-sided titanium frame window chamber is surgically implanted into the dorsal skin fold under sterile conditions using a laminar flow hood. Surgery involves carefully removing the epidermal and dermal layers of one side of a dorsal skin fold, exposing the blood vessels of the subcutaneous tissue adjacent to the striated muscles of the opposing skin fold, and then securing the 2 sides of the chamber to the skin using stainless steel screws and sutures. A glass window is placed in the chamber to cover the exposed tissue and secured with a snap ring. Subsequently, animals are kept at 32° C. to 34° C. until in vivo studies were performed 3 days after surgery.

Anesthetized animals with window chambers are placed on the stage of an Axoplan microscope (Carl Zeiss, Thornwood, N.Y.); temperature is maintained at 37° C. using a thermostatically controlled heating pad. All infusions are through the dorsal tail vein. Erythroid cells are cultured as described herein. Cells are then labeled with DiI or DiO (Molecular Probes, Eugene, Oreg.) dyes per manufacturer's instructions. Labeled cells (300 µL; hematocrit [Hct] 0.50 [50%] in PBS with Ca2+ and Mg2+) are infused, and RBC adhesion and blood flow dynamics are observed in subdermal vessels for at least 30 minutes using LD Achroplan 20×/0.40 Korr and Fluar 5×/0.25 objectives. Microcirculatory events and cell adhesion are simultaneously recorded using a Trinitron Color video monitor (PVM-1353 MD; Sony, Tokyo, Japan) and JVC video cassette recorder (BR-S3784; VCR King, Durham, N.C.) connected to a digital video camera C2400 (Hamamatsu Photonics KK, Hamamatsu City, Japan). Thirty segments of venules are examined for each set of conditions. Arterioles are distinguished from venules based on (1) observation of divergent flow as opposed to convergent flow; (2) birefringent appearance of vessel walls using transillumination, which is characteristic of arteriolar vascular smooth muscle; and (3) relatively straight vessel trajectory without evidence of tortuosity.

Measurement of red cell flux and adhesion is performed by examining videotapes produced using ×20 magnification. Cell adherence is quantitated by considering cells attached to the vessel walls and immobile for 1 minute. The percentage of the length of vessels with diameters up to 25 µm or more than 25 µm, occupied by SS RBCs, is quantified as follows: % venular length occupied by SS RBCs=(length of vessel wall with adherent cells/total length of the vessel segments analyzed)×100. Changes in RBC flux are calculated as follows: flux=number of circulating fluorescent human RBCs crossing a single point marked on vessels less than 50 µm in diameter per minute.

Example 62: Assessment of Vascular Occlusion—Platelets

Methods to assess vascular occlusion of platelets using human vascular endothelial cells (HUVECs) can be adapted from similar methods for eythroctyes. Briefly, a 2-mL volume of 0.05% hematocrit suspension is added to confluent HUVECs on tissue culture Petri dish. The cone-and-plate apparatus is assembled within 1 min after addition of platelets and placed on a Nikon Diaphot-TMD inverted-phase contrast microscope (Southern Micro Instruments, Atlanta, Ga.). The motor is started to turn the cone, and adherence is continuously monitored at 0.1 or 1 dyne/cm2 shear stress for 30 min. Temperature is maintained constant at 37° C. by an air curtain incubator (Nicholson Precision Instruments, Inc., Bethesda, Md.) blowing on the adhesion apparatus. Platelet adherence is visualized and recorded every 5 min by focusing on 8 different fields of view for 20 sec per field for each time point. The entire experiment is viewed under 400× total magnification through a CCD-72 series camera (Dage-MTI, Inc., Michigan City, Ind.) and recorded on videotape with a SVO 2000 video cassette recorder (Sony Electronics, San Jose, Calif.). Adherence is quantified off-line at the end of each experiment by counting individual adherent cells during manual playback of recorded video images. The cell counts in 8 fields for each time point are averaged and normalized to adherent red cells per square millimeter of endothelium.

Example 63: Assessment of Mass/Volume/Density with Resonator

A dual suspended microchannel resonator (SMR) system is used to characterize the mass, volume, and density of a population of terminally-differentiated erythroid cells based on Bryan et al, *LabChip*, 2014. At the start of a cell density measurement, the system is first flushed with filtered Percoll media, which serves as the high density fluid. Next, the sample bypass is filled with a dilute cell sample, and the vial heights at the sample inlet and outlet are adjusted to direct fluid flow into the first SMR. Pressure at the high density fluid inlet is used to set the density of Fluid 2, and pressure at the waste outlet controls the overall flow speed in the device. To minimize the likelihood of size biasing due to heavier cells settling at the bottom of the sample vial or tubing, a fresh sample is introduced at regular intervals by flushing the sample bypass channel. Data is acquired via LabVIEW and processed with MATLAB.

Cell concentration is monitored using a Coulter counter. Cell measurements are performed on cultures grown to $5 \times 10^5$-$1 \times 10^6$ cells/ml. High density fluid introduced for measurement in the second SMR is formulated as a solution of 50% (v/v) Percoll (Sigma), 1.38% (w/v) powdered L15 media (Sigma), 0.4% (w/v) glucose, 100 IU penicillin, and 100 µg mL-1 streptomycin. Media pH is adjusted to 7.2. This Percoll media is stored at 4° C. and filtered immediately prior to use in the dual SMR.

Example 64: Assessment of Phosphatidyl Serine Content by Annexin V

Erythroid cells are cultured as described herein. 50 µL cell suspension is washed in Ringer solution containing 5 mM $CaCl_2$ and then stained with Annexin-V-FITC (1:200 dilution; ImmunoTools, Friesoythe, Germany) in this solution at 37° C. for 20 min under protection from light. Cells are washed and stained by flow cytometry as described herein, and annexin-V fluorescence intensity is measured with an excitation wavelength of 488 nm and an emission wavelength of 530 nm. Relative phosphatidyl serine exposure is assessed from annexin-V fluorescence.

Example 65: Assessment of Lipid Content by Chromatography

Lipids are extracted from washed exogenous antigen-expressing EHCs by three extractions with methanol-chloroform 1:1 at room temperature in the presence of the antioxidant BHT (Sigma Aldrich). The pooled extracts are washed with 0.05M KCl in the method of Folch, Lees and Sloane Stanley1957, J Biol Chem 226:497. Briefly, for the first extraction, 15 mL methanol containing 0.05 mg/mL BHT are added to the washed complexes in a centrifuge tube and allowed to stand for 30 min with occasional stirring to break up sediment. 15 mL of chloroform is then added and the mixture is allowed to stand for 30 min with occasional stirring to break up clumps. The tubes are centrifuged for 5 minutes at 1500 g and the supernatant fractions decanted into separatory funnels fitted with Teflon stopcocks. The second and third extractions are performed similarly with 15 mL of the methanol-BHT added to the residue followed by 15 mL of chloroform, except the extracts stand for only 10 minutes with occasional stirring after each addition. After centrifugation, the supernatant fractions are pooled in a separatory funnel then 48 mL of chloroform and 28 mL of 0.05M KCl are added and mixed. The mixture is allowed to stand overnight in darkness at 4 C for phase separation. After being rewarmed to room temperature, the lower of the two clear phases is collected and evaporated to dryness in vacuo at 40 C in a rotary vacuum evaporator. The lipid is transferred quantitatively to a 10 mL volumetric flask with chloroform and stored at −22 C.

The concentration of free cholesterol in the lipid extract is determined as follows. The lipid extract is chromatographed on a 0.5 mm layer of Silica Gel HR (Brinkmann Instruments, Inc., Westbury, N.Y.) in hexane-diethyl ether-glacial acetic acid 80:20:1, the TLC plate is stained by spraying with 2,7-dichlorofluorescein solution (see below), the free cholesterol spot is scraped into a conical centrifuge tube and extracted once with 2.0 ml and three times with 1.0 ml of chloroform, the extract is evaporated to dryness in vacuo at 40° C. in a rotary vacuum evaporator, and the cholesterol is estimated by the ferric chloride method of Mann 1961 Clin Chem 7:275 without saponification. A free cholesterol standard, prepared from a commercial certified reagent grade material by isolation through the dibromide derivative (see e.g., Fieser J Amer Chem Soc 1953 75:5421), is taken through the chromatographic procedure and estimated with each set of determinations. The values for free cholesterol are corrected in each determination for the recovery of the standard, which averaged 95%. The TLC is necessary to remove the BHT, which otherwise interferes with the ferric chloride method by producing a brown product that absorbed at 560 nm.

The phospholipid distribution is determined in triplicate by TLC of aliquots of the total lipid extract at 4° C. on Silica Gel HR, 0.5 mm thick, in chloroformmethanol-glacial acetic acid-water 25:15:4:2 to which is added BHT at a concentration of 50 mg/100 ml to prevent autoxidation during chromatography; the TLC plates are prepared with water ("neutral" plates). Use of a "wedged-tip technique" for applying the lipid sample at the origin of the plate (see e.g., Stahl 1965 Thin-Layer Chromatography, Academic Press Inc.) results in excellent separations of the individual phospholipids. In particular, the method provides complete separation between phosphatidyl ethanolamine (PE), phosphatidyl serine (PS), lecithin, and sphingomyelin; a discrete spot migrates between PS and lecithin that is identified as phosphatidyl inositol (PI). The spots are made visible in UV light by spraying with a solution of 2,7-dichlorofluorescein (33.3 mg/100 ml of aqueous 2 mM NaOH) and then scraping directly into Kramer-Gittleman tubes, where the phospholipids are digested at 190° C. for 60 min with 1.0 ml of 70% perchloric acid. The remainder of the procedure is performed as described above, except that after color development, the silica gel is removed by centrifugation at 3000 g for 5 min and the absorbancy is determined on the clear supernatant solution. Corrections are made for the absorbancy of corresponding areas of blank lanes.

Gas-liquid chromatography is performed on hexane-dissolved samples with a Barber-Colman instrument, model 5000, equipped with paired 8-ft columns of EGSS-X (an ethylene glycol succinate polyester combined with a silicone) 8% on Gas-Chrom P, 100-120 mesh (Applied Science Laboratories Inc.) and dual flame ionization detectors. The nitrogen flow rate is 50 ml/min at the inlet. The column temperature is maintained at 165° C. for 10 min after injection of the sample, then increased at 2 C/min to 200° C.

Example 66: Assessment of Membrane Viscosity

The membrane viscosity of a population of cells can be assessed by fluorescence photobleaching assay. A 0.5-ml sample of erythroid cells is collected and washed once in HEPES-buffered saline (132 mM NaCl, 4.7 mM KCl, 2.0 mM CaCl2, 1.2 mM MgSO4, 20 mM HEPES, adjusted to pH 7.4). The packed cells are then washed once in 145 mM NaCl-10 mM NaHCO3, pH 9.5, and resuspended in the same buffer with 1 mg/ml DTAF (obtained from Research Organics, Cleveland, Ohio). The cells are incubated on ice for 1 h, then washed twice in 50 mM glycine-95 mM NaCl-10 mM NaHCO3, pH 9.5, to remove any dye that has not bound covalently to protein. Finally, the cells are washed twice and resuspended to ~2% hematocrit in HEPES-buffered saline with 1 mg/ml bovine serum albumin. The same treatment is applied to control native erythrocytes.

The flow chamber is mounted on the stage of a Leitz Diavert (Rockleigh, N.J.) inverted microscope equipped for incident-light fluorescence microscopy. The dichroic mirror and excitation/emission filters are the standard combination for use with fluorescein dyes (Leitz designation 12), with excitation wavelength in the range 450-490 nm. The objective is an oil immersion type with 100× magnification and 1.25 numerical aperture. A 100 watt high pressure mercury arc lamp (Osram, Munich) with an appropriate power supply and housing (Oriel, Stamford, Conn.) serves as the fluorescence excitation source.

A computer-controlled electronic shutter (Vincent Associates, Rochester, N.Y.) limits the exposure duration and is synchronized with a photon-counting electronic system for measuring fluorescence intensity. The field diaphragm of the incident light illuminator is used to limit excitation to a circular area of diameter 20-40 um. At regular intervals, an output pulse from the computer causes the shutter to open for a typical duration of 20 ms. Light from the brief fluorescent image is split with a series of prisms so that half the light is directed to a low-light-level SIT video camera (Model 66-SIT, Dage-MTI, Michigan City, Ind.) and half to a photomultiplier tube (Model 8850, RCA, Harrison, N.J.) enclosed in an ambient temperature housing. During the time that the electronic shutter is open, a video image processor (Model 794, Hughes Aircraft, Carlsbad, Calif.) is triggered to acquire the fluorescent image, providing a video snapshot that can be monitored to ensure that the subject remains in focus and that no foreign object intrudes into the field of view. Distances on the video screen are measured with a video caliper and calibrated by comparison with the video image of a stage micrometer. Also during the time the shutter is open, the photomultiplier signal is processed with the photon-counting technique. An amplifier/discriminator (Model AD6, Pacific Instruments, Concord, Calif.) generates a digital logic pulse for each signal pulse above a given magnitude, and those digital pulses are counted on a 100-MHz gated counter (Model 770, EG&G Ortec, Oak Ridge, Tenn.). The microcomputer controls the gating, resetting, and recording of the photon count.

A typical experiment consists of a number of preliminary fluorescence measurements made during brief (20 ms) pulses of excitation light, followed by an extended period of illumination (typically 30 s) during which the samples cells are bleached, followed by another series of brief exposures, every 15-30 s, until the fluorescence appears to have completed its recovery.

The recovery time and other parameter values obtained for cultured erythroid cells are compared to the same values obtained for primary erythroid cells.

Example 67: Assessment of Mean Corpuscular Volume with Advia Hematology Analyzer The Mean corpuscular volume (MCV) of the cultured erythroid cells is measured using electrical impedance in an Advia 120 hematology analyzer (Siemens Healthcare). The results are compared to that of natural human erythrocytes.

Example 68: Pathogen Testing of Cultured Erythroid Cells

RT-PCR is used to quantify adventitious virus presence in cultured erythroid cell populations and confirm non-contamination (Assay No. 003000.BSV, BioReliance). Sterility testing of unprocessed and final bulk, final vials, prebanking cells, and cell and virus banks is performed by directly inoculating the erythroid population into 2 different types of media that support the growth of aerobic and anaerobic bacteria respectively. Samples are incubated for 14 days followed by testing for microbial contaminants per BioReliance Sterility Testing protocol USP 71.

Example 69: Assessment of Osmotic Fragility

Osmotic fragility is evaluated to measure the resistance of the erythroid cells to lysis when exposed to hypotonic solutions. Solutions of NaCl in water were made at concentrations spanning 0% to 1%. Cells were incubated in each of the salt solutions for 15 minutes. The samples were centrifuged to pellet intact cells. Supernatant was assayed for hemoglobin content by absorption of light at 540 nm using a spectrophotometer. The point at which 50% hemolysis occurs is calculated and compared to the value obtained for primary erythrocytes.

Example 70: Assessment of Rosetting/Immunogenicity

The direct antiglobulin test, also known as Coombs test, assesses the agglutination or resetting of erythroid cells caused by the binding of polyclonal antibodies from serum to surface antigens on the cell. It can be performed with pooled human serum for general allogeneic immunogenicity assessment, or with serum from the intended recipient for specific immunogenicity prediction.

In brief, add 1-2 drops of cells stored in an EDTA tube to a reaction tube. Wash this tube three times with isotonic saline. After the third wash, prepare a 3% suspension from the washed cells. Label 2 tubes A and B. Add one drop of the washed 3% suspension to each tube. Wash these tubes one more time. When decanting, position the tubes so that the cell button is on top. This will prevent too many cells from being lost in the washing process. Drain well, and blot dry with a biowipe. Immediately add one drop human test serum to both tubes, and shake to mix. Allow the B tube to incubate at room temperature 5 minutes. Centrifuge the A tube for the time calibrated for the Coombs spin on the serofuge. Immediately resuspend gently and examine for agglutination using the lighted agglutination viewer (Beckton Dickinson). If the A tube is positive, it is not necessary to read the B tube nor is it necessary to examine the A tube microscopically. If the A tube is negative by lighted agglutination viewer, examine for agglutination under the microscope. If the A tube was negative through the microscopic reading, centrifuge the B tube after its incubation period and repeat steps 2-4 with the B tube sample. If the B tube is negative as well, add one drop of IgG-coated Coombs Control Cells (Check Cells) to the tube and centrifuge. Examine for agglutination. Agglutination should be present in this step, or the test is invalid.

If there is no agglutination in any of the steps before addition of the check cells (ccc), the test is interpreted as negative. If agglutination is observed in any of the steps before addition of the check cells, the test is interpreted as positive.

Example 71: Assessment of Oxygen-Binding Capacity

Equilibrium oxygen binding curves at 37° C. are determined in a tonometer linked to a 1-cm path length cuvette. Spectral measurements are performed with a spectrophotometer (Cary 50; Variant Inc), and the temperature is controlled with a Peltier module. Analyses are performed in 50 mM bis-Tris buffer (pH 7.2) containing 140 mM NaCl and 2 mM glucose. After thorough deoxygenation under nitrogen, the red cell suspensions are equilibrated at different partial pressures of oxygen by injection of known volumes of pure oxygen into the tonometer through a rubber cap with a Hamilton syringe. The fractional saturation is estimated by simulation of the absorption spectra in the visible and Soret regions as a linear combination of the fully deoxygenated and oxygenated spectra of the RBC suspension by least squares regression.

Example 72: Assessment of Metabolic State of Cells

The erythroid cell population may be verified as metabolically active using a variety of different enzyme based assays to quantify important metabolic end products. Active glycolysis is a crucial metabolic pathway to assess and may be measured with the following assay (Glycolysis cell-based assay kit, Cayman Chemical, Item 600450).

450 ul of assay buffer is aliquoted into a test tube, followed by 50 uL of the L-Lactic acid standard and mixed thoroughly. A titration curve is constructed using the lactic acid concentration standard, beginning with a 1 mM dilution.

Cells are added to a 96 well plate and centrifuged at 1000 RPM for 5 minutes. 100 uL of the standards are transferred into a separate 96 well plate. 90 uL of assay buffer is then added to each well. 10 ul of supernatant in each cell well is then transferred to corresponding new wells. Add 100 ul of reaction solution to each well using a repeating pipettor. The plates are then incubated on an orbital shaker for 30 minutes at RT. The absorbance is read at 490 nm with a plate reader. Results are compared to natural cells to identify any metabolic differences.

Example 73: Assessment of Platelet Aggregation

Aggregation propensity of cultured or primary sourced platelets can be monitored. Platelets are submitted to swirling analysis by shaking them in front of a light source, with the results expressed as presence or absence of birefringence. The units of platelet concentrates produced with a volume of 50-70 mL are left to rest for one hour and placed in a linear shaker (C-Mar®) at 70 rpm at a controlled temperature of 22±2° C. (71.6±3.6° F.).

The tests of platelets concentrates (platelet count, platelet aggregation and pH) are carried out on days 1, 3 and 5 after processing; a leukocyte count is performed only on day 1 and the microbiological control is performed only on the 5th day of storage. In order to obtain aliquots from samples of platelet concentrates, a sterile connection (Haemonetics®) is used which ensured the integrity of the environment. Platelet aggregation is achieved using the turbidimetric aggregometry technique using a dual-channel Chronolog (Crono-Log Corporation®) within four hours of blood collection. For this, the cells are initially obtained through light centrifugation at 1000 rpm for five minutes, and then centrifuged at 3000 rpm for fifteen minutes (Eppendorf®). Samples are subjected to a platelet count in an automatic counter (Human Count®).

After adjusting the platelet concentration, aggregation is evaluated using different concentrations of inducing agonists: collagen 2.0 pg/mL and ADP 7.0 pg/mL (Crono-Log Corporation®). For each test, 400 µL of PRP and 400 µL of PPP are used, each one in a different cuvette after waiting for spontaneous aggregation. The aggregation curve is observed after five minutes of stimulation by inducing agonists, and soon after, aggregation is measured and expressed as a percentage according to the curves formed during the tests. The result of the test is commonly expressed as a percentage of aggregation by the quantity of light transmitted through the test solution; aggregation is classified as normal, low or high.

Example 74: Autologous Culture Process

The culture of erythroid cells using autologously sourced progenitor CD34+ cells is done to optimize cell immunocompatibility for patients. CD34+ cells from the bone marrow are mobilized to the periphery in a patient using GM-CSF as described herein. Between $10^6$-$10^8$ CD34+ cells are collected and cultured using the aforementioned 22 day protocol using defined media. During Day 4 the cells are transfected with a lentiviral vector containing a gene that codes for the expression of a therapeutic agent. Upon completion of the culturing protocol, the cells are purified and assessed across several quality control metrics including physical properties that correlate with circulation viability, immunogenicity, replicative potential, purity, and therapeutic dose. The cells are then stored in appropriate stabilizing solution and formulated in a syringe or appropriate delivery vehicle. The cells are then infused into the same patient that donated the initial CD34+ cells.

Example 75: Autologous Loading Process

For the preparation of therapeutic erythroid cells loaded with a suitable exogenous antigen, autologously sourced erythrocytes can be used to optimize cell immunocompatibility for patients. Blood is drawn from the patient and centrifuged at 5000 g for 20 minutes. The buffy coat is removed and the remaining red cells are re-suspended in anticoagulant buffer at a density of $10^8$ cells/ml, giving a total of $10^{10}$ cells. The cells are loaded with a therapeutic exogenous antigen of interest by one of the methods described above. Upon completion of the loading protocol, the cells are purified and assessed across several quality control metrics including physical properties that correlate with circulation viability, immunogenicity, replicative potential, purity, and therapeutic dose. The cells are then stored in appropriate stabilizing solution and formulated in a syringe or appropriate delivery vehicle. The cells are infused into the same patient that donated the initial erythrocytes.

Example 76: Allogeneic Culture Process

To create a scalable, universal therapeutic, etyrhoid cells can be cultured from an allogeneic source. The culture of erythroid cells using allogeneically sourced progenitor CD34+ cells is done to streamline the process and culture a volume of therapeutic capable of treating patients at scale. Donors are blood-typed for major blood antigens, including A, B, Rh to identify universal donors (e.g., O Rh- or Bombay Rh-). CD34+ cells from the bone marrow are mobilized to the periphery in a suitable donor using GM-CSF as described herein. Between $10^6$-$10^8$ CD34+ cells are collected and cultured using the aforementioned 22 day protocol using defined media. During Day 4 the cells are transfected with a lentiviral vector containing a gene that codes for the expression of a therapeutic agent. Upon completion of the culturing protocol, the cells are purified and assessed across several quality control metrics including physical properties that correlate with circulation viability, immunogenicity, replicative potential, purity, and therapeutic dose. The cells are then stored in appropriate stabilizing solution and formulated in a syringe or appropriate delivery vehicle. The cells are then infused into patients irrespective of their major blood groups.

Example 77: Allogeneic Loading Process

The culture of erythroid cells using allogeneically sourced progenitor CD34+ cells is done to streamline the process to prepare larger volumes of therapeutic cells capable of treating patients at scale. Donors are blood-typed for major blood antigens, including A, B, Rh to identify universal donors (e.g., O Rh- or Bombay Rh-). The cells are loaded with a therapeutic exogenous antigen of interest by one of the methods described above. Upon completion of the loading protocol, the cells are purified and assessed across several quality control metrics including physical properties that correlate with circulation viability, immunogenicity, replicative potential, purity, and therapeutic dose. The cells are then stored in appropriate stabilizing solution and formulated in a syringe or appropriate delivery vehicle. The cells are then infused into patients irrespective of their major blood groups.

Example 78: Storage

1. Storage in Refrigerated Buffer Solution

Standard protocols for the storage of red blood cells are known in the art, see e.g., Meryman and Hornblower 1986, Transfusion 26(6):500. The standard protocol for the storage of red blood cells (for up to 42 days) is the collection of blood into anticoagulant solutions (citrate-dextrose-phosphate). Erythroid cells are cultured as described herein. Red cell concentrates are prepared by the removal of plasma by centrifugation. The cells are stored at 4±2° C. in a slightly hypertonic additive solution, SAGM (sodium, adenine, glucose, mannitol, 376 mOsm/L).

2. Storage in Frozen Buffer Solution

Methods for glycerolization, freezing, and thawing of erythroid cells are known in the art, see e.g., Meryman and Hornblower 1977 Transfusion 17(5):4348. Human blood in citrate phosphate dextrose is glycerolized and frozen within 4 days of collection. To prepare glycerolized RBCs, approximately 10 mL of whole blood is first centrifuged at 1,400 g for 10-15 min, and the plasma is removed. The resulting packed cells are then glycerolized in two steps using an aqueous glycerol solution with the following composition: 57.1 g glycerol, 0.03 g potassium chloride, 0.085 g magnesium chloride hexahydrate, 0.08 g disodium phosphate, and 1.6 g sodium lactate in a total volume of 100 mL, adjusted to a pH of 6.8.42 In the first step, 1.5 mL of this glycerol solution is added drop-wise to the packed cells with gentle agitation over a period of 3 min. The mixture is then allowed to equilibrate undisturbed for at least 5 min. In the second glycerolization step, 5 mL of the glycerol solution is added drop-wise while the mixture is gently agitated over a 3-min period, yielding a final glycerol composition of ~40% w/v. The entire glycerolization process is carried out at room temperature. The glycerolized RBCs are then divided into aliquots of 0.6-1.1 mL in cryogenic vials, placed in a NalgeneVR Cryo "Mr. Frosty" freezing container (Thermo Scientific, NC), and stored in a −80 C freezer for at least 12 h and up to 10 years. Frozen RBCs are thawed by placing the cryogenic vial in a 37 C water bath for 1 min. All glycerolized blood samples are used in deglycerolization experiments within 2 h of thawing.

3. Formulation as Syringe

The cell population may be intravenously administered via a syringe. The therapeutic cells are diluted to a density of $10^7$ cells/ml using standard saline buffer at 37 C such that 100 ml of volume, or $10^9$ cells, are delivered. The cell solution is loaded into a 150 cc syringe, 20 gauge needle and injected into the patient through the basilic vein at 5 cc/min. During injection the patient's vitals are monitored for any immunogenic or clotting reactions.

4. Formulation as Bag

The cell population may be intravenously administered via syringe connected to a bag and drip chamber (i.e. an IV drip). The therapeutic cells are diluted to a density of 10∂cells/ml using standard saline buffer at 37 C such that 100 ml of volume, or $10^9$ cells, are delivered. The cell solution is loaded into a 1 L plastic bag, connected to a catheter and allowed to drain via gravity into the patient through the basilic vein. During infusion the patient's vitals are monitored for any immunogenic or clotting reactions.

Example 79: Treatment of Diseases

1. Hemophilia

A patient suffering from hemophilia A is diagnosed. A composition of exogenous FVIII expressing enucleated hematopoietic cells is prepared as described herein. $10^9$ of the cells are administered intravenously to the patient. The clotting rate is assessed with a standard in vitro clotting time assay known in the art. Circulating antibodies against FVIII are detected in serum as described herein. The levels of circulating antibodies are assessed to track the effectiveness of immune tolerance induction. If the clotting cascade activity is insufficient to ensure healthy coagulation, recombinant or isolated FVIII are administered concurrently intravenously in order to reduce the symptoms of hemophilia A.

2. Atypical Hemolytic Uremic Syndrome

A patient suffering from atypical hemolytic uremic syndrome (aHUS) is diagnosed. A composition of exogenous CFH expressing enucleated hematopoietic cells is prepared as described herein. $10^9$ of the cells are administered intravenously to the patient. The symptomatic hemolysis rate is assessed with a standard urinary hemolysis assay known in the art. Circulating antibodies against CFH are detected in serum as described herein. The levels of circulating antibodies are assessed to track the effectiveness of immune tolerance induction. The patient is administered the treatment until the symptoms of the disease are seen to ameliorate using the assays described herein.

3. Multiple Sclerosis

An individual with multiple sclerosis (MS) receives a single infusion of $1\times10^9$ antigen expressing enucleated hematopoietic cells expressing the antigenic polypeptide myelin basic protein (MBP), produced and formulated as described herein. At the day of study drug administration, the patient is monitored in a phase 1 inpatient unit for 24 hours. Measurement of the primary outcome is performed at month 3 and additional safety follow-up is performed until month 6 with consecutive clinical, MRI, and general physical examinations as well as clinical and laboratory analyses to assess adverse events and monitor MS disease activity. The procedure is repeated until tolerance is induced such that the symptoms of MS are ameliorated in the individual. See, for example, Andreas Lutterotti et al. Sci Transl Med 5, 188ra75 (2013).

Frequency of different cell subsets is analyzed in whole blood (EDTA tubes) by flow cytometry with the following antibody panels: for immune cell subsets (granulocytes, eosinophils, monocytes, and B, T, NK, and NK T cells)- anti-CD45 (PE-Cy7, eBioscience), anti-CD16, (APC-Cy7, BioLegend), anti-CD19 [fluorescein isothiocyanate (FITC), BD], anti-CD14 (V450, BD), anti-CD3 [peridinin chlorophyll protein (PerCP), BD], and anti-CD56 [phycoerythrin (PE), eBioscience]; for T cell subsets including CD4+, FoxP3+ Tregs, regulatory CD8+CD57+ILT2+, and proinflammatory CD8+CD161high T cells-anti-CD3 (PE-Cy7, eBioscience), anti-CD4 (APC, eBioscience), anti-CD8 [Pacific Blue (PB), Dako-Biozol], anti-FoxP3 (PE, Miltenyi), anti-CD25 (APC, eBioscience), anti-CD57 (FITC, BD), anti-ILT2 (PE, Beckman), and anti-CD161 (APC, Miltenyi). The corresponding isotype controls are included in all stainings. Cells are analyzed with an LSR-II flow cytometer (BD) and FACSDiva Software (BD).

Peripheral blood mononuclear cells (PBMCs) are isolated by Ficoll density gradient centrifugation (PAA), and functional phenotype of T cells is evaluated by intracellular cytokine staining as follows: $5\times10^5$ freshly isolated PBMCs are incubated overnight in 200 ml of X-VIVO 15 (Lonza) in a sterile FACS tube. The next day, cells are stimulated with phorbol 12-myristate 13-acetate (50 ng/ml, Sigma) and ionomycin (1 mg/ml, Sigma) in the presence of brefeldin A (10 mg/ml, eBioscience) for 5 hours. After washing with phosphate-buffered saline, cells are stained with LiveDead kit (AmCyan, Invitrogen), fixed, permeabilized, and stained with different antibodies: anti-IL-17 (Alexa Fluor 647; eBioscience), anti-IL-4 (PE-Cy7, BioLegend), anti-IFN-g (FITC, BioLegend), anti-IL-10 (PE; BioLegend), anti-CD3 (PE, DakoCytomation), anti-CD4 (PB, DakoCytomation), and anti-CD8 (PB, BioLegend) or with the corresponding isotype controls.

The antigen-specific T cell responses toward the myelin peptide used in the study are measured in freshly isolated PBMCs before the tolerization procedure and after 3 months. Antigen-specific T cell responses are analyzed by proliferation assays with thymidine incorporation. Briefly, isolated PBMCs are seeded in 96-well plates at $1.5\times10^5$ PBMCs per well in X-VIVO 15 medium (Lonza) with 1 mM of peptide. Forty-eight wells are seeded per antigen, and six wells only with medium as negative control in each plate. TTx (5 mg/ml) (Novartis Behring) is used as positive control. On day 7, plates are incubated for 15 hours with 1 mCi of [3H] thymidine (Hartmann Analytic). [3H] thymidine-pulsed plates are analyzed with a scintillation b counter (Wallac 1450, PerkinElmer). The scintillation counts (CPM) of each well are measured. Wells showing CPM higher than the mean+3 SDs of the unstimulated wells are considered as positive.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

TABLES A-J

TABLE A

| Circulating cells | |
|---|---|
| Embryonic stem cells (ESC) | Induced pluripotent stem cells (iPSC) |
| Cord blood stem cell (CD-SC) | Mesenchymal stem cell |
| CD34+ cells | Polychromatic normoblasts |
| Hematopoietic stem cells (HSC) | Orthochromatic normoblasts |
| Spleen colony forming unit (CFU-S) | Proerythroblast |
| Common myeloid progenitor (CMP) cells capable of forming a granulocyte, erythrocyte, monocyte, or megakaryocyte (CFU-GEMM) | Polychromatophilic erythrocyte |
| Blastocyte colony-forming cells | Normoblast |
| Burst-forming unit erythroid (BFU-E) | Platelets |
| Megakaryocyte-erythroid progenitor (MEP) cell | Leukocytes |
| Colony-forming unit erythroid (CFU-E) | Lymphoid cells |
| Reticulocytes | T cells |
| Erythrocytes | B cells |

TABLE A1

| Erythroid cells | |
|---|---|
| Embryonic stem cells (ESC) | Induced pluripotent stem cells (iPSC) |
| Cord blood stem cell (CD-SC) | Polychromatic normoblasts |
| CD34+ cells | Orthochromatic normoblasts |
| Hematopoietic stem cells (HSC) | Proerythroblast |
| Spleen colony forming unit (CFU-S) | Polychromatophilic erythrocyte |
| Common myeloid progenitor (CMP) cells capable of forming a granulocyte, erythrocyte, monocyte, or megakaryocyte (CFU-GEMM) | Normoblast |
| Blastocyte colony-forming cells | |
| Burst-forming unit erythroid (BFU-E) | |
| Megakaryocyte-erythroid progenitor (MEP) cell | |
| Erythroid forming colony unit (CFU-E) | |
| Reticulocytes | |
| Erythrocytes | |

TABLE B

| Circulating cell associated proteins | | | | | |
|---|---|---|---|---|---|
| CD1 | CD23 | CD46 | CD72 | CD120 | CD195 |
| CD2 | CD24 | CD47 | CD73 | CD122 | CD197 |
| CD3 | CD25 | CD48 | CD74 | CD127 | CD199 |
| CD4 | CD26 | CD49a | CD80 | CD132 | CD209 |
| CD5 | CD27 | CD49b | CD81 | CD133 | CD202a |
| CD6 | CD28 | CD49c | CD82 | CD134 | CD220 |
| CD7 | CD29 | CD49d | CD83 | CD135 | CD221 |
| CD8 | CD30 | CD49e | CD86 | CD138 | CD235a |
| CD9 | CD31 | CD49f | CD87 | CD141 | CD271 |
| CD10 | CD32 | CD53 | CD88 | CD142 | CD279 |
| CD11a | CD33 | CD54 | CD89 | CD143 | CD303 |
| CD11b | CD34 | CD55 | CD90 | CD144 | CD304 |
| CD11c | CD35 | CD56 | CD91 | CD147 | CD309 |
| CD12w | CD36 | CD57 | CD95 | CD151 | CD326 |
| CD13 | CD37 | CD58 | CD96 | CD152 | TLR 1 |
| CD14 | CD38 | CD59 | CD100 | CD154 | TLR 2 |
| CD15 | CD39 | CD61 | CD103 | CD156 | TLR 4 |
| CD16 | CD40 | CD62E | CD105 | CD158 | TLR 5 |
| CD17 | CD41 | CD62L | CD106 | CD163 | TLR 6 |
| CD18 | CD42 | CD62P | CD107 | CD165 | |
| CD19 | CD43 | CD63 | CD107a | CD166 | |
| CD20 | CD44 | CD68 | CD107b | CD168 | |
| CD21 | CD45 | CD69 | CD109 | CD184 | |
| CD22 | | CD71 | CD117 | CD186 | |

TABLE C

| Erythrocyte associated proteins | | | |
|---|---|---|---|
| 2',3'-cyclic-nucleotide 3'-phosphodiesterase | Creatine kinase | Hypothetical protein XP_100510 | RAP1A or RAP1B |
| Acetylcholinesterase | DC 38 | Hypothetical protein XP_100619 | RAP2B |
| Actin alpha and beta chain | Duodenal cytochrome b | Hypothetical protein XP_100665 | Rh blood D group antigen polypeptide |
| Adenosine deaminase | Enhancer protein | Hypothetical protein XP_100925 | Rhesus D category VI type III protein |
| Adducin alpha subunit | Erythroblast membrane-associated protein | Hypothetical protein XP_103707 | Similar to adhesive plaque matrix protein precursor |
| Aldolase A | Far upstream element binding protein | Hypothetical protein XP_106269 | Similar to ankyrin 1 |
| Ankyrin 1 isoform 2 | Flotillin 1 | Ig heavy chain V-V region | Similar to flotillin 2 |
| Ankyrin 1 isoform 4 | Flotillin 2 47 | Kell | Similar to glycophorin A |
| Ankyrin 1 splice form 2 | Glucose transporter glycoprotein | KIAA0340 | Similar to Lutheran blood group |
| Aquaporin 1 | Glutathione transferase | KIAA1741 protein | Similar to RAS-related protein RAB-15 |

TABLE C-continued

| Erythrocyte associated proteins | | | |
|---|---|---|---|
| Arginase type 1 | Glyceraldehyde-3-phosphate dehydrogenase | Lyn B protein | Similar to RAS-related protein RAL-A |
| Arginase type 1 erythroid variant | Glycophorin A | Membrane protein p55 | Similar to tropomyosin |
| ATP-binding cassette half-transporter | Glycophorin A precursor | Phosphatidylinositol-4-phosphate 5 kinase type III | Similar to tropomyosin 4 18 |
| ATP-binding cassette subfamily C member 6 | Glycophorin C isoform 1 | Phosphoribosyl pyrophosphate synthetase | Solute carrier family 2 (facilitated glucose transporter) member 1 |
| bA421H8.2 (novel protein) | Hemoglobin alpha | Poly (A)-specific ribonuclease | Solute carrier family 29 (nucleoside transporter) member 1 |
| B-CAM protein | Hemoglobin beta | Presenilin-associated protein | Spectrin alpha chain |
| Block of proliferation 1 | Hemoglobin delta | Protein band 3 | Spectrin beta chain |
| C-1-tetrahydrofolate synthase | Hemoglobin epsilon | Protein band 4.1 | Translation initiation factor 2C |
| Calcium transporting ATPase 4 | Hemoglobin gamma | Protein band 4.1 (elliptocytosis 1, RH-linked) | Tropomodulin |
| CD55 | HGTD-P | Protein band 4.2 | Tropomyosin 3 |
| CD58 | Hypothetical protein XP_061743 or XP_089854 | Protein band 4.9 (dematin) | Tropomyosin isoform |
| CD59 antigen | Hypothetical protein XP_091430 | Protein band 7.2b, stomatin | Tropomyosinalpha chain (smooth muscle) 26 |
| Cell surface glycoprotein CD44 | Hypothetical protein XP_091724 | RAB 35 | Unknown protein |
| Channel-like integral membrane protein | Hypothetical protein XP_092517 | Rabphilin-3 A-integrating protein | Vesicle-associated membrane protein 2 (synaptobrevin 2) |
| Complement receptor 1 | Hypothetical protein XP_095819 | Ral A binding protein | Zona pellucida binding protein |
| Adipocyte plasma membrane-associated protein | Stomatin | Myosin-9 | Histone H1.1 |
| Ammonium transporter Rh type A | Stomatin-like protein 2 | Protein 4.1 | Histone H2A type 1-B/E |
| Aquaporin 1 | Thioredoxin-related transmembrane protein 4 | Spectrin alpha chain, erythrocyte | Histone H3.1 |
| Aquaporin 7 | TMCC2 | Spectrin beta chain, erythrocyte | Histone H4 |
| ATP-binding cassette sub-family B member 6, mitochondrial | Transferrin receptor protein 1 | Talin-1 | Lamin A/C |
| Band 3 anion transport protein | Transmembrane and coiled-coil domain family 2 | Talin-2 | Lamina-associated polypeptide 2, isoform alpha |
| Basigin | Urea transporter 1 | Tropomodulin-1 | Lamina-associated polypeptide 2, isoforms beta/gamma |
| CD44 | Zinc transporter 1 | Tropomyosin 1 (Alpha) isoform 4 | Lamin-B receptor |
| CD47 | 55 kDa erythrocyte membrane protein | Tropomyosin 3 | Lamin-B1 |
| Equilibrative nucleoside transporter 1 | Actin, alpha cardiac muscle | Tropomyosin alpha-3 chain | Lamin-B2 |
| Erythroid membrane-associated protein | Actin, cytoplasmic | Tubulin alpha-1 chain | Matrin-3 |
| Flotillin-1 | Actin-related protein 2 | Tubulin beta chain | Multiple inositol polyphosphate phosphatase 1 |
| Flotillin-2 | Actin-related protein 2/3 complex subunit 1B | Tubulin, alpha 1 (Testis specific) | N-acylneuraminate cytidylyltransferase |
| Glucose transporter, type 1 | Actin-related protein 2/3 complex subunit 2 | Tubulin, alpha 8 | Neutral alpha-glucosidase AB |
| Glycophorin-A | Actin-related protein 3 | Tubulin, beta 6 | Nuclear pore complex protein Nup93 |

TABLE C-continued

Erythrocyte associated proteins

| | | | |
|---|---|---|---|
| Glycophorin-B | Alpha-actinin-4 | Vinculin | Nuclear pore membrane glycoprotein 210 |
| Glycophorin-C | Alpha-adducin | 78 kDa glucose-regulated protein | Nucleolin |
| Immunoglobulin-like domain-containing receptor 1 | Ankyrin-1 | Antigen KI-67 | Nucleoporin NUP188 homolog |
| Integrin alpha-X | Ankyrin-3 | ATP-dependent RNA helicase DDX39A | Nucleoprotein TPR |
| Integrin beta-1 | Beta-actin-like protein 2 | Calnexin | Prelamin-A/C |
| Kell blood group glycoprotein | Beta-adducin | Calreticulin | Protein disulfide-isomerase |
| Large neutral amino acids transporter small subunit 3 | Capping protein (Actin filament) muscle Z-line, beta | DNA topoisomerase 1 | Protein disulfide-isomerase A4 |
| Membrane transport protein XK | Cortactin | DNA-dependent protein kinase catalytic subunit | Protein disulfide-isomerase A6 |
| Membrane-associated progesterone receptor component 2 | Dematin | Dolichyl-diphosphooligosaccharide-protein glycosyltransferase 48 kDa subunit | Protein ERGIC-53 |
| Monocarboxylate transporter 1 | Dynactin 2 (P50), isoform CRA_b | Dolichyl-diphosphooligosaccharide-protein glycosyltransferase subunit 1 | Ribophorin II |
| Multidrug resistance-associated protein 4 | Erythrocyte membrane protein band 4.2 | Endoplasmic reticulum resident protein 29 | Transitional endoplasmic reticulum ATPase |
| Neutral cholesterol ester hydrolase 1 | Filamin-A | Endoplasmic reticulum resident protein 44 | UDP-glucose:glycoprotein glucosyltransferase 1 |
| Plasma membrane calcium-transporting ATPase 1 | Gamma-adducin | Endoplasmin | CD59 |
| Plasma membrane calcium-transporting ATPase 3 | Gelsolin | ER-Golgi SNARE of 24 kDa | |
| Plasma membrane calcium-transporting ATPase 4 | Kinesin-1 heavy chain | FACT complex subunit SPT16 | |
| Probable E3 ubiquitin-protein ligase C12orf51 | Microtubule-associated protein RP/EB family member 1 | Glucosidase 2 subunit beta | |
| Rh blood group, CcEe antigens | Myosin light chain 4 | Heme oxygenase 1 | |
| SLC43A3 | Myosin light polypeptide 6 | Hemogen | |
| Sodium/calcium exchanger SCL8A3 | Myosin, heavy chain 11, smooth muscle | Heterochromatin protein 1-binding protein 3 | |
| Sodium/potassium-transporting ATPase subunit alpha-1 | Myosin-10 | High mobility group protein B1 | |
| Sodium/potassium-transporting ATPase subunit beta-3 | Myosin-14 | High mobility group protein B2 | |

TABLE C1

Erythrocyte transmembrane proteins

Aquaporin 1
Cell surface glycoprotein CD44
Channel-like integral membrane protein
Complement receptor 1
Erythroblast membrane-associated protein
Glucose transporter glycoprotein
Glycophorin A
Glycophorin A precursor
Glycophorin C isoform 1
Kell
Membrane protein p55
Protein band 3
Rh blood D group antigen polypeptide
Rhesus D category VI type III protein
Similar to glycophorin A
Similar to Lutheran blood group
Solute carrier family 2 (facilitated glucose transporter) member 1
Solute carrier family 29 (nucleoside transporter) member 1

TABLE C2

Erythrocyte GPI-linked proteins

Acetylcholinesterase
CD55
CD58
CD59 antigen

TABLE C3

Erythrocyte intracellular proteins

2',3'-cyclic-nucleotide 3'-phosphodiesterase
Actin alpha and beta chains
Adenosine deaminase
Adducin alpha subunit
Aldolase A
Ankyrin 1 isoform 2
Ankyrin 1 isoform 4
Ankyrin 1 splice form 2
Arginase type 1
Arginase type 1 erythroid variant
ATP-binding cassette half-transporter
ATP-binding cassette subfamily C member 6
bA421H8.2 (novel protein)
B-CAM protein
Block of proliferation 1
C-1-tetrahydrofolate synthase
Calcium transporting ATPase 4
Creatine kinase
DC 38
Duodenal cytochrome b
Enhancer protein
Far upstream element binding protein
Flotillin 1
Flotillin 2 47
Glutathione transferase
Glyceraldehyde-3-phosphate dehydrogenase
Hemoglobin alpha
Hemoglobin beta
Hemoglobin delta
Hemoglobin epsilon
Hemoglobin gamma
HGTD-P
Hypothetical protein XP_061743 or XP_089854
Hypothetical protein XP_091430
Hypothetical protein XP_091724
Hypothetical protein XP_092517
Hypothetical protein XP_095819
Hypothetical protein XP_100510
Hypothetical protein XP_100619
Hypothetical protein XP_100665
Hypothetical protein XP_100925
Hypothetical protein XP_103707
Hypothetical protein XP_106269
Ig heavy chain V-V region
KIAA0340
KIAA1741 protein
Lyn B protein
Phosphatidylinositol-4-phosphate 5 kinase type III
Phosphoribosyl pyrophosphate synthetase
Poly (A)-specific ribonuclease
Presenilin-associated protein
Protein band 4.1
Protein band 4.1 (elliptocytosis 1, RH-linked)
Protein band 4.2
Protein band 4.9 (dematin)
Protein band 7.2b, stomatin
RAB 35
Rabphilin-3 A-integrating protein
Ral A binding protein
RAP1A or RAP1B
RAP2B
Similar to adhesive plaque matrix protein precursor
Similar to ankyrin 1
Similar to flotillin 2
Similar to RAS-related protein RAB-15
Similar to RAS-related protein RAL-A

TABLE C3-continued

Erythrocyte intracellular proteins

Similar to tropomyosin
Similar to tropomyosin 4
Spectrin alpha chain
Spectrin beta chain
Translation initiation factor 2C
Tropomodulin
Tropomyosin 3
Tropomyosin isoform
Tropomyosinalpha chain (smooth muscle) 26
Unknown protein
Vesicle-associated membrane protein 2 (synaptobrevin 2)
Zona pellucida binding protein

TABLE D

Conjugation methods

Zero-length x-linker

EDC
EDC plus sulfo NHS
CMC
DCC
DIC
Woodward's reagent K
N,N'-carbonyldiimidazole
Schiff base + reductive amination

Homobifunctional NHS esters

DSP
DTSSP
DSS
BS^3
DST
Sulfo-DST
BSOCOES
Sulfo-BSOCOES
EGS
Sulfo-EGS
DSG
DSC

Homobifunctional Imidoesters

DMA
DMP
DMS
DTBP

Sulfhydryl reactive x-linkers

DPDPB
BMH
Difluorobenzene derivatives

DFDNB
DFDNPS

Photoreactive x-linker

BASED

Homobifunctional aldehydes

Formaldehyde
Glutaraldehyde
bis-epoxide 1,4-butanediol diglycidyl ether

Homobifunctional hydrazides adipic acid dihydrazide
carbohydrazide
Bis-diazonium derivative o-tolidine diazotized
Bis-diazotized benzidine

TABLE D-continued

Conjugation methods

Amine-sulfhydryl x-linker

SPDP, LC-SPDP, sulfo-LC-SPDP
SMPT and sulfo-LC-SMPT
SMCC and sulfo-SMCC
MBS and sulfo-MBS
SIAB and sulfo-SIAB
SMPB and sulfo-SMPB
GMBS and sulfo-GMBS
SIAX and SIAXX
SIAC and SIACX
NPIA
Carbonyl-sulfydryl x-linker MPBH
M2C2H
PDPH
amine-photoreactive x-linker NHS-ASA, Sulfo-NHS-ASA
Sulfo-NHS-LC-ASA
SASD
HSAB and sulfo-HSAB
SANPAH and sulfo-SANPAH
ANB-NOS
SAND
SADP and sulfo-SADP
Sulfo-SAPB
SAED
Sulfo-SAMCA
p-Nitrophenyl diazopyruvate
PNP-DTP
sulfhydryl-photoreactive x-linker ASIB
APDP
Benzophenone-4-iodoacetamide
Benzophenone-4-maleimide
Carbonyl-photoreactive x-linker ABH
Carboxylate-photoreactive x-linker ASBA
arginine-photoreactive x-linker APG
Bioorthogonal reactions Diels-alder reagent pairs
Hydrazine-aldehyde reagent pairs
Boronic acid salicylhydroxamate
Click chemistry
Staudinger ligation

TABLE D1

Enzymatic conjugation methods
Enzymatic reactions

SpyCatcher/SpyTag
Spy0128 derivatives
Transpeptidases
Isopeptidases
Sortase
DD-transpeptidase
Peptidyl transferase
G-glutamyl transpeptidase
D-glutamyl transpeptidase
Farnesyltransferase
Prenyltranferase
Dimethylallyltrans-transferase
Geranylgeranyl pyrophosphate synthase
Dehydrodolichol diphosphate synthase

TABLE E

Chemistry of reactive groups

Amine reactions

Isothyocyantes
Isocyanates
Acyl azides
NHS esters
Sulfonyl chlorides
Aldehydes and glyoxals
Epoxides and oxiranes
Carbonates
Arylating agents
Imidoesters
Carbodiimides
Anhydrides
Fuorphenyl esters
Hydroxymethyl phosphine derivatives
Guanidination of amines Thiol reactions Haloacetyl and alkl halide derivatives
Maleimides
Aziridines
Acryloyl derivatives
Arylating agents
Thil-disulfide exchange reagents
Vinylsulfone derivatives
Metal-thiol dative bonds Carboxylate rections Diazoalkanes and diazoacetyl compounds
Carbonyldiimidazole
Carbodiimides Hydroxyl reactions Epoxides and oxiranes
Carbonyldiimidazole
N,N'0disuccinimidyl carbonate
N-hydroxysuccinimidyl chloroformate
Oxidation with periodate
Enzymatic oxidation
Alkyl halogens
Isocyanates Aldehyde and Ketone reactions Hydrazine derivatives
Schiff base formation
Reductive amination
Mannich condensation
Active hydrogen reactions Diazonium derivatives
Mannich condensation
Iodination reactions
Cycloaddition reactions Diels-Alder reaction
Complex formation with boronic acid derivatives
Click chemistry: Cu-promoted Azide-
Alkyne [3 + 2] cycloaddition

TABLE F

Autoimmune diseases and antigens

| Disease | Known antigen |
| --- | --- |
| Acute rheumatic fever | cross reactive antibodies to cardiac muscle |
| alopecia areata | Trychohyalin, keratin 16 |
| ANCA-associated vasculitis | Neutrophil cytoplasmic antigen, proteinase 3, myeloperodixase, bacterial permiability increasing factor |
| autoimmune gastritis | H, K adenosine triphosphatase |
| autoimmune hemolytic anemia | Rh blood group antigens, I antigen |
| autoimmune hepatitis | nuclear protein, liver-kidney microsome type 1, liver cytosol type 1 |
| autoimmune myocarditis | cardiac myosin |
| Autoimmune thyroiditis | Thyroid peroxidase, thyroglobulin, thyroid-stimulating hormone receptor |
| Autoimmune uveitis | Retinal arrestin (S-antigen) |
| dermatomyositis | Mi2 ATPase |
| diabetes (type 1) | Pancreatic beta cell antigen |
| goodpasture's syndrome | Noncollagenous domain of basement membrane collagen type IV |
| Graves' disease | Thyroid stimulating hormone receptor |
| Guillain-Barré syndrome | Neurofascin-186, gliomedin, nodal adhesion molecueles |
| Hypoglycemia | Insulin receptor |
| idiopathic thrombocytopenic purpura | Platelet integrin GpIIb, GpIIIa |
| Insulin resistant diabetes | Insulin receptor |
| Membranous nephritis | Phospholipase A2 |
| mixed essential cryoglobulinemia | rheumatoid factor IgG complexes |
| multiple sclerosis | Myelin basic protein, proteolipid protein, myelin oligodendrocyte glycoprotein |
| myasthenia gravis | Acetylcholine receptor |
| Myasthenia gravis - MUSC | Muscarinic receptor |
| pemphigus/pemphigoid | Epidermal cadherin |
| pernicious anemia | intrinsic factor (Gastric) |
| polymyositis | nuclear and nucleolar antigen |
| primary biliary cirrhosis | neutrophil nuclear antigen, mitochondrial multienzyme complex |
| psoriasis | PSO p27 |
| rheumatoid arthritis | rheumatoid factor IgG complexes, synovial joint antigen, citrullinated protein, carbamylated protein |
| scleroderma/systemic sclerosis | Scl-86, nucleolar scleroderma antigen |
| Sjögren's syndrome | SS-B, Lupus La protein |
| systemic lupus erythematosus | DNA, histones, ribosomes, snRNP, scRNP |
| vitiligo | VIT-90, VIT-75, VIT-40 |
| Wegener's granulomatosis | neutrophil nuclear antigen |
| Antiphospholipid syndrome (APS) & catastrophic APS | Beta-2 glycoprotein 1 |
| Chemotherapy induced peripheral neuropathy | Neuronal antigens |
| Thrombotic thrombocytopenic purpura | ADAMTS13 |
| Atypical hemolytic uremic syndrome | Complement factor H |

TABLE G

Inflammatory diseases and antigens

| Disease | Antigen |
| --- | --- |
| Crohn's disease | Flagellin, microbial antigens |
| Ulcerative colitis | Neutrophil cytoplasmic antigen, microbial antigens |
| Celiac disease | Gluten |
| Inflammatory bowel disease | Microbial antigens |

TABLE H

Allergic disease triggers

| Allergy | Antigen |
| --- | --- |
| Animal dander | fel d 1, can f6 |
| Black walnut | 2S albumin, vicilin-like (7S) protein |

TABLE H-continued

Allergic disease triggers

| Allergy | Antigen |
| --- | --- |
| Brazil nut | 2S albumin, legumin-like (11S) seed storage protein |
| Cashew nut | 7S vicilin-like protein, legumin-like 11S seed storage protein |
| Chestnut | Chitinase 1b, lipid transfer protein Cas s8 |
| Dust mites | Der p2 |
| Egg | Ovomucoid, ovalbumin, ovotransferrin, lysozyme, alpha-livetin |
| English walnut | 2S albumin, 7S vicilin-like protein, lipid transfer protein, legumin-like 11S seed storage protein |
| Fish | Parvalbumins |
| Hazelnut | Bet v1 homologue, profilin, lipid transfer protein, 11s globulin-like protein, 7S vicilin-like protein |
| Insect venom | Melittin, phospholipase A2, hyaluronidase, acid phosphatase, protease, antigen 5, Api m1-4, Bom p1, p4, Dol m1, 2, 5; Vesp c1, c5; Pol a1, a2, a5; Ves v1, v2, v5; Sol I 1-4 |
| Latex | Hev b 1, 2, 3, 5, 6.01, 6.02, 8, 9, 11 |
| Milk | Alpha s1 casein, beta-lactoglobulin |
| Mold | enzymes, toxins, cell wall components |
| Peanut | Ara h1, Ara h2, Ara h3, Ara h6 |
| Pollen | Aconitate hydratase, fructose bisphosphate aldolase, ATP synthase, luminal binding protein, calmodulin, calreticulin, chaperonin, enolase, lipid transfer protein 1, lipid transfer protein 2, profilins |
| Pollen, grass | Phl p 1, 2, 4, 5, 6, 11, 12, 13 |
| Shellfish | arginine kinase, tropomyosin, myosin light chain, sarcoplasmic calcium binding protein, triose phosphate isomerase, aldolase, titin |
| Soy | Gly m1 soybean hydrophobic protein, gly m4, gly m5, gly m6, Gly m 2s albumin, lipid transfer proteins, alpha-globulin, |
| Tree nuts | Lipid transfer proteins, profilins, Bet v1-related family, legumins, vicilins, 2S albumins |
| Wheat | gluten, prolamins, 2S albumins, lipid transer proteins, a-amylase/protease inhibitors, puroindoline, alpha-globulin, alpha-gliadin, beta-gliadin, gamma-gliadin, fast-omega-gliadin, slow-omega-gliadin |

TABLE I

Therapeutic proteins to treat diseases

| Brand Name | Company | Indication |
| --- | --- | --- |
| Amevive | Astellas Pharma | Moderate to severe chronic plaque psoriasis |
| BayGam | Bayer | Hepatitis A, measles, varicella, rubella, immunoglobulin deficiency |
| CinnoVex | CinnaGen | Multiple Sclerosis |
| Synagis | Medlummne | Respiratory syncytial virus (RSV) infections |
| Lucentis | Roche Genentech | Wet age-related macular degeneration (AMD) |
| Actemra | Hoffman-La Roche | Rheumatoid Arthritis |
| Avastin | Roche Genentech | Various cancers |
| Benefix | Pfizer | Heamophelia B/Christmas disease (coagulation factor IX defficiency) |
| Benlysta | HGS, GlaxoSmithKline | Systemic lupus erythematosus (SLE) |
| Bexxar | GlaxoSmithKline, Corixa | CD20+. follicular, NHL |
| Campath | Genzyme | B-cell chronic lymphocytic leukemia (B-CLL |
| Ceredase | Genzyme | Type I Gaucher disease |
| Cerezyme | Genzyme | Type 1 Gaucher's disease |
| Erbitux | Lilly | Metastatic colorectal cancer |
| Helixate FS | CSL Behring | Haemophilia A |
| Herceptin | Roche Genentech | Breast cancer |
| Kogenate FS | Bayer Healthcare | Haemophilia A |
| Lumizyme | Genzyme | Pompe disease (glycogen storage disease type II) |
| NovoSeven | Novo Nordisk | Hemophilia A or B patients with inhibitors to Factor VIII or Factor IX and in patients with acquired hemophilia |
| Privigen | CSL Behring | IVIG therapy |
| Recombinate | Baxter, Wyeth | Haemophilia A |
| Refacto | Pfizer | Haemophilia A |
| Remicade | Jannssen Biotech (J&J) | Rheumatoid Arthritis, Crohn's Disease, Ankylosing Spondylitis, Plaque Psoriasis, Ulcerative Colitis |

TABLE I-continued

Therapeutic proteins to treat diseases

| Brand Name | Company | Indication |
|---|---|---|
| ReoPro | Lilly | PTCA (Angioplasty) adjunct |
| Rituxan/MabThera | Roche Genentech/Biogen Idec | Blood cancers and rheumatoid arthritis |
| Simulect | Novartis | Organ rejection prophylaxis |
| Soliris | Alexion Pharmaceuticals | Paroxysmal nocturnal hemoglobinuria (PNH), atypical hemolytic uremic syndrome (aHUS) |
| Tysabri | Biogen Idec, Elan Pharma. | Multiple Sclerosis, Crohn's Disease |
| Vectibix | Amgen | Treatment of epidermal growth factor receptor (EGFR)-expressing, metastatic colorectal carcinoma (mCRC) |
| Xyntha | Wyeth | Haemophilia A (factor VIII defficiency) |
| Zenapax | Roche/PDL | Prophylaxis of acute organ rejection in patients receiving renal transplants |
| Arcalyst | Regeneron Pharmaceuticals | Cryopyrin-Associated Periodic Syndromes (CAPS), including FCAS and MWS |
| Betaseron | Bayer Healthcare | Multiple Sclerosis, myocardial disease |
| Cetrotide | Merck Serono | Infertility |
| Cimzia | UCB | Rheumatoid Arthritis, Crohn's Disease |
| Copaxone | Teva Pharmaceuticals | Multiple Sclerosis, Crohn's disease, glaucoma, motor neurone disease, Huntingtons chorea, neurodegenerative disease |
| Enbrel | Amgen, Wyeth | Rheumatoid Arthritis, psoriasis |
| Epogen | Amgen | Anemia |
| Humira | Abbott | Rheumatoid Arthritis, Crohn's Disease |
| Kineret | Amgen, Biovitrum | Active Rheumatoid Arthritis |
| Lantus | Sanofi-Aventis | Diabetes |
| Pegasys | Roche Genentech | Chronic hepatitis C, chronic hepatitis B |
| Prolia | Amgen, GSK | Osteoporosis, therapy-induced bone loss (breast or ovarian cancer), bone metastatase, giant cell tumor of bone, multiple myeloma |
| — | — | — |
| Rebif | Merck Serono, Pfizer | Multiple Sclerosis (relapsing) |
| Simponi | Johnson & Johnson | Rheumatoid Arthritis, Crohn's Disease, Ulcerative Cilitis, Ankylosing Spondylitis, Psoriatic Arthritis |
| Stelara | Centocor, Janssen-Cilag | Moderate to severe plaque psoriasis who are candidates for phototherapy or systemic therapy. |
| Vivaglobin | CSL Behring | Primary Immune Deficiency (PID) |
| Xgeva | Amgen | Bone Metastasis from Solid Tumors |
| Xolair | Roche Genentech, Novartis | Moderate to severe persistent allergic asthma |
| Avonex | Biogen Idec | Multiple Sclerosis (relapsing) |
| Aranesp | Amgen | Anemia |
| Orencia | Bristol-Myers-Squibb | Rheumatoid arthritis, juvenile ideopathic arthritis |
| Procrit | Jannssen Biotech (J&J) | Anemia |
| Erwinaze | Jazz | Acute lymphoblastic luekemia |

TABLE J

Therapeutic protein classes to treat diseases

AAV capsid protein
alglucosidase alpha
Anti C5
Anti gp Iib/IIIa
Anti IGE
Anti IL-12, Anti IL-23
Anti RANK ligand
Anti-alpha 4 integrin
Anti-APRIL
Anti-BAFF
Anti-CD20
Anti-CD52
Anti-EGFR
Anti-Her2
Anti-IL2 receptor
Anti-IL6 receptor
Anti-PD1

TABLE J-continued

Therapeutic protein classes to treat diseases

Anti-RSV protein F
Anti-TNFa
Anti-VEGF
Asparaginase
CTLA4
Erythropoietin
Factor IX
Factor VII
Factor VIII
Glatiramer acetate
glucocerebrosidase
GnRH antagonist
IgG
IL1R antagonist
IL1R or IL1 antagonist
Insulin
Interferon alpha

TABLE J-continued

Therapeutic protein classes to treat diseases interferon beta
Lentivirus capsid protein
LFA3-Fc
Retrovirus capsid protein
TACI-Ig
TNF-receptor

TABLES 1-8

TABLE 1

| Erythroid Polypeptides and Non-Exogenous antigen Polypeptides | | | |
|---|---|---|---|
| ABO blood groups | Stomatin | Peters | DAF Cromer |
| Aquaporin 3 | Tropomyosin | Rasmussen | Gerbich (GYPC) |
| Aubergers | Glucose transporter | Reid | CD47 |
| Band 3 | Adducin | REIT | Glycophorin A, B, C |
| Basigin | Rabphilin | SARA | Band 3 (AE3) |
| C41 | C1 tetrahydrofolate synthase | Rhesus blood D group | GYPB Ss |
| CD44 | Vel group | Aldolase | C4A, C4B Chido, Rodgers C4 component of complement |
| Cis AB | Lan antigen | Tropomodulin | HLA Bg HLA class I |
| Diego (Di) | At antigen | Arginase | RHAG Rh-associated Ammonium transport glycoprotein |
| Colton antigen | Jr antigen | Creatine kinase | |
| Complement Component 4 | AnWj antigen | B-Cam protein | Colton (Co) Water channel protein |
| alpha(1,3) fucosyltransferase | Sd antigen | Rap1A | ACHE Cartwright (Yt) Acetylcholinesterase |
| CR1 | Batty | Bennett-Goodspeed | Glutathione transferase |
| DAF | Bilkes | P antigen system | Glycophorin C |
| Diego | Wright (Wr) | Rh blood group | Aquaporin |
| Duffy | Box | Xg antigen system | Erythroblast associated membrane protein |
| Hh/Bombay antigen | Christiansen | XK protein | CD44 |
| ii antigen | alpha(1,2) fucosyltransferase | Yt/Cartwright antigen system | Synaptobrevin 2 |
| Indian blood group | HJK | CD58 | Ribonuclease |
| Kell | HOFM | Rh | ABO glycosyl transferases |
| Kidd | JFV | AnWj Adhesion receptor | CD59 |
| Lewis antigen | JONEs | Scianna | CD44 |
| Lutheran antigen | Jensen | Radin | MER2 |
| MNS antigen system | Katagiri | Duodenal cytochrome B | DOK Dombrock ADP-ribosyltransferase |
| Cost group | Livesay | DARC (Duffy) | SEMA7A JMH Putative adhesion receptor |
| Er group | Milne | CR1 Knops-McCoy | UMOD Sda Tamm-Horsfall protein (uromodulin) |
| Dematin | Oldeide | FP Family | Anion exchanger channel protein (band 3, AE1) |
| Indian (In) | Annexin Family | Tweety Family | CTL Family |
| Kidd (Jk) Urea transporter | Bcl-2 Family | UT Family | DAACS Family |
| FUT3 Lewis (Le) | Bestrophin Family | VIC Family | DASS family |
| Adenosine deaminase | BNip3 Family | AAAP Family | DMT family |
| OK Oka Neurothelin, putative adhesion molecule | CD20 Family | transferrin receptor | ENT Family |
| LW Adhesion receptor | CLIC Family | c-KIT | GPH Family |
| FUT2 Secretor (Se) | Connexin Family | Insulin receptors 1 & 2 | GUP Family |
| FUT1 Hh alpha | CRAC-C Family | Estrogen receptor | LCT Family |
| LU Lutheran (Lu) Adhesion receptor | Ctr Family | Dexamethasone receptor | MC family |
| P1 Glycosyltransferase | E-CIC Family | JAK2 kinase | MET Family |
| XK Kx Putative neurotransmitter transporter | ENaC Family | ABC family | MFS Family |
| XG Xg formerly called PBDX | GIC Family | ArsAB family | MOP Family |
| MIC2 | ICC Family | F-ATPase Family | MTC Family |
| Hemoglobin | Innexin Family | IISP Family | NCS2 Family |
| Ankyrin | IRK-C Family | MPT Family | Nramp Family |
| Spectrin | LIC Family | P-ATPase Family | NSS Family |
| KEL Kell (K, k, Kp, Js) Metalloproteinase | MIP Family | AE family | OAT Family |

TABLE 1-continued

Erythroid Polypeptides and Non-Exogenous antigen Polypeptides

| | | | |
|---|---|---|---|
| Torkildsen | MIT family | APC Family | OST Family |
| Rab 35 | NSCC2 Family | ArsB Family | Oxa1 Family |
| Ral A binding protein | PCC Family | BASS Family | PiT Family |
| Zona pellucida binding protein | Plamolipin Family | CaCA Family | PNaS Family |
| Lyn B protein | PLB Family | CCC Family | POT Family |
| KIaa1741 protein | PLM Family | CDF Family | RFC Family |
| DC38 | Presenilin Family | CIC Family | RND Family* |
| Calciums transporting ATPase | RIR-CaC Family | CNT Family | SSS Family |
| ACC Family | TRIC Family | CPA1 Family | STRA6 Family |
| Amt Family | TRP-CC Family | CPA2 Family | SulP Family |
| ZIP Family | HCC Family | NIPA Family | N-MDE Family |
| ATP-E Family | LPI Family | PPI Family | Epo receptor |
| dsRNA-T Family | MagT1 Family | PPI2 Family | MgtE Family |

TABLE 2

Erythroid Promoters

| Promoter | Gene |
|---|---|
| beta globin promoter | beta globin |
| 3' beta-globin enhancer | beta globin |
| beta globin locus control region | beta globin |
| GATA-1 promoter | GATA-1 |
| GYPA promoter | Glycophorin A |
| HK1 promoter | Hexokinase |

TABLE 3

Sequences of Complement Receptor 1

4A. CR1 isoform S precursor, *Homo sapiens* NCBI Reference Sequence No. NP_000642.3

```
   1 mgassprspe pvgppapglp fccggsllav vvllalpvaw gqcnapewlp farptnltde
  61 fefpigtyln yecrpgysgr pfsiiclkns vwtgakdrcr rkscrnppdp vngmvhvikg
 121 iqfgsqikys ctkgyrligs ssatciisgd tviwdnetpi cdripcglpp titngdfist
 181 nrenfhygsv vtyrcnpgsg grkvfelvge psiyctsndd qvgiwsgpap qciipnkctp
 241 pnvengilvs dnrslfslne vvefrcqpgf vmkgprrvkc qalnkwepel pscsrvcqpp
 301 pdvlhaertq rdkdnfspgq evfyscepgy dlrgaasmrc tpqgdwspaa ptcevkscdd
 361 fmgqllngrv lfpvnlqlga kvdfvcdegf qlkgssasyc vlagmeslwn ssvpvceqif
 421 cpsppvipng rhtgkplevf pfgktvnytc dphpdrgtsf dligestirc tsdpqgngvw
 481 sspaprcgil ghcqapdhfl faklktqtna sdfpigtslk yecrpeyygr pfsitcldnl
 541 vwsspkdvck rkscktppdp vngmvhvitd iqvgsrinys cttghrligh ssaecilsgn
 601 aahwstkppi cqripcglpp tiangdfist nrenfhygsv vtyrcnpgsg grkvfelvge
 661 psiyctsndd qvgiwsgpap qciipnkctp pnvengilvs dnrslfslne vvefrcqpgf
 721 vmkgprrvkc qalnkwepel pscsrvcqpp pdvlhaertq rdkdnfspgq evfyscepgy
 781 dirgaasmrc tpqgdwspaa ptcevkscdd fmgqllngrv lfpvnlqlga kvdfvcdegf
 841 qlkgssasyc vlagmeslwn ssvpvceqif cpsppvipng rhtgkplevf pfgktvnytc
 901 dphpdrgtsf dligestirc tsdpqgngvw sspaprcgil ghcqapdhfl faklktqtna
 961 sdfpigtslk yecrpeyygr pfsitcldnl vwsspkdvck rkscktppdp vngmvhvitd
1021 iqvgsrinys cttghrligh ssaecilsgn aahwstkppi cqripcglpp tiangdfist
1081 nrenfhygsv vtyrcnpgsg grkvfelvge psiyctsndd qvgiwsgpap qciipnkctp
1141 pnvengilvs dnrslfslne vvefrcqpgf vmkgprrvkc qalnkwepel pscsrvcqpp
```

TABLE 3-continued

Sequences of Complement Receptor 1

```
1201 pdvlhaertq rdkdnfspgq evfyscepgy dirgaasmrc tpqgdwspaa ptcevkscdd 1261 fmgqllngrv lfpvnlqlga kvdfvcdegf qlkgssasyc vlagmeslwn ssvpvceqif 1321 cpsppvipng rhtgkplevf pfgkavnytc dphpdrgtsf dligestirc tsdpqgngvw 1381 sspaprcgil ghcqapdhfl faklktqtna sdfpigtslk yecrpeyygr pfsitcldnl 1441 vwsspkdvck rksckctppdp vngmvhvitd iqvgsrinys cttghrligh ssaecilsgn 1501 tahwstkppi cgripcglpp tiangdfist nrenfhygsv vtyrcnlgsr grkvfelvge 1561 psiyctsndd qvgiwsgpap qciipnkctp pnvengilvs dnrslfslne vvefrcqpgf 1621 vmkgprrvkc qalnkwepel pscsrvcqpp peilhgehtp shqdnfspgq evfyscepgy 1681 dlrgaaslhc tpqgdwspea prcavkscdd flgqlphgrv lfplnlqlga kvsfvcdegf 1741 rlkgssvshc vlvgmrslwn nsvpvcehif cpnppailng rhtgtpsgdi pygkeisytc 1801 dphpdrgmtf nligestirc tsdphgngvw sspaprcels vraghcktpe qfpfasptip 1861 indfefpvgt slnyecrpgy fgkmfsiscl enlvwssved ncrrkscgpp pepfngmvhi 1921 ntdtqfgstv nyscnegfrl igspsttclv sgnnvtwdkk apiceiisce ppptisngdf 1981 ysnnrtsfhn gtvvtyqcht gpdgeqlfel vgersiycts kddqvgvwss ppprcistnk 2041 ctapevenai rvpgnrsfft lteiirfrcq pgfvmvgsht vqcqtngrwg pklphcsrvc 2101 qpppeilhge htlshqdnfs pgqevfysce psydlrgaas lhctpqgdws peaprctvks 2161 cddflgqlph grvllplnlq lgakvsfvcd egfrlkgrsa shcvlagmka lwnssvpvce 2221 qifcpnppai lngrhtgtpf gdipygkeis yacdthpdrg mtfnligess irctsdpqgn 2281 gvwsspaprc elsvpaacph ppkiqnghyi gghvslylpg mtisyicdpg yllvgkgfif 2341 ctdqgiwsql dhyckevncs fplfmngisk elemkkvyhy gdyvtlkced gytlegspws 2401 qcqaddrwdp plakctsrth dalivgtlsg tiffilliif lswiilkhrk gnnahenpke 2461 vaihlhsqgg ssvhprtlqt neensrvlp
(Seq. ID No. 1)
```

4B. CR1 isoform F precursor, *Homo sapiens* NCBI Reference
Sequence No. NP_000564.2

```
  1 mgassprspe pvgppapglp fccggsllav vvllalpvaw gqcnapewlp farptnltde 61 fefpigtyln yecrpgysgr pfsiiclkns vwtgakdrcr rkscrnppdp vngmvhvikg 121 iqfgsqikys ctkgyrligs ssatciisgd tviwdnetpi cdripcglpp titngdfist 181 nrenfhygsv vtyrcnpgsg grkvfelvge psiyctsndd qvgiwsgpap qciipnkctp 241 pnvengilvs dnrslfslne vvefrcqpgf vmkgprrvkc qalnkwepel pscsrvcqpp 301 pdvlhaertq rdkdnfspgq evfyscepgy dlrgaasmrc tpqgdwspaa ptcevkscdd 361 fmgqllngrv lfpvnlqlga kvdfvcdegf qlkgssasyc vlagmeslwn ssvpvceqif 421 cpsppvipng rhtgkplevf pfgktvnytc dphpdrgtsf dligestirc tsdpqgngvw 481 sspaprcgil ghcqapdhfl faklktqtna sdfpigtslk yecrpeyygr pfsitcldnl 541 vwsspkdvck rksckctppdp vngmvhvitd iqvgsrinys cttghrligh ssaecilsgn 601 aahwstkppi cqripcglpp tiangdfist nrenfhygsv vtyrcnpgsg grkvfelvge 661 psiyctsndd qvgiwsgpap qciipnkctp pnvengilvs dnrslfslne vvefrcqpgf 721 vmkgprrvkc qalnkwepel pscsrvcqpp pdvlhaertq rdkdnfspgq evfyscepgy 781 dlrgaasmrc tpqgdwspaa ptcevkscdd fmgqllngrv lfpvnlqlga kvdfvcdegf 841 qlkgssasyc vlagmeslwn ssvpvceqif cpsppvipng rhtgkplevf pfgkavnytc
```

TABLE 3-continued

Sequences of Complement Receptor 1

```
 901 dphpdrgtsf dligestirc tsdpqgngvw sspaprcgil ghcqapdhfl faklktqtna 961 sdfpigtslk yecrpeyygr pfsltcldnl vwsspkdvck rkscktppdp vngmvhvitd 1021 iqvgsrinys cttghrligh ssaecilsgn tahwstkppi cqripcglpp tiangdfist 1081 nrenfhygsv vtyrcnlgsr grkvfelvge psiyctsndd qvgiwsgpap qciipnkctp 1141 pnvengilvs dnrslfslne vvefrcqpgf vmkgprrvkc qalnkwepel pscsrvcqpp 1201 peilhgehtp shqdnfspgq evfyscepgy dlrgaaslhc tpqgdwspea prcavkscdd 1261 flgqlphgrv lfplnlqlga kvsfvcdegf rlkgssvshc vlvgmrslwn nsvpvcehif 1321 cpnppailng rhtgtpsgdi pygkeisytc dphpdrgmtf nligestirc tsdphgngvw 1381 sspaprcels vraghcktpe qfpfasptip indfefpvgt slnyecrpgy fgkmfsiscl 1441 enlvwssved ncrrkscgpp pepfngmvhi ntdtqfgstv nyscnegfrl igspsttclv 1501 sgnnvtwdkk apiceiisce ppptisngdf ysnnrtsfhn gtvvtyqcht qpdgeqlfel 1561 vgersiycts kddqvgvwss pppcrcistnk ctapevenai rvpgnrsfft lteiirfrcq 1621 pgfvmvgsht vqcqtngrwg pklphcsrvc qpppeilhge htlshqdnfs pgqevfysce 1681 psydlrgaas lhctpqgdws peaprctvks cddflgqlph grvllplnlq lgakvsfvcd 1741 egfrlkgrsa shcvlagmka lwnssvpvce qifcpnppai lngrhtgtpf gdipygkeis 1801 yacdthpdrg mtfnligess irctsdpqgn gvwsspaprc elsvpaacph ppkiqnghyi 1861 gghvslylpg mtisyicdpg yllvgkgfif ctdqgiwsql dhyckevncs fplfmngisk 1921 elemkkvyhy gdyvtlkced gytlegspws qcqaddrwdp plakctsrth dalivgtlsg 1981 tiffilliif lswiilkhrk gnnahenpke vaihlhsqgg ssvhprtlqt neensrvlp
(Seq. ID No. 2)
```

4C. Predicted CR1 isoform X1, *Homo sapiens*, NCBI Reference Sequence No. XP_005273121.1

```
   1 mclgrmgass prspepvgpp apglpfccgg sllavvvlla lpvawgqcna pewlpfarpt 61 nltdefefpi gtylnyecrp gysgrpfsii clknsvwtga kdrcrrkscr nppdpvngmv 121 hvikgiqfgs qikysctkgy rligsssatc iisgdtviwd netpicdrip cglpptitng 181 dfistnrenf hygsvvtyrc npgsggrkvf elvgepsiyc tsnddqvgiw sgpapqciip 241 nkctppnven gilvsdnrsl fslnevvefr cqpgfvmkgp rrvkcqalnk wepelpscsr 301 vcqpppdvlh aertqrdkdn fspgqevfys cepgydlrga asmrctpqgd wspaaptcev 361 kscddfmgql ingrvlfpvn lqlgakvdfv cdegfqlkgs sasycvlagm eslwnssvpv 421 ceqifcpspp vipngrhtgk plevfpfgkt vnytcdphpd rgtsfdlige stirctsdpq 481 gngvwsspap rcgilghcqa pdhflfaklk tqtnasdfpi gtslkyecrp eyygrpfsit 541 cldnlvwssp kdvckrksck tppdpvngmv hvitdiqvgs rinyscttgh rlighssaec 601 ilsgnaahws tkppicqrip cglpptiang dfistnrenf hygsvvtyrc npgsggrkvf 661 elvgepsiyc tsnddqvgiw sgpapqciip nkctppnven gilvsdnrsl fslnevvefr 721 cqpgfvmkgp rrvkcqalnk wepelpscsr vcqpppdvlh aertqrdkdn fspgqevfys 781 cepgydlrga asmrctpqgd wspaaptcev kscddfmgql lngrvlfpvn lqlgakvdfv 841 cdegfqlkgs sasycvlagm eslwnssvpv ceqifcpspp vipngrhtgk plevfpfgkt 901 vnytcdphpd rgtsfdlige stirctsdpq gngvwsspap rcgilghcqa pdhflfaklk 961 tqtnasdfpi gtslkyecrp eyygrpfsit cldnlvwssp kdvckrksck tppdpvngmv 1021 hvitdiqvgs rinyscttgh rlighssaec ilsgnaahws tkppicqlcq pppdvlhaer
```

TABLE 3-continued

Sequences of Complement Receptor 1

```
1081 tqrdkdnfsp gqevfyscep gydlrgaasm rctpqgdwsp aaptcevksc ddfmgqllng 1141 rvlfpvnlql gakvdfvcde gfqlkgssas ycvlagmesl wnssvpvceq ifcpsppvip 1201 ngrhtgkple vfpfgkavny tcdphpdrgt sfdligesti rctsdpqgng vwsspaprcg 1261 ilghcqapdh flfaklktqt nasdfpigts lkyecrpeyy grpfsitcld nlvwsspkdv 1321 ckrkscktpp dpvngmvhvi tdiqvgsrin yscttghrli ghssaecils gntahwstkp 1381 picgripcgl pptiangdfi stnrenfhyg svvtyronlg srgrkvfelv gepsiyctsn 1441 ddqvgiwsgp apqciipnkc tppnvengil vsdnrslfsl nevvefrcqp gfvmkgprrv 1501 kcqalnkwep elpscsrvcq pppeilhgeh tpshqdnfsp gqevfyscep gydlrgaasl 1561 hctpqgdwsp eaprcavksc ddflgqlphg rvlfplnlql gakvsfvcde gfrlkgssvs 1621 hcvlvgmrsl wnnsvpvceh ifcpnppail ngrhtgtpsg dipygkeisy tcdphpdrgm 1681 tfnligesti rctsdphgng vwsspaprce lsvraghckt peqfpfaspt ipindfefpv 1741 gtslnyecrp gyfgkmfsis clenlvwssv edncrrkscg pppepfngmv hintdtqfgs 1801 tvnyscnegf rligspsttc lvsgnnvtwd kkapiceiis ceppptisng dfysnnrtsf 1861 hngtvvtyqc htgpdgeqlf elvgersiyc tskddqvgvw sspprcist nkctapeven 1921 airvpgnrsf ftlteiirfr cqpgfvmvgs htvqcqtngr wgpklphcsr vcqpppeilh 1981 gehtlshqdn fspgqevfys cepsydlrga aslhctpqgd wspeaprctv kscddflgql 2041 phgrvllpln lqlgakvsfv cdegfrlkgr sashcvlagm kalwnssvpv ceqifcpnpp 2101 aiingrhtgt pfgdipygke isyacdthpd rgmtfnlige ssirctsdpq gngvwsspap 2161 rcelsvpaac phppkiqngh yigghvslyl pgmtisyicd pgyllvgkgf ifctdqgiws 2221 qldhyckevn csfplfmngi skelemkkvy hygdyvtlkc edgytlegsp wsqcqaddrw 2281 dpplakctsr thdalivgtl sgtiffilli iflswiilkh rkgnnahenp kevaihlhsq 2341 ggssvhprtl qtneensrvl p
(Seq. ID No. 3)
```

TABLE 4

| Targets |||||
|---|---|---|---|
| General Classes of Targets |||||
| Microbes | Polypeptides | DNA | Amino Acids |
| Fungi | Toxins | RNA | Prions |
| Bacteria | Lipids | Parasites | Cytokines |
| Virus | Cells | Cellular debris | Complement-associated molecules |
| Complement-Related Targets |||||
| Immune complexes | C3dg | C4a | C6 |
| Factor B | C3dk | C4b | C7 |
| Factor D | C3e | C2 | C8 |
| Properdin | Bb | C4bp | C9 |
| C3 | membrane attack complex | Mannose-Binding Lectin (MBL) ||
| C3a | C1q | MBL-Associated Serine Protease 1 (MASP1) ||
| C3b | C1r | MBL-Associated Serine Protease 2 (MASP2) ||
| iC3b | C1s | C5 ||
| C3c | C4 | C5a ||
| Infectious Disease-Related Targets |||||
| Lipopolysaccharides | Cell invasion protein | Intermedilysin | Secreted effector protein sptP |
| Zona occludens toxin | Cholera enterotoxin | Invasion protein sipA | Seeligeriolysin |
| Actin polymerization protein RickA | Cysteine protease | Iota toxin component Ia | Serine protease |

TABLE 4-continued

| Targets | | | |
|---|---|---|---|
| Actin polymerization protein RickA | Cytolethal distending toxin | Ivanolysin | Shiga toxin |
| Adenosine monophosphate-protein transferase vopS adenylate cyclase | Cytolysin | LepB | Sphingomyelinase |
| | Cytotoxic necrotizing factor | Lethal factor | Staphylokinase |
| Adenylate cyclase ExoY | Cytotoxin | Leukotoxin | Streptokinase |
| ADP-ribosyltransferase enzymatic component | Dermonecrotic toxin | Listeriolysin | Streptolysin |
| Aerolysin | Deubiquitinase | Microbial collagenase | Streptopain |
| Alpha-toxin | Diphtheria toxin | Outer membrane protein IcsA autotransporter | Suilysin |
| Alveolysin | Enterohemolysin | Panton-Valentine Leucocidin F | Superantigen |
| Alveolysin | Enterotoxin | Perfringolysin | T3SS secreted effector EspF |
| Anthrolysin O | Epidermal cell differentiation inhibitor | Pertussis toxin | Tetanus toxin |
| Arp2/3 complex-activating protein rickA | Exoenzyme | Phospholipase | Tir |
| Binary ADP-ribosyltransferase CDT toxin | Exotoxin | Plasminogen activator | TolC |
| *Botulinum* neurotoxin | G-nucleotide exchange factor | Pneumolysin | Toxic shock syndrome toxin |
| C2 toxin, component II | Guanine nucleotide exchange factor sopE | Protective antigen | Zink-carboxypeptidase |
| CagA | Heat stable enterotoxin | Protein kinase | Zink-carboxypeptidase |
| Calmodulin-sensitive adenylate cyclase | IgA-specific serine endopeptidase autotransporter | Pyolysin | Zn-dependent peptidase |
| Cell cycle inhibiting factor | Inositol phosphate phosphatase sopB | RTX toxin | |
| Other Molecular Targets | | | |
| G-CSF | IL3 | IL10 | MIP1a |
| GM-CSF | IL4 | IL12 | MIP1b |
| M-CSF | IL5 | IFNa | TGFb |
| IL1a | IL6 | IFNb | TNFa |
| IL1b | IL7 | IFNg | TNFb |
| IL2 | IL8 | Self-antibodies | Non-self antibodies |
| PRP | PRPc | PRPsc | PRPres |
| Lipid & Cell Targets | | | |
| Circulating tumor cells | very low density lipid (VLDL) | triglycerides | Fatty acids |
| Metastases | high density lipoprotein | chylomicrons | Cholesterol |
| Eukaryotic cells | low density lipoprotein | apolipoproteins | |

TABLE 5

| Diseases and Conditions | | | |
|---|---|---|---|
| Cancers | | | |
| Acute lymphoblastic leukaemia (ALL) | Colorectal cancer | Macroglobulinemia, Waldenström | Pleuropulmonary Blastoma, Childhood |
| Acute myeloid leukaemia (AML) | Craniopharyngioma, Childhood | Male Breast Cancer | Pregnancy and Breast Cancer |
| Adrenocortical Carcinoma | Cutaneous T-Cell Lymphoma | Malignant Fibrous Histiocytoma of Bone and Osteosarcoma | Primary Central Nervous System (CNS) Lymphoma |
| AIDS-Related Kaposi Sarcoma | Ductal Carcinoma In Situ (DCIS) | Melanoma | Prostate Cancer |
| AIDS-Related lymphoma | Embryonal Tumors, Childhood | Merkel Cell Carcinoma | Rare cancers |
| Anal Cancer | Endometrial Cancer | Mesothelioma | Rectal Cancer |
| Appendix Cancer | Ependymoma, Childhood | Metastatic Squamous Neck Cancer with Occult Primary | Renal cell carcinoma |

TABLE 5-continued

| Diseases and Conditions | | | |
|---|---|---|---|
| Astrocytomas, Childhood | Epithelial cancer | Midline Tract Carcinoma Involving NUT Gene | Renal Pelvis and Ureter, Transitional Cell Cancer |
| Atypical Teratoid/Rhabdoid Tumor, Childhood | Esophageal Cancer | Molar pregnancy | Retinoblastoma |
| Basal Cell Carcinoma | Esthesioneuroblastoma, Childhood | Mouth and oropharyngeal cancer | Rhabdomyosarcoma |
| Bile duct cancer | Ewing sarcoma | Multiple Endocrine Neoplasia Syndromes, Childhood | Salivary Gland Cancer |
| Bladder cancer | Extragonadal Germ Cell Tumor | Multiple Myeloma/Plasma Cell Neoplasm | Sarcoma |
| Bone cancer | Extrahepatic Bile Duct Cancer | Mycosis Fungoides | Secondary cancers |
| Bowel cancer | Eye Cancer | Myelodysplastic Syndromes | Sézary Syndrome |
| Brain Stem Glioma, Childhood | Gallbladder Cancer | Myelodysplastic/ Myeloproliferative Neoplasms | Skin Cancer |
| Brain tumours | Gastric cancer | Myeloproliferative Disorders, Chronic | Skin cancer (non melanoma) |
| Breast cancer | Gastrointestinal Carcinoid Tumor | Nasal Cavity and Paranasal Sinus Cancer | Small Cell Lung Cancer |
| Bronchial Tumors, Childhood | Germ Cell Tumor | Nasopharyngeal cancer | Small Intestine Cancer |
| Burkitt Lymphoma | Gestational trophoblastic tumours (GTT) | Neuroblastoma | Soft Tissue Sarcoma |
| Cancer of unknown primary | Glioma | Non-Hodgkin Lymphoma | Squamous Cell Carcinoma |
| Cancer spread to bone | Hairy cell leukaemia | Non-Small Cell Lung Cancer | Squamous Neck Cancer with Occult Primary, Metastatic |
| Cancer spread to brain | Head and neck cancer | Oesophageal cancer | Stomach (Gastric) Cancer |
| Cancer spread to liver | Heart Cancer, Childhood | Oral Cancer | Stomach cancer |
| Cancer spread to lung | Hepatocellular (Liver) Cancer | Oral Cavity Cancer | T-Cell Lymphoma, Cutaneous - see Mycosis Fungoides and Sézary Syndrome |
| Carcinoid Tumor | Histiocytosis, Langerhans Cell | Oropharyngeal Cancer | Testicular cancer |
| Carcinoma of Unknown Primary | Hodgkin Lymphoma | Osteosarcoma (Bone Cancer) | Throat Cancer |
| Cardiac (Heart) Tumors, Childhood | Hypopharyngeal Cancer | Osteosarcoma and Malignant Fibrous Histiocytoma | Thymoma and Thymic Carcinoma |
| Central Nervous System Atypical Teratoid/Rhabdoid Tumor, Childhood | Intraocular Melanoma | Ovarian Cancer | Thyroid Cancer |
| Central Nervous System Embryonal Tumors, Childhood | Islet Cell Tumors, Pancreatic Neuroendocrine Tumors | Pancreatic Cancer | Transitional Cell Cancer of the Renal Pelvis and Ureter |
| Central Nervous System, Childhood | Kidney cancer | Pancreatic Neuroendocrine Tumors (Islet Cell Tumors) | Unknown primary cancer |
| Cervical cancer | Langerhans Cell Histiocytosis | Papillomatosis, Childhood | Ureter and Renal Pelvis, Transitional Cell Cancer |
| Chordoma, Childhood | Laryngeal Cancer | Paraganglioma | Urethral Cancer |
| Choriocarcinoma | Leukemia | Parathyroid Cancer | Uterine Cancer, Endometrial |
| Chronic Lymphocytic Leukemia (CLL) | Lip and Oral Cavity Cancer | Penile Cancer | Uterine Sarcoma |
| Chronic myeloid leukaemia (CML) | Liver cancer | Pharyngeal Cancer | Vaginal cancer |
| Chronic Myeloproliferative Disorders | Lobular Carcinoma In Situ (LCIS) | Pheochromocytoma | Vulvar Cancer |
| Colon cancer | Low Malignant Potential Tumor | Pituitary Tumor | Waldenström Macroglobulinemia |
| Lymphoma | Lung Cancer | Plasma Cell Neoplasm/Multiple Myeloma | Wilms Tumor |

TABLE 5-continued

| Diseases and Conditions | | | |
|---|---|---|---|
| Complement and Immune Complex-Related Diseases | | | |
| Age-related macular degeneration | ANCA-associated vasculitis (Includes Pauci-immune) | Glomerulonephritis - sparse hair - telangiectasis | MYH9-related disease |
| Atypical hemolytic uremic syndrome | Anti-glomerular basement membrane disease (Goodpasture's) | Goodpasture's sndrome | Nail-patella syndrome |
| Autoimmune hemolytic anemia | Arthus Reaction | Granulomatosis with polyangiitis (ANCA and Wegeners) | Nail-patella-like renal disease |
| C1 inhibitor deficiency | Asthma | Guillain-Barre syndrome | Nephritis |
| C1q deficiency | Atypical hemolytic uremic syndrome | Hemolytic angioedema (HAE) | Non-amyloid monoclonal immunoglobulin deposition disease |
| C1r deficiency | Autoimmune inner ear disease (AIED) Sensorineural hearing loss | Henoch-Schonlein purpura | Pauci-immune glomerulonephritis |
| C1s deficiency | Autoimmune uveitis | HIVICK | Pediatric systemic lupus erythematosus |
| C2 deficiency | Autosomal dominant intermediate Charcot-Marie-Tooth disease type E | Hypersensitivty vasculitis | Pierson syndrome |
| C3 deficiency | Behçet disease | Hypocomplementemic urticarial vasculitis | Polyarteritis |
| C4 deficiency | Berger (IgA) Nephropathy | Idiopathic membranous glomerulonephritis | polyarteritis nodosa |
| C5 deficiency | Buergers disease | Idiopathic nephrotic syndrome | Polymyalgia rheumatica |
| C6 deficiency | Central nervous system vasculitis | IgA nephropathy (Berger's disease) | Polymyositis |
| C7 deficiency | Choroiditis | IgA nephropathy/vasculitis (Henoch-Schonlein purpura) | Polymyositis/ dermatomyositis |
| C8 deficiency | Chronic demyelinating polyneuropathy (CIDP) | Immune thrombocytopenia | Poststaphilococcal glomerulonephritis |
| C9 deficiency | Churg-strauss syndrome | Immunobullous diseases | Poststeptococcal glomerulonephritis |
| CD55 deficiency | Cogan's syndrome | Immunotactoid or fibrillary glomerulopathy | Primary membranoproliferative glomerulonephritis |
| CD59 deficiency | Collagen type III glomerulopathy | Infection-related glomerulonephritis | Rapidly progressive glomerulonephritis (Crescentic) |
| Complement Factor I deficiency | Congenital and infantile nephrotic syndrome | Inflammatory myopathies | Rapidly progressive glomerulonephritis (RPGN) |
| Complement factor-H related 1(CFHR1) deficiency | Congenital membranous nephropathy due to maternal anti-neutral endopeptidase alloimmunization | Juvenile dermatomyositis | Rasmussen syndrome |
| Complement factor-H related 3(CFHR3) deficiency | Cryoglobulinaemia/Cold agglutinin diease | Juvenile polymyositis | Reactive arthritis |
| CR3/CR4 defieciency (leukocyte adhesion deficiency 1) | Cryoglobulinemic vasculitis | Kawasaki disease | Relapsing polychondritis |
| Factor B deficiency | Cutaneous vasculitis | Lipoprotein glomerulopathy | Renal amyloidosis |
| Factor D deficiency | Demyelinating myopathies (paraprotein associated) | Lupus nephritis | Reynolds syndrome |
| Factor H deficiency | Denys-Drash syndrome | Lupus nephropathy | Rheumatoid arthritis |
| Factor I deficiency | Dermatomyositis | May Hegglin anomaly | Sarcoidosis (Nesnier Boeck Schuamann Disease) |
| Ficolin 3 deficiency | Dermatomyositis | Membranoglomerular nephritis | Schimke immuno-osseous dysplasia |
| MASP2 deficiency | Diabetic nephropathy | Membranoproliferative glomerulonephritis | Scleroderma |
| MBL deficiency | Drug-induced immune complex vasculitis | Membranoproliferative glomerulonephritis Type I (MPGN Type I) | Sebastian syndrome |

TABLE 5-continued

| Diseases and Conditions | | | |
|---|---|---|---|
| Non-alcoholic steatohepatitis | Eosinophilic granulomatosis with polyangiitis (Churgg-Strauss) | Membranoproliferative glomerulonephritis Type II (Dense Deposit Disease, MPGN Type II) | Secondary amyloidosis |
| Paroxysmal nocturnal hemoglobinuria | Epstein Syndrome | Membranoproliferative glomerulonephritis Type III (MPGN Type III) | Severe or recurring *C diff* colitis |
| Properdin deficiency | Essential mixed cryoglobulinemia | Membranouse glomerulonephritis | Sjogren's syndrome |
| Action myoclonus - renal failure syndrome | Familial Mediterranean fever | Menieres disease | Staphylococcal or streptococcal sepsis |
| Acute respiratory disease syndrome (ARDS)/Severe acute respiratory syndrome (SARS) | Familial renal amyloidosis | Microscopic polyangiitis | Stiff person syndrome |
| Acute serum sickness | Familial steroid-resistant nephrotic syndrome with sensorineural deafness | Minimal change disease | Systemic lupus erythematosus |
| Adult-onset Still disease | Farmer's lung | Mixed connective tissue disease | Systemic sclerosis |
| Age-related macular degeneration | Fechtner Syndrome | Mostly large vessel vasculitis | Takayasu arteritis |
| AL amyloidosis | Fibronectin glomerulopathy | mostly medium vessel vasculitis | Toxic epidermal necrolysis (Stevens Johnson syndrome) |
| Alport's syndrome | Fibrosing alveolitis | Mostly small vessel vsculitis | Transplantation/reperfusion (solid organ) |
| Alzheimer's disease | Focal segmental glomerular | Muckle-Wells syndrome | Vasculitis |
| Amyloidosis (AL, AA, MIDD, Other) | Focal segmental glomerulosclerosis | Myasthenia gravis | Wegener's granulomatosis |
| Giant cell arteritis | Frasier syndrome | Galloway-Mowat syndrome | |
| Type 1 diabetes | Myasthenia gravis | Graves' disease | Pernicious anemia |
| Crohn's disease | alopecia areata | thrombocytopenic purpura | Primary biliary cirrhosis |
| Ulcerative colitis | autoimmune hepatitis | Guillain-Barre syndrome | Psoriasis |
| Inflammatory bowel syndrome | autoimmune deramtomyositis | Autoimmune myocarditis | Rheumatoid arthritis |
| Multiple sclerosis | Juvenile idiopathic arthritis | Autoimmune pemphigus | Vitiligo |
| Enzyme Deficiencies & Vascular Diseases | | | |
| 2,4-dienoyl-CoA reductase deficiency | Fabry disease (1:80,000 to 1:117,000) | Isobutyryl-CoA dehydrogenase | Peripheral neuropathy |
| 2-Methyl-3-hydroxy butyric aciduria | Familial hypercholesterolemia (1:500) | Isovaleric acidemia | Peroxisomal disorders (1:50,000; e.g., Zellweger syndrome, neonatal adrenoleukodystrophy, Refsum's disease) |
| 2-methylbutyryl-CoA dehydrogenase | Familial myocardial infarct/stroke | Lactase deficiency (common) | Phenylketonuria |
| 3-hydroxy-3-methylglutaryl (HMG) aciduria | Fatty acid oxidation disorders (1:10,000) | Lesch-Nyhan syndrome | Primary hyperoxaluria |
| 3-methylglutaconic aciduria | Galactokinase deficiency | Lipoprotein lipase deficiency (rare) | Propionic acidemia |
| 3-oxothiolase deficiency (1:100,000) | Galactose epimerase | long-chain l-3-hdroxyacyl-CoA dehydrogenase | Recurrent emesis |
| 4-hydroxybutyric aciduria | Galactosemia | Lysinuric protein intolerance (rare) | Short-chain acyl-CoA dehydrogenase |
| 5,10-methylenetetra-hydrofolate reductase deficiency (common) | Galactosemia (1:40,000) | Lysinuric protein intolerance (rare) | Sucrase-isomaltase deficiency (rare) |
| 5-Oxoprolinuria (pyroglutamic aciduria) | Gaucher's disease | Malonic acidemia | Symptoms of pancreatitis |
| Abetalipoproteinemia (rare) | Glutaric acidemia type I | Maple syrup urine disease | Transferase deficient galactosemia (Galactosemia type 1) |

TABLE 5-continued

| Diseases and Conditions | | | |
|---|---|---|---|
| Acute Intermittent Porphyria | Glutaric acidemia Type II | Medium chain acyl-CoA dehydrogenase | Trifunctional protein deficiency |
| Alkaptonuria | Glutathione Synthetase Deficiency w/5-oxoprolinuria | Medium/short chain L-3-hydroxy acyl-CoA dehydrogenase | Tyrosinemia type 1 |
| Argininemia | Glutathione Synthetase Deficiency w/o 5-oxoprolinuria | Medum-chain ketoacyl-coA thiolase | Tyrosinemia type 2 |
| argininosuccinate aciduria | Glycogenolysis disorders (1:20,000) | Metachromatic leukodystrophy (1:100,000) | Tyrosinemia type 3 |
| Benign hyperphenylalaninemia | Glycogenosis, type I (1:70,000) | Metachromatic leukodystrophy (1:100,000) | Upward gaze paralysis |
| beta ketothiolase deficiency | Hemolytic anemia due to adenylate kinase deficiency | Methylmalonic acidemia (Cbl C) | Very long chain acyl-CoA dehydrogenase |
| Biopterin cofactor biosynthesis defects | Hemolytic anemia due to deficiency in Glucose 6 phosphate dehydrogenase | Methylmalonic acidemia (Cbl D) | Wilson Disease |
| Biopterin cofactor regeneration defects | Hemolytic anemia due to diphosphoglycerate mutase deficiency | Methylmalonic acidemia (vitamin b12 non-responsive) | Aicardi-Goutieres Syndrome (may be an allelic form of CLE) |
| biotin-unresponsive 3-methylcrotonyl-CoA carboxylase deficiency | Hemolytic anemia due to erythrocyte adenosine deaminase overproduction | Methylmalonic acidemia w/0 homocystinuria | Cutaneous lupus erythematosus |
| Carbamoyl phosphate synthetase | Hemolytic anemia due to glucophosphate isomerase deficiency | Methylmalonic aciduria and homocystinuria | Dermatitis herpetiformis |
| Carnitine acylcarnitine translocase | Hemolytic anemia due to glutathione reductase deficiency | Mitochondrial disorders (1:30,000) | hemophilia A |
| Carnitine palmitoyltransferase I | Hemolytic anemia due to glyceraldehyde-3-phosphate dehydrogenase deficiency | Mitochondrial disorders (1:30,000; e.g., cytochrome-c oxidase deficiency; MELAS syndrome; Pearson's syndrome [all rare]) | hemophilia B |
| Carnitine palmitoyltransferase II | Hemolytic anemia due to pyrimidine 5' nucleotidase deficiency | Mitochondrial disorders (1:30,000; e.g., Leigh disease, Kearns-Sayre syndrome [rare]) | Idiopathic steroid sensitive nephrotic syndrome (same as focal segmental glomerulaosclerosis) |
| Carnitine uptake defect | Hemolytic anemia due to red cell pyruvate kinase deficiency | Mitochondrial disorders (1:30,000; e.g., lipoamide dehydrogenase deficiency [rare]) | Immune thrombocytopenic purpura |
| citrullinemia type I | HHH syndrome (rare) | Mitochondrial disorders (1:30,000; e.g., Pearson's syndrome [rare]) | Myasthenia gravis |
| Citrullinemia type II | homocysteinuria | Multiple carboxylase (holocarboxylase synthetase) | Oligoarticular juvenile arthritis |
| Congenital disorders of glycosylation (rare) | Homocystinuria (1:200,000) | Multiple carboxylase deficiency (e.g., holocarboxylase synthetase [rare]) and biotinidase deficiencies (1:60,000) | Scleroderma |
| D-2-hydroxyglutaric aciduria | hyperammonemia/ornithinemia/ citrullinemia (ornithine transporter defect) | Muscle cramps/spasticity | Solar urticaria (maybe protophyria erythema) |
| D-2-hydroxyglutaricaciduria (rare) | Hyperlipoproteinemia, types I and IV (rare) | Myoadenylate deaminase deficiency (1:100,000) | Thrombotic thrombocytopenic purpura |
| Enteropeptidase deficiency (rare) | Hypermethioninemia due to glycine N-methyltransferase deficiency | Niemann-Pick disease, type C (rare) | Tubulointerstitial nephritis with Uveitis/ ATIN |
| Ethylmalonic encephalopathy | Hypermethioninemia encephalopathy due to adenosine kinase deficiency | Nonketotic hyperglycinemia | Von willebrand disease |
| | | Hyperprolinemia | |
| Infectious Diseases & agents | | | |
| *Acinetobacter* | Dengue haemorrhagic fever | Infection-induced immune complex vasculitis | Sepsis |

TABLE 5-continued

| Diseases and Conditions | | | |
|---|---|---|---|
| *Arcobacter butzleri* infection - blood infection | Disseminated infection with *mycobacterium* avium complex - blood infection | *Klebsiella* | *Serratia* |
| *Arcobacter cryaerophilus* infection - blood infection | *E. coli* | Leprosy/Hansen's disease | *Staphylococcus Aureus* |
| *Arcobacter* infection - blood infection | *Enterobacter* | Malaria | *Stenotrophomonas maltophilia* - blood infection |
| Bacteremia | *Enterococcus* | Meningococcus | Streptococcal Group A invasive disease - blood infection |
| Bacterial endocarditis | Glanders - blood infection | Methicillin Resistant *Staphylococcus Aureus* | *Streptococcus pneumoniae* |
| *Campylobacter fetus* infection - blood infection | Gonorrhea | *Pseudomonas* | *Streptococcus pyogenes* |
| *Campylobacter jejuni* infection - blood infection | Hepatitis | *Rhodococcus equi* - blood infection | Trypanosomiasis |
| *Candida* | Human Immunodeficiency Virus Coagulase-negative *Staphylococcus* | *Salmonella* | Yellow fever |

TABLE 6

| Exogenous antigens | | | |
|---|---|---|---|
| General Classes of Exogenous antigens | | | |
| Antibodies | Ankyrin repeat proteins | Fibronectins | Lyases |
| Antibodies | Complement receptors | GPI-linked polypeptides | Nanobodies |
| Aptamers | Cyclic peptides | HEAT repeat proteins | Nucleic Acids |
| ARM repeat proteins | DARPins | Hydrolases | Polypeptides |
| Carbohydrates | DNAses | Kinases | Single-chain variable fragments (scFv) |
| Cell surface receptors | Enzymes | Lipoproteins | Tetratricopeptide repeat proteins |
| Complement-Related Exogenous antigens | | | |
| C1 inhibitor | C4 binding protein | CR3 | Factor I |
| C3 Beta chain Receptor | CD59 | CR4 | Homologous restriction factor |
| C3aR | CR1 | Decay-accelerating factor (DAF) | Membrane cofactor protein (MCP) |
| C3eR | CR2 | Factor H | PRELP |
| Enzymes | | | |
| triacylglycerol lipase | bile-acid-CoA hydrolase | feruloyl esterase | phosphatidate phosphatase |
| (S)-methylmalonyl-CoA hydrolase | bis(2-ethylhexyl)phthalate esterase | formyl-CoA hydrolase | phosphatidylglycerophosphatase |
| [acyl-carrier-protein] phosphodiesterase | bisphosphoglycerate phosphatase | fructose-bisphosphatase | phosphatidylinositol deacylase |
| [phosphorylase] phosphatase | Carboxylic-Ester Hydrolases | fumarylacetoacetase | phosphodiesterase I |
| 1,4-lactonase | carboxymethylenebutenolidase | fusarinine-C ornithinesterase | phosphoglycerate phosphatase |
| 11-cis-retinyl-palmitate hydrolase | cellulose-polysulfatase | galactolipase | phosphoglycolate phosphatase |
| 1-alkyl-2-acetylglycerophosphocholine esterase | cephalosporin-C deacetylase | gluconolactonase | phosphoinositide phospholipase C |
| 2'-hydroxybiphenyl-2-sulfinate desulfinase | cerebroside-sulfatase | glucose-1-phosphatase | phospholipase A1 |
| 2-pyrone-4,6-dicarboxylate lactonase | cetraxate benzylesterase | glucose-6-phosphatase | phospholipase A2 |
| 3',5'-bisphosphate nucleotidase | chlorogenate hydrolase | glutathione thiolesterase | phospholipase C |
| 3-hydroxyisobutyryl-CoA hydrolase | chlorophyllase | glycerol-1-phosphatase | phospholipase D |
| 3'-nucleotidase | cholinesterase | glycerol-2-phosphatase | phosphonoacetaldehyde hydrolase |
| 3-oxoadipate enol-lactonase | choline-sulfatase | glycerophosphocholine phosphodiesterase | phosphonoacetate hydrolase |

TABLE 6-continued

| Exogenous antigens | | | |
|---|---|---|---|
| 3-phytase | choloyl-CoA hydrolase | Glycosidases, i.e. enzymes that hydrolyse O- and S-glycosyl compounds | phosphonopyruvate hydrolase |
| 4-hydroxybenzoyl-CoA thioesterase | chondro-4-sulfatase | glycosulfatase | phosphoprotein phosphatase |
| 4-methyloxaloacetate esterase | chondro-6-sulfatase | Glycosylases | Phosphoric-diester hydrolases |
| 4-phytase | citrate-lyase deacetylase | histidinol-phosphatase | Phosphoric-monoester hydrolases |
| 4-pyridoxolactonase | cocaine esterase | hormone-sensitive lipase | Phosphoric-triester hydrolases |
| 5'-nucleotidase | cutinase | Hydrolysing N-glycosyl compounds | phosphoserine phosphatase |
| 6-acetylglucose deacetylase | cyclamate sulfohydrolase | Hydrolysing S-glycosyl compounds | poly(3-hydroxybutyrate) depolymerase |
| 6-phosphogluconolactonase | Cysteine endopeptidases | hydroxyacylglutathione hydrolase | poly(3-hydroxyoctanoate) depolymerase |
| a-amino-acid esterase | Cysteine-type carboxypeptidases | hydroxybutyrate-dimer hydrolase | polyneuridine-aldehyde esterase |
| a-Amino-acyl-peptide hydrolases | D-arabinonolactonase | hydroxymethylglutaryl-CoA hydrolase | protein-glutamate methylesterase |
| acetoacetyl-CoA hydrolase | deoxylimonate A-ring-lactonase | iduronate-2-sulfatase | quorum-quenching N-acyl-homoserine lactonase |
| acetoxybutynylbithiophene deacetylase | dGTPase | inositol-phosphate phosphatase | retinyl-palmitate esterase |
| acetylajmaline esterase | dihydrocoumarin hydrolase | juvenile-hormone esterase | Serine dehyrdatase or serine hydroxymethyl transferase |
| acetylalkylglycerol acetylhydrolase | Dipeptidases | kynureninase | Serine endopeptidases |
| acetylcholinesterase | Dipeptide hydrolases | L-arabinonolactonase | serine-ethanolaminephosphate phosphodiesterase |
| acetyl-CoA hydrolase | Dipeptidyl-peptidases and tripeptidyl-peptidases | limonin-D-ring-lactonase | Serine-type carboxypeptidases |
| acetylesterase | Diphosphoric-monoester hydrolases | lipoprotein lipase | S-formylglutathione hydrolase |
| acetylpyruvate hydrolase | disulfoglucosamine-6-sulfatase | L-rhamnono-1,4-lactonase | sialate O-acetylesterase |
| acetylsalicylate deacetylase | dodecanoyl-[acyl-carrier-protein] hydrolase | lysophospholipase | sinapine esterase |
| acetylxylan esterase | Endodeoxyribonucleases producing 3'-phosphomonoesters | mannitol-1-phosphatase | Site specific endodeoxyribonucleases: cleavage is not sequence specific |
| acid phosphatase | Endodeoxyribonucleases producing 5'-phosphomonoesters | Metallocarboxypeptidases | Site-specific endodeoxyribonucleases that are specific for altered bases. |
| Acting on acid anhydrides to catalyse transmembrane movement of substances | Endopeptidases of unknown catalytic mechanism | Metalloendopeptidases. | Site-specific endodeoxyribonucleases: cleavage is sequence specific |
| Acting on acid anhydrides to facilitate cellular and subcellular movement | Endoribonucleases producing 3'-phosphomonoesters | methylphosphothioglycerate phosphatase | sphingomyelin phosphodiesterase |
| Acting on GTP to facilitate cellular and subcellular movement | Endoribonucleases producing 5'-phosphomonoesters | methylumbelliferyl-acetate deacetylase | S-succinylglutathione hydrolase |
| Acting on phosphorus-nitrogen bonds | Endoribonucleases that are active with either ribo- or deoxyribonucleic acids and produce 3'-phosphomonoesters | monoterpene e-lactone hydrolase | steroid-lactonase |
| Acting on sulfur-nitrogen bonds | Endoribonucleases that are active with either ribo- or deoxyribonucleic acids and produce 5'-phosphomonoesters | N-acetylgalactosamine-4-sulfatase | sterol esterase |
| actinomycin lactonase | Enzymes acting on acid anhydrides | N-acetylgalactosamine-6-sulfatase | steryl-sulfatase |
| acylcarnitine hydrolase | Enzymes Acting on carbon-carbon bonds | N-acetylgalactosaminoglycan deacetylase | succinyl-CoA hydrolase |
| acyl-CoA hydrolase | Enzymes acting on carbon-nitrogen bonds, other than peptide bonds | N-acetylglucosamine-6-sulfatase | sucrose-phosphate phosphatase |
| acylglycerol lipase | Enzymes acting on carbon-phosphorus bonds | N-sulfoglucosamine sulfohydrolase | sugar-phosphatase |
| acyloxyacyl hydrolase | Enzymes acting on carbon-sulfur bonds | oleoyl-[acyl-carrier-protein] hydrolase | Sulfuric-ester hydrolases |
| acylpyruvate hydrolase | Enzymes Acting on ether bonds | Omega peptidases | tannase |
| ADAMTS13 | Enzymes acting on halide bonds | orsellinate-depside hydrolase | Thioester hydrolases |

TABLE 6-continued

| Exogenous antigens | | | |
|---|---|---|---|
| Adenosine deaminase | Enzymes acting on peptide bonds (peptidases) | oxaloacetase | Thioether and trialkylsulfonium hydrolases |
| adenylyl-[glutamate-ammonia ligase] hydrolase | Enzymes acting on phosphorus-nitrogen bonds | palmitoyl[protein] hydrolase | Threonine endopeptidases |
| ADP-dependent medium-chain-acyl-CoA hydrolase | Enzymes acting on sulfur-nitrogen bonds | palmitoyl-CoA hydrolase | thymidine phosphorylase |
| ADP-dependent short-chain-acyl-CoA hydrolase | Enzymes acting on sulfur-sulfur bonds | pectinesterase | trehalose-phosphatase |
| ADP-phosphoglycerate phosphatase | Ether hydrolases. | Peptidyl peptide hydrolases | triacetate-lactonase |
| alkaline phosphatase | Exodeoxyribonucleases producing 5'-phosphomonoesters | Peptidyl-amino-acid hydrolases | Triphosphoric-monoester hydrolases |
| all-trans-retinyl-palmitate hydrolase | Exonucleases that are active with either ribo- or deoxyribonucleic acids and produce 3'-phosphomonoesters | Peptidylamino-acid hydrolases or acylamino-acid hydrolases | trithionate hydrolase |
| aminoacyl-tRNA hydrolase | Exonucleases that are active with either ribo- or deoxyribonucleic acids and produce 5'-phosphomonoesters | Peptidyl-dipeptidases | tropinesterase |
| Aminopeptidases | Exoribonucleases producing 3'-phosphomonoesters | phenylacetyl-CoA hydrolase | ubiquitin thiolesterase |
| arylesterase | Exoribonucleases producing 5'-phosphomonoesters. | Phenylalanine ammonia lyase | UDP-sulfoquinovose synthase |
| arylsulfatase | Factor IX | Phenylalanine hydroxylase | uricase |
| Asparaginase | Factor VIII | pheophorbidase | uronolactonase |
| Aspartic endopeptidases | fatty-acyl-ethyl-ester synthase | phloretin hydrolase | wax-ester hydrolase |
| | b-diketone hydrolase | phorbol-diester hydrolase | xylono-1,4-lactonase |

TABLE 7

Selected Diseases, Exogenous antigens and Targets

| Category | Disease | Exogenous antigen | Target |
|---|---|---|---|
| Amyloidoses | AA Amyloidosis | an an antibody-like binder to serum amyloid A protein or serum amyloid P component | Serum amyloid A protein and amyloid placques |
| Amyloidoses | beta2 microglobulin amyloidosis | an an antibody-like binder to beta-2 microbulin or serum amyloid P component | Beta2 microglobulin or amyloid placques |
| Amyloidoses | Light chain amyloidosis | an an antibody-like binder to light chain, serum amyloid P component | Antibody light chain or amyloid placques |
| Cell clearance | Cancer | an an antibody-like binder to CD44 | a circulating tumor cell |
| Cell clearance | Cancer | an an antibody-like binder to EpCam | a circulating tumor cell |
| Cell clearance | Cancer | an an antibody-like binder to Her2 | a circulating tumor cell |
| Cell clearance | Cancer | an an antibody-like binder to EGFR | a circulating tumor cell |
| Cell clearance | Cancer (B cell) | an an antibody-like binder to CD20 | a cancerous B cell |
| Cell clearance | Cancer (B cell) | an an antibody-like binder to CD19 | a cancerous B cell |
| Clearance Ab | Antiphospholipid syndrome | beta2-glycoprotein-1 | pathogenic self-antibody against beta2-glycoprotein-1 |
| Clearance Ab | Catastrophic antiphospholipid syndrome | beta2-glycoprotein-1 | pathogenic self-antibody against beta2-glycoprotein-1 |
| Clearance Ab | Cold agglutinin disease | I/i antigen | Pathogenic self-antibody against I/i antigen |
| Clearance Ab | Goodpasture syndrome | a3 NC1 domain of collagen (IV) | pathogenic self-antibody against a3 NC1 domain of Collagen (IV) |
| Clearance Ab | Immune thrombocytopenia purpura | Platelet Glycoproteins (Ib-IX, IIb-IIIa, IV, Ia-IIa) | pathogenic self-antibody against platelet glycoprotein |
| Clearance Ab | Membranous Nephropathy | Phospholipase A2 receptor | pathogenic self-antibody against phospholipase A2 receptor |
| Clearance Ab | Warm antibody hemolytic anemia | Glycophorin A, glycophorin B, and/or glycophorin C, Rh antigen | pathogenic self-antibody against glycophorins and/or Rh antigen |
| Complement | Age-related macular degeneration | a suitable complement regulatory protein | active complement |
| Complement | Atypical hemolytic uremic syndrome | complement factor H, or a suitable complement regulatory protein | active complement |

TABLE 7-continued

Selected Diseases, Exogenous antigens and Targets

| Category | Disease | Exogenous antigen | Target |
|---|---|---|---|
| Complement | Autoimmune hemolytic anemia | a suitable complement regulatory molecule | active complement |
| Complement | Complement Factor I deficiency | Complement factor I, a suitable complement regulatory protein | active complement |
| Complement | Non-alcoholic steatohepatitis | a suitable complement regulatory molecule | active complement |
| Complement | Paroxysmal nocturnal hemoglobinuria | a suitable complement regulatory protein | active complement |
| Enzyme | 3-methylcrotonyl-CoA carboxylase deficiency | 3-methylcrotonyl-CoA carboxylase | 3-hydroxyvalerylcarnitine, 3-methylcrotonylglycine (3-MCG) and 3-hydroxyisovaleric acid (3-HIVA) |
| Enzyme | Acute Intermittent Porphyria | Porphobilinogen deaminase | Porphobilinogen |
| Enzyme | Acute lymphoblastic leukemia | Asparaginase | Asparagine |
| Enzyme | Acute lymphocytic leukemia, acute myeloid leukemia | Asparaginase | Asparagine |
| Enzyme | Acute myeloblastic leukemia | Asparaginase | Asparagine |
| Enzyme | Adenine phosphoribosyltransferase deficiency | adenine phosphoribosyltransferase | Insoluble purine 2,8-dihydroxyadenine |
| Enzyme | Adenosine deaminase deficiency | Adenosine deaminase | Adenosine |
| Enzyme | Afibrinogenomia | FI | enzyme replacement |
| Enzyme | Alcohol poisoning | Alcohol dehydrogenase/oxidase | Ethanol |
| Enzyme | Alexander's disease | FVII | enzyme replacement |
| Enzyme | Alkaptonuria | homogentisate oxidase | homogentisate |
| Enzyme | Argininemia | Ammonia monooxygenase | ammonia |
| Enzyme | argininosuccinate aciduria | Ammonia monooxygenase | ammonia |
| Enzyme | citrullinemia type I | Ammonia monooxygenase | ammonia |
| Enzyme | Citrullinemia type II | Ammonia monooxygenase | ammonia |
| Enzyme | Complete LCAT deficiency, Fish-eye disease, atherosclerosis, hypercholesterolemia | Lecithin-cholesterol acyltransferase (LCAT) | Cholesterol |
| Enzyme | Cyanide poisoning | Thiosulfate-cyanide sulfurtransferase | Cyanide |
| Enzyme | Diabetes | Hexokinase, glucokinase | Glucose |
| Enzyme | Factor II Deficiency | FII | enzyme replacement |
| Enzyme | Familial hyperarginemia | Arginase | Arginine |
| Enzyme | Fibrin Stabilizing factor Def. | FXIII | enzyme replacement |
| Enzyme | Glutaric acidemia type I | lysine oxidase | 3-hydroxyglutaric and glutaric acid (C5-DC), lysine |
| Enzyme | Gout | Uricase | Uric Acid |
| Enzyme | Gout - hyperuricemia | Uricase | Uric acid (Urate crystals) |
| Enzyme | Hageman Def. | FXII | enzyme replacement |
| Enzyme | Hemolytic anemia due to pyrimidine 5' nucleotidase deficiency | pyrimidine 5' nucleotidase | pyrimidines |
| Enzyme | Hemophilia A | Factor VIII | Thrombin (factor II a) or Factor X |
| Enzyme | Hemophilia B | Factor IX | Factor XIa or Factor X |
| Enzyme | Hemophilia C | FXI | enzyme replacement |
| Enzyme | Hepatocellular carcinoma, melanoma | Arginine deiminase | Arginine |
| Enzyme | Homocystinuria | Cystathionine B synthase | homocysteine |
| Enzyme | hyperammonemia/ornithinemia/citrullinemia (ornithine transporter defect) | Ammonia monooxygenase | Ammonia |
| Enzyme | Isovaleric acidemia | Leucine metabolizing enzyme | leucine |
| Enzyme | Lead poisoning | d-aminolevulinate dehydrogenase | lead |
| Enzyme | Lesch-Nyhan syndrome | Uricase | Uric acid |
| Enzyme | Maple syrup urine disease | Leucine metabolizing enzyme | Leucine |
| Enzyme | Methylmalonic acidemia (vitamin b12 non-responsive) | methylmalonyl-CoA mutase | methylmalonate |
| Enzyme | Mitochondrial neurogastrointestinal encephalomyopathy | thymidine phosphorylase | thymidine |
| Enzyme | Mitochondrial neurogastrointestinal encephalomyopathy (MNGIE) | Thymidine phosphorylase | Thymidine |
| Enzyme | Owren's disease | FV | enzyme replacement |
| Enzyme | p53-null solid tumor | Serine dehyrdatase or serine hydroxymethyl transferase | serine |
| Enzyme | Pancreatic adenocarcinoma | Asparaginase | asparagine |
| Enzyme | Phenylketonuria | Phenylalanine hydroxylase, phenylalanine ammonia lyase | Phenylalanine |
| Enzyme | Primary hyperoxaluria | Oxalate oxidase | Oxalate |
| Enzyme | Propionic acidemia | Propionate conversion enzyme? | Proprionyl coA |
| Enzyme | Purine nucleoside phosphorylase deficiency | Purine nucleoside phosphorylase | Inosine, dGTP |

TABLE 7-continued

Selected Diseases, Exogenous antigens and Targets

| Category | Disease | Exogenous antigen | Target |
|---|---|---|---|
| Enzyme | Stuart-Power Def. | FX | enzyme replacement |
| Enzyme | Thrombotic Thrombocytopenic Purpura | ADAMTS13 | ultra-large von willebrand factor (ULVWF) |
| Enzyme | Transferase deficient galactosemia (Galactosemia type 1) | galactose dehydrogenase | Galactose-1-phosphate |
| Enzyme | Tyrosinemia type 1 | tyrosine phenol-lyase | tyrosine |
| Enzyme | von Willebrand disease | vWF | enzyme replacement |
| IC clearance | IgA Nephropathy | Complement receptor 1 | Immune complexes |
| IC clearance | Lupus nephritis | Complement receptor 1 | immune complex |
| IC clearance | Systemic lupus erythematosus | Complement receptor 1 | immune complex |
| Infectious | Anthrax (*B. anthracis*) infection | an an antibody-like binder to *B. anthracis* surface protein | *B. anthracis* |
| Infectious | *C. botulinum* infection | an an antibody-like binder to *C. botulinum* surface protein | *C. botulinum* |
| Infectious | *C. difficile* infection | an antibody-like binder to *C. difficile* surface protein | *C. difficile* |
| Infectious | *Candida* infection | an antibody-like binder to *candida* surface protein | *candida* |
| Infectious | *E. coli* infection | an antibody-like binder to *E. coli* surface protein | *E. coli* |
| Infectious | Ebola infection | an antibody-like binder to Ebola surface protein | Ebola |
| Infectious | Hepatitis B (HBV) infection | an antibody-like binder to HBV surface protein | HBV |
| Infectious | Hepatitis C (HCV) infection | an antibody-like binder to HCV surface protein | HCV |
| Infectious | Human immunodeficiency virus (HIV) infection | an antibody-like binder to HIV envelope proteins or CD4 or CCR5 or | HIV |
| Infectious | *M. tuberculosis* infection | an antibody-like binder to *M. tuberculosis* surface protein | *M. tuberculosis* |
| Infectious | Malaria (*P. falciparum*) infection | an antibody-like binder to *P. falciparum* surface protein | *P. falciparum* |
| Lipid | Hepatic lipase deficiency, hypercholesterolemia | Hepatic lipase (LIPC) | Lipoprotein, intermediate density (IDL) |
| Lipid | Hyperalphalipoproteinemia 1 | Cholesteryl ester transfer protein(CETP) | Lipoprotein, high density (HDL) |
| Lipid | hypercholesterolemia | an antibody-like binder to low-density lipoprotein (LDL), LDL receptor | LDL |
| Lipid | hypercholesterolemia | an antibody-like binder to high-density lipoprotein (HDL) or HDL receptor | HDL |
| Lipid | lipoprotein lipase deficiency | lipoprotein lipase | chilomicrons and very low density lipoproteins (VLDL) |
| Lipid | Lipoprotein lipase deficiency, disorders of lipoprotein metabolism | lipoprotein lipase (LPL) | Lipoprotein, very low density (VLDL) |
| Lysosomal storage | Aspartylglucosaminuria (208400) | N-Aspartylglucosaminidase | glycoproteins |
| Lysosomal storage | Cerebrotendinous xanthomatosis (cholestanol lipidosis; 213700) | Sterol 27-hydroxylase | lipids, cholesterol, and bile acid |
| Lysosomal storage | Ceroid lipofuscinosis Adult form (CLN4, Kufs' disease; 204300) | Palmitoyl-protein thioesterase-1 | lipopigments |
| Lysosomal storage | Ceroid lipofuscinosis Infantile form (CLN1, Santavuori-Haltia disease; 256730) | Palmitoyl-protein thioesterase-1 | lipopigments |
| Lysosomal storage | Ceroid lipofuscinosis Juvenile form (CLN3, Batten disease, Vogt-Spielmeyer disease; 204200) | Lysosomal transmembrane CLN3 protein | lipopigments |
| Lysosomal storage | Ceroid lipofuscinosis Late infantile form (CLN2, Jansky-Bielschowsky disease; 204500) | Lysosomal pepstatin-insensitive peptidase | lipopigments |
| Lysosomal storage | Ceroid lipofuscinosis Progressive epilepsy with intellectual disability (600143) | Transmembrane CLN8 protein | lipopigments |
| Lysosomal storage | Ceroid lipofuscinosis Variant late infantile form (CLN6; 601780) | Transmembrane CLN6 protein | lipopigments |
| Lysosomal storage | Ceroid lipofuscinosis Variant late infantile form, Finnish type (CLN5; 256731) | Lysosomal transmembrane CLN5 protein | lipopigments |
| Lysosomal storage | Cholesteryl ester storage disease (CESD) | lisosomal acid lipase | lipids and cholesterol |
| Lysosomal storage | Congenital disorders of N-glycosylation CDG Ia (solely neurologic and neurologic-multivisceral forms; 212065) | Phosphomannomutase-2 | N-glycosylated protein |
| Lysosomal storage | Congenital disorders of N-glycosylation CDG Ib (602579) | Mannose (Man) phosphate (P) isomerase | N-glycosylated protein |

TABLE 7-continued

Selected Diseases, Exogenous antigens and Targets

| Category | Disease | Exogenous antigen | Target |
|---|---|---|---|
| Lysosomal storage | Congenital disorders of N-glycosylation CDG Ic (603147) | Dolicho-P-Glc: Man9GlcNAc2-PP-dolichol glucosyltransferase | N-glycosylated protein |
| Lysosomal storage | Congenital disorders of N-glycosylation CDG Id (601110) | Dolicho-P-Man: Man5GlcNAc2-PP-dolichol mannosyltransferase | N-glycosylated protein |
| Lysosomal storage | Congenital disorders of N-glycosylation CDG Ie (608799) | Dolichol-P-mannose synthase | N-glycosylated protein |
| Lysosomal storage | Congenital disorders of N-glycosylation CDG If (609180) | Protein involved in mannose-P-dolichol utilization | N-glycosylated protein |
| Lysosomal storage | Congenital disorders of N-glycosylation CDG Ig (607143) | Dolichyl-P-mannose: Man-7-GlcNAc-2-PP-dolichyl-α-6-mannosyltransferase | N-glycosylated protein |
| Lysosomal storage | Congenital disorders of N-glycosylation CDG Ih (608104) | Dolichyl-P-glucose: Glc-1-Man-9-GlcNAc-2-PP-dolichyl-α-3-glucosyltransferase | N-glycosylated protein |
| Lysosomal storage | Congenital disorders of N-glycosylation CDG Ii (607906) | α-1,3-Mannosyltransferase | N-glycosylated protein |
| Lysosomal storage | Congenital disorders of N-glycosylation CDG IIa (212066) | Mannosyl-α-1,6-glycoprotein-β-1,2-N-acetylglucosminyltransferase | N-glycosylated protein |
| Lysosomal storage | Congenital disorders of N-glycosylation CDG IIb (606056) | Glucosidase I | N-glycosylated protein |
| Lysosomal storage | Congenital disorders of N-glycosylation CDG IIc (Rambam-Hasharon syndrome; 266265 | GDP-fucose transporter-1 | N-glycosylated protein |
| Lysosomal storage | Congenital disorders of N-glycosylation CDG IId (607091) | β-1,4-Galactosyltransferase | N-glycosylated protein |
| Lysosomal storage | Congenital disorders of N-glycosylation CDG IIe (608779) | Oligomeric Golgi complex-7 | N-glycosylated protein |
| Lysosomal storage | Congenital disorders of N-glycosylation CDG Ij (608093) | UDP-GlcNAc: dolichyl-P NAcGlc phosphotransferase | N-glycosylated protein |
| Lysosomal storage | Congenital disorders of N-glycosylation CDG Ik (608540) | β-1,4-Mannosyltransferase | N-glycosylated protein |
| Lysosomal storage | Congenital disorders of N-glycosylation CDG Il (608776) | α-1,2-Mannosyltransferase | N-glycosylated protein |
| Lysosomal storage | Congenital disorders of N-glycosylation, type I (pre-Golgi glycosylation defects) | α-1,2-Mannosyltransferase | N-glycosylated protein |
| Lysosomal storage | Cystinosis | Cystinosin (lysosomal cystine transporter) | Cysteine |
| Lysosomal storage | Fabry's disease (301500) | Trihexosylceramide α-galactosidase | globotriaosylceramide |
| Lysosomal storage | Farber's disease (lipogranulomatosis; 228000) | Ceramidase | lipids |
| Lysosomal storage | Fucosidosis (230000) | α-L-Fucosidase | fucose and complex sugars |
| Lysosomal storage | Galactosialidosis (Goldberg's syndrome, combined neuraminidase and β-galactosidase deficiency; 256540) | Protective protein/cathepsin A (PPCA) | lysosomal content |
| Lysosomal storage | Gaucher's disease | Glucosylceramide β-glucosidase | sphingolipids |
| Lysosomal storage | Glutamyl ribose-5-phosphate storage disease (305920) | ADP-ribose protein hydrolase | glutamyl ribose 5-phosphate |
| Lysosomal storage | Glycogen storage disease type 2 (Pompe's disease) | alpha glucosidase | glycogen |
| Lysosomal storage | GM1 gangliosidosis, generalized | Ganglioside β-galactosidase | acidic lipid material, gangliosides |
| Lysosomal storage | GM2 activator protein deficiency (Tay-Sachs disease AB variant, GM2A; 272750) | GM2 activator protein | gangliosides |
| Lysosomal storage | GM2 gangliosidosis | Ganglioside β-galactosidase | gangliosides |
| Lysosomal storage | Infantile sialic acid storage disorder (269920) | Na phosphate cotransporter, sialin | sialic acid |
| Lysosomal storage | Krabbe's disease (245200) | Galactosylceramide β-galactosidase | sphingolipids |
| Lysosomal storage | Lysosomal acid lipase deficiency (278000) | Lysosomal acid lipase | cholesteryl esters and triglycerides |
| Lysosomal storage | Metachromatic leukodystrophy (250100) | Arylsulfatase A | sulfatides |
| Lysosomal storage | Mucolipidosis ML II (I-cell disease; 252500) | N-Acetylglucosaminyl-1-phosphotransfeerase catalytic subunit | N-linked glycoproteins |
| Lysosomal storage | Mucolipidosis ML III (pseudo-Hurler's polydystrophy) | N-acetylglucosaminyl-1-phosphotransfeerase | N-linked glycoproteins |
| Lysosomal storage | Mucolipidosis ML III (pseudo-Hurler's polydystrophy) Type III-A (252600) | Catalytic subunit | N-linked glycoproteins |
| Lysosomal storage | Mucolipidosis ML III (pseudo-Hurler's polydystrophy) Type III-C (252605) | Substrate-recognition subunit | N-linked glycoproteins |
| Lysosomal storage | Mucopolysaccharidosis MPS I H/S (Hurler-Scheie syndrome; 607015) | α-I-Iduronidase | glycosaminoglycans |
| Lysosomal storage | Mucopolysaccharidosis MPS I-H (Hurler's syndrome; 607014) | α-I-Iduronidase | glycosaminoglycans |

TABLE 7-continued

Selected Diseases, Exogenous antigens and Targets

| Category | Disease | Exogenous antigen | Target |
|---|---|---|---|
| Lysosomal storage | Mucopolysaccharidosis MPS II (Hunter's syndrome; 309900) | Iduronate sulfate sulfatase | glycosaminoglycans |
| Lysosomal storage | Mucopolysaccharidosis MPS III (Sanfilippo's syndrome) Type III-A (252900) | Heparan-S-sulfate sulfamidase | glycosaminoglycans |
| Lysosomal storage | Mucopolysaccharidosis MPS III (Sanfilippo's syndrome) Type III-B (252920) | N-acetyl-D-glucosaminidase | glycosaminoglycans |
| Lysosomal storage | Mucopolysaccharidosis MPS III (Sanfilippo's syndrome) Type III-C (252930) | Acetyl-CoA-glucosaminide N-acetyltransferase | glycosaminoglycans |
| Lysosomal storage | Mucopolysaccharidosis MPS III (Sanfilippo's syndrome) Type III-D (252940) | N-acetyl-glucosaminine-6-sulfate sulfatase | glycosaminoglycans |
| Lysosomal storage | Mucopolysaccharidosis MPS I-S (Scheie's syndrome; 607016) | α-I-Iduronidase | glycosaminoglycans |
| Lysosomal storage | Mucopolysaccharidosis MPS IV (Morquio's syndrome) Type IV-A (253000) | Galactosamine-6-sulfate sulfatase | glycosaminoglycans |
| Lysosomal storage | Mucopolysaccharidosis MPS IV (Morquio's syndrome) Type IV-B (253010) | β-Galactosidase | glycosaminoglycans |
| Lysosomal storage | Mucopolysaccharidosis MPS IX (hyaluronidase deficiency; 601492) | Hyaluronidase deficiency | glycosaminoglycans |
| Lysosomal storage | Mucopolysaccharidosis MPS VI (Maroteaux-Lamy syndrome; 253200) | N-Acetyl galactosamine α-4-sulfate sulfatase (arylsulfatase B) | glycosaminoglycans |
| Lysosomal storage | Mucopolysaccharidosis MPS VII (Sly's syndrome; 253220) | β-Glucuronidase | glycosaminoglycans |
| Lysosomal storage | Mucosulfatidosis (multiple sulfatase deficiency; 272200) | Sulfatase-modifying factor-1 | sulfatides |
| Lysosomal storage | Niemann-Pick disease type A | Sphingomyelinase | sphingomyelin |
| Lysosomal storage | Niemann-Pick disease type B | Sphingomyelinase | sphingomyelin |
| Lysosomal storage | Niemann-Pick disease Type C1/Type D ((257220) | NPC1 protein | sphingomyelin |
| Lysosomal storage | Niemann-Pick disease Type C2 (607625) | Epididymal secretory protein 1 (HE1; NPC2 protein) | sphingomyelin |
| Lysosomal storage | Prosaposin deficiency (176801) | Prosaposin | sphingolipids |
| Lysosomal storage | Pycnodysostosis (265800) | Cathepsin K | kinins |
| Lysosomal storage | Sandhoff's disease; 268800 | β-Hexosaminidase B | gangliosides |
| Lysosomal storage | Saposin B deficiency (sulfatide activator deficiency) | Saposin B | sphingolipids |
| Lysosomal storage | Saposin C deficiency (Gaucher's activator deficiency) | Saposin C | sphingolipids |
| Lysosomal storage | Schindler's disease Type I (infantile severe form; 609241) | N-Acetyl-galactosaminidase | glycoproteins |
| Lysosomal storage | Schindler's disease Type II (Kanzaki disease, adult-onset form; 609242) | N-Acetyl-galactosaminidase | glycoproteins |
| Lysosomal storage | Schindler's disease Type III (intermediate form; 609241) | N-Acetyl-galactosaminidase | glycoproteins |
| Lysosomal storage | Sialidosis (256550) | Neuraminidase 1 (sialidase) | mucopolysaccharides and mucolipids |
| Lysosomal storage | Sialuria Finnish type (Salla disease; 604369) | Na phosphate cotransporter, sialin | sialic acid |
| Lysosomal storage | Sialuria French type (269921) | UDP-N-acetylglucosamine-2-epimerase/N-acetylmannosamine kinase, sialin | sialic acid |
| Lysosomal storage | Sphingolipidosis Type I (230500) | Ganglioside β-galactosidase | sphingolipids |
| Lysosomal storage | Sphingolipidosis Type II (juvenile type; 230600) | Ganglioside β-galactosidase | sphingolipids |
| Lysosomal storage | Sphingolipidosis Type III (adult type; 230650) | Ganglioside β-galactosidase | sphingolipids |
| Lysosomal storage | Tay-Sachs disease; 272800 | β-Hexosaminidase A | gangliosides |
| Lysosomal storage | Winchester syndrome (277950) | Metalloproteinase-2 | mucopolysaccharides |
| Lysosomal storage | Wolman's disease | lysosomal acid lipase | lipids and cholesterol |
| Lysosomal storage | α-Mannosidosis (248500), type I (severe) or II (mild) | α-D-Mannosidase | carbohydrates and glycoproteins |
| Lysosomal storage | β-Mannosidosis (248510) | β-D-Mannosidase | carbohydrates and glycoproteins |
| Toxic Molecule | alpha hemolysin poisoning | an antibody-like binder to alpha hemolysin | alpha hemolysin |
| Toxic Molecule | antrax toxin poisoning | an antibody-like binder to anthrax toxin | anthrax toxin |
| Toxic Molecule | bacterial toxin-induced shock | an antibody-like binder to bacterial toxin | bacterial toxin |
| Toxic Molecule | botulinum toxin poisoning | an antibody-like binder to botulinum toxin | botulinum toxin |
| Toxic Molecule | Hemochromatosis (iron poisoning) | iron chelator | molecular iron |

TABLE 7-continued

Selected Diseases, Exogenous antigens and Targets

| Category | Disease | Exogenous antigen | Target |
|---|---|---|---|
| Toxic Molecule | Methanol poisoning | Methanol dehdrogenase | Methanol |
| Toxic Molecule | Nerve gas poisoning | Butyryl cholinesterase | Sarin |
| Toxic Molecule | Prion disease caused by PRP | an antibody-like binder to prion protein PRP | Prion protein PRP |
| Toxic Molecule | Prion disease caused by PRPc | an antibody-like binder to prion protein PRPc | Prion protein PRPc |
| Toxic Molecule | Prion disease caused by PRPsc | an antibody-like binder to prion protein PRPsc | Prion protein PRPsc |
| Toxic Molecule | Prion disease cuased by PRPres | an antibody-like binder to prion protein PRPres | Prion protein PRPres |
| Toxic Molecule | Sepsis or cytokine storm | an antibody-like binder to cytokines or Duffy antigen receptor of chemokines (DARC) | cytokines |
| Toxic Molecule | spider venom poisoning | an antibody-like binder to spider venom | spider venom |
| Toxic Molecule | Wilson disease | copper chelator | molecular copper |

TABLE 8

Complement & Complement Regulatory Molecules
Soluble molecules

Alternative Pathway

Factor B
Factor D
Properdin
C3
C3a
C3b
iC3b
C3c
C3dg
C3dk
C3e
Bb
Factor I

Classical Pathway

C1q
C1r
C1s
C4
C4a
C4b
C2
C4bp

Lectin Pathway

Mannose-Binding Lectin (MBL)
MBL-Associated Serine Protease 1 (MASP1)
MBL-Associated Serine Protease 2 (MASP2)

TABLE 8-continued

Complement & Complement Regulatory Molecules
Soluble molecules

Late Components

C5
C5a
C6
C7
C8
C9

Receptors

CR1
CR2
CR3
CR4
C3aR
C3eR
Decay-accelerating factor (DAF)
Membrane cofactor protein (MCP)
CD59
C3 Beta chain Receptor
Homologous restriction factor

Control Proteins

C1 inhibitor
C4 binding protein
Factor I
Factor H

---

What is claimed is:

1. A method of inducing immune tolerance in a human subject suffering from immune activation in response to an antigen that mediates an autoimmune disease, the method comprising: administering to the human subject a pharmaceutical composition comprising an enucleated erythroid cell comprising at least 1,000 copies of an exogenous fusion polypeptide comprising the antigen, or an antigenic fragment thereof, fused to an intracellular domain of a transmembrane protein, wherein:
   the antigen, or the antigenic fragment thereof, is localized on the intracellular side of the enucleated erythroid cell,
   the exogenous fusion polypeptide does not comprise a ligand-binding domain,
   the exogenous fusion polypeptide was expressed from a transgene introduced into a nucleated erythroid cell precursor used to generate the enucleated erythroid cell,
   the enucleated erythroid cell is not a hypotonically dialysed cell; and
   the pharmaceutical composition is administered in an amount and frequency sufficient to mediate the induction of the immune tolerance in the subject.

2. The method of claim 1, wherein the enucleated erythroid cell comprises at least 10,000 copies of the antigen.

3. The method of claim 1, wherein the antigen is selected from the group consisting of: insulin, proinsulin, preproinsulin, GAD65, IA-2, myelin oligodendrocyte glycoprotein, myelin basic protein, and proteolipid protein, or an antigenic fragment thereof.

4. The method of claim 1, wherein the enucleated erythroid cell is a reticulocyte.

5. The method of claim 1, wherein the pharmaceutical composition comprises a population of erythroid cells that is greater than 60% enucleated.

6. The method of claim 1, wherein the enucleated erythroid cell is an erythrocyte.

7. The method of claim 1, wherein the antigen is a viral capsid protein, or an antigenic fragment thereof.

8. The method of claim 1, wherein the antigen is insulin or an antigenic fragment thereof.

9. The method of claim 1, wherein the antigen is proinsulin or an antigenic fragment thereof.

10. The method of claim 1, wherein the antigen is preproinsulin or an antigenic fragment thereof.

11. The method of claim 1, wherein the antigen is GAD65 or an antigenic fragment thereof.

12. A method of inducing immune tolerance in a human subject suffering from immune activation in response to an antigen that mediates an autoimmune disease, the method comprising administering to the human subject a pharmaceutical composition comprising a population of enucleated erythroid cells that comprise an exogenous fusion polypeptide comprising the antigen, or an antigenic fragment thereof, fused to an intracellular domain of a transmembrane protein, wherein:
   the antigen, or the antigenic fragment thereof, is localized on the intracellular side of the enucleated erythroid cells;
   the exogenous fusion polypeptide does not comprise a ligand-binding domain;
   the exogenous fusion polypeptide was expressed from a transgene introduced into a nucleated erythroid cell precursor used to generate the population of enucleated erythroid cells;

the enucleated erythroid cells are not hypotonically dialysed cells;

the pharmaceutical composition comprises a population of erythroid cells that is greater than 70% enucleated; and the pharmaceutical composition is administered in an amount and frequency to mediate the induction of the immune tolerance in the subject.

13. The method of claim 12, wherein the antigen is selected from the group consisting of: insulin, proinsulin, preproinsulin, GAD65, IA-2, myelin oligodendrocyte glycoprotein, myelin basic protein, and proteolipid protein, or an antigenic fragment thereof.

14. The method of claim 12, wherein the antigen is a viral capsid protein, or an antigenic fragment thereof.

15. The method of claim 12, wherein the antigen is insulin or an antigenic fragment thereof.

16. The method of claim 12, wherein the antigen is proinsulin or an antigenic fragment thereof.

17. The method of claim 12, wherein the antigen is preproinsulin or an antigenic fragment thereof.

18. The method of claim 12, wherein the antigen is GAD65 or an antigenic fragment thereof.

* * * * *

SEQUENCE LISTING

<160> NUMBER OF SEQ ID NOS: 30

<210> SEQ ID NO 1
<211> LENGTH: 2489
<212> TYPE: PRT
<213> ORGANISM: Homo sapiens

<400> SEQUENCE: 1

Met Gly Ala Ser Ser Pro Arg Ser Pro Glu Pro Val Gly Pro Pro Ala
1               5                   10                  15

Pro Gly Leu Pro Phe Cys Cys Gly Gly Ser Leu Leu Ala Val Val Val
            20                  25                  30

Leu Leu Ala Leu Pro Val Ala Trp Gly Gln Cys Asn Ala Pro Glu Trp

```
            35                  40                  45
Leu Pro Phe Ala Arg Pro Thr Asn Leu Thr Asp Glu Phe Glu Phe Pro
 50                  55                  60

Ile Gly Thr Tyr Leu Asn Tyr Glu Cys Arg Pro Gly Tyr Ser Gly Arg
 65                  70                  75                  80

Pro Phe Ser Ile Ile Cys Leu Lys Asn Ser Val Trp Thr Gly Ala Lys
                 85                  90                  95

Asp Arg Cys Arg Arg Lys Ser Cys Arg Asn Pro Pro Asp Pro Val Asn
            100                 105                 110

Gly Met Val His Val Ile Lys Gly Ile Gln Phe Gly Ser Gln Ile Lys
            115                 120                 125

Tyr Ser Cys Thr Lys Gly Tyr Arg Leu Ile Gly Ser Ser Ser Ala Thr
            130                 135                 140

Cys Ile Ile Ser Gly Asp Thr Val Ile Trp Asp Asn Glu Thr Pro Ile
145                 150                 155                 160

Cys Asp Arg Ile Pro Cys Gly Leu Pro Pro Thr Ile Thr Asn Gly Asp
                165                 170                 175

Phe Ile Ser Thr Asn Arg Glu Asn Phe His Tyr Gly Ser Val Val Thr
                180                 185                 190

Tyr Arg Cys Asn Pro Gly Ser Gly Gly Arg Lys Val Phe Glu Leu Val
            195                 200                 205

Gly Glu Pro Ser Ile Tyr Cys Thr Ser Asn Asp Asp Gln Val Gly Ile
210                 215                 220

Trp Ser Gly Pro Ala Pro Gln Cys Ile Ile Pro Asn Lys Cys Thr Pro
225                 230                 235                 240

Pro Asn Val Glu Asn Gly Ile Leu Val Ser Asp Asn Arg Ser Leu Phe
                245                 250                 255

Ser Leu Asn Glu Val Val Glu Phe Arg Cys Gln Pro Gly Phe Val Met
                260                 265                 270

Lys Gly Pro Arg Arg Val Lys Cys Gln Ala Leu Asn Lys Trp Glu Pro
            275                 280                 285

Glu Leu Pro Ser Cys Ser Arg Val Cys Gln Pro Pro Pro Asp Val Leu
            290                 295                 300

His Ala Glu Arg Thr Gln Arg Asp Lys Asp Asn Phe Ser Pro Gly Gln
305                 310                 315                 320

Glu Val Phe Tyr Ser Cys Glu Pro Gly Tyr Asp Leu Arg Gly Ala Ala
                325                 330                 335

Ser Met Arg Cys Thr Pro Gln Gly Asp Trp Ser Pro Ala Ala Pro Thr
            340                 345                 350

Cys Glu Val Lys Ser Cys Asp Asp Phe Met Gly Gln Leu Leu Asn Gly
            355                 360                 365

Arg Val Leu Phe Pro Val Asn Leu Gln Leu Gly Ala Lys Val Asp Phe
            370                 375                 380

Val Cys Asp Glu Gly Phe Gln Leu Lys Gly Ser Ser Ala Ser Tyr Cys
385                 390                 395                 400

Val Leu Ala Gly Met Glu Ser Leu Trp Asn Ser Ser Val Pro Val Cys
                405                 410                 415

Glu Gln Ile Phe Cys Pro Ser Pro Val Ile Pro Asn Gly Arg His
                420                 425                 430

Thr Gly Lys Pro Leu Glu Val Phe Pro Phe Gly Lys Thr Val Asn Tyr
            435                 440                 445

Thr Cys Asp Pro His Pro Asp Arg Gly Thr Ser Phe Asp Leu Ile Gly
            450                 455                 460
```

-continued

```
Glu Ser Thr Ile Arg Cys Thr Ser Asp Pro Gln Gly Asn Gly Val Trp
465                 470                 475                 480

Ser Ser Pro Ala Pro Arg Cys Gly Ile Leu Gly His Cys Gln Ala Pro
            485                 490                 495

Asp His Phe Leu Phe Ala Lys Leu Lys Thr Gln Thr Asn Ala Ser Asp
        500                 505                 510

Phe Pro Ile Gly Thr Ser Leu Lys Tyr Glu Cys Arg Pro Glu Tyr Tyr
            515                 520                 525

Gly Arg Pro Phe Ser Ile Thr Cys Leu Asp Asn Leu Val Trp Ser Ser
        530                 535                 540

Pro Lys Asp Val Cys Lys Arg Lys Ser Cys Lys Thr Pro Pro Asp Pro
545                 550                 555                 560

Val Asn Gly Met Val His Val Ile Thr Asp Ile Gln Val Gly Ser Arg
            565                 570                 575

Ile Asn Tyr Ser Cys Thr Thr Gly His Arg Leu Ile Gly His Ser Ser
        580                 585                 590

Ala Glu Cys Ile Leu Ser Gly Asn Ala Ala His Trp Ser Thr Lys Pro
        595                 600                 605

Pro Ile Cys Gln Arg Ile Pro Cys Gly Leu Pro Pro Thr Ile Ala Asn
        610                 615                 620

Gly Asp Phe Ile Ser Thr Asn Arg Glu Asn Phe His Tyr Gly Ser Val
625                 630                 635                 640

Val Thr Tyr Arg Cys Asn Pro Gly Ser Gly Gly Arg Lys Val Phe Glu
            645                 650                 655

Leu Val Gly Glu Pro Ser Ile Tyr Cys Thr Ser Asn Asp Asp Gln Val
            660                 665                 670

Gly Ile Trp Ser Gly Pro Ala Pro Gln Cys Ile Ile Pro Asn Lys Cys
        675                 680                 685

Thr Pro Pro Asn Val Glu Asn Gly Ile Leu Val Ser Asp Asn Arg Ser
        690                 695                 700

Leu Phe Ser Leu Asn Glu Val Val Glu Phe Arg Cys Gln Pro Gly Phe
705                 710                 715                 720

Val Met Lys Gly Pro Arg Arg Val Lys Cys Gln Ala Leu Asn Lys Trp
            725                 730                 735

Glu Pro Glu Leu Pro Ser Cys Ser Arg Val Cys Gln Pro Pro Pro Asp
            740                 745                 750

Val Leu His Ala Glu Arg Thr Gln Arg Asp Lys Asp Asn Phe Ser Pro
        755                 760                 765

Gly Gln Glu Val Phe Tyr Ser Cys Glu Pro Gly Tyr Asp Leu Arg Gly
        770                 775                 780

Ala Ala Ser Met Arg Cys Thr Pro Gln Gly Asp Trp Ser Pro Ala Ala
785                 790                 795                 800

Pro Thr Cys Glu Val Lys Ser Cys Asp Asp Phe Met Gly Gln Leu Leu
            805                 810                 815

Asn Gly Arg Val Leu Phe Pro Val Asn Leu Gln Leu Gly Ala Lys Val
            820                 825                 830

Asp Phe Val Cys Asp Glu Gly Phe Gln Leu Lys Gly Ser Ser Ala Ser
        835                 840                 845

Tyr Cys Val Leu Ala Gly Met Glu Ser Leu Trp Asn Ser Ser Val Pro
        850                 855                 860

Val Cys Glu Gln Ile Phe Cys Pro Ser Pro Pro Val Ile Pro Asn Gly
865                 870                 875                 880
```

-continued

```
Arg His Thr Gly Lys Pro Leu Glu Val Phe Pro Gly Lys Thr Val
                885                 890                 895

Asn Tyr Thr Cys Asp Pro His Pro Asp Arg Gly Thr Ser Phe Asp Leu
                900                 905                 910

Ile Gly Glu Ser Thr Ile Arg Cys Thr Ser Asp Pro Gln Gly Asn Gly
            915                 920                 925

Val Trp Ser Ser Pro Ala Pro Arg Cys Gly Ile Leu Gly His Cys Gln
            930                 935                 940

Ala Pro Asp His Phe Leu Phe Ala Lys Leu Lys Thr Gln Thr Asn Ala
945                 950                 955                 960

Ser Asp Phe Pro Ile Gly Thr Ser Leu Lys Tyr Glu Cys Arg Pro Glu
                965                 970                 975

Tyr Tyr Gly Arg Pro Phe Ser Ile Thr Cys Leu Asp Asn Leu Val Trp
                980                 985                 990

Ser Ser Pro Lys Asp Val Cys Lys Arg Lys Ser Cys Lys Thr Pro Pro
                995                 1000                1005

Asp Pro Val Asn Gly Met Val His Val Ile Thr Asp Ile Gln Val
            1010                1015                1020

Gly Ser Arg Ile Asn Tyr Ser Cys Thr Thr Gly His Arg Leu Ile
            1025                1030                1035

Gly His Ser Ser Ala Glu Cys Ile Leu Ser Gly Asn Ala Ala His
            1040                1045                1050

Trp Ser Thr Lys Pro Pro Ile Cys Gln Arg Ile Pro Cys Gly Leu
            1055                1060                1065

Pro Pro Thr Ile Ala Asn Gly Asp Phe Ile Ser Thr Asn Arg Glu
            1070                1075                1080

Asn Phe His Tyr Gly Ser Val Val Thr Tyr Arg Cys Asn Pro Gly
            1085                1090                1095

Ser Gly Gly Arg Lys Val Phe Glu Leu Val Gly Glu Pro Ser Ile
            1100                1105                1110

Tyr Cys Thr Ser Asn Asp Asp Gln Val Gly Ile Trp Ser Gly Pro
            1115                1120                1125

Ala Pro Gln Cys Ile Ile Pro Asn Lys Cys Thr Pro Pro Asn Val
            1130                1135                1140

Glu Asn Gly Ile Leu Val Ser Asp Asn Arg Ser Leu Phe Ser Leu
            1145                1150                1155

Asn Glu Val Val Glu Phe Arg Cys Gln Pro Gly Phe Val Met Lys
            1160                1165                1170

Gly Pro Arg Arg Val Lys Cys Gln Ala Leu Asn Lys Trp Glu Pro
            1175                1180                1185

Glu Leu Pro Ser Cys Ser Arg Val Cys Gln Pro Pro Pro Asp Val
            1190                1195                1200

Leu His Ala Glu Arg Thr Gln Arg Asp Lys Asp Asn Phe Ser Pro
            1205                1210                1215

Gly Gln Glu Val Phe Tyr Ser Cys Glu Pro Gly Tyr Asp Leu Arg
            1220                1225                1230

Gly Ala Ala Ser Met Arg Cys Thr Pro Gln Gly Asp Trp Ser Pro
            1235                1240                1245

Ala Ala Pro Thr Cys Glu Val Lys Ser Cys Asp Asp Phe Met Gly
            1250                1255                1260

Gln Leu Leu Asn Gly Arg Val Leu Phe Pro Val Asn Leu Gln Leu
            1265                1270                1275

Gly Ala Lys Val Asp Phe Val Cys Asp Glu Gly Phe Gln Leu Lys
```

```
            1280                1285                1290
Gly Ser Ser Ala Ser Tyr Cys Val Leu Ala Gly Met Glu Ser Leu
        1295                1300                1305
Trp Asn Ser Ser Val Pro Val Cys Glu Gln Ile Phe Cys Pro Ser
        1310                1315                1320
Pro Pro Val Ile Pro Asn Gly Arg His Thr Gly Lys Pro Leu Glu
        1325                1330                1335
Val Phe Pro Phe Gly Lys Ala Val Asn Tyr Thr Cys Asp Pro His
        1340                1345                1350
Pro Asp Arg Gly Thr Ser Phe Asp Leu Ile Gly Glu Ser Thr Ile
        1355                1360                1365
Arg Cys Thr Ser Asp Pro Gln Gly Asn Gly Val Trp Ser Ser Pro
        1370                1375                1380
Ala Pro Arg Cys Gly Ile Leu Gly His Cys Gln Ala Pro Asp His
        1385                1390                1395
Phe Leu Phe Ala Lys Leu Lys Thr Gln Thr Asn Ala Ser Asp Phe
        1400                1405                1410
Pro Ile Gly Thr Ser Leu Lys Tyr Glu Cys Arg Pro Glu Tyr Tyr
        1415                1420                1425
Gly Arg Pro Phe Ser Ile Thr Cys Leu Asp Asn Leu Val Trp Ser
        1430                1435                1440
Ser Pro Lys Asp Val Cys Lys Arg Lys Ser Cys Lys Thr Pro Pro
        1445                1450                1455
Asp Pro Val Asn Gly Met Val His Val Ile Thr Asp Ile Gln Val
        1460                1465                1470
Gly Ser Arg Ile Asn Tyr Ser Cys Thr Thr Gly His Arg Leu Ile
        1475                1480                1485
Gly His Ser Ser Ala Glu Cys Ile Leu Ser Gly Asn Thr Ala His
        1490                1495                1500
Trp Ser Thr Lys Pro Pro Ile Cys Gln Arg Ile Pro Cys Gly Leu
        1505                1510                1515
Pro Pro Thr Ile Ala Asn Gly Asp Phe Ile Ser Thr Asn Arg Glu
        1520                1525                1530
Asn Phe His Tyr Gly Ser Val Val Thr Tyr Arg Cys Asn Leu Gly
        1535                1540                1545
Ser Arg Gly Arg Lys Val Phe Glu Leu Val Gly Glu Pro Ser Ile
        1550                1555                1560
Tyr Cys Thr Ser Asn Asp Asp Gln Val Gly Ile Trp Ser Gly Pro
        1565                1570                1575
Ala Pro Gln Cys Ile Ile Pro Asn Lys Cys Thr Pro Pro Asn Val
        1580                1585                1590
Glu Asn Gly Ile Leu Val Ser Asp Asn Arg Ser Leu Phe Ser Leu
        1595                1600                1605
Asn Glu Val Val Glu Phe Arg Cys Gln Pro Gly Phe Val Met Lys
        1610                1615                1620
Gly Pro Arg Arg Val Lys Cys Gln Ala Leu Asn Lys Trp Glu Pro
        1625                1630                1635
Glu Leu Pro Ser Cys Ser Arg Val Cys Gln Pro Pro Glu Ile
        1640                1645                1650
Leu His Gly Glu His Thr Pro Ser His Gln Asp Asn Phe Ser Pro
        1655                1660                1665
Gly Gln Glu Val Phe Tyr Ser Cys Glu Pro Gly Tyr Asp Leu Arg
        1670                1675                1680
```

-continued

Gly Ala Ala Ser Leu His Cys Thr Pro Gln Gly Asp Trp Ser Pro
1685                1690                1695

Glu Ala Pro Arg Cys Ala Val Lys Ser Cys Asp Asp Phe Leu Gly
1700                1705                1710

Gln Leu Pro His Gly Arg Val Leu Phe Pro Leu Asn Leu Gln Leu
1715                1720                1725

Gly Ala Lys Val Ser Phe Val Cys Asp Glu Gly Phe Arg Leu Lys
1730                1735                1740

Gly Ser Ser Val Ser His Cys Val Leu Val Gly Met Arg Ser Leu
1745                1750                1755

Trp Asn Asn Ser Val Pro Val Cys Glu His Ile Phe Cys Pro Asn
1760                1765                1770

Pro Pro Ala Ile Leu Asn Gly Arg His Thr Gly Thr Pro Ser Gly
1775                1780                1785

Asp Ile Pro Tyr Gly Lys Glu Ile Ser Tyr Thr Cys Asp Pro His
1790                1795                1800

Pro Asp Arg Gly Met Thr Phe Asn Leu Ile Gly Glu Ser Thr Ile
1805                1810                1815

Arg Cys Thr Ser Asp Pro His Gly Asn Gly Val Trp Ser Ser Pro
1820                1825                1830

Ala Pro Arg Cys Glu Leu Ser Val Arg Ala Gly His Cys Lys Thr
1835                1840                1845

Pro Glu Gln Phe Pro Phe Ala Ser Pro Thr Ile Pro Ile Asn Asp
1850                1855                1860

Phe Glu Phe Pro Val Gly Thr Ser Leu Asn Tyr Glu Cys Arg Pro
1865                1870                1875

Gly Tyr Phe Gly Lys Met Phe Ser Ile Ser Cys Leu Glu Asn Leu
1880                1885                1890

Val Trp Ser Ser Val Glu Asp Asn Cys Arg Arg Lys Ser Cys Gly
1895                1900                1905

Pro Pro Pro Glu Pro Phe Asn Gly Met Val His Ile Asn Thr Asp
1910                1915                1920

Thr Gln Phe Gly Ser Thr Val Asn Tyr Ser Cys Asn Glu Gly Phe
1925                1930                1935

Arg Leu Ile Gly Ser Pro Ser Thr Thr Cys Leu Val Ser Gly Asn
1940                1945                1950

Asn Val Thr Trp Asp Lys Lys Ala Pro Ile Cys Glu Ile Ile Ser
1955                1960                1965

Cys Glu Pro Pro Pro Thr Ile Ser Asn Gly Asp Phe Tyr Ser Asn
1970                1975                1980

Asn Arg Thr Ser Phe His Asn Gly Thr Val Val Thr Tyr Gln Cys
1985                1990                1995

His Thr Gly Pro Asp Gly Glu Gln Leu Phe Glu Leu Val Gly Glu
2000                2005                2010

Arg Ser Ile Tyr Cys Thr Ser Lys Asp Asp Gln Val Gly Val Trp
2015                2020                2025

Ser Ser Pro Pro Pro Arg Cys Ile Ser Thr Asn Lys Cys Thr Ala
2030                2035                2040

Pro Glu Val Glu Asn Ala Ile Arg Val Pro Gly Asn Arg Ser Phe
2045                2050                2055

Phe Thr Leu Thr Glu Ile Ile Arg Phe Arg Cys Gln Pro Gly Phe
2060                2065                2070

```
Val Met Val Gly Ser His Thr Val Gln Cys Gln Thr Asn Gly Arg
2075                2080                2085

Trp Gly Pro Lys Leu Pro His Cys Ser Arg Val Cys Gln Pro Pro
2090                2095                2100

Pro Glu Ile Leu His Gly Glu His Thr Leu Ser His Gln Asp Asn
2105                2110                2115

Phe Ser Pro Gly Gln Glu Val Phe Tyr Ser Cys Glu Pro Ser Tyr
2120                2125                2130

Asp Leu Arg Gly Ala Ala Ser Leu His Cys Thr Pro Gln Gly Asp
2135                2140                2145

Trp Ser Pro Glu Ala Pro Arg Cys Thr Val Lys Ser Cys Asp Asp
2150                2155                2160

Phe Leu Gly Gln Leu Pro His Gly Arg Val Leu Leu Pro Leu Asn
2165                2170                2175

Leu Gln Leu Gly Ala Lys Val Ser Phe Val Cys Asp Glu Gly Phe
2180                2185                2190

Arg Leu Lys Gly Arg Ser Ala Ser His Cys Val Leu Ala Gly Met
2195                2200                2205

Lys Ala Leu Trp Asn Ser Ser Val Pro Val Cys Glu Gln Ile Phe
2210                2215                2220

Cys Pro Asn Pro Pro Ala Ile Leu Asn Gly Arg His Thr Gly Thr
2225                2230                2235

Pro Phe Gly Asp Ile Pro Tyr Gly Lys Glu Ile Ser Tyr Ala Cys
2240                2245                2250

Asp Thr His Pro Asp Arg Gly Met Thr Phe Asn Leu Ile Gly Glu
2255                2260                2265

Ser Ser Ile Arg Cys Thr Ser Asp Pro Gln Gly Asn Gly Val Trp
2270                2275                2280

Ser Ser Pro Ala Pro Arg Cys Glu Leu Ser Val Pro Ala Ala Cys
2285                2290                2295

Pro His Pro Pro Lys Ile Gln Asn Gly His Tyr Ile Gly Gly His
2300                2305                2310

Val Ser Leu Tyr Leu Pro Gly Met Thr Ile Ser Tyr Ile Cys Asp
2315                2320                2325

Pro Gly Tyr Leu Leu Val Gly Lys Gly Phe Ile Phe Cys Thr Asp
2330                2335                2340

Gln Gly Ile Trp Ser Gln Leu Asp His Tyr Cys Lys Glu Val Asn
2345                2350                2355

Cys Ser Phe Pro Leu Phe Met Asn Gly Ile Ser Lys Glu Leu Glu
2360                2365                2370

Met Lys Lys Val Tyr His Tyr Gly Asp Tyr Val Thr Leu Lys Cys
2375                2380                2385

Glu Asp Gly Tyr Thr Leu Glu Gly Ser Pro Trp Ser Gln Cys Gln
2390                2395                2400

Ala Asp Asp Arg Trp Asp Pro Pro Leu Ala Lys Cys Thr Ser Arg
2405                2410                2415

Thr His Asp Ala Leu Ile Val Gly Thr Leu Ser Gly Thr Ile Phe
2420                2425                2430

Phe Ile Leu Leu Ile Ile Phe Leu Ser Trp Ile Ile Leu Lys His
2435                2440                2445

Arg Lys Gly Asn Asn Ala His Glu Asn Pro Lys Glu Val Ala Ile
2450                2455                2460

His Leu His Ser Gln Gly Gly Ser Ser Val His Pro Arg Thr Leu
```

-continued

```
                2465                2470                2475
        Gln Thr Asn Glu Glu Asn Ser Arg Val Leu Pro
            2480                2485

<210> SEQ ID NO 2
<211> LENGTH: 2039
<212> TYPE: PRT
<213> ORGANISM: Homo sapiens

<400> SEQUENCE: 2

Met Gly Ala Ser Ser Pro Arg Ser Pro Glu Pro Val Gly Pro Pro Ala
1               5                   10                  15

Pro Gly Leu Pro Phe Cys Cys Gly Gly Ser Leu Leu Ala Val Val Val
            20                  25                  30

Leu Leu Ala Leu Pro Val Ala Trp Gly Gln Cys Asn Ala Pro Glu Trp
        35                  40                  45

Leu Pro Phe Ala Arg Pro Thr Asn Leu Thr Asp Glu Phe Glu Phe Pro
    50                  55                  60

Ile Gly Thr Tyr Leu Asn Tyr Glu Cys Arg Pro Gly Tyr Ser Gly Arg
65                  70                  75                  80

Pro Phe Ser Ile Ile Cys Leu Lys Asn Ser Val Trp Thr Gly Ala Lys
                85                  90                  95

Asp Arg Cys Arg Arg Lys Ser Cys Arg Asn Pro Pro Asp Pro Val Asn
            100                 105                 110

Gly Met Val His Val Ile Lys Gly Ile Gln Phe Gly Ser Gln Ile Lys
        115                 120                 125

Tyr Ser Cys Thr Lys Gly Tyr Arg Leu Ile Gly Ser Ser Ala Thr
    130                 135                 140

Cys Ile Ile Ser Gly Asp Thr Val Ile Trp Asp Asn Glu Thr Pro Ile
145                 150                 155                 160

Cys Asp Arg Ile Pro Cys Gly Leu Pro Pro Thr Ile Thr Asn Gly Asp
                165                 170                 175

Phe Ile Ser Thr Asn Arg Glu Asn Phe His Tyr Gly Ser Val Val Thr
            180                 185                 190

Tyr Arg Cys Asn Pro Gly Ser Gly Gly Arg Lys Val Phe Glu Leu Val
        195                 200                 205

Gly Glu Pro Ser Ile Tyr Cys Thr Ser Asn Asp Asp Gln Val Gly Ile
    210                 215                 220

Trp Ser Gly Pro Ala Pro Gln Cys Ile Ile Pro Asn Lys Cys Thr Pro
225                 230                 235                 240

Pro Asn Val Glu Asn Gly Ile Leu Val Ser Asp Asn Arg Ser Leu Phe
                245                 250                 255

Ser Leu Asn Glu Val Val Glu Phe Arg Cys Gln Pro Gly Phe Val Met
            260                 265                 270

Lys Gly Pro Arg Arg Val Lys Cys Gln Ala Leu Asn Lys Trp Glu Pro
        275                 280                 285

Glu Leu Pro Ser Cys Ser Arg Val Cys Gln Pro Pro Asp Val Leu
    290                 295                 300

His Ala Glu Arg Thr Gln Arg Asp Lys Asp Asn Phe Ser Pro Gly Gln
305                 310                 315                 320

Glu Val Phe Tyr Ser Cys Glu Pro Gly Tyr Asp Leu Arg Gly Ala Ala
                325                 330                 335

Ser Met Arg Cys Thr Pro Gln Gly Asp Trp Ser Pro Ala Ala Pro Thr
            340                 345                 350
```

```
Cys Glu Val Lys Ser Cys Asp Asp Phe Met Gly Gln Leu Asn Gly
            355                 360                 365
Arg Val Leu Phe Pro Val Asn Leu Gln Leu Gly Ala Lys Val Asp Phe
    370                 375                 380
Val Cys Asp Glu Gly Phe Gln Leu Lys Gly Ser Ser Ala Ser Tyr Cys
385                 390                 395                 400
Val Leu Ala Gly Met Glu Ser Leu Trp Asn Ser Ser Val Pro Val Cys
                405                 410                 415
Glu Gln Ile Phe Cys Pro Ser Pro Val Ile Pro Asn Gly Arg His
                420                 425                 430
Thr Gly Lys Pro Leu Glu Val Phe Pro Phe Gly Lys Thr Val Asn Tyr
            435                 440                 445
Thr Cys Asp Pro His Pro Asp Arg Gly Thr Ser Phe Asp Leu Ile Gly
    450                 455                 460
Glu Ser Thr Ile Arg Cys Thr Ser Asp Pro Gln Gly Asn Gly Val Trp
465                 470                 475                 480
Ser Ser Pro Ala Pro Arg Cys Gly Ile Leu Gly His Cys Gln Ala Pro
                485                 490                 495
Asp His Phe Leu Phe Ala Lys Leu Lys Thr Gln Thr Asn Ala Ser Asp
                500                 505                 510
Phe Pro Ile Gly Thr Ser Leu Lys Tyr Glu Cys Arg Pro Glu Tyr Tyr
            515                 520                 525
Gly Arg Pro Phe Ser Ile Thr Cys Leu Asp Asn Leu Val Trp Ser Ser
    530                 535                 540
Pro Lys Asp Val Cys Lys Arg Lys Ser Cys Lys Thr Pro Pro Asp Pro
545                 550                 555                 560
Val Asn Gly Met Val His Val Ile Thr Asp Ile Gln Val Gly Ser Arg
                565                 570                 575
Ile Asn Tyr Ser Cys Thr Thr Gly His Arg Leu Ile Gly His Ser Ser
                580                 585                 590
Ala Glu Cys Ile Leu Ser Gly Asn Ala Ala His Trp Ser Thr Lys Pro
            595                 600                 605
Pro Ile Cys Gln Arg Ile Pro Cys Gly Leu Pro Pro Thr Ile Ala Asn
    610                 615                 620
Gly Asp Phe Ile Ser Thr Asn Arg Glu Asn Phe His Tyr Gly Ser Val
625                 630                 635                 640
Val Thr Tyr Arg Cys Asn Pro Gly Ser Gly Gly Arg Lys Val Phe Glu
                645                 650                 655
Leu Val Gly Glu Pro Ser Ile Tyr Cys Thr Ser Asn Asp Asp Gln Val
                660                 665                 670
Gly Ile Trp Ser Gly Pro Ala Pro Gln Cys Ile Ile Pro Asn Lys Cys
            675                 680                 685
Thr Pro Pro Asn Val Glu Asn Gly Ile Leu Val Ser Asp Asn Arg Ser
    690                 695                 700
Leu Phe Ser Leu Asn Glu Val Val Glu Phe Arg Cys Gln Pro Gly Phe
705                 710                 715                 720
Val Met Lys Gly Pro Arg Arg Val Lys Cys Gln Ala Leu Asn Lys Trp
                725                 730                 735
Glu Pro Glu Leu Pro Ser Cys Ser Arg Val Cys Gln Pro Pro Pro Asp
                740                 745                 750
Val Leu His Ala Glu Arg Thr Gln Arg Asp Lys Asp Asn Phe Ser Pro
            755                 760                 765
Gly Gln Glu Val Phe Tyr Ser Cys Glu Pro Gly Tyr Asp Leu Arg Gly
```

```
              770               775               780
Ala Ala Ser Met Arg Cys Thr Pro Gln Gly Asp Trp Ser Pro Ala Ala
785               790               795               800

Pro Thr Cys Glu Val Lys Ser Cys Asp Asp Phe Met Gly Gln Leu Leu
              805               810               815

Asn Gly Arg Val Leu Phe Pro Val Asn Leu Gln Leu Gly Ala Lys Val
              820               825               830

Asp Phe Val Cys Asp Glu Gly Phe Gln Leu Lys Gly Ser Ser Ala Ser
              835               840               845

Tyr Cys Val Leu Ala Gly Met Glu Ser Leu Trp Asn Ser Ser Val Pro
              850               855               860

Val Cys Glu Gln Ile Phe Cys Pro Ser Pro Pro Val Ile Pro Asn Gly
865               870               875               880

Arg His Thr Gly Lys Pro Leu Glu Val Phe Pro Phe Gly Lys Ala Val
              885               890               895

Asn Tyr Thr Cys Asp Pro His Pro Asp Arg Gly Thr Ser Phe Asp Leu
              900               905               910

Ile Gly Glu Ser Thr Ile Arg Cys Thr Ser Asp Pro Gln Gly Asn Gly
              915               920               925

Val Trp Ser Ser Pro Ala Pro Arg Cys Gly Ile Leu Gly His Cys Gln
930               935               940

Ala Pro Asp His Phe Leu Phe Ala Lys Leu Lys Thr Gln Thr Asn Ala
945               950               955               960

Ser Asp Phe Pro Ile Gly Thr Ser Leu Lys Tyr Glu Cys Arg Pro Glu
              965               970               975

Tyr Tyr Gly Arg Pro Phe Ser Ile Thr Cys Leu Asp Asn Leu Val Trp
              980               985               990

Ser Ser Pro Lys Asp Val Cys Lys Arg Lys Ser Cys Lys Thr Pro Pro
              995               1000              1005

Asp Pro Val Asn Gly Met Val His Val Ile Thr Asp Ile Gln Val
    1010              1015              1020

Gly Ser Arg Ile Asn Tyr Ser Cys Thr Thr Gly His Arg Leu Ile
    1025              1030              1035

Gly His Ser Ser Ala Glu Cys Ile Leu Ser Gly Asn Thr Ala His
    1040              1045              1050

Trp Ser Thr Lys Pro Pro Ile Cys Gln Arg Ile Pro Cys Gly Leu
    1055              1060              1065

Pro Pro Thr Ile Ala Asn Gly Asp Phe Ile Ser Thr Asn Arg Glu
    1070              1075              1080

Asn Phe His Tyr Gly Ser Val Val Thr Tyr Arg Cys Asn Leu Gly
    1085              1090              1095

Ser Arg Gly Arg Lys Val Phe Glu Leu Val Gly Glu Pro Ser Ile
    1100              1105              1110

Tyr Cys Thr Ser Asn Asp Asp Gln Val Gly Ile Trp Ser Gly Pro
    1115              1120              1125

Ala Pro Gln Cys Ile Ile Pro Asn Lys Cys Thr Pro Pro Asn Val
    1130              1135              1140

Glu Asn Gly Ile Leu Val Ser Asp Asn Arg Ser Leu Phe Ser Leu
    1145              1150              1155

Asn Glu Val Val Glu Phe Arg Cys Gln Pro Gly Phe Val Met Lys
    1160              1165              1170

Gly Pro Arg Arg Val Lys Cys Gln Ala Leu Asn Lys Trp Glu Pro
    1175              1180              1185
```

```
Glu Leu Pro Ser Cys Ser Arg Val Cys Gln Pro Pro Pro Glu Ile
    1190                1195                1200

Leu His Gly Glu His Thr Pro Ser His Gln Asp Asn Phe Ser Pro
    1205                1210                1215

Gly Gln Glu Val Phe Tyr Ser Cys Glu Pro Gly Tyr Asp Leu Arg
    1220                1225                1230

Gly Ala Ala Ser Leu His Cys Thr Pro Gln Gly Asp Trp Ser Pro
    1235                1240                1245

Glu Ala Pro Arg Cys Ala Val Lys Ser Cys Asp Asp Phe Leu Gly
    1250                1255                1260

Gln Leu Pro His Gly Arg Val Leu Phe Pro Leu Asn Leu Gln Leu
    1265                1270                1275

Gly Ala Lys Val Ser Phe Val Cys Asp Glu Gly Phe Arg Leu Lys
    1280                1285                1290

Gly Ser Ser Val Ser His Cys Val Leu Val Gly Met Arg Ser Leu
    1295                1300                1305

Trp Asn Asn Ser Val Pro Val Cys Glu His Ile Phe Cys Pro Asn
    1310                1315                1320

Pro Pro Ala Ile Leu Asn Gly Arg His Thr Gly Thr Pro Ser Gly
    1325                1330                1335

Asp Ile Pro Tyr Gly Lys Glu Ile Ser Tyr Thr Cys Asp Pro His
    1340                1345                1350

Pro Asp Arg Gly Met Thr Phe Asn Leu Ile Gly Glu Ser Thr Ile
    1355                1360                1365

Arg Cys Thr Ser Asp Pro His Gly Asn Gly Val Trp Ser Ser Pro
    1370                1375                1380

Ala Pro Arg Cys Glu Leu Ser Val Arg Ala Gly His Cys Lys Thr
    1385                1390                1395

Pro Glu Gln Phe Pro Phe Ala Ser Pro Thr Ile Pro Ile Asn Asp
    1400                1405                1410

Phe Glu Phe Pro Val Gly Thr Ser Leu Asn Tyr Glu Cys Arg Pro
    1415                1420                1425

Gly Tyr Phe Gly Lys Met Phe Ser Ile Ser Cys Leu Glu Asn Leu
    1430                1435                1440

Val Trp Ser Ser Val Glu Asp Asn Cys Arg Arg Lys Ser Cys Gly
    1445                1450                1455

Pro Pro Pro Glu Pro Phe Asn Gly Met Val His Ile Asn Thr Asp
    1460                1465                1470

Thr Gln Phe Gly Ser Thr Val Asn Tyr Ser Cys Asn Glu Gly Phe
    1475                1480                1485

Arg Leu Ile Gly Ser Pro Ser Thr Thr Cys Leu Val Ser Gly Asn
    1490                1495                1500

Asn Val Thr Trp Asp Lys Lys Ala Pro Ile Cys Glu Ile Ile Ser
    1505                1510                1515

Cys Glu Pro Pro Pro Thr Ile Ser Asn Gly Asp Phe Tyr Ser Asn
    1520                1525                1530

Asn Arg Thr Ser Phe His Asn Gly Thr Val Val Thr Tyr Gln Cys
    1535                1540                1545

His Thr Gly Pro Asp Gly Glu Gln Leu Phe Glu Leu Val Gly Glu
    1550                1555                1560

Arg Ser Ile Tyr Cys Thr Ser Lys Asp Asp Gln Val Gly Val Trp
    1565                1570                1575
```

```
Ser Ser Pro Pro Pro Arg Cys Ile Ser Thr Asn Lys Cys Thr Ala
    1580                1585                1590

Pro Glu Val Glu Asn Ala Ile Arg Val Pro Gly Asn Arg Ser Phe
    1595                1600                1605

Phe Thr Leu Thr Glu Ile Ile Arg Phe Arg Cys Gln Pro Gly Phe
    1610                1615                1620

Val Met Val Gly Ser His Thr Val Gln Cys Gln Thr Asn Gly Arg
    1625                1630                1635

Trp Gly Pro Lys Leu Pro His Cys Ser Arg Val Cys Gln Pro Pro
    1640                1645                1650

Pro Glu Ile Leu His Gly Glu His Thr Leu Ser His Gln Asp Asn
    1655                1660                1665

Phe Ser Pro Gly Gln Glu Val Phe Tyr Ser Cys Glu Pro Ser Tyr
    1670                1675                1680

Asp Leu Arg Gly Ala Ala Ser Leu His Cys Thr Pro Gln Gly Asp
    1685                1690                1695

Trp Ser Pro Glu Ala Pro Arg Cys Thr Val Lys Ser Cys Asp Asp
    1700                1705                1710

Phe Leu Gly Gln Leu Pro His Gly Arg Val Leu Leu Pro Leu Asn
    1715                1720                1725

Leu Gln Leu Gly Ala Lys Val Ser Phe Val Cys Asp Glu Gly Phe
    1730                1735                1740

Arg Leu Lys Gly Arg Ser Ala Ser His Cys Val Leu Ala Gly Met
    1745                1750                1755

Lys Ala Leu Trp Asn Ser Ser Val Pro Val Cys Glu Gln Ile Phe
    1760                1765                1770

Cys Pro Asn Pro Pro Ala Ile Leu Asn Gly Arg His Thr Gly Thr
    1775                1780                1785

Pro Phe Gly Asp Ile Pro Tyr Gly Lys Glu Ile Ser Tyr Ala Cys
    1790                1795                1800

Asp Thr His Pro Asp Arg Gly Met Thr Phe Asn Leu Ile Gly Glu
    1805                1810                1815

Ser Ser Ile Arg Cys Thr Ser Asp Pro Gln Gly Asn Gly Val Trp
    1820                1825                1830

Ser Ser Pro Ala Pro Arg Cys Glu Leu Ser Val Pro Ala Ala Cys
    1835                1840                1845

Pro His Pro Pro Lys Ile Gln Asn Gly His Tyr Ile Gly Gly His
    1850                1855                1860

Val Ser Leu Tyr Leu Pro Gly Met Thr Ile Ser Tyr Ile Cys Asp
    1865                1870                1875

Pro Gly Tyr Leu Leu Val Gly Lys Gly Phe Ile Phe Cys Thr Asp
    1880                1885                1890

Gln Gly Ile Trp Ser Gln Leu Asp His Tyr Cys Lys Glu Val Asn
    1895                1900                1905

Cys Ser Phe Pro Leu Phe Met Asn Gly Ile Ser Lys Glu Leu Glu
    1910                1915                1920

Met Lys Lys Val Tyr His Tyr Gly Asp Tyr Val Thr Leu Lys Cys
    1925                1930                1935

Glu Asp Gly Tyr Thr Leu Glu Gly Ser Pro Trp Ser Gln Cys Gln
    1940                1945                1950

Ala Asp Asp Arg Trp Asp Pro Pro Leu Ala Lys Cys Thr Ser Arg
    1955                1960                1965

Thr His Asp Ala Leu Ile Val Gly Thr Leu Ser Gly Thr Ile Phe
```

-continued

```
              1970                1975                1980
Phe Ile Leu Leu Ile Ile Phe Leu Ser Trp Ile Ile Leu Lys His
            1985                1990                1995
Arg Lys Gly Asn Asn Ala His Glu Asn Pro Lys Glu Val Ala Ile
            2000                2005                2010
His Leu His Ser Gln Gly Gly Ser Ser Val His Pro Arg Thr Leu
            2015                2020                2025
Gln Thr Asn Glu Glu Asn Ser Arg Val Leu Pro
            2030                2035

<210> SEQ ID NO 3
<211> LENGTH: 2361
<212> TYPE: PRT
<213> ORGANISM: Homo sapiens

<400> SEQUENCE: 3

Met Cys Leu Gly Arg Met Gly Ala Ser Ser Pro Arg Ser Pro Glu Pro
1               5                   10                  15
Val Gly Pro Pro Ala Pro Gly Leu Pro Phe Cys Cys Gly Gly Ser Leu
                20                  25                  30
Leu Ala Val Val Val Leu Leu Ala Leu Pro Val Ala Trp Gly Gln Cys
            35                  40                  45
Asn Ala Pro Glu Trp Leu Pro Phe Ala Arg Pro Thr Asn Leu Thr Asp
50                  55                  60
Glu Phe Glu Phe Pro Ile Gly Thr Tyr Leu Asn Tyr Glu Cys Arg Pro
65                  70                  75                  80
Gly Tyr Ser Gly Arg Pro Phe Ser Ile Ile Cys Leu Lys Asn Ser Val
                85                  90                  95
Trp Thr Gly Ala Lys Asp Arg Cys Arg Arg Lys Ser Cys Arg Asn Pro
            100                 105                 110
Pro Asp Pro Val Asn Gly Met Val His Val Ile Lys Gly Ile Gln Phe
        115                 120                 125
Gly Ser Gln Ile Lys Tyr Ser Cys Thr Lys Gly Tyr Arg Leu Ile Gly
    130                 135                 140
Ser Ser Ser Ala Thr Cys Ile Ile Ser Gly Asp Thr Val Ile Trp Asp
145                 150                 155                 160
Asn Glu Thr Pro Ile Cys Asp Arg Ile Pro Cys Gly Leu Pro Pro Thr
                165                 170                 175
Ile Thr Asn Gly Asp Phe Ile Ser Thr Asn Arg Glu Asn Phe His Tyr
            180                 185                 190
Gly Ser Val Val Thr Tyr Arg Cys Asn Pro Gly Ser Gly Gly Arg Lys
        195                 200                 205
Val Phe Glu Leu Val Gly Glu Pro Ser Ile Tyr Cys Thr Ser Asn Asp
    210                 215                 220
Asp Gln Val Gly Ile Trp Ser Gly Pro Ala Pro Gln Cys Ile Ile Pro
225                 230                 235                 240
Asn Lys Cys Thr Pro Pro Asn Val Glu Asn Gly Ile Leu Val Ser Asp
                245                 250                 255
Asn Arg Ser Leu Phe Ser Leu Asn Glu Val Val Glu Phe Arg Cys Gln
            260                 265                 270
Pro Gly Phe Val Met Lys Gly Pro Arg Arg Val Lys Cys Gln Ala Leu
        275                 280                 285
Asn Lys Trp Glu Pro Glu Leu Pro Ser Cys Ser Arg Val Cys Gln Pro
    290                 295                 300
```

```
Pro Pro Asp Val Leu His Ala Glu Arg Thr Gln Arg Asp Lys Asp Asn
305                 310                 315                 320

Phe Ser Pro Gly Gln Glu Val Phe Tyr Ser Cys Glu Pro Gly Tyr Asp
            325                 330                 335

Leu Arg Gly Ala Ala Ser Met Arg Cys Thr Pro Gln Gly Asp Trp Ser
                340                 345                 350

Pro Ala Ala Pro Thr Cys Glu Val Lys Ser Cys Asp Asp Phe Met Gly
                355                 360                 365

Gln Leu Leu Asn Gly Arg Val Leu Phe Pro Val Asn Leu Gln Leu Gly
        370                 375                 380

Ala Lys Val Asp Phe Val Cys Asp Glu Gly Phe Gln Leu Lys Gly Ser
385                 390                 395                 400

Ser Ala Ser Tyr Cys Val Leu Ala Gly Met Glu Ser Leu Trp Asn Ser
                405                 410                 415

Ser Val Pro Val Cys Glu Gln Ile Phe Cys Pro Ser Pro Pro Val Ile
                420                 425                 430

Pro Asn Gly Arg His Thr Gly Lys Pro Leu Glu Val Phe Pro Phe Gly
                435                 440                 445

Lys Thr Val Asn Tyr Thr Cys Asp Pro His Pro Asp Arg Gly Thr Ser
450                 455                 460

Phe Asp Leu Ile Gly Glu Ser Thr Ile Arg Cys Thr Ser Asp Pro Gln
465                 470                 475                 480

Gly Asn Gly Val Trp Ser Ser Pro Ala Pro Arg Cys Gly Ile Leu Gly
                485                 490                 495

His Cys Gln Ala Pro Asp His Phe Leu Phe Ala Lys Leu Lys Thr Gln
                500                 505                 510

Thr Asn Ala Ser Asp Phe Pro Ile Gly Thr Ser Leu Lys Tyr Glu Cys
                515                 520                 525

Arg Pro Glu Tyr Tyr Gly Arg Pro Phe Ser Ile Thr Cys Leu Asp Asn
530                 535                 540

Leu Val Trp Ser Ser Pro Lys Asp Val Cys Lys Arg Lys Ser Cys Lys
545                 550                 555                 560

Thr Pro Pro Asp Pro Val Asn Gly Met Val His Val Ile Thr Asp Ile
                565                 570                 575

Gln Val Gly Ser Arg Ile Asn Tyr Ser Cys Thr Thr Gly His Arg Leu
                580                 585                 590

Ile Gly His Ser Ser Ala Glu Cys Ile Leu Ser Gly Asn Ala Ala His
        595                 600                 605

Trp Ser Thr Lys Pro Pro Ile Cys Gln Arg Ile Pro Cys Gly Leu Pro
        610                 615                 620

Pro Thr Ile Ala Asn Gly Asp Phe Ile Ser Thr Asn Arg Glu Asn Phe
625                 630                 635                 640

His Tyr Gly Ser Val Val Thr Tyr Arg Cys Asn Pro Gly Ser Gly Gly
                645                 650                 655

Arg Lys Val Phe Glu Leu Val Gly Glu Pro Ser Ile Tyr Cys Thr Ser
                660                 665                 670

Asn Asp Asp Gln Val Gly Ile Trp Ser Gly Pro Ala Pro Gln Cys Ile
                675                 680                 685

Ile Pro Asn Lys Cys Thr Pro Pro Asn Val Glu Asn Gly Ile Leu Val
                690                 695                 700

Ser Asp Asn Arg Ser Leu Phe Ser Leu Asn Glu Val Val Glu Phe Arg
705                 710                 715                 720

Cys Gln Pro Gly Phe Val Met Lys Gly Pro Arg Arg Val Lys Cys Gln
```

```
                   725               730              735
Ala Leu Asn Lys Trp Glu Pro Glu Leu Pro Ser Cys Ser Arg Val Cys
            740              745             750

Gln Pro Pro Asp Val Leu His Ala Glu Arg Thr Gln Arg Asp Lys
            755              760             765

Asp Asn Phe Ser Pro Gly Gln Glu Val Phe Tyr Ser Cys Glu Pro Gly
            770              775             780

Tyr Asp Leu Arg Gly Ala Ala Ser Met Arg Cys Thr Pro Gln Gly Asp
785              790              795             800

Trp Ser Pro Ala Ala Pro Thr Cys Glu Val Lys Ser Cys Asp Asp Phe
                805              810             815

Met Gly Gln Leu Leu Asn Gly Arg Val Leu Phe Pro Val Asn Leu Gln
                820              825             830

Leu Gly Ala Lys Val Asp Phe Val Cys Asp Glu Gly Phe Gln Leu Lys
                835              840             845

Gly Ser Ser Ala Ser Tyr Cys Val Leu Ala Gly Met Glu Ser Leu Trp
            850              855             860

Asn Ser Ser Val Pro Val Cys Glu Gln Ile Phe Cys Pro Ser Pro Pro
865              870              875             880

Val Ile Pro Asn Gly Arg His Thr Gly Lys Pro Leu Glu Val Phe Pro
                885              890             895

Phe Gly Lys Thr Val Asn Tyr Thr Cys Asp Pro His Pro Asp Arg Gly
            900              905             910

Thr Ser Phe Asp Leu Ile Gly Glu Ser Thr Ile Arg Cys Thr Ser Asp
            915              920             925

Pro Gln Gly Asn Gly Val Trp Ser Ser Pro Ala Pro Arg Cys Gly Ile
930              935              940

Leu Gly His Cys Gln Ala Pro Asp His Phe Leu Phe Ala Lys Leu Lys
945              950              955             960

Thr Gln Thr Asn Ala Ser Asp Phe Pro Ile Gly Thr Ser Leu Lys Tyr
            965              970             975

Glu Cys Arg Pro Glu Tyr Tyr Gly Arg Pro Phe Ser Ile Thr Cys Leu
            980              985             990

Asp Asn Leu Val Trp Ser Ser Pro Lys Asp Val Cys Lys Arg Lys Ser
            995              1000            1005

Cys Lys Thr Pro Pro Asp Pro Val Asn Gly Met Val His Val Ile
            1010             1015            1020

Thr Asp Ile Gln Val Gly Ser Arg Ile Asn Tyr Ser Cys Thr Thr
            1025             1030            1035

Gly His Arg Leu Ile Gly His Ser Ser Ala Glu Cys Ile Leu Ser
            1040             1045            1050

Gly Asn Ala Ala His Trp Ser Thr Lys Pro Pro Ile Cys Gln Leu
            1055             1060            1065

Cys Gln Pro Pro Pro Asp Val Leu His Ala Glu Arg Thr Gln Arg
            1070             1075            1080

Asp Lys Asp Asn Phe Ser Pro Gly Gln Glu Val Phe Tyr Ser Cys
            1085             1090            1095

Glu Pro Gly Tyr Asp Leu Arg Gly Ala Ala Ser Met Arg Cys Thr
            1100             1105            1110

Pro Gln Gly Asp Trp Ser Pro Ala Ala Pro Thr Cys Glu Val Lys
            1115             1120            1125

Ser Cys Asp Asp Phe Met Gly Gln Leu Leu Asn Gly Arg Val Leu
            1130             1135            1140
```

```
Phe Pro Val Asn Leu Gln Leu Gly Ala Lys Val Asp Phe Val Cys
    1145                1150                1155

Asp Glu Gly Phe Gln Leu Lys Gly Ser Ser Ala Ser Tyr Cys Val
    1160                1165                1170

Leu Ala Gly Met Glu Ser Leu Trp Asn Ser Ser Val Pro Val Cys
    1175                1180                1185

Glu Gln Ile Phe Cys Pro Ser Pro Val Ile Pro Asn Gly Arg
    1190                1195                1200

His Thr Gly Lys Pro Leu Glu Val Phe Pro Phe Gly Lys Ala Val
    1205                1210                1215

Asn Tyr Thr Cys Asp Pro His Pro Asp Arg Gly Thr Ser Phe Asp
    1220                1225                1230

Leu Ile Gly Glu Ser Thr Ile Arg Cys Thr Ser Asp Pro Gln Gly
    1235                1240                1245

Asn Gly Val Trp Ser Ser Pro Ala Pro Arg Cys Gly Ile Leu Gly
    1250                1255                1260

His Cys Gln Ala Pro Asp His Phe Leu Phe Ala Lys Leu Lys Thr
    1265                1270                1275

Gln Thr Asn Ala Ser Asp Phe Pro Ile Gly Thr Ser Leu Lys Tyr
    1280                1285                1290

Glu Cys Arg Pro Glu Tyr Tyr Gly Arg Pro Phe Ser Ile Thr Cys
    1295                1300                1305

Leu Asp Asn Leu Val Trp Ser Ser Pro Lys Asp Val Cys Lys Arg
    1310                1315                1320

Lys Ser Cys Lys Thr Pro Pro Asp Pro Val Asn Gly Met Val His
    1325                1330                1335

Val Ile Thr Asp Ile Gln Val Gly Ser Arg Ile Asn Tyr Ser Cys
    1340                1345                1350

Thr Thr Gly His Arg Leu Ile Gly His Ser Ser Ala Glu Cys Ile
    1355                1360                1365

Leu Ser Gly Asn Thr Ala His Trp Ser Thr Lys Pro Pro Ile Cys
    1370                1375                1380

Gln Arg Ile Pro Cys Gly Leu Pro Pro Thr Ile Ala Asn Gly Asp
    1385                1390                1395

Phe Ile Ser Thr Asn Arg Glu Asn Phe His Tyr Gly Ser Val Val
    1400                1405                1410

Thr Tyr Arg Cys Asn Leu Gly Ser Arg Gly Arg Lys Val Phe Glu
    1415                1420                1425

Leu Val Gly Glu Pro Ser Ile Tyr Cys Thr Ser Asn Asp Asp Gln
    1430                1435                1440

Val Gly Ile Trp Ser Gly Pro Ala Pro Gln Cys Ile Ile Pro Asn
    1445                1450                1455

Lys Cys Thr Pro Pro Asn Val Glu Asn Gly Ile Leu Val Ser Asp
    1460                1465                1470

Asn Arg Ser Leu Phe Ser Leu Asn Glu Val Val Glu Phe Arg Cys
    1475                1480                1485

Gln Pro Gly Phe Val Met Lys Gly Pro Arg Arg Val Lys Cys Gln
    1490                1495                1500

Ala Leu Asn Lys Trp Glu Pro Glu Leu Pro Ser Cys Ser Arg Val
    1505                1510                1515

Cys Gln Pro Pro Pro Glu Ile Leu His Gly Glu His Thr Pro Ser
    1520                1525                1530
```

His Gln Asp Asn Phe Ser Pro Gly Gln Glu Val Phe Tyr Ser Cys
1535                    1540                1545

Glu Pro Gly Tyr Asp Leu Arg Gly Ala Ala Ser Leu His Cys Thr
1550                    1555                1560

Pro Gln Gly Asp Trp Ser Pro Glu Ala Pro Arg Cys Ala Val Lys
1565                    1570                1575

Ser Cys Asp Asp Phe Leu Gly Gln Leu Pro His Gly Arg Val Leu
1580                    1585                1590

Phe Pro Leu Asn Leu Gln Leu Gly Ala Lys Val Ser Phe Val Cys
1595                    1600                1605

Asp Glu Gly Phe Arg Leu Lys Gly Ser Ser Val Ser His Cys Val
1610                    1615                1620

Leu Val Gly Met Arg Ser Leu Trp Asn Asn Ser Val Pro Val Cys
1625                    1630                1635

Glu His Ile Phe Cys Pro Asn Pro Pro Ala Ile Leu Asn Gly Arg
1640                    1645                1650

His Thr Gly Thr Pro Ser Gly Asp Ile Pro Tyr Gly Lys Glu Ile
1655                    1660                1665

Ser Tyr Thr Cys Asp Pro His Pro Asp Arg Gly Met Thr Phe Asn
1670                    1675                1680

Leu Ile Gly Glu Ser Thr Ile Arg Cys Thr Ser Asp Pro His Gly
1685                    1690                1695

Asn Gly Val Trp Ser Ser Pro Ala Pro Arg Cys Glu Leu Ser Val
1700                    1705                1710

Arg Ala Gly His Cys Lys Thr Pro Glu Gln Phe Pro Phe Ala Ser
1715                    1720                1725

Pro Thr Ile Pro Ile Asn Asp Phe Glu Phe Pro Val Gly Thr Ser
1730                    1735                1740

Leu Asn Tyr Glu Cys Arg Pro Gly Tyr Phe Gly Lys Met Phe Ser
1745                    1750                1755

Ile Ser Cys Leu Glu Asn Leu Val Trp Ser Ser Val Glu Asp Asn
1760                    1765                1770

Cys Arg Arg Lys Ser Cys Gly Pro Pro Pro Glu Pro Phe Asn Gly
1775                    1780                1785

Met Val His Ile Asn Thr Asp Thr Gln Phe Gly Ser Thr Val Asn
1790                    1795                1800

Tyr Ser Cys Asn Glu Gly Phe Arg Leu Ile Gly Ser Pro Ser Thr
1805                    1810                1815

Thr Cys Leu Val Ser Gly Asn Asn Val Thr Trp Asp Lys Lys Ala
1820                    1825                1830

Pro Ile Cys Glu Ile Ile Ser Cys Glu Pro Pro Pro Thr Ile Ser
1835                    1840                1845

Asn Gly Asp Phe Tyr Ser Asn Asn Arg Thr Ser Phe His Asn Gly
1850                    1855                1860

Thr Val Val Thr Tyr Gln Cys His Thr Gly Pro Asp Gly Glu Gln
1865                    1870                1875

Leu Phe Glu Leu Val Gly Glu Arg Ser Ile Tyr Cys Thr Ser Lys
1880                    1885                1890

Asp Asp Gln Val Gly Val Trp Ser Ser Pro Pro Pro Arg Cys Ile
1895                    1900                1905

Ser Thr Asn Lys Cys Thr Ala Pro Glu Val Glu Asn Ala Ile Arg
1910                    1915                1920

Val Pro Gly Asn Arg Ser Phe Phe Thr Leu Thr Glu Ile Ile Arg

```
                1925                1930                1935

Phe Arg Cys Gln Pro Gly Phe Val Met Val Gly Ser His Thr Val
    1940                1945                1950

Gln Cys Gln Thr Asn Gly Arg Trp Gly Pro Lys Leu Pro His Cys
    1955                1960                1965

Ser Arg Val Cys Gln Pro Pro Glu Ile Leu His Gly Glu His
    1970                1975                1980

Thr Leu Ser His Gln Asp Asn Phe Ser Pro Gly Gln Glu Val Phe
    1985                1990                1995

Tyr Ser Cys Glu Pro Ser Tyr Asp Leu Arg Gly Ala Ala Ser Leu
    2000                2005                2010

His Cys Thr Pro Gln Gly Asp Trp Ser Pro Glu Ala Pro Arg Cys
    2015                2020                2025

Thr Val Lys Ser Cys Asp Asp Phe Leu Gly Gln Leu Pro His Gly
    2030                2035                2040

Arg Val Leu Leu Pro Leu Asn Leu Gln Leu Gly Ala Lys Val Ser
    2045                2050                2055

Phe Val Cys Asp Glu Gly Phe Arg Leu Lys Gly Arg Ser Ala Ser
    2060                2065                2070

His Cys Val Leu Ala Gly Met Lys Ala Leu Trp Asn Ser Ser Val
    2075                2080                2085

Pro Val Cys Glu Gln Ile Phe Cys Pro Asn Pro Ala Ile Leu
    2090                2095                2100

Asn Gly Arg His Thr Gly Thr Pro Phe Gly Asp Ile Pro Tyr Gly
    2105                2110                2115

Lys Glu Ile Ser Tyr Ala Cys Asp Thr His Pro Asp Arg Gly Met
    2120                2125                2130

Thr Phe Asn Leu Ile Gly Glu Ser Ser Ile Arg Cys Thr Ser Asp
    2135                2140                2145

Pro Gln Gly Asn Gly Val Trp Ser Ser Pro Ala Pro Arg Cys Glu
    2150                2155                2160

Leu Ser Val Pro Ala Ala Cys Pro His Pro Pro Lys Ile Gln Asn
    2165                2170                2175

Gly His Tyr Ile Gly Gly His Val Ser Leu Tyr Leu Pro Gly Met
    2180                2185                2190

Thr Ile Ser Tyr Ile Cys Asp Pro Gly Tyr Leu Leu Val Gly Lys
    2195                2200                2205

Gly Phe Ile Phe Cys Thr Asp Gln Gly Ile Trp Ser Gln Leu Asp
    2210                2215                2220

His Tyr Cys Lys Glu Val Asn Cys Ser Phe Pro Leu Phe Met Asn
    2225                2230                2235

Gly Ile Ser Lys Glu Leu Glu Met Lys Lys Val Tyr His Tyr Gly
    2240                2245                2250

Asp Tyr Val Thr Leu Lys Cys Glu Asp Gly Tyr Thr Leu Glu Gly
    2255                2260                2265

Ser Pro Trp Ser Gln Cys Gln Ala Asp Asp Arg Trp Asp Pro Pro
    2270                2275                2280

Leu Ala Lys Cys Thr Ser Arg Thr His Asp Ala Leu Ile Val Gly
    2285                2290                2295

Thr Leu Ser Gly Thr Ile Phe Phe Ile Leu Leu Ile Ile Phe Leu
    2300                2305                2310

Ser Trp Ile Ile Leu Lys His Arg Lys Gly Asn Asn Ala His Glu
    2315                2320                2325
```

```
Asn Pro  Lys Glu Val Ala Ile  His Leu His Ser Gln  Gly Gly Ser
    2330                2335                2340

Ser Val  His Pro Arg Thr Leu  Gln Thr Asn Glu Glu  Asn Ser Arg
    2345                2350                2355

Val Leu  Pro
    2360

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7
<211> LENGTH: 54
<212> TYPE: DNA
<213> ORGANISM: Thosea asigna virus

<400> SEQUENCE: 7
gagggcagag gaagtcttct aacatgcggt gacgtggagg sgsstcccgg ccct          54

<210> SEQ ID NO 8
<211> LENGTH: 27
<212> TYPE: DNA
<213> ORGANISM: Human influenza virus

<400> SEQUENCE: 8
tacccctatg acgtgcccga ctatgcc                                        27

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tcctgaggag aagtctgccg t                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggagtggaca gatccccaaa g                                              21

<210> SEQ ID NO 11
```

<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
tctcctgccg acaagaccaa    20

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
gcagtggctt agcttgaagt tg    22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
caacttcaag ctaagccact gc    22

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
cggtgctcac agaagccag    19

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
gactgctgtc aatgccctgt    20

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
aaaggcacct agcaccttct t    21

<210> SEQ ID NO 17
<211> LENGTH: 25

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cactggagct acagacaaga aggtg                                            25

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tctcccacca tagaagatac cagg                                             24

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aagagcctca ggatccagca c                                                21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tcagcagtga tggatggaca c                                                21

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cgcagctagg aataatggaa tagg                                             24

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
catggcctca gttccgaaa                                                   19

<210> SEQ ID NO 23
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 23

Gly Gly Gly Ser Gly Gly Gly Ser
1               5

<210> SEQ ID NO 24
<211> LENGTH: 5
<212> TYPE: PRT
<213> ORGANISM: Unknown
<220> FEATURE:
<223> OTHER INFORMATION: Description of Unknown:
      Sortase A peptide
<220> FEATURE:
<221> NAME/KEY: MOD_RES
<222> LOCATION: (3)..(3)
<223> OTHER INFORMATION: Any amino acid

<400> SEQUENCE: 24

Leu Pro Xaa Thr Gly
1               5

<210> SEQ ID NO 25
<211> LENGTH: 5
<212> TYPE: PRT
<213> ORGANISM: Unknown
<220> FEATURE:
<223> OTHER INFORMATION: Description of Unknown:
      Sortase A peptide
<220> FEATURE:
<221> NAME/KEY: MOD_RES
<222> LOCATION: (3)..(3)
<223> OTHER INFORMATION: Any amino acid

<400> SEQUENCE: 25

Leu Pro Xaa Thr Ala
1               5

<210> SEQ ID NO 26
<211> LENGTH: 8
<212> TYPE: PRT
<213> ORGANISM: Gallus gallus

<400> SEQUENCE: 26

Ser Ile Ile Asn Phe Glu Lys Leu
1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 27

His His His His His His
1               5

<210> SEQ ID NO 28
<211> LENGTH: 20
<212> TYPE: PRT
<213> ORGANISM: Mus sp.

<400> SEQUENCE: 28
```

-continued

```
His Trp Met Val Leu Pro Trp Leu Pro Gly Thr Leu Asp Gly Gly Ser
1               5                   10                  15

Gly Cys Arg Gly
            20

<210> SEQ ID NO 29
<211> LENGTH: 6
<212> TYPE: PRT
<213> ORGANISM: Unknown
<220> FEATURE:
<223> OTHER INFORMATION: Description of Unknown:
      Sortase A peptide

<400> SEQUENCE: 29

Leu Pro Glu Thr Gly Gly
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: PE-Kb-Ser

<400> SEQUENCE: 30

Ser Ile Ile Asn Phe Glu Lys Leu
1               5
```